US010260069B2

(12) United States Patent
Oestergaard et al.

(10) Patent No.: US 10,260,069 B2
(45) Date of Patent: Apr. 16, 2019

(54) SELECTIVE ANTISENSE COMPOUNDS AND USES THEREOF

(71) Applicant: Ionis Pharmaceuticals, Inc., Carlsbad, CA (US)

(72) Inventors: Michael Oestergaard, Carlsbad, CA (US); Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/765,633

(22) PCT Filed: Feb. 4, 2014

(86) PCT No.: PCT/US2014/014722
§ 371 (c)(1),
(2) Date: Aug. 4, 2015

(87) PCT Pub. No.: WO2014/121287
PCT Pub. Date: Aug. 7, 2014

(65) Prior Publication Data

US 2015/0376625 A1 Dec. 31, 2015

Related U.S. Application Data

(60) Provisional application No. 61/760,610, filed on Feb. 4, 2013.

(51) Int. Cl.
*C12N 15/11* (2006.01)
*C12N 15/113* (2010.01)
*C07H 21/02* (2006.01)

(52) U.S. Cl.
CPC ......... *C12N 15/1138* (2013.01); *C07H 21/02* (2013.01); *C12N 15/113* (2013.01); *C12N 2310/11* (2013.01); *C12N 2310/31* (2013.01); *C12N 2310/315* (2013.01); *C12N 2310/322* (2013.01); *C12N 2310/3231* (2013.01); *C12N 2310/33* (2013.01); *C12N 2310/335* (2013.01); *C12N 2310/3341* (2013.01); *C12N 2310/341* (2013.01); *C12N 2310/351* (2013.01); *C12N 2320/34* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 2005/0176045 A1 | 8/2005 | Federov et al. | |
| 2007/0123484 A1 | 5/2007 | Bhat et al. | |
| 2011/0213010 A1* | 9/2011 | Hayden | C12N 15/111 514/44 A |
| 2015/0051389 A1 | 2/2015 | Seth et al. | |

FOREIGN PATENT DOCUMENTS

| | | |
|---|---|---|
| JP | 2008-513507 | 5/2008 |
| WO | WO 2006/034348 | 3/2006 |
| WO | WO 2008/147887 | 12/2008 |
| WO | WO 2011/097643 | 8/2011 |
| WO | WO 2011/097644 | 8/2011 |
| WO | WO 2012/109395 | 8/2012 |
| WO | WO 2013/022967 | 2/2013 |

OTHER PUBLICATIONS

Carroll et al., "Potent and Selective Antisense Oligonucleotides Targeting Single-Nucleotide Polymorphisms in the Huntington Disease Gene / Allele-Specific Silencing of Mutant Huntingtin" Molecular Therapy (2011) 19(12):2178-2185.
Fluiter et al., "Killing cancer by targeting genes that cancer cells have lost: allele-specific inhibition, a novel approach to the treatment of genetic disorders." Cell Mol Life Sci (2003) 60: 834-43.
Gagnon et al. "Allele-selective inhibition of mutatn huntington expression with antisense oligonucleotides targeting the expanded CAG repeat" Biochemistry (2010) 49:10166-78.
Ostergaard et al. "Rational design of antisense oligonucleotides targeting single nucleotide polymorphisms for potent and allele selective suppression of mutant Huntingtin in the CNS." Nucleic Acids Res. (2013) 41:9634-50.
Persichetti et al., "Differential expression of normal and mutant Huntington's disease gene alleles." Neurobiol Dis (1996) 3(3): 183-190.
Pfister et al., "Five siRNAs targeting three SNPs may provide therapyfor three-quarters of Huntington's Disease patients," Current Biology (2009) 19:774-778.
Southwell et al. "Antisense oligonuceltide therapeutics for inherited neurodegenerative diseases" Trends Mol Med (2012) 18:634-43.
International Search Report for application PCT/US14/14722 dated Aug. 25, 2014.
Liu et al., "Linking SNP Identity to CAG Repeat Length in Huntington's Disease Patients," Nature Methods, 2008, 5(11):951-953.
Extended European Search Report for application No. EP 17206749.8 dated Feb. 13, 2018, 9 pages.
Bruge et al., "A novel Real Time PCR strategy to detect SOD3 SNP using LNA probes," Mutation Res, 2009, 669(1):80-84.

* cited by examiner

*Primary Examiner* — Dana H Shin
(74) *Attorney, Agent, or Firm* — McNeill Baur PLLC

(57) ABSTRACT

The present disclosure provides oligomeric compounds. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell. In certain embodiments, certain oligomeric compounds selectively reduce the expression of a target nucleic acid transcript relative to a non-target nucleic acid transcript.

12 Claims, No Drawings

Specification includes a Sequence Listing.

SELECTIVE ANTISENSE COMPOUNDS AND USES THEREOF

SEQUENCE LISTING

The present application is being filed along with a Sequence Listing in electronic format. The Sequence Listing is provided as a file entitled CORE0113USASEQ_ST25.txt, created Aug. 4, 2015 which is 316 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY OF THE INVENTION

In certain embodiments, the present invention provides oligomeric compounds comprising oligonucleotides. In certain embodiments, such oligonucleotides comprise a region having a gapmer motif. In certain embodiments, such oligonucleotides consist of a region having a gapmer motif. The present disclosure provides the following non-limiting numbered embodiments:
We Claim:

EMBODIMENT 1

A oligomeric compound comprising a modified oligonucleotide consisting of 10 to 30 linked nucleosides, wherein the modified oligonucleotide has a modification motif comprising: a 5'-region consisting of 1-9 linked 5'-region nucleosides, each independently selected from among a modified nucleoside and an unmodified deoxynucleoside, provided that at least one 5'-region nucleoside is a modified nucleoside and wherein the 3'-most 5'-region nucleoside is a modified nucleoside;

a 3'-region consisting of 2-10 linked 3'-region nucleosides, wherein each 3'-region nucleoside comprises a modified nucleoside; and a central region between the 5'-region and the 3'-region consisting of 6-10 linked central region nucleosides, each independently selected from among: a modified nucleoside and an unmodified deoxynucleoside, wherein the 5'-most central region nucleoside is an unmodified deoxynucleoside and the 3'-most central region nucleoside is an unmodified deoxynucleoside; and wherein the modified oligonucleotide has a nucleobase sequence complementary to the nucleobase sequence of a target region of a nucleic acid associated with a huntingtin transcript.

EMBODIMENT 2

The oligomeric compound of embodiment 1, wherein the nucleobase sequence of the target region of the target nucleic acid differs from the nucleobase sequence of at least one non-target nucleic acid by 1-3 differentiating nucleobases.

EMBODIMENT 3

The oligomeric compound of embodiment 1, wherein the nucleobase sequence of the target region of the target nucleic acid differs from the nucleobase sequence of at least one non-target nucleic acid by a single differentiating nucleobase.

EMBODIMENT 4

The oligomeric compound of embodiment 2 or 3, wherein the target nucleic acid and the non-target nucleic acid are transcripts from different genes.

EMBODIMENT 5

The oligomeric compound of any of embodiments 2 to 4, wherein the non-target nucleic acid is bone morphogenetic protein receptor, type IA.

EMBODIMENT 6

The oligomeric compound of embodiment 2 or 3, wherein the target nucleic acid and the non-target nucleic acid are alleles of the same gene.

EMBODIMENT 7

The oligomeric compound of embodiment 6, wherein the single differentiating nucleobase is a single-nucleotide polymorphism.

EMBODIMENT 8

The oligomeric compound of embodiment 7, wherein the single-nucleotide polymorphism is associated with a disease.

EMBODIMENT 9

The oligomeric compound of embodiment 8, wherein the disease is Huntington's disease.

EMBODIMENT 10

The oligomeric compound of embodiment 7, wherein the single-nucleotide polymorphism is selected from among: rs6446723, rs3856973, rs2285086, rs363092, rs916171, rs6844859, rs7691627, rs4690073, rs2024115, rs11731237, rs362296, rs10015979, rs7659144, rs363096, rs362273, rs16843804, rs362271, rs362275, rs3121419, rs362272, rs3775061, rs34315806, rs363099, rs2298967, rs363088, rs363064, rs363102, rs2798235, rs363080, rs363072, rs363125, rs362303, rs362310, rs10488840, rs362325, rs35892913, rs363102, rs363096, rs11731237, rs10015979, rs363080, rs2798235, rs1936032, rs2276881, rs363070, rs35892913, rs12502045, rs6446723, rs7685686, rs3733217, rs6844859, and rs362331.

EMBODIMENT 11

The oligomeric compound of embodiment 8, wherein the single-nucleotide polymorphism is selected from among:

rs7685686, rs362303 rs4690072, rs362273, rs2024115, rs6446723, rs363064, and rs363088.

EMBODIMENT 12

The oligomeric compound of embodiment 8, wherein the single-nucleotide polymorphism is selected from among: rs7685686, rs363088, rs362303, rs362273, rs2024115, rs6446723, and rs363064.

EMBODIMENT 13

The oligomeric compound of embodiment 8, wherein the single-nucleotide polymorphism is rs7685686.

EMBODIMENT 14

The oligomeric compound of embodiment 8, wherein the single-nucleotide polymorphism is rs363088.

EMBODIMENT 15

The oligomeric compound of embodiment 8, wherein the single-nucleotide polymorphism is rs362303.

EMBODIMENT 16

The oligomeric compound of embodiment 8, wherein the single-nucleotide polymorphism is rs362273.

EMBODIMENT 17

The oligomeric compound of embodiment 8, wherein the single-nucleotide polymorphism is rs2024115.

EMBODIMENT 18

The oligomeric compound of embodiment 8, wherein the single-nucleotide polymorphism is rs6446723.

EMBODIMENT 19

The oligomeric compound of embodiment 8, wherein the single-nucleotide polymorphism is rs363064.

EMBODIMENT 20

The oligomeric compound of any of embodiments 1-19, wherein the 3'-most 5'-region nucleoside comprises a bicyclic sugar moiety.

EMBODIMENT 21

The oligomeric compound of embodiment 20, wherein the 3'-most 5'-region nucleoside comprises a cEt sugar moiety.

EMBODIMENT 22

The oligomeric compound of embodiment 20, wherein the 3'-most 5'-region nucleoside comprises an LNA sugar moiety.

EMBODIMENT 23

The oligomeric compound of any of embodiments 1-22, wherein the central region consists of 6-10 linked nucleosides.

EMBODIMENT 24

The oligomeric compound of any of embodiments 1-23, wherein the central region consists of 6-9 linked nucleosides.

EMBODIMENT 25

The oligomeric compound of embodiment 24, wherein the central region consists of 6 linked nucleosides.

EMBODIMENT 26

The oligomeric compound of embodiment 24, wherein the central region consists of 7 linked nucleosides.

EMBODIMENT 27

The oligomeric compound of embodiment 24, wherein the central region consists of 8 linked nucleosides.

EMBODIMENT 28

The oligomeric compound of embodiment 24, wherein the central region consists of 9 linked nucleosides.

EMBODIMENT 29

The oligomeric compound of any of embodiments 1-28, wherein each central region nucleoside is an unmodified deoxynucleoside.

EMBODIMENT 30

The oligomeric compound of any of embodiments 1-28, wherein at least one central region nucleoside is a modified nucleoside.

EMBODIMENT 31

The oligomeric compound of embodiment 30, wherein one central region nucleoside is a modified nucleoside and each of the other central region nucleosides is an unmodified deoxynucleoside.

EMBODIMENT 32

The oligomeric compound of any of embodiments 30-31, wherein the modified central region nucleoside comprises a modified nucleobase.

EMBODIMENT 33

The oligomeric compound of embodiment 32, wherein the modified nucleobase is selected from among a 2-thio pyrimidine and a 5-propyne pyrimidine.

EMBODIMENT 34

The oligomeric compound of embodiment 32, wherein the modified nucleobase is 2-thiothymine.

EMBODIMENT 35

The oligomeric compound of any of embodiments 30-34, wherein the $2^{nd}$ nucleoside from the 5'-end of the central region is a modified nucleoside.

EMBODIMENT 36

The oligomeric compound of any of embodiments 30-34, wherein the $8^{th}$ nucleoside from the 3'-end of the central region is a modified nucleoside.

EMBODIMENT 37

The oligomeric compound of any of embodiments 30-34, wherein the $7^{th}$ nucleoside from the 3'-end of the central region is a modified nucleoside.

EMBODIMENT 38

The oligomeric compound of any of embodiments 30-34, wherein the modified nucleoside is a 2-thio pyrimidine.

EMBODIMENT 39

The oligomeric compound of any of embodiments 30-34, wherein the modified nucleobase is 2-thiothymine.

EMBODIMENT 40

The oligomeric compound of any of embodiments 1-39, wherein the central region has a nucleoside motif selected from among: DDDDDDD, DDDDDDDD, DDDDDDDDD, DXDDDDD, DXDDDDDD, and DXDDDDDDD; wherein each D is an unmodified deoxynucleoside; and each X is a modified nucleoside.

EMBODIMENT 41

The oligomeric compound of embodiment 40, wherein each X comprises a modified nucleobase.

EMBODIMENT 42

The oligomeric compound of embodiment 40, wherein each X comprises 2-thio-thymidine.

EMBODIMENT 43

The oligomeric compound of any of embodiments 1-42, wherein the 5' region consists of 1 nucleoside.

EMBODIMENT 44

The oligomeric compound of any of embodiments 1-42, wherein the 5' region consists of 2 linked 5'-region nucleosides.

EMBODIMENT 45

The oligomeric compound of any of embodiments 1-42, wherein the 5' region consists of 3 linked 5'-region nucleosides.

EMBODIMENT 46

The oligomeric compound of any of embodiments 1-42, wherein the 5' region consists of 4 linked 5'-region nucleosides.

EMBODIMENT 47

The oligomeric compound of any of embodiments 1-42, wherein the 5' region consists of 5 linked 5'-region nucleosides.

EMBODIMENT 48

The oligomeric compound of any of embodiments 1-42, wherein the 5' region consists of 6 linked 5'-region nucleosides.

EMBODIMENT 49

The oligomeric compound of any of embodiments 1-42, wherein the 5' region consists of 7 linked 5'-region nucleosides.

EMBODIMENT 50

The oligomeric compound of any of embodiments 1-42, wherein the 5' region consists of 8 linked 5'-region nucleosides.

EMBODIMENT 51

The oligomeric compound of any of embodiments 1-42, wherein the 5' region consists of 9 linked 5'-region nucleosides.

EMBODIMENT 52

The oligomeric compound of any of embodiments 1-51 wherein at least one 5'-region nucleoside is an RNA-like nucleoside.

EMBODIMENT 53

The oligomeric compound of any of embodiments 1-51 wherein each 5'-region nucleoside is an RNA-like nucleoside.

EMBODIMENT 54

The oligomeric compound of any of embodiments 1-53 comprising at least one modified 5'-region nucleoside comprising a modified sugar.

EMBODIMENT 55

The oligomeric compound of embodiment 54 comprising at least one modified 5'-region nucleoside comprising a bicyclic sugar moiety.

EMBODIMENT 56

The oligomeric compound of embodiment 55 comprising at least one modified 5'-region nucleoside comprising a cEt sugar moiety.

EMBODIMENT 57

The oligomeric compound of embodiment 55 comprising at least one modified 5'-region nucleoside comprising an LNA sugar moiety.

EMBODIMENT 58

The oligomeric compound of any of embodiments 54-57 comprising at least one modified 5'-region nucleoside comprising a 2'-substituted sugar moiety.

EMBODIMENT 59

The oligomeric compound of any of embodiments 54-58 comprising at least one modified 5'-region nucleoside comprising a 2'-MOE sugar moiety.

EMBODIMENT 60

The oligomeric compound of any of embodiments 1-59, wherein the 5'-region has a motif selected from among: eeeedk, eeeee, eeeeedk, eeeeeeeek, eeeeeeek, eeeeek, eeeek, eeeekk, eeek, eeek, eeekk, eek, eekk, ek, ekek, ekek, ekk, ekkdk, ekkkk, and k, wherein each “e” is a 2'MOE modified nucleoside, each “k” is a cEt modified nucleoside, and each “d” is an unmodified deoxynucleoside.

EMBODIMENT 61

The oligomeric compound of any of embodiments 1-60, wherein the 3' region consists of 2 linked 3'-region nucleosides.

EMBODIMENT 62

The oligomeric compound of any of embodiments 1-60, wherein the 3' region consists of 3 linked 3'-region nucleosides.

EMBODIMENT 63

The oligomeric compound of any of embodiments 1-60, wherein the 3' region consists of 4 linked 3'-region nucleosides.

EMBODIMENT 64

The oligomeric compound of any of embodiments 1-60, wherein the 3' region consists of 5 linked 3'-region nucleosides.

EMBODIMENT 65

The oligomeric compound of any of embodiments 1-60, wherein the 3' region consists of 6 linked 3'-region nucleosides.

EMBODIMENT 66

The oligomeric compound of any of embodiments 1-60, wherein the 3' region consists of 7 linked 3'-region nucleosides.

EMBODIMENT 67

The oligomeric compound of any of embodiments 1-60, wherein the 3' region consists of 8 linked 3'-region nucleosides.

EMBODIMENT 68

The oligomeric compound of any of embodiments 1-60, wherein the 3' region consists of 9 linked 3'-region nucleosides.

EMBODIMENT 69

The oligomeric compound of any of embodiments 1-60, wherein the 3' region consists of 10 linked 3'-region nucleosides.

EMBODIMENT 70

The oligomeric compound of any of embodiments 1-69, wherein each 3'-region nucleoside is a modified nucleoside.

EMBODIMENT 71

The oligomeric compound of any of embodiments 1-69, wherein at least one 3'-region nucleoside is an RNA-like nucleoside.

EMBODIMENT 72

The oligomeric compound of any of embodiments 1-69, wherein each 3'-region nucleoside is an RNA-like nucleoside.

EMBODIMENT 73

The oligomeric compound of any of embodiments 1-72, comprising at least one modified 3'-region nucleoside comprising a modified sugar.

EMBODIMENT 74

The oligomeric compound of embodiment 73, comprising at least one modified 3'-region nucleoside comprising a bicyclic sugar moiety.

EMBODIMENT 75

The oligomeric compound of embodiment 74, comprising at least one modified 3'-region nucleoside comprising a cEt sugar moiety.

EMBODIMENT 76

The oligomeric compound of embodiment 74, comprising at least one modified 3'-region nucleoside comprising an LNA sugar moiety.

EMBODIMENT 77

The oligomeric compound of any of embodiments 1-73 wherein each modified 3'-region nucleoside comprises a 2'-substituted sugar moiety.

EMBODIMENT 78

The oligomeric compound of any of embodiments 1-73 wherein at least one modified 3'-region nucleoside comprises a 2'-substituted sugar moiety.

EMBODIMENT 79

The oligomeric compound of embodiment 77 or 78, wherein the modified 3'-region nucleoside is a 2'-MOE sugar moiety.

EMBODIMENT 80

The oligomeric compound of any of embodiments 1-73, wherein the 3'-region has a motif selected from among: eee, eeee, eeeee, eeeeee, eeeeeee, eeeeeeee, eeeeeeeee, eeeeeeeeee, eeeekek, eeeekeke, eeek, eeeke, eeekek, eeekeke, eeekekee, eeekk, eeke, eekek, eekeke, eekekee, eekk, kee, keee, keeee, keeeke, keeekee, keek, keeke, keekee, keekeee, keekk, keke, kekee, kke, kkeee, kkeek, and kkke, wherein each "e" is a 2'MOE modified nucleoside and each "k" is a cEt modified nucleoside.

EMBODIMENT 81

The oligomeric compound of embodiments 1-80, wherein the 5'-region has a motif selected from among: eeeedk, eeeee, eeeeedk, eeeeeeeek, eeeeeek, eeeeek, eeeek, eeeekk, eeek, eeek, eeekk, eek, eekk, ek, ekek, ekek, ekk, ekkdk, ekkkk, and k;

wherein the 3'-region has a motif selected from among: eee, eeee, eeeee, eeeeee, eeeeeee, eeeeeeee, eeeeeeeee, eeeeeeeeee, eeeekek, eeeekeke, eeek, eeeke, eeekek, eeekeke, eeekekee, eeekk, eeke, eekek, eekeke, eekekee, eekk, kee, keee, keeee, keeeke, keeekee, keek, keeke, keekee, keekeee, keekk, keke, kekee, kke, kkeee, kkeek, and kkke;

wherein the central region has a nucleoside motif selected from among: DDDDDDD, DDDDDDDD, DDDDDDDDD, DXDDDDD, DXDDDDDD, and DXDDDDDDD; and wherein each "e" is a 2'MOE modified nucleoside, each "k" is a cEt modified nucleoside, each "d" is an unmodified deoxynucleoside, and each "X" is a modified nucleoside or a modified nucleobase.

EMBODIMENT 82

The oligomeric compound of embodiment 81, wherein each X comprises a 2-thio-thymidine.

EMBODIMENT 83

The oligomeric compound of any of embodiments 1-82 comprising at least one modified internucleoside linkage.

EMBODIMENT 84

The oligomeric compound of embodiment 83, wherein each internucleoside linkage is a modified internucleoside linkage.

EMBODIMENT 85

The oligomeric compound of embodiment 83 or 84 comprising at least one phosphorothioate internucleoside linkage.

EMBODIMENT 86

The oligomeric compound of embodiment 84, wherein each internucleoside linkage is a phosphorothioate internucleoside linkage.

EMBODIMENT 87

The oligomeric compound of embodiment 83, wherein the 5'-most internucleoside linkage of the 5'-region is a phosphorothioate internucleoside linkage, wherein the 3'-most internucleoside linkage of the 3'-region is a phosphorothioate internucleoside linkage, and wherein each internucleoside linkage of the central region is a phosphorothioate internucleoside linkage.

EMBODIMENT 88

The oligomeric compound of embodiment 83, wherein the 5'-most internucleoside linkage of the 5'-region is a phosphorothioate internucleoside linkage, wherein the 3'-most internucleoside linkage of the 3'-region is a phosphorothioate internucleoside linkage, wherein each internucleoside linkage of the central region is a phosphorothioate internucleoside linkage, and wherein each remaining internucleoside linkage is a phosphodiester internucleoside linkage.

EMBODIMENT 89

The oligomeric compound of embodiment 87, wherein the oligomeric compound contains 2 phosphodiester internucleoside linkages.

EMBODIMENT 90

The oligomeric compound of embodiment 87, wherein the oligomeric compound contains 3 phosphodiester internucleoside linkages.

EMBODIMENT 91

The oligomeric compound of embodiment 87, wherein the oligomeric compound contains 4 phosphodiester internucleoside linkages.

EMBODIMENT 92

The oligomeric compound of embodiment 87, wherein the oligomeric compound contains 5 phosphodiester internucleoside linkages.

EMBODIMENT 93

The oligomeric compound of embodiment 87, wherein the oligomeric compound contains 6 phosphodiester internucleoside linkages.

EMBODIMENT 94

The oligomeric compound of embodiment 87, wherein the 5'-region of the oligomeric compound contains 1 phosphodiester internucleoside linkage.

EMBODIMENT 95

The oligomeric compound of embodiment 87, wherein the 5'-region of the oligomeric compound contains 2 phosphodiester internucleoside linkages.

EMBODIMENT 96

The oligomeric compound of embodiment 87, wherein the 5'-region of the oligomeric compound contains 3 phosphodiester internucleoside linkages.

EMBODIMENT 97

The oligomeric compound of any of embodiments 87 or 94 to 96, wherein the 3'-region of the oligomeric compound contains 1 phosphodiester internucleoside linkage.

EMBODIMENT 98

The oligomeric compound of any of embodiments 87 or 94 to 96, wherein the 3'-region of the oligomeric compound contains 2 phosphodiester internucleoside linkages.

EMBODIMENT 99

The oligomeric compound of any of embodiments 87 or 94 to 96, wherein the 3'-region of the oligomeric compound contains 3 phosphodiester internucleoside linkages.

EMBODIMENT 100

The oligomeric compound of any of embodiments 87 or 94 to 96, wherein the 3'-region of the oligomeric compound contains 4 phosphodiester internucleoside linkages.

EMBODIMENT 101

The oligomeric compound of any of embodiments 87 or 94 to 96, wherein the 3'-region of the oligomeric compound contains 5 phosphodiester internucleoside linkages.

EMBODIMENT 102

The oligomeric compound of any of embodiments 87 or 94 to 96, wherein the 3'-region of the oligomeric compound contains 6 phosphodiester internucleoside linkages.

EMBODIMENT 103

The oligomeric compound of any of embodiments 87 or 94 to 96, wherein the 2nd, internucleoside bond from 3'-end of the oligomeric compound is a phosphodiester internucleoside linkage.

EMBODIMENT 104

The oligomeric compound of any of embodiments 87 or 94 to 96, wherein the 3rd, internucleoside bond from 3'-end of the oligomeric compound is a phosphodiester internucleoside linkage.

EMBODIMENT 105

The oligomeric compound of any of embodiments 87 or 94 to 96, wherein the rd, 3rd and $4^{th}$ internucleoside bonds from 3'-end of the oligomeric compound are phosphodiester internucleoside linkages.

EMBODIMENT 106

The oligomeric compound of any of embodiments 87 or 94 to 96, wherein the $3^{rd}$ and $4^{th}$ internucleoside bonds from 3'-end of the oligomeric compound are phosphodiester internucleoside linkages.

EMBODIMENT 107

The oligomeric compound of any of embodiments 87 or 94 to 96, wherein the $3^{rd}$, $4^{th}$, and $5^{th}$, internucleoside bonds from 3'-end of the oligomeric compound are phosphodiester internucleoside linkages.

EMBODIMENT 108

The oligomeric compound of any of embodiments 87 or 94 to 96, wherein the $4^{th}$ and $5^{th}$ internucleoside bonds from 3'-end of the oligomeric compound are phosphodiester internucleoside linkages.

EMBODIMENT 109

The oligomeric compound of any of embodiments 87 or 94 to 96, wherein the $3^{rd}$, $4^{th}$, $5^{th}$, and $6^{th}$, internucleoside bonds from 3'-end of the oligomeric compound are phosphodiester internucleoside linkages.

EMBODIMENT 110

The oligomeric compound of any of embodiments 87 or 94 to 96, wherein the $2^{nd}$, $3^{rd}$, $4^{th}$, $5^{th}$, and $6^{th}$, internucleoside bonds from 3'-end of the oligomeric compound are phosphodiester internucleoside linkages.

EMBODIMENT 111

The oligomeric compound of any of embodiments 87 or 97 to 110, wherein the $2^{nd}$ internucleoside bond from 5'-end of the oligomeric compound is a phosphodiester internucleoside linkage.

EMBODIMENT 112

The oligomeric compound of any of embodiments 87 or 97 to 110, wherein the $3^{rd}$ internucleoside bond from 5'-end of the oligomeric compound is a phosphodiester internucleoside linkage.

EMBODIMENT 113

The oligomeric compound of any of embodiments 87 or 97 to 110, wherein the $2^{nd}$ and $3^{rd}$ internucleoside bonds from 5'-end of the oligomeric compound are phosphodiester internucleoside linkages.

EMBODIMENT 114

The oligomeric compound of any of embodiments 87 or 97 to 110, wherein the $2^{nd}$ $3^{rd}$, and $4^{th}$ internucleoside bonds from 5'-end of the oligomeric compound are phosphodiester internucleoside linkages.

EMBODIMENT 115

The oligomeric compound of any of embodiments 87 or 97 to 110, wherein the $3^{rd}$ and $4^{th}$ internucleoside bonds from 5'-end of the oligomeric compound are phosphodiester internucleoside linkages.

EMBODIMENT 116

The oligomeric compound of any of embodiments 87 or 97 to 110, wherein the $2^{nd}$, $3^{rd}$, $4^{th}$, and $5^{th}$ internucleoside bonds from 5'-end of the oligomeric compound are phosphodiester internucleoside linkages.

EMBODIMENT 117

The oligomeric compound of any of embodiments 87 or 97 to 110, wherein the $3^{rd}$, $4^{th}$, and $5^{th}$ internucleoside bonds from 5'-end of the oligomeric compound are phosphodiester internucleoside linkages.

EMBODIMENT 118

The oligomeric compound of any of embodiments 87 or 97 to 110, wherein the $3^{rd}$, $4^{th}$, $5^{th}$, and $6^{th}$ internucleoside bonds from 5'-end of the oligomeric compound are phosphodiester internucleoside linkages.

EMBODIMENT 119

The oligomeric compound of any of embodiments 87 or 97 to 110, wherein the $3^{rd}$, $4^{th}$, $5^{th}$, $6^{th}$, and $7^{th}$ internucleoside bonds from 5'-end of the oligomeric compound are phosphodiester internucleoside linkages.

EMBODIMENT 120

The oligomeric compound of any of embodiments 1-119 comprising at least one conjugate group.

EMBODIMENT 121

The oligomeric compound of embodiment 1-120, wherein the conjugate group consists of a conjugate.

EMBODIMENT 122

The oligomeric compound of embodiment 120, wherein the conjugate group consists of a conjugate and a conjugate linker.

EMBODIMENT 123

The oligomeric compound of any of embodiments 1-122, wherein the nucleobase sequence of the modified oligonucleotide is 100% complementary to the nucleobase sequence of the target region of the target nucleic acid.

EMBODIMENT 124

The oligomeric compound of any of embodiments 1-122, wherein the nucleobase sequence of the modified oligonucleotide contains one mismatch relative to the nucleobase sequence of the target region of the target nucleic acid.

EMBODIMENT 125

The oligomeric compound of any of embodiments 1-122, wherein the nucleobase sequence of the modified oligonucleotide contains two mismatches relative to the nucleobase sequence of the target region of the target nucleic acid.

EMBODIMENT 126

The oligomeric compound of any of embodiments 1-122, wherein the nucleobase sequence of the modified oligonucleotide comprises a hybridizing region and at least one non-targeting region, wherein the nucleobase sequence of the hybridizing region is complementary to the nucleobase sequence of the target region of the target nucleic acid.

EMBODIMENT 127

The oligomeric compound of embodiment 126, wherein the nucleobase sequence of the hybridizing region is 90% complementary to the nucleobase sequence of the target region of the target nucleic acid.

EMBODIMENT 128

The oligomeric compound of embodiment 126, wherein the nucleobase sequence of the hybridizing region is 95% complementary to the nucleobase sequence of the target region of the target nucleic acid.

EMBODIMENT 129

The oligomeric compound of embodiment 126, wherein the nucleobase sequence of the hybridizing region is 100% complementary to the nucleobase sequence of the target region of the target nucleic acid.

EMBODIMENT 130

The oligomeric compound of embodiment 126, wherein the nucleobase sequence of the hybridizing region contains one mismatch relative to the nucleobase sequence of the target region of the target nucleic acid.

EMBODIMENT 131

The oligomeric compound of any of embodiments 126-129, wherein the nucleobase sequence of at least one non-targeting region is complementary to a portion of the hybridizing region of the modified oligonucleotide.

EMBODIMENT 132

The oligomeric compound of embodiment 126, wherein the nucleobase sequence of at least one non-targeting region is 100% complementary to a portion of the hybridizing region of the modified oligonucleotide.

EMBODIMENT 133

The oligomeric compound of embodiment 126 wherein the nucleobase sequence of the modified oligonucleotide comprises two non-targeting regions flanking a central hybridizing region.

EMBODIMENT 134

The oligomeric compound of embodiment 133, wherein the two non-targeting regions are complementary to one another.

EMBODIMENT 135

The oligomeric compound of embodiment 134, wherein the two non-targeting regions are 100% complementary to one another.

EMBODIMENT 136

The oligomeric compound of any of embodiments 2-135, wherein the nucleobase sequence of the modified oligonucleotide aligns with the nucleobase sequence of the target region of the target nucleic acid such that a distinguishing nucleobase of the target region of the target nucleic acid aligns with a target-selective nucleoside within the central region of the modified oligonucleotide.

EMBODIMENT 137

The oligomeric compound of any of embodiments 3-135, wherein the nucleobase sequence of the modified oligonucleotide aligns with the nucleobase of the target region of the target nucleic acid such that the single distinguishing nucleobase of the target region of the target nucleic acid aligns with a target-selective nucleoside within the central region of the modified oligonucleotide.

EMBODIMENT 138

The oligomeric compound of embodiment 136 or 137, wherein the target-selective nucleoside is the 5'-most nucleoside of the central region.

EMBODIMENT 139

The oligomeric compound of embodiment 136 or 137, wherein the target-selective nucleoside is the $2^{nd}$ nucleoside from the 5'-end of the central region.

EMBODIMENT 140

The oligomeric compound of embodiment 136 or 137, wherein the target-selective nucleoside is at the $3^{rd}$ nucleoside from the 5'-end of the central region.

EMBODIMENT 141

The oligomeric compound of embodiment 136 or 137, wherein the target-selective nucleoside is at the $4^{th}$ nucleoside from the 5'-end of the central region.

EMBODIMENT 142

The oligomeric compound of embodiment 136 or 137, wherein the target-selective nucleoside is at the $5^{th}$ nucleoside from the 5'-end of the central region.

EMBODIMENT 143

The oligomeric compound of embodiment 136 or 137, wherein the target-selective nucleoside is at the $6^{th}$ nucleoside from the 5'-end of the central region.

EMBODIMENT 144

The oligomeric compound of embodiment 136 or 137, wherein the target-selective nucleoside is at the $7^{th}$ nucleoside from the 5'-end of the central region.

EMBODIMENT 145

The oligomeric compound of embodiment 136 or 137, wherein the target-selective nucleoside is at the $8^{th}$ nucleoside from the 5'-end of the central region.

EMBODIMENT 146

The oligomeric compound of embodiment 136 or 137, wherein the target-selective nucleoside is at the $9^{th}$ nucleoside from the 5'-end of the central region.

EMBODIMENT 147

The oligomeric compound of any of embodiments 136 or 137, wherein the target-selective nucleoside is at the $2^{nd}$ nucleoside from the 3'-end of the central region.

EMBODIMENT 148

The oligomeric compound of any of embodiments 136 or 137, wherein the target-selective nucleoside is at the $3^{rd}$ nucleoside from the 3'-end of the central region.

EMBODIMENT 149

The oligomeric compound of any of embodiments 136 or 137, wherein the target-selective nucleoside is at the $4^{th}$ nucleoside from the 3'-end of the central region.

EMBODIMENT 150

The oligomeric compound of any of embodiments 136 or 137, wherein the target-selective nucleoside is at the $5^{th}$ nucleoside from the 3'-end of the central region.

EMBODIMENT 151

The oligomeric compound of any of embodiments 136 or 137, wherein the target-selective nucleoside is at the $6^{th}$ nucleoside from the 3'-end of the central region.

EMBODIMENT 152

The oligomeric compound of any of embodiments 136 or 137, wherein the target-selective nucleoside is at the $7^{th}$ nucleoside from the 3'-end of the central region.

EMBODIMENT 153

The oligomeric compound of any of embodiments 136 or 137, wherein the target-selective nucleoside is at the $8^{th}$ nucleoside from the 3'-end of the central region.

EMBODIMENT 154

The oligomeric compound of any of embodiments 136 or 137, wherein the target-selective nucleoside is at the $9^{th}$ nucleoside from the 3'-end of the central region.

EMBODIMENT 155

The oligomeric compound of any of embodiments 1-154, wherein the oligomeric compound has a nucleobase sequence comprising a nucleobase sequence selected from among SEQ ID NO. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39.

EMBODIMENT 156

The oligomeric compound of any of embodiments 1-154, wherein the oligomeric compound has a nucleobase sequence selected from among SEQ ID NO. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39.

EMBODIMENT 157

The oligomeric compound of any of embodiments 1-156, wherein target-selective nucleoside is an unmodified deoxy-nucleoside.

EMBODIMENT 158

The oligomeric compound of any of embodiments 1-156, wherein target-selective nucleoside is a modified nucleoside.

EMBODIMENT 159

The oligomeric compound of any of embodiments 1-156, wherein the target-selective nucleoside is a sugar modified nucleoside.

EMBODIMENT 160

The oligomeric compound of embodiment 159, wherein the target-selective nucleoside comprises a sugar modification selected from among: 2'-MOE and cEt.

EMBODIMENT 161

The oligomeric compound of any of embodiments 1-160, wherein the target-selective nucleoside comprises a nucleobase modification.

EMBODIMENT 162

The oligomeric compound of embodiment 161, wherein the modified nucleobase is selected from among: a 2-thio pyrimidine and a 5-propyne pyrimidine.

EMBODIMENT 163

The oligomeric compound of any of embodiments 1-162, wherein the oligomeric compound is an antisense compound.

EMBODIMENT 164

The oligomeric compound of embodiment 163, wherein the oligomeric compound selectively reduces expression of the target relative to the non-target.

EMBODIMENT 165

The oligomeric compound of embodiment 164, wherein the oligomeric compound reduces expression of target at least two-fold more than it reduces expression of the non-target.

EMBODIMENT 166

The oligomeric compound of embodiment 165, having an $EC_{50}$ for reduction of expression of target that is at least two-fold lower than its $EC_{50}$ for reduction of expression of the non-target, when measured in cells.

EMBODIMENT 167

The oligomeric compound of claim 165, having an $ED_{50}$ for reduction of expression of target that is at least two-fold lower than its $ED_{50}$ for reduction of expression of the non-target, when measured in an animal.

EMBODIMENT 168

A method comprising contacting a cell with an oligomeric compound of any of claims 1-167.

EMBODIMENT 169

The method of claim 168, wherein the cell is in vitro.

EMBODIMENT 170

The method of claim 168, wherein the cell is in an animal.

EMBODIMENT 171

The method of claim 170, wherein the animal is a human.

EMBODIMENT 172

The method of claim 170, wherein the animal is a mouse.

EMBODIMENT 173

A pharmaceutical composition comprising an oligomeric compound of any of claims 1-167 and a pharmaceutically acceptable carrier or diluent.

EMBODIMENT 174

A method of administering a pharmaceutical composition of claim 173 to an animal.

EMBODIMENT 175

The method of claim 174, wherein the animal is a human.

EMBODIMENT 176

The method of claim 174, wherein the animal is a mouse.

EMBODIMENT 177

Use of an oligomeric compound of any of claims 1-167 for the preparation of a medicament for the treatment or amelioration of Huntington's disease.

EMBODIMENT 178

A method of ameliorating a symptom of Huntington's disease, comprising administering an oligomeric compound of any of claims 1-167 to an animal in need thereof.

EMBODIMENT 179

The method of claim 178, wherein the animal is a human.

EMBODIMENT 180

The method of claim 178, wherein the animal is a mouse.

In certain embodiments, including but not limited to any of the above numbered embodiments, oligomeric compounds including oligonucleotides described herein are capable of modulating expression of a target RNA. In certain embodiments, the target RNA is associated with a disease or disorder, or encodes a protein that is associated with a disease or disorder. In certain embodiments, the oligomeric compounds or oligonucleotides provided herein modulate the expression of function of such RNA to alleviate one or more symptom of the disease or disorder.

In certain embodiments, oligomeric compounds including oligonucleotides describe herein are useful in vitro. In certain embodiments such oligomeric compounds are used in diagnostics and/or for target validation experiments.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21st edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means $—OCH_2CH_2OCH_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

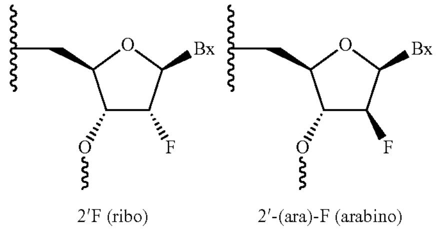

2'F (ribo) 2'-(ara)-F (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$—O-2' bridge.

As used herein, "locked nucleic acid nucleoside" or "LNA" means a nucleoside comprising a bicyclic sugar moiety comprising a 4'-$CH_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($—C(O)R_{aa}$), carboxyl ($—C(O)O—R_{aa}$), aliphatic groups, alicyclic groups, alkoxy, substituted oxy ($—O—R_{aa}$), aryl, aralkyl, heterocyclic radical, heteroaryl, heteroarylalkyl, amino ($—N(R_{bb})(R_{cc})$), imino($=NR_{bb}$), amido ($—C(O)N(R_{bb})(R_{cc})$ or $—N(R_{bb})C(O)R_{aa}$), azido ($—N_3$), nitro ($—NO_2$), cyano ($—CN$), carbamido ($—OC(O)N(R_{bb})(R_{cc})$ or $—N(R_{bb})C(O)OR_{aa}$), ureido ($—N(R_{bb})C(O)N(R_{bb})(R_{cc})$), thioureido ($—N(R_{bb})C(S)N(R_{bb})—(R_{cc})$), guanidinyl ($—N(R_{bb})C(=NR_{bb})N(R_{bb})(R_{cc})$), amidinyl ($—C(=NR_{bb})N(R_{bb})(R_{cc})$ or $—N(R_{bb})C(=NR_{bb})(R_{aa})$), thiol ($—SR_{bb}$), sulfinyl ($—S(O)R_{bb}$), sulfonyl ($—S(O)_2R_{bb}$) and sulfonamidyl ($—S(O)_2N(R_{bb})(R_{cc})$ or $—N(R_{bb})S—(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "huntingtin transcript" means a transcript transcribed from a huntingtin gene.

B. Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonucleotides comprising at least one modified nucleoside. Such modified nucleosides comprise a modified sugar moiety, a modified nucleobase, or both a modified sugar moiety and a modified nucleobase.

i. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2'; 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-$CH(CH_3)$—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA, and (K) Ethylene(methoxy) (4'-(CH($CH_2$OMe)-O-2') BNA (also referred to as constrained MOE or cMOE) as depicted below.

(A)

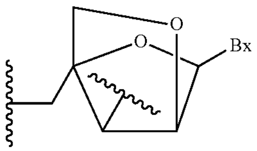

(B)

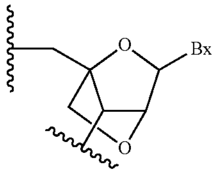

(C)

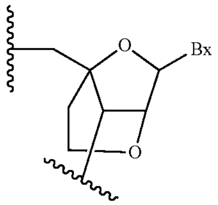

(D)

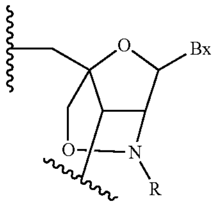

-continued (E)

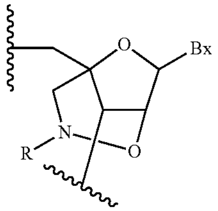

(F)

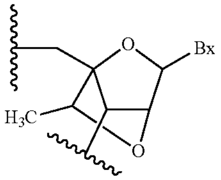

(G)

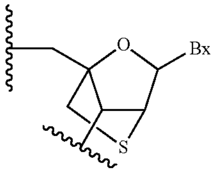

(H)

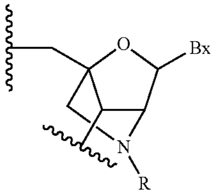

(I)

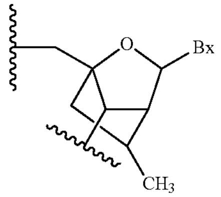

(J)

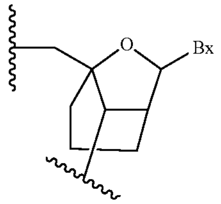

(K)

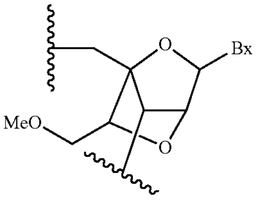

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A,* 2000, 97, 5633-5638; Kumar et al., *Bioorg. Med. Chem. Lett.,* 1998, 8, 2219-2222; Singh et al., *J. Org. Chem.,* 1998, 63, 10035-

10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

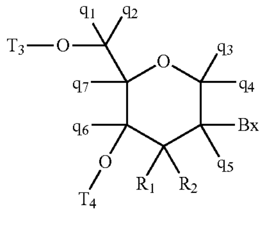

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. In certain embodiments, modified nucleobases are selected from: 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si$(H)_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

i. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

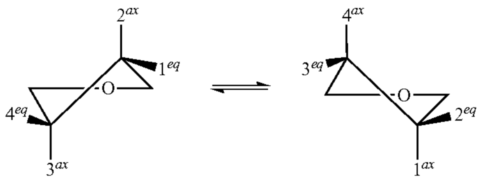

C2'-endo/Southern C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as exemplified in Example 35, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

c. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2' deoxynucleoside. In certain embodiments, the modified nucleobase is selected from: a 2-thio pyrimidine and a 5-propyne pyrimidine. In certain embodiments, one nucleoside comprising a modified nucleobases is the $5^{th}$ nucleobase from the 5'-end of the oligonucleotide. In certain embodiments, the $5^{th}$ nucleobase from the 5'-end of the oligonucleotide is 2-thio-thymine.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or “wings” and a central or internal region or “gap.” The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

iv. Certain 5'-Wings

In certain embodiments, the 5'-wing of a gapmer consists of 1 to 9 linked nucleosides. In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides. In certain embodiments, the 5'-wing of a gapmer consists of 7 linked nucleosides. In certain embodiments, the 5'-wing of a gapmer consists of 8 linked nucleosides. In certain embodiments, the 5'-wing of a gapmer consists of 9 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer has a nucleoside motif selected from among the following: eeeedk, eeeee, eeeeedk, eeeeeeeek, eeeeeeek, eeeeek, eeeek, eeeekk, eeek, eeekdx, eeekk, eek, eekk, ek, ekek, ekekdx, ekk, ekkdk, ekkkk, and k, wherein each “e” is a 2'MOE modified nucleoside, each “k” is a cEt modified nucleoside, each “dx” is a 2-thiothymidine, and each “d” is an unmodified deoxynucleoside.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any nucleoside motif.

v. Certain 3'-Wings

In certain embodiments, the 3'-wing of a gapmer consists of 1 to 10 linked nucleosides. In certain embodiments, the 3'-wing of a gapmer consists of 1 to 9 linked nucleosides. In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides. In certain embodiments, the 3'-wing of a gapmer consists of 7 linked nucleosides. In certain embodiments, the 3'-wing of a gapmer consists of 8 linked nucleosides. In certain embodiments, the 3'-wing of a gapmer consists of 9 linked nucleosides. In certain embodiments, the 3'-wing of a gapmer consists of 10 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a nucleoside motif selected from among the following: eee, eeee, eeeee, eeeeee, eeeeeee, eeeeeeee, eeeeeeeee, eeeeeeeeee, eeeekek, eeeekeke, eeek, eeeke, eeekek, eeekeke, eeekekee, eeekk, eeke, eekek, eekeke, eekekee, eekk, kee, keee, keeee, keeeke, keeekee, keek, keeke, keekee, keekeee, keekk, keke, kekee, kke, kkeee, kkeek, and kkke, wherein each "e" is a 2'MOE modified nucleoside and each "k" is a cEt modified nucleoside.

vi. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

In certain embodiments, the gap comprises a nucleoside motif selected from among the following: DDDDDDD, DDDDDDDD, DDDDDDDDD, DXDDDDD, DXDDDDDD, and DXDDDDDDD, wherein each D is an unmodified deoxynucleoside and each X is a modified nucleoside.

In certain embodiments, each X comprises an unmodified 2'-deoxyfuranose sugar moiety. In certain embodiments, each X comprises a modified sugar moiety. In certain embodiments, each X comprises a 2'-substituted sugar moiety. In certain embodiments, each X comprises a 2'-substituted sugar moiety selected from among F, (ara)-F, $OCH_3$ and $O(CH_2)_2$—$OCH_3$. In certain embodiments, each X comprises a 5'-substituted sugar moiety. In certain embodiments, each X comprises a 2-thio-thymidine nucleoside. In certain embodiments, each X comprises a 5'-substituted sugar moiety selected from among 5'-Me, and 5'-(R)-Me. In certain embodiments, each X comprises a bicyclic sugar moiety. In certain embodiments, each X comprises a bicyclic sugar moiety selected from among cEt, cMOE, LNA, α-L-LNA, ENA and 2'-thio LNA. In certain embodiments, each X comprises a modified nucleobase. In certain embodiments, each X comprises a modified nucleobase selected from among 2-thio-thymidine and 5-propyne uridine. In certain embodiments, each X comprises an HNA. In certain embodiments, each C comprises an F-HNA. In certain embodiments, X represents the location of a single differentiating nucleobase.

vii. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among any of those listed in the tables above and any 5'-wing may be paired with any gap and any 3'-wing.

In certain embodiments, a gapmer has a sugar motif other than: E-K-K-$(D)_9$-K-K-E; E-E-E-E-K-$(D)_9$-E-E-E-E-E; E-K-K-K-$(D)_9$-K-K-K-E; K-E-E-K-$(D)_9$-K-E-E-K; K-D-D-K-$(D)_9$-K-D-D-K; K-E-K-E-K-$(D)_9$-K-E-K-E-K; K-D-K-D-K-$(D)_9$-K-D-K-D-K; E-K-E-K-$(D)_9$-K-E-K-E; E-E-E-E-E-K-$(D)_8$-E-E-E-E-E; or E-K-E-K-E-$(D)_9$-E-K-E-K-E, E-E-E-K-K-$(D)_7$-E-E-K, E-K-E-K-K-K-$(D)_7$-K-E-K-E, E-K-E-K-E-K-$(D)_7$-K-E-K-E, wherein K is a nucleoside comprising a cEt sugar moiety and E is a nucleoside comprising a 2'-MOE sugar moiety.

viii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, the oligonucleotide comprises a mixture of phosphorothioate internucleoside linkages and phosphodiester internucleoside linkages. In certain embodiments, a modified oligonucleotide has one or more phosphodiester internucleoside linkages in the 5'-wing region or 3'-wing region. In certain embodiments, a modified oligonucleotide has one or more phosphodiester internucleoside linkages in the 5'-wing region and each of the remaining internucleoside linkages comprise phosphorothioate internucleoside linkages. In certain embodiments, a modified oligonucleotide has one or more phosphodiester internucleoside linkages in the 3'-wing region and each of the remaining internucleoside linkages comprise phosphorothioate internucleoside linkages. In certain embodiments, a modified oligonucleotide has one or more phosphodiester internucleoside linkages in the 5'-wing region and the 3'-wing region and each of the remaining internucleoside linkages comprise phosphorothioate internucleoside linkages.

The following non-limiting Table further illustrates certain internucleoside linkage motifs:

TABLE 1

Certain Internucleoside Linkage Motifs

| 5'-wing region | Central gap region | 3'-wing region |
|---|---|---|
| $E_s E_o E_o E_o E_o K_s$ | $D_s D_s D_s D_s D_s D_s D_s$ | $K_s E_s E$ |
| $E_s E_o E_o E_o E_o K_s$ | $D_s D_s D_s D_s D_s D_s D_s$ | $E_s E_s E$ |
| $E_s K_o E_o K_s$ | $D_s D_s D_s D_s D_s D_s D_s D_s D_s$ | $K_o E_s K_s E$ |
| $E_s E_o E_o E_o E_s D_s K_s$ | $D_s D_s D_s D_s D_s D_s D_s$ | $E_o E_o E_s E_s E$ |
| $E_s E_s E_o E_o E_s K_s$ | $D_s D_s D_s D_s D_s D_s D_s$ | $E_o E_o E_o E_s E_s E$ |
| $E_s E_o E_o E_s K_s$ | $D_s D_s D_s D_s D_s D_s D_s$ | $E_s E_o E_o E_o E_s E_s E$ |
| $E_s E_o E_s K_s$ | $D_s D_s D_s D_s D_s D_s D_s$ | $E_s E_o E_o E_o E_o E_s E_s E$ |
| $E_s E_o K_s$ | $D_s D_s D_s D_s D_s D_s D_s$ | $E_s E_s E_o E_o E_o E_o E_s E_s E$ |
| $E_s K_s$ | $D_s D_s D_s D_s D_s D_s D_s$ | $E_s E_s E_o E_o E_o E_o E_o E_s E_s E$ |
| $E_s E_s E_o E_o E_o E_o E_s K_s$ | $D_s D_s D_s D_s D_s D_s D_s$ | $E_o E_s E_s E$ |
| $E_s E_s E_o E_o E_o E_o E_o E_s K_s$ | $D_s D_s D_s D_s D_s D_s D_s$ | $E_s E_s E$ |
| $E_s E_o K_o K_s$ | $D_s D_s D_s D_s D_s D_s D_s D_s$ | $K_o K_o E_s E_s E$ |
| $E_s K_s$ | $D_s D_s D_s D_s D_s D_s D_s D_s D_s$ | $K_o K_o K_s E$ |
| $E_s E_o E_o E_s K_s$ | $D_s D_s D_s D_s D_s D_s D_s$ | $K_s E_o E_o E_s E$ |
| $E_s E_s E_o K_o K_s$ | $D_s D_s D_s D_s D_s D_s D_s$ | $K_o K_o E_s E_s E$ |
| $E_s E_o K_o K_s$ | $D_s D_s D_s D_s D_s D_s D_s D_s$ | $K_o K_o E_s E_s E$ |
| $E_s K_o E_o K_s$ | $D_s D_s D_s D_s D_s D_s D_s D_s$ | $K_o E_o K_s E_s E$ |
| $E_s E_o K_o K_s$ | $D_s D_s D_s D_s D_s D_s D_s D_s$ | $K_o K_o E_s E_s E$ |

TABLE 1-continued

| Certain Internucleoside Linkage Motifs | | |
|---|---|---|
| 5'-wing region | Central gap region | 3'-wing region |
| $E_s K_s$ | $D_s D_s D_s D_s D_s D_s D_s D_s$ | $E_s E_s E_o K_s K$ |
| $K_s$ | $D_s D_s D_s D_s D_s D_s D_s D_s$ | $E_s E_o K_o E_s K_s E$ |
| $K_s$ | $D_s D_s D_s D_s D_s D_s D_s D_s$ | $E_s E_s E_o K_o E_s K_s E$ |
| $K_s$ | $D_s D_s D_s D_s D_s D_s D_s D_s D_s$ | $E_s E_o K_o E_s K_s E_s E$ |
| $K_s$ | $D_s D_s D_s D_s D_s D_s D_s D_s$ | $E_s E_s E_o K_o E_s K_s E_s E$ |
| $K_s$ | $D_s D_s D_s D_s D_s D_s D_s D_s$ | $K_s E_s E_o E_o K_s E_s E$ |
| $K_s$ | $D_s D_s D_s D_s D_s D_s D_s D_s D_s$ | $K_s E_o E_o K_s E_s E_s E$ |
| $E_s E_s K_s$ | $D_s D_s D_s D_s D_s D_s D_s D_s$ | $E_o E_s E_s K$ |
| $E_s E_s K_s$ | $D_s D_s D_s D_s D_s D_s D_s D_s D_s$ | $E_o E_s K_s E$ |
| $E_s E_s K_s$ | $D_s D_s D_s D_s D_s D_s D_s D_s$ | $E_o E_o E_s K_s E$ |
| $E_s E_s K_s$ | $D_s D_s D_s D_s D_s D_s D_s D_s$ | $E_s E_o E_o K_s E_s K$ |
| $E_s E_s K_s$ | $D_s D_s D_s D_s D_s D_s D_s D_s$ | $K_o E_s E_s E$ |
| $E_s E_s K_s$ | $D_s D_s D_s D_s D_s D_s D_s D_s$ | $K_s E_o E_o E_s K_s E$ |
| $E_s K_s$ | $D_s D_s D_s D_s D_s D_s D_s$ | $E_s E_s E_s E_o K_o E_s K_s E$ |
| $E_s K_s$ | $D_s D_s D_s D_s D_s D_s D_s D_s$ | $K_s E_s E_o E_o K_s E_s E$ |
| $E_s K_s$ | $D_s D_s D_s D_s D_s D_s D_s D_s$ | $E_s E_o E_o K_s E_s K$ |
| $E_s E_s K_s$ | $D_s D_s D_s D_s D_s D_s D_s D_s D_s$ | $E_o E_o K_s E_s K$ |
| $E_s K_s$ | $D_s D_s D_s D_s D_s D_s D_s D_s$ | $E_s E_s E_o K_o E_s K_s E$ |
| $K_s$ | $D_s D_s D_s D_s D_s D_s D_s D_s D_s$ | $E_s E_o K_o E_s K_s E_s E$ |
| $E_s K_s$ | $D_s D_s D_s D_s D_s D_s D_s D_s$ | $E_s E_s E_o K_o E_s K_s E$ |
| $E_s K_s K_s$ | $D_s X_s D_s D_s D_s D_s D_s D_s D_s$ | $K_s K_s E$ |
| $E_s K_o E_o K_s$ | $D_s X_s D_s D_s D_s D_s D_s D_s D_s$ | $K_o E_s K_s E$ |
| $E_s K_s E_s K_s$ | $D_s X_s D_s D_s D_s D_s D_s D_s D_s$ | $K_s E_s E_s E$ |
| $E_s E_s E_s K_s$ | $D_s X_s D_s D_s D_s D_s D_s D_s D_s$ | $K_s E_s E_s E$ |
| $E_s K_s E_s K_s$ | $D_s X_s D_s D_s D_s D_s D_s D_s D_s$ | $K_s E_s K_s E$ |
| $E_s K_s$ | $D_s D_s D_s D_s D_s D_s D_s D_s D_s$ | $E_s E_o K_s K$ |
| $E_s K_s$ | $D_s D_s D_s D_s D_s D_s D_s D_s D_s$ | $K_s E_o E_s K$ |
| $K_s$ | $D_s D_s D_s D_s D_s D_s D_s D_s D_s$ | $E_s E_o K_s E_s K$ |
| $K_s$ | $D_s D_s D_s D_s D_s D_s D_s D_s D_s$ | $K_s E_o E_s K_s K$ |
| $E_s E_s K_s$ | $D_s D_s D_s D_s D_s D_s D_s D_s$ | $K_o K_o E_s E_s K$ |
| $E_s E_s K_s$ | $D_s D_s D_s D_s D_s D_s D_s D_s D_s$ | $K_s E_o E_s K_s E$ |
| $E_s K_s$ | $D_s D_s D_s D_s D_s D_s D_s D_s D_s$ | $E_s E_o K_o E_s K_s E$ |
| $E_s K_s$ | $D_s D_s D_s D_s D_s D_s D_s D_s$ | $E_s E_s E_o K_o E_s K_s E$ |
| $E_s K_s$ | $D_s D_s D_s D_s D_s D_s D_s D_s D_s$ | $K_s E_o E_o K_s E_s E$ |
| $E_s K_s$ | $D_s D_s D_s D_s D_s D_s D_s D_s D_s$ | $E_o E_o K_s E_s K$ |
| $E_s K_s$ | $D_s D_s D_s D_s D_s D_s D_s$ | $E_s E_s E_o E_o K_s E_s K$ |
| $E_s K_s$ | $D_s D_s D_s D_s D_s D_s D_s D_s D_s$ | $E_s E_o K_o E_s K_s E$ |

wherein each "E" is a 2'MOE modified nucleoside, each "K" is a cEt modified nucleoside, each "D" is an unmodified deoxynucleoside, each "X" comprises a 2-thiothymidine, each "s" is a phosphorothioate internucleoside linkage, and each "o" is a phosphodiester internucleoside linkage.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

i. Certain Modification Motifs

Modification motifs define oligonucleotides by nucleoside motif (sugar motif and nucleobase motif) and linkage motif. For example, certain oligonucleotides have the following modification motif:

$$A_sA_sA_sD_sD_sD_sD_s({}^{N}D)_sD_sD_sD_sD_sB_sB_sB;$$

wherein each A is a modified nucleoside comprising a 2'-substituted sugar moiety; each D is an unmodified 2'-deoxynucleoside; each B is a modified nucleoside comprising a bicyclic sugar moiety; ${}^{N}D$ is a modified nucleoside comprising a modified nucleobase; and s is a phosphorothioate internucleoside linkage. Thus, the sugar motif is a gapmer motif. The nucleobase modification motif is a single modified nucleobase at $8^{th}$ nucleoside from the 5'-end. Combining the sugar motif and the nucleobase modification motif, the nucleoside motif is an interrupted gapmer where the gap of the sugar modified gapmer is interrupted by a nucleoside comprising a modified nucleobase. The linkage motif is uniform phosphorothioate.

The following non-limiting Table further illustrates certain modification motifs:

TABLE 2

| Certain Modification Motifs | | |
|---|---|---|
| 5'-wing region | Central gap region | 3'-wing region |
| $A_s B_s B_s$ | $D_s D_s D_s D_s D_s D_s D_s D_s D_s$ | $B_s B_s A$ |
| $A_s A_s A_s A_s B_s B_s$ | $D_s D_s D_s D_s D_s D_s D_s$ | $B_s B_s A$ |
| $A_s A_s A_s B_s B_s$ | $D_s D_s D_s D_s D_s D_s D_s$ | $B_s B_s A$ |
| $A_s B_s B_s$ | $D_s X_s D_s D_s D_s D_s D_s D_s D_s$ | $B_s B_s A$ |
| $A_s A_s A_s A_s A_s B_s$ | $D_s D_s D_s D_s D_s D_s D_s$ | $A_s A_s A$ |
| $A_s A_s A_s A_s A_s B_s$ | $D_s D_s D_s D_s D_s D_s D_s$ | $B_s B_s A$ |

TABLE 2-continued

| Certain Modification Motifs | | |
|---|---|---|
| 5'-wing region | Central gap region | 3'-wing region |
| $A_s A_s A_s A_s B_s B_s$ | $D_s D_s D_s D_s D_s D_s D_s$ | $B_s A_s A$ |
| $A_s A_s A_s A_s A_s B_s$ | $D_s D_s D_s D_s D_s D_s D_s$ | $B_s A_s A$ |
| $A_s A_o A_o A_o A_o B_s$ | $D_s D_s D_s D_s D_s D_s D_s$ | $B_s A_s A$ |
| $A_s A_o A_o A_o A_o B_s$ | $D_s D_s D_s D_s D_s D_s D_s$ | $A_s A_s A$ |
| $A_s B_o A_o B_s$ | $D_s X_s D_s D_s D_s D_s D_s D_s D_s$ | $B_o A_s B_s A$ |
| $A_s A_o A_o A_s D_s B_s$ | $D_s D_s D_s D_s D_s D_s D_s$ | $A_o A_o A_s A_s A$ |
| $A_s A_s A_o A_o A_s B_s$ | $D_s D_s D_s D_s D_s D_s D_s$ | $A_o A_o A_o A_s A_s A$ |
| $A_s A_o A_o A_s B_s$ | $D_s D_s D_s D_s D_s D_s D_s$ | $A_s A_o A_o A_o A_s A_s A$ |
| $A_s A_o A_s B_s$ | $D_s D_s D_s D_s D_s D_s D_s$ | $A_s A_o A_o A_o A_o A_s A_s A$ |
| $A_s A_o B_s$ | $D_s D_s D_s D_s D_s D_s D_s$ | $A_s A_s A_o A_o A_o A_o A_s A_s A$ |
| $A_s B_s$ | $D_s D_s D_s D_s D_s D_s D_s$ | $A_s A_s A_o A_o A_o A_o A_o A_s A_s A$ |
| $A_s A_s A_o A_o A_o A_o A_s B_s$ | $D_s D_s D_s D_s D_s D_s D_s$ | $A_o A_s A_s A$ |
| $A_s A_s A_o A_o A_o A_o A_o A_s B_s$ | $D_s D_s D_s D_s D_s D_s D_s$ | $A_s A_s A$ |
| $A_s A_o B_o B_s$ | $D_s D_s D_s D_s D_s D_s D_s D_s$ | $B_o B_o A_s A_s A$ |
| $A_s B_s A_s B_s$ | $D_s X_s D_s D_s D_s D_s D_s D_s D_s$ | $B_s A_s A_s A$ |
| $A_s A_s A_s B_s$ | $D_s X_s D_s D_s D_s D_s D_s D_s D_s$ | $B_s A_s A_s A$ |
| $A_s A_s A_s B_s B_s$ | $D_s D_s D_s D_s D_s D_s D_s$ | $B_s B_s A$ |
| $A_s B_s A_s B_s$ | $D_s X_s D_s D_s D_s D_s D_s D_s D_s$ | $B_s A_s B_s A$ |
| $A_s A_s A_s A_s B_s B_s$ | $D_s D_s D_s D_s D_s D_s D_s$ | $B_s B_s A$ |
| $A_s B_s B_s D_s B_s$ | $D_s D_s D_s D_s D_s D_s D_s$ | $B_s B_s A$ |
| $A_s B_s B_s B_s B_s$ | $D_s D_s D_s D_s D_s D_s D_s$ | $B_s B_s A$ |
| $A_s B_s$ | $D_s D_s D_s D_s D_s D_s D_s D_s D_s$ | $B_o B_o B_s A$ |
| $A_s A_s A_s A_s B_s$ | $D_s D_s D_s D_s D_s D_s D_s$ | $B_s A_s A_s A$ |
| $A_s A_s A_s A_s D_s B_s$ | $D_s D_s D_s D_s D_s D_s D_s$ | $B_s A_s A_s A$ |
| $A_s A_o A_o A_s B_s$ | $D_s D_s D_s D_s D_s D_s D_s$ | $B_s A_o A_o A_s A$ |
| $A_s A_s A_o B_o B_s$ | $D_s D_s D_s D_s D_s D_s D_s$ | $B_o B_o A_s A_s A$ |
| $A_s A_o B_o B_s$ | $D_s D_s D_s D_s D_s D_s D_s D_s$ | $B_o B_o A_s A_s A$ |
| $A_s B_o A_o B_s$ | $D_s D_s D_s D_s D_s D_s D_s D_s$ | $B_o A_o B_s A_s A$ |
| $A_s A_o B_o B_s$ | $D_s D_s D_s D_s D_s D_s D_s D_s$ | $B_o B_o A_s A_s A$ |
| $A_s B_s$ | $D_s D_s D_s D_s D_s D_s D_s D_s$ | $A_s A_s A_o B_s B$ |
| $B_s$ | $D_s D_s D_s D_s D_s D_s D_s D_s D_s$ | $A_s A_o B_o A_s B_s A$ |
| $B_s$ | $D_s D_s D_s D_s D_s D_s D_s D_s$ | $A_s A_s A_o B_o A_s B_s A$ |
| $B_s$ | $D_s D_s D_s D_s D_s D_s D_s D_s D_s$ | $A_s A_o B_o A_s B_s A_s A$ |
| $B_s$ | $D_s D_s D_s D_s D_s D_s D_s D_s$ | $A_s A_s A_o B_o A_s B_s A_s A$ |
| $B_s$ | $D_s D_s D_s D_s D_s D_s D_s D_s$ | $B_s A_s A_o A_o B_s A_s A$ |
| $B_s$ | $D_s D_s D_s D_s D_s D_s D_s D_s D_s$ | $B_s A_o A_o B_s A_s A_s A$ |
| $A_s A_s B_s$ | $D_s D_s D_s D_s D_s D_s D_s D_s$ | $A_o A_s A_s B$ |
| $A_s A_s B_s$ | $D_s D_s D_s D_s D_s D_s D_s D_s D_s$ | $A_o A_s B_s A$ |
| $A_s A_s B_s$ | $D_s D_s D_s D_s D_s D_s D_s D_s$ | $A_o A_o A_s B_s A$ |
| $A_s A_s B_s$ | $D_s D_s D_s D_s D_s D_s D_s D_s$ | $A_s A_o A_o B_s A_s B$ |
| $A_s A_s B_s$ | $D_s D_s D_s D_s D_s D_s D_s D_s$ | $B_o A_s A_s A$ |
| $A_s A_s B_s$ | $D_s D_s D_s D_s D_s D_s D_s D_s$ | $B_s A_o A_o A_s B_s A$ |
| $A_s B_s$ | $D_s D_s D_s D_s D_s D_s D_s$ | $A_s A_s A_s A_o B_o A_s B_s A$ |
| $A_s B_s$ | $D_s D_s D_s D_s D_s D_s D_s D_s$ | $B_s A_s A_o A_o B_s A_s A$ |
| $A_s B_s$ | $D_s D_s D_s D_s D_s D_s D_s D_s$ | $A_s A_o A_o B_s A_s B$ |
| $A_s A_s B_s$ | $D_s D_s D_s D_s D_s D_s D_s D_s D_s$ | $A_o A_o B_s A_s B$ |
| $A_s B_s$ | $D_s D_s D_s D_s D_s D_s D_s D_s$ | $A_s A_s A_o B_o A_s B_s A$ |
| $B_s$ | $D_s D_s D_s D_s D_s D_s D_s D_s D_s$ | $A_s A_o B_o A_s B_s A_s A$ |
| $A_s B_s$ | $D_s D_s D_s D_s D_s D_s D_s D_s$ | $A_s A_s A_o B_o A_s B_s A$ |
| $A_s A_s A_s A_s A_s$ | $D_s D_s D_s D_s D_s D_s D_s D_s D_s D_s$ | $A_s A_s A_s A_s A$ |
| $A_s A_s A_s A_s A_s$ | $D_s D_s D_s D_s D_s D_s D_s D_s D_s D_s$ | $A_s A_s A_s A_s A$ |
| $A_s B_s$ | $D_s D_s D_s D_s D_s D_s D_s D_s D_s$ | $A, A_o B_s B$ |
| $A_s B_s$ | $D_s D_s D_s D_s D_s D_s D_s D_s D_s$ | $B_s A_o A_s B$ |
| $B_s$ | $D_s D_s D_s D_s D_s D_s D_s D_s D_s$ | $A_s A_o B_s A_s B$ |
| $B_s$ | $D_s D_s D_s D_s D_s D_s D_s D_s D_s$ | $B_s A_o A_s B_s B$ |
| $A_s A_s B_s$ | $D_s D_s D_s D_s D_s D_s D_s D_s$ | $B_o B_o A_s A_s B$ |
| $A_s A_s B_s$ | $D_s D_s D_s D_s D_s D_s D_s D_s D_s$ | $B_s A_o A_s B_s A$ |
| $A_s B_s$ | $D_s D_s D_s D_s D_s D_s D_s D_s D_s$ | $A_s A_o B_o A_s B_s A$ |
| $A_s B_s$ | $D_s D_s D_s D_s D_s D_s D_s D_s$ | $A_s A_s A_o B_o A_s B_s A$ |
| $A_s B_s$ | $D_s D_s D_s D_s D_s D_s D_s D_s D_s$ | $B_s A_o A_o B_s A_s A$ |
| $A_s B_s$ | $D_s D_s D_s D_s D_s D_s D_s D_s D_s$ | $A_o A_o B_s A_s B$ |
| $A_s B_s$ | $D_s D_s D_s D_s D_s D_s D_s$ | $A_s A_s A_o A_o B_s A_s B$ |
| $A_s B_s$ | $D_s D_s D_s D_s D_s D_s D_s D_s D_s$ | $A_s A_o B_o A_s B_s A$ |

In certain embodiments, each A comprises a modified sugar moiety. In certain embodiments, each A comprises a 2'-substituted sugar moiety. In certain embodiments, each A comprises a 2'-substituted sugar moiety selected from among F, (ara)-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each A comprises an HNA. In certain embodiments, each A comprises an F-HNA. In certain embodiments, each "X" comprises a 2-thiothymidine, each "s" comprises a phosphorothioate internucleoside linkage, and each "o" comprises a phosphodiester internucleoside linkage.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety. In certain embodiments, B is an LNA nucleoside and A comprises a 2'-OMe sugar moiety. In certain embodiments, B is a cEt nucleoside and A comprises a 2'-OMe sugar moiety. In certain embodiments, B is an α-L-LNA nucleoside and A comprises a 2'-OMe sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety. In certain embodiments, A is a cEt nucleoside and B comprises a 2'-MOE sugar moiety.

The following non-limiting Table further illustrates certain modification motifs:

TABLE 3

| Certain Modification Motifs | | |
|---|---|---|
| 5'-wing region | Central gap region | 3'-wing region |
| $E_s K_s K_s$ | $D_s D_s D_s D_s D_s D_s D_s D_s D_s$ | $K_s K_s E$ |
| $E_s E_s E_s E_s K_s K_s$ | $D_s D_s D_s D_s D_s D_s D_s$ | $K_s K_s E$ |
| $E_s E_s E_s K_s K_s$ | $D_s D_s D_s D_s D_s D_s D_s$ | $K_s K_s E$ |
| $E_s K_s K_s$ | $D_s X_s D_s D_s D_s D_s D_s D_s D_s$ | $K_s K_s E$ |
| $E_s E_s E_s E_s E_s K_s$ | $D_s D_s D_s D_s D_s D_s D_s$ | $E_s E_s E$ |
| $E_s E_s E_s E_s E_s K_s$ | $D_s D_s D_s D_s D_s D_s D_s$ | $K_s K_s E$ |
| $E_s E_s E_s E_s K_s K_s$ | $D_s D_s D_s D_s D_s D_s D_s$ | $K_s E_s E$ |
| $E_s E_s E_s E_s E_s K_s$ | $D_s D_s D_s D_s D_s D_s D_s$ | $K_s E_s E$ |
| $E_s E_o E_o E_o E_o K_s$ | $D_s D_s D_s D_s D_s D_s D_s$ | $K_s E_s E$ |
| $E_s E_o E_o E_o E_o K_s$ | $D_s D_s D_s D_s D_s D_s D_s$ | $E_s E_s E$ |
| $E_s K_o E_o K_s$ | $D_s X_s D_s D_s D_s D_s D_s D_s D_s$ | $K_o E_s K_s E$ |
| $E_s E_o E_o E_o E_s D_s K_s$ | $D_s D_s D_s D_s D_s D_s D_s$ | $E_o E_o E_s E_s E$ |
| $E_s E_s E_o E_o E_s K_s$ | $D_s D_s D_s D_s D_s D_s D_s$ | $E_o E_o E_o E_s E_s E$ |
| $E_s E_o E_o E_s K_s$ | $D_s D_s D_s D_s D_s D_s D_s$ | $E_s E_o E_o E_o E_s E_s E$ |
| $E_s E_o E_s K_s$ | $D_s D_s D_s D_s D_s D_s D_s$ | $E_s E_o E_o E_o E_o E_s E_s E$ |
| $E_s E_o K_s$ | $D_s D_s D_s D_s D_s D_s D_s$ | $E_s E_s E_o E_o E_o E_o E_s E_s E$ |
| $E_s K_s$ | $D_s D_s D_s D_s D_s D_s D_s$ | $E_s E_s E_o E_o E_o E_o E_o E_s E_s E$ |
| $E_s E_s E_o E_o E_o E_o E_s K_s$ | $D_s D_s D_s D_s D_s D_s D_s$ | $E_o E_s E_s E$ |
| $E_s E_s E_o E_o E_o E_o E_o E_s K_s$ | $D_s D_s D_s D_s D_s D_s D_s$ | $E_s E_s E$ |
| $E_s E_o K_o K_s$ | $D_s D_s D_s D_s D_s D_s D_s D_s$ | $K_o K_o E_s E_s E$ |
| $E_s K_s E_s K_s$ | $D_s xD_s D_s D_s D_s D_s D_s D_s D_s$ | $K_s E_s E_s E$ |
| $E_s E_s E_s K_s$ | $D_s xD_s D_s D_s D_s D_s D_s D_s D_s$ | $K_s E_s E_s E$ |
| $E_s E_s E_s K_s K_s$ | $D_s D_s D_s D_s D_s D_s D_s$ | $K_s K_s E$ |
| $E_s K_s E_s K_s$ | $D_s xD_s D_s D_s D_s D_s D_s D_s D_s$ | $K_s E_s K_s E$ |
| $E_s E_s E_s E_s K_s K_s$ | $D_s D_s D_s D_s D_s D_s D_s$ | $K_s K_s E$ |
| $E_s K_s K_s D_s K_s$ | $D_s D_s D_s D_s D_s D_s D_s$ | $K_s K_s E$ |
| $E_s K_s K_s K_s K_s$ | $D_s D_s D_s D_s D_s D_s D_s$ | $K_s K_s E$ |
| $E_s K_s$ | $D_s D_s D_s D_s D_s D_s D_s D_s D_s$ | $K_o K_o K_s E$ |
| $E_s E_s E_s E_s K_s$ | $D_s D_s D_s D_s D_s D_s D_s$ | $K_s E_s E_s E$ |
| $E_s E_s E_s E_s D_s K_s$ | $D_s D_s D_s D_s D_s D_s D_s$ | $K_s E_s E_s E$ |
| $E_s E_o E_o E_s K_s$ | $D_s D_s D_s D_s D_s D_s D_s$ | $K_s E_o E_o E_s E$ |
| $E_s E_s E_o K_o K_s$ | $D_s D_s D_s D_s D_s D_s D_s$ | $K_o K_o E_s E_s E$ |
| $E_s E_o K_o K_s$ | $D_s D_s D_s D_s D_s D_s D_s D_s$ | $K_o K_o E_s E_s E$ |
| $E_s K_o E_o K_s$ | $D_s D_s D_s D_s D_s D_s D_s D_s$ | $K_o E_o K_s E_s E$ |
| $E_s E_o K_o K_s$ | $D_s D_s D_s D_s D_s D_s D_s D_s$ | $K_o K_o E_s E_s E$ |
| $E_s K_s$ | $D_s D_s D_s D_s D_s D_s D_s D_s$ | $E_s E_s E_o K_s K$ |
| $K_s$ | $D_s D_s D_s D_s D_s D_s D_s D_s D_s$ | $E_s E_o K_o E_s K_s E$ |
| $K_s$ | $D_s D_s D_s D_s D_s D_s D_s D_s$ | $E_s E_s E_o K_o E_s K_s E$ |
| $K_s$ | $D_s D_s D_s D_s D_s D_s D_s D_s D_s$ | $E_s E_o K_o E_s K_s E_s E$ |
| $K_s$ | $D_s D_s D_s D_s D_s D_s D_s D_s$ | $E_s E_s E_o K_o E_s K_s E_s E$ |
| $K_s$ | $D_s D_s D_s D_s D_s D_s D_s D_s$ | $K_s E_s E_o E_o K_s E_s E$ |
| $K_s$ | $D_s D_s D_s D_s D_s D_s D_s D_s D_s$ | $K_s E_o E_o K_s E_s E_s E$ |
| $E_s E_s K_s$ | $D_s D_s D_s D_s D_s D_s D_s D_s$ | $E_o E_s E_s K$ |
| $E_s E_s K_s$ | $D_s D_s D_s D_s D_s D_s D_s D_s D_s$ | $E_o E_s K_s E$ |
| $E_s E_s K_s$ | $D_s D_s D_s D_s D_s D_s D_s D_s$ | $E_o E_o E_s K_s E$ |
| $E_s E_s K_s$ | $D_s D_s D_s D_s D_s D_s D_s D_s$ | $E_s E_o E_o K_s E_s K$ |
| $E_s E_s K_s$ | $D_s D_s D_s D_s D_s D_s D_s D_s$ | $K_o E_s E_s E$ |
| $E_s E_s K_s$ | $D_s D_s D_s D_s D_s D_s D_s D_s$ | $K_s E_o E_o E_s K_s E$ |
| $E_s K_s$ | $D_s D_s D_s D_s D_s D_s D_s$ | $E_s E_s E_s E_o K_o E_s K_s E$ |
| $E_s K_s$ | $D_s D_s D_s D_s D_s D_s D_s D_s$ | $K_s E_s E_o E_o K_s E_s E$ |
| $E_s K_s$ | $D_s D_s D_s D_s D_s D_s D_s D_s$ | $E_s E_o E_o K_s E_s K$ |
| $E_s E_s K_s$ | $D_s D_s D_s D_s D_s D_s D_s D_s D_s$ | $E_o E_o K_s E_s K$ |
| $E_s K_s$ | $D_s D_s D_s D_s D_s D_s D_s D_s$ | $E_s E_s E_o K_o E_s K_s E$ |

TABLE 3-continued

| Certain Modification Motifs | | |
|---|---|---|
| 5'-wing region | Central gap region | 3'-wing region |
| $K_s$ | $D_s$ $D_s$ $D_s$ $D_s$ $D_s$ $D_s$ $D_s$ $D_s$ $D_s$ | $E_s$ $E_o$ $K_o$ $E_s$ $K_s$ $E_s$ E |
| $E_s$ $K_s$ | $D_s$ $D_s$ $D_s$ $D_s$ $D_s$ $D_s$ $D_s$ $D_s$ | $E_s$ $E_s$ $E_o$ $K_o$ $E_s$ $K_s$ E |
| $E_s$ $E_s$ $E_s$ $E_s$ $E_s$ | $D_s$ $D_s$ $D_s$ $D_s$ $D_s$ $D_s$ $D_s$ $D_s$ $D_s$ $D_s$ | $E_s$ $E_s$ $E_s$ $E_s$ E |
| $E_s$ $E_s$ $E_s$ $E_s$ $E_s$ | $D_s$ $D_s$ $D_s$ $D_s$ $D_s$ $D_s$ $D_s$ $D_s$ $D_s$ $D_s$ | $E_s$ $E_s$ $E_s$ $E_s$ E |
| $E_s$ $K_s$ | $D_s$ $D_s$ $D_s$ $D_s$ $D_s$ $D_s$ $D_s$ $D_s$ $D_s$ | $E_s$ $E_o$ $K_s$ K |
| $E_s$ $K_s$ | $D_s$ $D_s$ $D_s$ $D_s$ $D_s$ $D_s$ $D_s$ $D_s$ $D_s$ | $K_s$ $E_o$ $E_s$ K |
| $K_s$ | $D_s$ $D_s$ $D_s$ $D_s$ $D_s$ $D_s$ $D_s$ $D_s$ $D_s$ | $E_s$ $E_o$ $K_s$ $E_s$ K |
| $K_s$ | $D_s$ $D_s$ $D_s$ $D_s$ $D_s$ $D_s$ $D_s$ $D_s$ $D_s$ | $K_s$ $E_o$ $E_s$ $K_s$ K |
| $E_s$ $E_s$ $K_s$ | $D_s$ $D_s$ $D_s$ $D_s$ $D_s$ $D_s$ $D_s$ $D_s$ | $K_o$ $K_o$ $E_s$ $E_s$ K |
| $E_s$ $E_s$ $K_s$ | $D_s$ $D_s$ $D_s$ $D_s$ $D_s$ $D_s$ $D_s$ $D_s$ $D_s$ | $K_s$ $E_o$ $E_s$ $K_s$ E |
| $E_s$ $K_s$ | $D_s$ $D_s$ $D_s$ $D_s$ $D_s$ $D_s$ $D_s$ $D_s$ $D_s$ | $E_s$ $E_o$ $K_o$ $E_s$ $K_s$ E |
| $E_s$ $K_s$ | $D_s$ $D_s$ $D_s$ $D_s$ $D_s$ $D_s$ $D_s$ $D_s$ | $E_s$ $E_s$ $E_o$ $K_o$ $E_s$ $K_s$ E |
| $E_s$ $K_s$ | $D_s$ $D_s$ $D_s$ $D_s$ $D_s$ $D_s$ $D_s$ $D_s$ $D_s$ | $K_s$ $E_o$ $E_o$ $K_s$ $E_s$ E |
| $E_s$ $K_s$ | $D_s$ $D_s$ $D_s$ $D_s$ $D_s$ $D_s$ $D_s$ $D_s$ $D_s$ | $E_o$ $E_o$ $K_s$ $E_s$ K |
| $E_s$ $K_s$ | $D_s$ $D_s$ $D_s$ $D_s$ $D_s$ $D_s$ $D_s$ | $E_s$ $E_s$ $E_o$ $E_o$ $K_s$ $E_s$ K |
| $E_s$ $K_s$ | $D_s$ $D_s$ $D_s$ $D_s$ $D_s$ $D_s$ $D_s$ $D_s$ $D_s$ | $E_s$ $E_o$ $K_o$ $E_s$ $K_s$ E |

wherein each "E" is a 2'MOE modified nucleoside, each "K" is a cEt modified nucleoside, each "D" is an unmodified deoxynucleoside, each "X" comprises a 2-thiothymidine, each "s" is a phosphorothioate internucleoside linkage, and each "o" is a phosphodiester internucleoside linkage.

d. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

f. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

C. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

b. Certain Selective Antisense Compounds

In certain embodiments, antisense compounds provided are selective for a target relative to a non-target nucleic acid. In certain embodiments, antisense compounds provided are selective for a target relative to one or more non-target nucleic acids. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the nucleobase sequences of the target and non-target nucleic acids are identical in the targeted region.

In certain embodiments, the target and non-target nucleic acids are transcripts from different genes. In certain embodiments, the target nucleic acid is a transcript from the huntingtin gene and the non-target nucleic acid is a transcript from a different gene. In certain embodiments, the non-target nucleic acid is a transcript from a gene encoding bone morphogenetic protein receptor, type IA and the target nucleic acid is a transcript from a different gene. In certain embodiments, the target nucleic acid is a transcript from the huntingtin gene and the non-target nucleic acid is a transcript from a gene encoding bone morphogenetic protein receptor, type IA. In certain embodiments, the target and non-target nucleic acids are different alleles for the same gene. In certain embodiments, the introduction of a mismatch between an antisense compound and a non-target nucleic acid may alter the RNase H cleavage site of a target nucleic acid compared to a non-target nucleic acid. In certain embodiments, the target and non-target nucleic acids are not functionally related to one another (e.g., are transcripts from different genes). In certain embodiments, the target and non-target nucleic acids are allelic variants of one another. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (e.g. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

In certain embodiments, an antisense compound binds its intended target to form a target duplex. In certain embodiments, RNase H cleaves the target nucleic acid of the target duplex. In certain such embodiments, there is a primary cleavage site between two particular nucleosides of the target nucleic acid (the primary target cleavage site), which accounts for the largest amount of cleavage of the target nucleic acid. In certain embodiments, there are one or more secondary target cleavage sites. In certain embodiments, the same antisense compound hybridizes to a non-target to form a non-target duplex. In certain such embodiments, the non-target differs from the target by a single nucleobase within the target region, and so the antisense compound hybridizes with a single mismatch. Because of the mismatch, in certain embodiments, RNase H cleavage of the non-target may be reduced compared to cleavage of the target, but still occurs. In certain embodiments, though, the primary site of that cleavage of the non-target nucleic acid (primary non-target cleavage site) is different from that of the target. That is, the primary site is shifted due to the mismatch. In such a circumstance, one may use a modification placed in the antisense compound to disrupt RNase H cleavage at the primary non-target cleavage site. Such modification will result in reduced cleavage of the non-target, but will result little or no decrease in cleavage of the target. In certain embodiments, the modification is a modified sugar, nucleobase and/or linkage.

In certain embodiments, the primary non-target cleavage site is towards the 5'-end of the antisense compound, and the 5'-end of an antisense compound may be modified to prevent RNaseH cleavage. In this manner, it is thought that one having skill in the art may modify the 5'-end of an antisense compound, or modify the nucleosides in the gap region of the 5'-end of the antisense compound, or modify the 3'-most 5'-region nucleosides of the antisense compound to selectively inhibit RNaseH cleavage of the non-target nucleic acid duplex while retaining RNase H cleavage of the target nucleic acid duplex. In certain embodiments, 1-3 of the 3'-most 5'-region nucleosides of the antisense compound comprises a bicyclic sugar moiety.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to the target nucleic acid. The mismatch between the antisense compound and the non-target nucleic acid may destabilize the antisense compound non-target nucleic acid duplex, and consequently the cleavage site of RNaseH may shift upstream towards the 5'-end of the antisense compound. Modification of the 5'-end of the antisense compound or the gap region near the 5'-end of the antisense compound, or one or more of the 3'-most nucleosides of the 5'-wing region, will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more downstream, towards the 3' end of the antisense compound. Accordingly, modifications at the 5'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 3'-most nucleosides of the 5'-wing region comprises a bicyclic sugar moiety. In certain embodiments, one or more of the 3'-most nucleosides of the 5'-wing region comprises a bicyclic sugar moiety selected from cEt and LNA. In certain embodiments, one or more of the 3'-most nucleosides of the 5'-wing region comprises cEt. In certain embodiments, one or more of the 3'-most nucleosides of the 5'-wing region comprises LNA.

In certain embodiments, the introduction of a mismatch between an antisense compound and a target nucleic acid may alter the RNase H cleavage site of a target nucleic acid compared to a non-target nucleic acid by shifting the RNaseH cleavage site downstream from the mismatch site and towards the 3'-end of the antisense compound. In certain embodiments where the cleavage site of a target nucleic acid compared to a non-target nucleic acid has shifted downstream towards the 3'-end of the antisense compound, the 3'-end of an antisense compound may be modified to prevent RNaseH cleavage. In this manner, it is thought that one having skill in the art may modify the 3'-end of an antisense compound, or modify the nucleosides in the gap region near the 3'-end of antisense compound, to selectively inhibit RNaseH cleavage of the non-target nucleic acid while retaining RNase H cleavage of the target nucleic acid.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to target nucleic acid. The mismatch between the antisense compound and the non-target nucleic acid may destabilize the antisense compound-non-target nucleic acid duplex, and consequently the cleavage site of RNaseH may shift downstream towards the 3'-end of the antisense compound. Modification of the 3'-end of the antisense compound, or one or more of the 5'-most nucleosides of the 3'-wing region, or the gap region of the antisense compound near the 3'-end will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more upstream, towards the 5' end of the antisense compound. Accordingly, modifications at the 3'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 5'-most nucleosides of the 3'-wing region comprises a bicyclic sugar moiety. In certain embodiments, one or more of the 5'-most nucleosides of the 3'-wing region comprises a bicyclic sugar moiety selected from cEt and LNA. In certain embodiments, one or more of the 5'-most nucleosides of the 3'-wing region comprises cEt. In certain embodiments, one or more of the 5'-most nucleosides of the 3'-wing region comprises LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside. In certain embodiments, the selectivity of antisense compounds having certain gaps, e.g. gaps of 7 nucleosides or longer, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicyclic nucleosides at the 5'-most 3'-wing nucleoside.

In certain embodiments, the selectivity of antisense compounds having certain gaps, e.g. gaps of 7 nucleosides or shorter, may be improved by the addition of one or more bicyclic nucleosides at the 3'-most 5'-wing nucleoside. In certain embodiments, the selectivity of antisense compounds having certain gaps, e.g. gaps of 7 nucleosides or shorter, may be improved by the addition of two or more bicyclic nucleosides at the 3'-most 5'-wing nucleoside. In certain embodiments, the selectivity of antisense compounds having certain gaps, e.g. gaps of 7 nucleosides or shorter, may be improved by the addition of one bicyclic nucleoside at the 3'-most 5'-wing nucleoside. In certain embodiments, the selectivity of antisense compounds having certain gaps, e.g. gaps of 7 nucleosides or shorter, may be improved by the addition of two bicyclic nucleosides at the 3'-most 5'-wing nucleoside. In certain embodiments, the selectivity of antisense compounds having certain gaps, e.g. gaps of 7 nucleosides or shorter, may be improved by the addition of three bicyclic nucleosides at the 3'-most 5'-wing nucleoside. In certain embodiments, the selectivity of antisense compounds having certain gaps, e.g. gaps of 7 nucleosides or shorter, may be improved by the addition of four bicyclic nucleosides at the 3'-most 5'-wing nucleoside. In certain embodiments, the selectivity of antisense compounds having certain gaps, e.g. gaps of 7 nucleosides or shorter, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

In certain embodiments, for example, in certain embodiments described above, the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to the target nucleic acid, and which also has one or more mismatches towards any other non-target nucleic acid. In this manner one having skill in the art may design a selective antisense compound that has full complementarity to the target nucleic acid, a single mismatch to its allelic variant, and one or more mismatches towards any other non-target nucleic acid.

In certain embodiments, a selective antisense compound having a single nucleobase mismatch relative to its allelic variant (e.g. a non-target nucleic having a single nucleobase mismatch from the target nucleic acid) may, based on its nucleobase sequence, have full complementarity to one or more other non-target nucleic acids. In such certain embodiments, the sequence of the selective antisense compound may be moved upstream or downstream, so long as the selective antisense compound has a single nucleobase mismatch relative to its allelic variant. For example, in certain embodiments, the $6^{th}$ nucleobase from the 5'-end of the selective antisense compound represents the single nucleobase mismatch relative to its allelic variant. A new selective antisense compound may then be designed wherein the sequence of the selective antisense compound is shifted closer to the 5'-end, and wherein the $3^{rd}$ nucleobase from the 5'-end of the newly designed selective antisense compound represents the single nucleobase mismatch relative to its allelic variant. In this manner, the newly designed selective antisense compound will continue to have a single nucleobase mismatch relative to its allelic variant, but now the newly designed selective antisense compound may have 1 or more mismatches with other non-target nucleic acids. Since the target nucleic acid differs from its allelic variant by only a single nucleobase mismatch, full complementarity between the selective antisense compound and the target nucleic acid may be maintained, while at the same time reducing complementarity between the selective antisense compound and other non-target nucleic acids. In certain embodiments, such modifications will have no impact or only a small impact on the selectivity of the selective antisense compound relative to its allelic variant, but will reduce the selectivity of the selective antisense compound relative to other non-target nucleic acids.

Any of the modifications discussed herein may be used to design a selective antisense compound that reduces the amount or activity of a target nucleic acid, while having little to no selectivity towards the allelic variant of the target nucleic acid or any other non-target nucleic acids. In certain embodiments, the target nucleic acid is a transcript from the huntingtin gene and the non-target nucleic acid is a transcript from a gene encoding bone morphogenetic protein receptor, type IA. In certain embodiments, the target nucleic acid is a transcript from a mutant huntingtin gene and the non-target nucleic acid is a transcript from a normal huntingtin gene. In certain embodiments, the target nucleic acid is a transcript from a mutant huntingtin gene and one non-target nucleic acid is a transcript from a normal huntingtin gene and another non-target nucleic acid is a nucleic acid encoding bone morphogenetic protein receptor, type IA.

In certain embodiments, it is desirable to have a selective antisense compound that selectively reduces the amount or activity of a target nucleic acid and which does not significantly reduce the amount or activity of any other non-target nucleic acid. In certain embodiments, it is desirable to have a selective antisense compound that selectively reduces the amount or activity of a target nucleic acid associated with Hungtinton's Disease and which does not significantly reduce the amount or activity of any other non-target nucleic acid, for example BMPR1A.

In certain embodiments, a selective antisense compound that selectively reduces the amount or activity of mutant huntingtin allele associated with a SNP may closely align with the nucleobase sequence of another non-target nucleic acid. For example, in certain embodiments, an antisense compound may be complementary to a target nucleic acid that corresponds to a mutant huntingtin allele associated with a SNP, and this mutant huntingtin allele associated with a SNP may have a high degree of homology with another non-target nucleic acid. For example, in certain embodiments, an antisense compound may be complementary to a target nucleic acid that corresponds to a mutant huntingtin allele associated with a SNP, and also complementary to a non-target nucleic acid encoding bone morphogenetic protein receptor, type IA. For example, in certain embodiments, an antisense compound may be complementary to a target nucleic acid that corresponds to a mutant huntingtin allele associated with a SNP, for example rs7685686, and also complementary to a non-target nucleic acid encoding bone morphogenetic protein receptor, type IA. In certain such embodiments, it is desirable to design an antisense compound that selectively reduces the target nucleic acid associated with SNP rs7685686 and the mutant allele associated with Huntington's disease, but at the same time minimizes reduction between non-target nucleic acids that have high degree of sequence homology with the target nucleic acid nucleobase sequence surrounding SNP rs7685686.

In certain embodiments, the nucleobase sequence surrounding SNP rs7685686 has a high degree of homology between portions of the non-target nucleic acid that encodes bone morphogenetic protein receptor, type IA. In certain embodiments, the present disclosure provides compounds having specific modification motifs and nucleobase sequences targeted to SNP rs7685686 that selectively reduce the amount or activity of a mutant huntintin allele of a huntingtin transcript but do not significantly reduce the amount or activity of a wild-type huntingtin allele and do not significantly reduce the amount or activity of a nucleic acid that encodes bone morphogenetic protein receptor, type IA.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

In certain embodiments, it is desirable to have a selective antisense compound that selectively reduces the amount or activity of a target nucleic acid associated with Hungtinton's Disease and which does not significantly reduce the amount or activity of any other non-target nucleic acid, for example BMPR1A.

In certain embodiments, a compound consists of ISIS 606561. In certain embodiments, a compound consists of ISIS 606562. In certain embodiments, a compound consists of ISIS 611714. In certain embodiments, a compound consists of ISIS 611715. In certain embodiments, a compound consists of ISIS 611717. In certain embodiments, a compound consists of ISIS 611718. In certain embodiments, a compound consists of ISIS 611719. In certain embodiments, a compound consists of ISIS 611720. In certain embodiments, a compound consists of ISIS 611721. In certain embodiments, a compound consists of ISIS 611722. In certain embodiments, a compound consists of ISIS 611723. In certain embodiments, a compound consists of ISIS 613581. In certain embodiments, a compound consists of ISIS 613582. In certain embodiments, a compound consists of ISIS 613583. In certain embodiments, a compound consists of ISIS 613584. In certain embodiments, a compound consists of ISIS 613585. In certain embodiments, a compound consists of ISIS 613586. In certain embodiments, a compound consists of ISIS 613588.

In certain embodiments, a compound consists of ISIS 613589. In certain embodiments, a compound consists of ISIS 617104. In certain embodiments, a compound consists of ISIS 617105. In certain embodiments, a compound consists of ISIS 617106. In certain embodiments, a compound consists of ISIS 617107. In certain embodiments, a compound consists of ISIS 617108. In certain embodiments, a compound consists of ISIS 617109. In certain embodiments, a compound consists of ISIS 617110. In certain embodiments, a compound consists of ISIS 617111. In certain embodiments, a compound consists of ISIS 617115. In certain embodiments, a compound consists of ISIS 617116. In certain embodiments, a compound consists of ISIS 617117. In certain embodiments, a compound consists of ISIS 617118. In certain embodiments, a compound consists of ISIS 617119. In certain embodiments, a compound consists of ISIS 617425. In certain embodiments, a compound consists of ISIS 623181. In certain embodiments, a compound consists of ISIS 623182. In certain embodiments, a compound consists of ISIS 623198. In certain embodiments, a compound consists of ISIS 623199.

In certain embodiments, a compound consists of ISIS 623202. In certain embodiments, a compound consists of ISIS 623203. In certain embodiments, a compound consists of ISIS 623205. In certain embodiments, a compound consists of ISIS 623206. In certain embodiments, a compound consists of ISIS 623208. In certain embodiments, a compound consists of ISIS 623212. In certain embodiments, a compound consists of ISIS 623214. In certain embodiments, a compound consists of ISIS 623218. In certain embodiments, a compound consists of ISIS 623220. In certain embodiments, a compound consists of ISIS 623221. In certain embodiments, a compound consists of ISIS 623224. In certain embodiments, a compound consists of ISIS 623227. In certain embodiments, a compound consists of ISIS 623230.

In certain embodiments, a compound consists of ISIS 623232. In certain embodiments, a compound consists of ISIS 623233. In certain embodiments, a compound consists of ISIS 623235. In certain embodiments, a compound consists of ISIS 623236. In certain embodiments, a compound consists of ISIS 623237. In certain embodiments, a compound consists of ISIS 623238. In certain embodiments, a compound consists of ISIS 623239. In certain embodiments, a compound consists of ISIS 623241. In certain embodiments, a compound consists of ISIS 623242. In certain embodiments, a compound consists of ISIS 623243. In certain embodiments, a compound consists of ISIS 623254. In certain embodiments, a compound consists of ISIS 623262. In certain embodiments, a compound consists of ISIS 623490. In certain embodiments, a compound consists of ISIS 623493. In certain embodiments, a compound consists of ISIS 623494.

i. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

ii. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{th}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

In certain embodiments, a target-selective nucleoside comprises a modified nucleoside. In certain embodiments, a target-selective nucleoside comprises a modified sugar. In certain embodiments, a target-selective nucleoside comprises a sugar surrogate. In certain embodiments, a target-selective nucleoside comprises a sugar surrogate selected from among HNA and F-HNA. In certain embodiments, a target-selective nucleoside comprises a 2'-substituted sugar moiety. In certain embodiments, a target-selective nucleoside comprises a 2'-substituted sugar moiety selected from among MOE, F and (ara)-F. In certain embodiments, a target-selective nucleoside comprises a 5'-substituted sugar moiety. In certain embodiments, a target-selective nucleoside comprises a 5'-substituted sugar moiety selected from 5'-(R)-Me DNA. In certain embodiments, a target-selective nucleoside comprises a bicyclic sugar moiety. In certain embodiments, a target-selective nucleoside comprises a bicyclic sugar moiety selected from among cEt, and α-L-LNA. In certain embodiments, a target-selective nucleoside comprises a modified nucleobase. In certain embodiments, a target-selective nucleoside comprises a modified nucleobase selected from among 2-thio-thymidine and 5-propyne uridine.

i. Alignment of Differentiating Nucleobase/Selectivity Against One or More Non-Target Nucleic Acid Transcripts In certain embodiments, a target region and a region of one or more non-target nucleic acids differ by 0-4 differentiating nucleobases. In such embodiments, selective antisense compounds have a nucleobase sequence that aligns with one or more non-target nucleic acids with 0-4 mismatches. In certain such embodiments, selective antisense compounds have a nucleobase sequence that aligns with a first non-target nucleic acid with 1-4 mismatches and a second non-target nucleic acid with 0-4 mismatches. In certain embodiments, selective antisense compounds have a nucleobase sequence that aligns with a first non-target nucleic acid with 1 mismatch and a second non-target nucleic acid with 0 mismatches. In certain embodiments, selective antisense compounds have a nucleobase sequence that aligns with a first non-target nucleic acid with 1 mismatch and a second non-target nucleic acid with 1 mismatch.

In certain embodiments, a selective antisense compound may be selective against one non-target nucleic acid transcript, but not be selective against another non-target nucleic acid transcript. For example, in certain embodiments, a selective antisense compound may be selective for a target relative to a first non-target nucleic acid, but may also be selective towards a second non-target nucleic acid relative to the first non-target nucleic acid, wherein the first and second non-target nucleic acids differ by 0-4 differentiating nucleobases. For example, in certain embodiments, a selective antisense compound may be selective for a target relative to a first non-target nucleic acid based on a mismatch of a single differentiating nucleobase, but also be selective for a second non-target nucleic acid relative to the first non-target nucleic acid. In certain embodiments, it is preferred to have a selective antisense compound be selective for a target relative to a first non-target nucleic acid and also be selective for a target relative to a second non-target nucleic acid. In certain embodiments, it is preferred to have a selective antisense compound be selective for a mutant huntingtin allele associated with Huntington's disease, and not be selective relative to any other non-target nucleic acids.

In certain embodiments where a selective antisense compound is selective for a target relative to a first non-target nucleic acid based on a single differentiating nucleobase, but wherein the selective antisense compound is also selective relative to a second non-target nucleic acid, it is possible to alter the position of the target-selective nucleoside within the gap region of the selective antisense compound to maintain selectivity relative to the first non-target nucleic acid and to increase selectivity relative to the second non-target nucleic acid. For example, in certain embodiments, a target-selective nucleoside is the $3^{rd}$ nucleoside of the gap from the 5'-end of the selective antisense compound, wherein the 5'-wing of the selective antisense compound consists of 4 nucleosides.

In certain embodiments, a selective antisense compound may be redesigned wherein the overall length of the selective antisense compound remains the same, but wherein the length of the 5'-wing is shortened to 1-4 nucleosides and/or the position of the target-selective nucleoside is moved closer to the 5'-end of the gap, for example the $1^{st}$ or $2^{nd}$ nucleoside of the gap from the 5'-end. In certain embodiments, a selective antisense compound may be redesigned wherein the overall length of the selective antisense compound remains the same, but wherein the length of the 5'-wing is increased to 1-9 nucleosides and/or the position of the target-selective nucleoside is moved closer to the 5'-end of the gap, for example the $1^{st}$ or $2^{nd}$ nucleoside of the gap from the 5'-end. In certain embodiments, a selective antisense compound may be redesigned wherein the overall length of the selective antisense compound remains the same, but wherein the length of the 5'-wing is increased to 1-9 nucleosides and/or the position of the target-selective nucleoside is moved closer to the 3'-end of the gap, for example the $1^{st}$ or $2^{nd}$ nucleoside of the gap from the 3'-end. In certain embodiments, a selective antisense compound may be redesigned wherein the overall length of the selective antisense compound remains the same, but wherein the length of the 5'-wing is shortened to 1-4 nucleosides and/or the position of the target-selective nucleoside is moved closer to the 3'-end of the gap, for example the $1^{st}$ or $2^{nd}$ nucleoside of the gap from the 3'-end. In this manner, the selectivity of the selective antisense compound relative to the first non-target nucleic acid may be retained, while also achieving selectivity of the selective antisense compound relative to the second non-target nucleic acid. In certain embodiments, redesign of the selective antisense compound will retain a single-differentiating nucleobase relative to the first non-target nucleic acid and increase the number of differentiating nucleobases between the selective antisense compound and the second non-target nucleic acid. In certain embodiments, the first non-target nucleic acid is wild-type huntingtin and the second non-target nucleic acid is bone morphogenetic protein receptor, type IA.

In certain embodiments, a selective antisense compound may be redesigned wherein the overall length of the selective antisense compound remains the same, but wherein the length of the 3'-wing is increased to 1-10 nucleosides and/or the position of the target-selective nucleoside is moved closer to the 5'-end of the gap, for example the $1^{st}$ or $2^{nd}$ nucleoside of the gap from the 5'-end. In certain embodiments, a selective antisense compound may be redesigned wherein the overall length of the selective antisense compound remains the same, but wherein the length of the 3'-wing is increased to 1-10 nucleosides and/or the position of the target-selective nucleoside is moved closer to the 3'-end of the gap, for example the $1^{st}$ or $2^{nd}$ nucleoside of the gap from the 3'-end. In certain embodiments, a selective antisense compound may be redesigned wherein the overall length of the selective antisense compound remains the same, but wherein the length of the 3'-wing is increased to 1-10 nucleosides and/or the position of the target-selective nucleoside is moved closer to the 3'-end of the gap, for example the $1^{st}$ or $2^{nd}$ nucleoside of the gap from the 3'-end. In certain embodiments, a selective antisense compound may be redesigned wherein the overall length of the selective antisense compound remains the same, but wherein the length of the 3'-wing is increased to 1-10 nucleosides and/or the position of the target-selective nucleoside is moved closer to the 5'-end of the gap, for example the $1^{st}$ or $2^{nd}$ nucleoside of the gap from the 5'-end. In this manner, the selectivity of the selective antisense compound relative to the first non-target nucleic acid may be retained, while also increasing selectivity of the selective antisense compound relative to the second non-target nucleic acid. In certain embodiments, redesign of the selective antisense compound will retain a single-differentiating nucleobase relative to the first non-target nucleic acid and increase the number of differentiating nucleobases between the selective antisense compound and the second non-target nucleic acid. In certain embodiments, the first non-target nucleic acid is wild-type huntingtin and the second non-target nucleic acid is bone morphogenetic protein receptor, type IA.

ii. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

iii. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

ABCXXXXXXXXXC'B'A';

ABCXXXXXXX(X/C')(X/B')(X/A');

(X/A)(X/B)(X/C)XXXXXXXXXC'B'A' where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

iv. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

D. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

a. Single-Nucleotide Polymorphism

In certain embodiments, the invention provides selective antisense compounds that have greater activity for a target nucleic acid than for a homologous or partially homologous non-target nucleic acid. In certain such embodiments, the target and non-target nucleic acids are not functionally related to one another (e.g., are transcripts from different genes). In certain embodiments, the target and not-target nucleic acids are allelic variants of one another. Certain embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congential myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congential myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

i. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 incorporated herein as SEQ ID NO: 1, and NM_002111.6, incorporated herein as SEQ ID NO: 2.

Table 4 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a T at SNP position rs6446723.

TABLE 4

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | C |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C |

E. Certain Indications

In certain embodiments, provided herein are methods of treating an animal or individual comprising administering one or more pharmaceutical compositions as described herein. In certain embodiments, the individual or animal has Huntington's disease.

In certain embodiments, compounds targeted to huntingtin as described herein may be administered to reduce the severity of physiological symptoms of Huntington's disease. In certain embodiments, compounds targeted to huntingtin as described herein may be administered to reduce the rate of degeneration in an individual or an animal having Huntington's disease. In certain embodiments, compounds targeted to huntingtin as described herein may be administered regeneration function in an individual or an animal having Huntington's disease. In certain embodiments, symptoms of Huntingtin's disease may be reversed by treatment with a compound as described herein.

In certain embodiments, compounds targeted to huntingtin as described herein may be administered to ameliorate one or more symptoms of Huntington's disease. In certain embodiments administration of compounds targeted to huntingtin as described herein may improve the symptoms of Huntington's disease as measured by any metric known to those having skill in the art. In certain embodiments, administration of compounds targeted to huntingtin as described herein may improve a rodent's rotaraod assay performance. In certain embodiments, administration of compounds targeted to huntingtin as described herein may improve a rodent's plus maze assay. In certain embodiments, administration of compounds targeted to huntingtin as described herein may improve a rodent's open field assay performance.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual or animal in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

F. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

G. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

H. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

To allow assessment of the relative effects of nucleobase sequence and chemical modification, throughout the examples, oligomeric compounds are assigned a "Sequence Code." Oligomeric compounds having the same Sequence Code have the same nucleobase sequence. Oligomeric compounds having different Sequence Codes have different nucleobase sequences.

EXAMPLE 1: SINGLE NUCLEOTIDE POLYMORPHISMS (SNPS) IN THE HUNTINGTIN (HTT) GENE SEQUENCE

SNP positions (identified by Hayden et al, WO/2009/135322) associated with the HTT gene were mapped to the HTT genomic sequence, designated herein as SEQ ID NO: 1 (NT_006081.18 truncated from nucleotides 1566000 to 1768000). Table 5 provides SNP positions associated with the HTT gene. Table 5 provides a reference SNP ID number from the Entrez SNP database at the National Center for Biotechnology Information (NCBI, ncbi.nlm.nih.gov/sites/entrez?db=snp), incorporated herein by reference. Table 5 furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 1. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

TABLE 5

Single Nuclear Polymorphisms (SNPs) and their positions on SEQ ID NO: 1

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |

TABLE 5-continued

Single Nuclear Polymorphisms (SNPs) and their positions on SEQ ID NO: 1

| RS No. | SNP position | Polymorphism | Major allele | Minor allele |
|---|---|---|---|---|
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

EXAMPLE 2: MODIFIED OLIGONUCLEOTIDES TARGETING HUNTINGTIN (HTT) SNPS AND BONE MORPHOGENETIC PROTEIN RECEPTOR 1A (BMPR1A)

A series of modified oligonucleotides were designed to target SNP positions associated with the HTT gene. These modified oligonucleotides were evaluated for their ability to selectively inhibit mutant (mut) HTT while leaving the expression of the wild-type (wt) HTT and BMPR1A intact. In the tables, 'k' subscript indicates an (S)-cEt modification; 'e' subscript indicates MOE modification; 'm' before the cytosine residue indicates a 5-methyl cytosine; 'x' before the thymine residue indicates a 2-thiothymine; the number along with 'd' indicates the number of deoxyribose nucleosides; 'o' subscript after the sugar modification subscripts indicates a phosphodiester internucleoside linkage; 's' subscript after the nucleoside indicates a phosphorothioate internucleoside linkage.

As described above in Example 1, certain SNPs may have two or more allelic variants. For example, the two allelic variants for SNP rs7685686 are A and G. In certain embodiments, antisense oligonucleotides can be designed that target either allelic variant. In certain embodiments, a higher percentage of the population may have a particular allelic variant. Modified oligonucleotides were designed to target the G allelic variant of rs7685686. These modified oligonucleotides are described further in Table 6.

The modified oligonucleotides were tested in vitro. Selective inhibition of the modified oligonucleotides targeting BMPR1A and HTT SNP rs7685686 or rs7685686 (G) was evaluated. Selective inhibition of modified oligonucleotides targeting SNP rs6446723 with 4 mismatches to BMPR1A and targeting SNP rs363064 with 3 or 4 mismatches to BMPR1A were also evaluated. Human patient fibroblasts GM04022 cell line was used. Cultured GM04022 cells at a density of 35,000 cells per well were transfected using electroporation at 130V with 0.0, 0.37, 1.1, 3.3 and 10 μM concentrations of modified oligonucleotides. After a treatment period of approximately 24 hours, RNA was isolated from the cells. Target message for HTT and BMPR1A were measured by quantitative real-time PCR using ABI assay C_2229297_10 and RTS2623, respectively. The target mRNA levels were adjusted according to total RNA content, as measured by RIBOGREEN and the results are presented in Table 7.

The $IC_{50}$ of each modified oligonucleotide presented in Table 7 was calculated by plotting the concentrations of oligonucleotides used versus the percent inhibition of HTT or BMPR1A mRNA expression achieved at each concentration, and noting the concentration of oligonucleotide at which 50% inhibition of HTT or BMPR1A mRNA expression was achieved compared to the control. Selectivity for HTT was calculated by dividing the $IC_{50}$ for inhibition of the wild-type HTT versus the $IC_{50}$ for inhibiting expression of the mutant HTT mRNA. Selectivity for BMPR1A was calculated by dividing the $IC_{50}$ for inhibition of BMPR1A versus the $IC_{50}$ for inhibiting expression of the mutant HTT mRNA.

ISIS 141923 and 387916 were included in the study as negative and positive controls. ISIS 460209 or 572772 was also included in the study for comparison.

TABLE 6

Modified oligonucleotides targeting Huntingtin (HTT) SNPs and/or BMPR1A

| Isis No. | SNP | Sequence (5' to 3') | Motif | SEQ ID. NO. |
|---|---|---|---|---|
| 460209 | rs7685686 | $T_{es}$ $A_{ks}$ $A_{ks}$ Ads $T_{ds}$ $T_{ds}$ $G_{ds}$ $T_{ds}$ $mC_{ds}$ $A_{ds}$ $T_{ds}$ $mC_{ds}$ $A_{ks}$ $mC_{ks}$ $mC_{e}$ | ekk-d9-kke | 3 |
| 572772 | rs7685686 | $A_{es}$ $T_{es}$ $A_{es}$ $A_{es}$ $A_{ks}$ $T_{ks}$ $T_{ds}$ $G_{ds}$ $T_{ds}$ $mC_{ds}$ $A_{ds}$ $T_{ds}$ $mC_{ds}$ $A_{ks}$ $mC_{ks}$ $mC_{e}$ | eeeekk-d7-kke | 4 |
| 551429 | rs7685686 | $T_{es}$ $A_{es}$ $A_{es}$ $A_{ks}$ $T_{ks}$ $T_{ds}$ $G_{ds}$ $T_{ds}$ $mC_{ds}$ $A_{ds}$ $T_{ds}$ $mC_{ds}$ $A_{ks}$ $mC_{ks}$ $mC_{e}$ | eeekk-d7-kke | 3 |
| 556845 | rs7685686 | $T_{es}$ $A_{ks}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ks}$ $mC_{ks}$ $mC_{e}$ | ekk-d9-kke | 3 |
| 617425 | rs7685686 | $A_{es}$ $T_{es}$ $A_{es}$ $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{e}$ | eeeeek-d7-eee | 4 |
| 617115 | rs7685686 | $A_{es}$ $T_{es}$ $A_{es}$ $A_{es}$ $A_{es}$ $T_{ds}$ $T_{ds}$ $G_{ds}$ $T_{ds}$ $mC_{ds}$ $A_{ds}$ $T_{ds}$ $mC_{ds}$ $A_{ks}$ $mC_{ks}$ $mC_{e}$ | eeeeek-d7-kke | 4 |
| 617116 | rs7685686 | $A_{es}$ $T_{es}$ $A_{es}$ $A_{es}$ $A_{ks}$ $T_{ks}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{e}$ | eeeekk-d7-kee | 4 |
| 617117 | rs7685686 | $A_{es}$ $T_{es}$ $A_{es}$ $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{e}$ | eeeeek-d7-kee | 4 |
| 617118 | rs7685686 | $A_{es}$ $T_{eo}$ $A_{eo}$ $A_{eo}$ $A_{eo}$ $T_{ks}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{e}$ | eeeeek-d7-kee | 4 |
| 617119 | rs7685686 | $A_{es}$ $T_{eo}$ $A_{eo}$ $A_{eo}$ $A_{eo}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{e}$ | eeeeek-d7-eee | 4 |
| 617111 | rs7685686 | $A_{es}$ $T_{ko}$ $A_{eo}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ko}$ $mC_{es}$ $mC_{ks}$ $A_{e}$ | ekek-d9-keke | 5 |
| 613581 | rs7685686 | $A_{es}$ $A_{eo}$ $T_{eo}$ $A_{eo}$ $A_{es}$ $A_{ds}$ $T_{ks}$ $T_{ds}$ $G_{ds}$ $T_{ds}$ $mC_{ds}$ $A_{ds}$ $T_{ds}$ $mC_{ds}$ $A_{eo}$ $mC_{eo}$ $mC_{es}$ $A_{es}$ $G_{e}$ | eeeee-d-k-d7-eeeee | 6 |
| 613582 | rs7685686 | $A_{es}$ $T_{es}$ $A_{eo}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{eo}$ $mC_{eo}$ $mC_{eo}$ $A_{es}$ $G_{es}$ $A_{e}$ | eeeeek-d7-eeeeee | 7 |
| 613583 | rs7685686 | $T_{es}$ $A_{eo}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{eo}$ $mC_{eo}$ $A_{eo}$ $G_{es}$ $A_{es}$ $A_{e}$ | eeeek-d7-eeeeeee | 8 |
| 613584 | rs7685686 | $A_{es}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{eo}$ $mC_{eo}$ $A_{eo}$ $G_{eo}$ $A_{es}$ $A_{es}$ $A_{e}$ | eeek-d7-eeeeeeee | 9 |
| 613585 | rs7685686 | $A_{es}$ $A_{eo}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{eo}$ $A_{eo}$ $G_{eo}$ $A_{eo}$ $A_{es}$ $A_{es}$ $A_{e}$ | eek-d7-eeeeeeeee | 10 |
| 613586 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{eo}$ $A_{eo}$ $G_{eo}$ $A_{eo}$ $A_{eo}$ $A_{es}$ $A_{es}$ $A_{e}$ | ek-d7-eeeeeeeeee | 11 |
| 613588 | rs7685686 | $T_{es}$ $A_{es}$ $A_{eo}$ $T_{eo}$ $A_{eo}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{eo}$ $mC_{es}$ $mC_{es}$ $A_{e}$ | eeeeeeek-d7-eeee | 12 |
| 613589 | rs7685686 | $T_{es}$ $T_{es}$ $A_{eo}$ $A_{eo}$ $T_{eo}$ $A_{eo}$ $A_{eo}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{e}$ | eeeeeeeek-d7-eee | 13 |
| 617105 | rs7685686 | $A_{es}$ $A_{eo}$ $A_{ko}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ke}$ $mC_{ko}$ $A_{es}$ $G_{es}$ $A_{e}$ | eekk-d8-kkeee | 14 |

TABLE 6 -continued

Modified oligonucleotides targeting Huntingtin (HTT) SNPs and/or BMPR1A

| Isis No. | SNP | Sequence (5' to 3') | Motif | SEQ ID. NO. |
|---|---|---|---|---|
| 606561 | rs7685686 | $A_{es}$ $T_{ks}$ $A_{es}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{es}$ $A_{e}$ | ekek-d9-keee | 5 |
| 606562 | rs7685686 | $A_{es}$ $T_{es}$ $A_{es}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{es}$ $A_{e}$ | eeek-d9-keee | 5 |
| 611714 | rs7685686 (G) | $T_{es}$ $A_{es}$ $A_{es}$ $A_{ks}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{ks}$ $mC_{e}$ | eeekk-d7-kke | 15 |
| 611715 | rs7685686 (G) | $A_{es}$ $T_{ks}$ $A_{es}$ $A_{ks}$ $A_{ds}$ $xT_{ds}$ $T_{ds}$ $G_{ds}$ $mC_{ds}$ $mC_{ds}$ $A_{ds}$ $T_{ds}$ $mC_{ds}$ $A_{ks}$ $mC_{es}$ $mC_{ks}$ $A_{e}$ | ekek-d9-keke | 16 |
| 611717 | rs7685686 (G) | $A_{es}$ $T_{es}$ $A_{es}$ $A_{es}$ $A_{ks}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{ks}$ $mC_{e}$ | eeeekk-d7-kke | 17 |
| 611718 | rs7685686 (G) | $T_{es}$ $A_{ks}$ $A_{ks}$ $A_{ds}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{ks}$ mCe | ekk-d-k-d7-kke | 15 |
| 611719 | rs7685686 (G) | $T_{es}$ $A_{ks}$ $A_{ks}$ $A_{ks}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{ks}$ $mC_{e}$ | eldckk-d7-kke | 15 |
| 611720 | rs7685686 (G) | $A_{es}$ $T_{ks}$ $T_{ds}$ $G_{ds}$ $mC_{ds}$ $mC_{ds}$ $A_{ds}$ $T_{ds}$ $mC_{ds}$ $A_{ds}$ $mC_{ds}$ $mC_{ko}$ $A_{ko}$ $G_{ks}$ $A_{e}$ | ek-d9-kkke | 18 |
| 611721 | rs7685686 (G) | $T_{es}$ $A_{es}$ $A_{es}$ $A_{es}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{es}$ $mC_{es}$ $A_{e}$ | eeeek-d7-keee | 19 |
| 611722 | rs7685686 (G) | $A_{es}$ $T_{es}$ $A_{es}$ $A_{es}$ $A_{ds}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{es}$ $mC_{es}$ $A_{e}$ | eeee-d-k-d7-keee | 16 |
| 611723 | rs7685686 (G) | $T_{es}$ $A_{eo}$ $A_{eo}$ $A_{es}$ $T_{ks}$ $T_{ds}$ $G_{ds}$ $mC_{ds}$ $mC_{ds}$ $A_{ds}$ $T_{ds}$ $mC_{ds}$ $A_{ks}$ $mC_{eo}$ $mC_{eo}$ $A_{es}$ $G_{e}$ | eeeek-d7-keeee | 20 |
| 617104 | rs6446723 | $T_{es}$ $A_{es}$ $A_{eo}$ $T_{ko}$ $T_{ks}$ $T_{ds}$ $T_{ds}$ $mC_{ds}$ $T_{ds}$ $A_{ds}$ $G_{ds}$ $A_{ds}$ $mC_{ko}$ $T_{ko}$ $T_{es}$ $T_{es}$ $A_{e}$ | eeekk-d7-kkeee | 21 |
| 617106 | rs6446723 | $T_{es}$ $A_{eo}$ $A_{ko}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ko}$ $T_{ko}$ $T_{es}$ $T_{es}$ $A_{e}$ | eekk-d8-kkeee | 21 |
| 617107 | rs363064 | $A_{es}$ $A_{eo}$ $T_{ko}$ $A_{ks}$ $mC_{ds}$ $G_{ds}$ $G_{ds}$ $G_{ds}$ $T_{ds}$ $A_{ds}$ $A_{ds}$ $mC_{ds}$ $A_{ko}$ $T_{ko}$ $T_{es}$ $T_{es}$ $T_{e}$ | eekk-d8-kkeee | 38 |
| 617108 | rs6446723 | $T_{es}$ $A_{ko}$ $A_{eo}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ko}$ $T_{eo}$ $T_{ks}$ $T_{es}$ $A_{e}$ | ekek-d8-kekee | 21 |
| 617109 | rs6446723 | $A_{es}$ $A_{eo}$ $T_{ko}$ $T_{ks}$ $T_{ds}$ $T_{ds}$ $mC_{ds}$ $T_{ds}$ $A_{ds}$ $G_{ds}$ $A_{ds}$ $mC_{ds}$ $T_{ko}$ $T_{ko}$ $T_{es}$ $A_{es}$ $T_{e}$ | eekk-d8-kkeee | 22 |
| 617110 | rs363064 | $G_{es}$ $A_{es}$ $A_{eo}$ $T_{ko}$ $A_{ks}$ $mC_{ds}$ $G_{ds}$ $G_{ds}$ $G_{ds}$ $T_{ds}$ $A_{ds}$ $A_{ds}$ $mC_{ko}$ $A_{ko}$ $T_{es}$ $T_{es}$ $T_{e}$ | eeekk-d7-kkeee | 39 |
| 623182 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{es}$ $A_{eo}$ $G_{ks}$ $A_{k}$ | ek-d8-eeekk | 23 |
| 623202 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{es}$ $A_{eo}$ $G_{ko}$ $A_{es}$ $A_{ks}$ $A_{e}$ | k-d9-eekeke | 24 |
| 623203 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{es}$ $A_{eo}$ $G_{ko}$ $A_{es}$ $A_{ks}$ $A_{e}$ | k-d8-eeekeke | 24 |
| 623205 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{es}$ $A_{eo}$ $G_{ko}$ $A_{es}$ $A_{ks}$ $A_{es}$ $A_{e}$ | k-d9-eekekee | 25 |
| 623206 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{es}$ $A_{eo}$ $G_{ko}$ $A_{es}$ $A_{ks}$ $A_{es}$ $A_{e}$ | k-d8-eeekekee | 25 |
| 623212 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ks}$ $mC_{es}$ $A_{eo}$ $G_{eo}$ $A_{ks}$ $A_{es}$ $A_{e}$ | k-d8-keeekee | 24 |
| 623214 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{ks}$ $A_{eo}$ $G_{eo}$ $A_{ks}$ $A_{es}$ $A_{es}$ $A_{e}$ | k-d9-keekeee | 25 |
| 623218 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{eo}$ $mC_{es}$ $A_{es}$ $G_{k}$ | eek-d8-eeek | 26 |

TABLE 6 -continued

| Modified oligonucleotides targeting Huntingtin (HTT) SNPs and/or BMPR1A | | | | |
|---|---|---|---|---|
| Isis No. | SNP | Sequence (5' to 3') | Motif | SEQ ID. NO. |
| 623220 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{eo}$ $A_{es}$ $G_{ks}$ $A_{e}$ | eek-d9-eeke | 27 |
| 623221 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{eo}$ $mC_{eo}$ $A_{es}$ $G_{ks}$ $A_{e}$ | eek-d8-eeeke | 27 |
| 623224 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{e}$o $A_{eo}$ $G_{ks}$ $A_{es}$ $A_{k}$ | eek-d8-eeekek | 28 |
| 623227 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ko}$ $mC_{es}$ $A_{es}$ $G_{e}$ | eek-d8-keee | 26 |
| 623233 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ks}$ $mC_{eo}$ $A_{eo}$ $G_{es}$ $A_{ks}$ $A_{e}$ | eek-d8-keeeke | 28 |
| 623237 | rs7685686 | $A_{es}$ $T_{ds}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{es}$ $A_{eo}$ $G_{ko}$ $A_{es}$ $A_{ks}$ $A_{e}$ | ek-d7-eeeekeke | 29 |
| 623239 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ks}$ $mC_{es}$ $A_{eo}$ $G_{eo}$ $A_{ks}$ $A_{es}$ $A_{e}$ | ek-d8-keeekee | 29 |
| 623242 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{eo}$ $A_{eo}$ $G_{ks}$ $A_{es}$ $A_{k}$ | ek-d8-eeekek | 30 |
| 623254 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{eo}$ $mC_{eo}$ $G_{ks}$ $A_{es}$ $A_{k}$ | eek-d9-eekek | 31 |
| 623262 | rs7685686 | $A_{es}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{es}$ $mC_{eo}$ $G_{ko}$ $A_{es}$ $A_{ks}$ $A_{e}$ | ek-d8-eeekeke | 32 |
| 623490 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{es}$ $A_{eo}$ $G_{ko}$ $mC_{es}$ $A_{ks}$ $A_{es}$ $A_{e}$ | k-d9-eekekee | 33 |
| 623494 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{es}$ $mC_{es}$ $A_{eo}$ $G_{ko}$ $T_{es}$ $A_{ks}$ $A_{e}$ | ek-d8-eeekeke | 34 |
| 387916 (pos control) | | $mC_{e}$s $mC_{es}$ $T_{es}$ $T_{es}$ $mC_{es}$ $mC_{ds}$ $mC_{ds}$ $T_{ds}$ $G_{ds}$ $A_{ds}$ $A_{ds}$ $G_{ds}$ $G_{ds}$ $T_{ds}$ $T_{ds}$ $mC_{es}$ $mC_{es}$ $T_{es}$ $mC_{es}$ $mC_{e}$ | eeeee-d10-eeeee | 35 |
| 141923 (neg control) | | $T_{es}$ $mC_{es}$ $T_{es}$ $mC_{es}$ $T_{es}$ $A_{ds}$ $T_{ds}$ $T_{ds}$ $G_{ds}$ $mC_{ds}$ $A_{ds}$ $mC_{ds}$ $A_{ds}$ $T_{ds}$ $T_{ds}$ $mC_{es}$ $mC_{es}$ $A_{es}$ $A_{es}$ $G_{e}$ | eeeee-d10-eeeee | 36 |

TABLE 7

Selectivity of modified oligonucleotides targeting Huntingtin (HTT) SNPs and/or BMPR1A

| ISIS NO. | SNP | HTT Mut $IC_{50}$ (μM) | BMPR1A $IC_{50}$ (μM) | HTT Selectivity | BMPR1A Selectivity | Motif | SEQ ID NO. |
|---|---|---|---|---|---|---|---|
| 460209[1] | rs7685686 | <0.4 | 1.35 | 5.6 | 3.4 | ekk-d9-kke | 3 |
| 572772[2] | rs7685686 | 0.27 | 2.23 | >37 | 8.3 | eeeekk-d7-kke | 4 |
| 551429 | rs7685686 | <0.4 | 1.2 | >25 | >3 | eeekk-d7-kke | 3 |
| 556845 | rs7685686 | <0.4 | 1.5 | >25 | >3.8 | ekk-d9-kke | 3 |
| 617425 | rs7685686 | 1.3 | 5 | >8 | 3.8 | eeeeek-d7-eee | 4 |
| 617115 | rs7685686 | <0.4 | 1.9 | >25 | >5 | eeeeek-d7-kke | 4 |
| 617116 | rs7685686 | <0.4 | 1.7 | >25 | >4 | eeeekk-d7-kee | 4 |
| 617117 | rs7685686 | 0.7 | 3.1 | >14 | 4 | eeeeek-d7-kee | 4 |
| 617118 | rs7685686 | 0.4 | 1.8 | >25 | 5 | eeeeek-d7-kee | 4 |
| 617119 | rs7685686 | 0.8 | 2.9 | >13 | 4 | eeeeek-d7-eee | 4 |
| 617111 | rs7685686 | <0.4 | 1.0 | >25 | 3 | ekek-d9-keke | 5 |
| 613581 | rs7685686 | 0.9 | 4.4 | >11 | 5 | eeeeedk-d7-eeeee | 6 |
| 613582 | rs7685686 | 0.4 | 5.1 | >25 | 13 | eeeeek-d7-eeeeee | 7 |
| 613583 | rs7685686 | 0.7 | 4.9 | >14 | 7 | eeeek-d7-eeeeeee | 8 |
| 613584 | rs7685686 | 0.4 | 5.6 | >25 | 14 | eeek-d7-eeeeeeee | 9 |
| 613585 | rs7685686 | 0.4 | 4.8 | >25 | 11 | eek-d7-eeeeeeeee | 10 |
| 613586 | rs7685686 | 0.7 | >10 | >14 | 15 | ek-d7-eeeeeeeeee | 11 |
| 613588 | rs7685686 | 0.7 | 4.4 | >14 | 6 | eeeeeeek-d7-eeee | 12 |
| 613589 | rs7685686 | 1.2 | 5.6 | >8 | 5 | eeeeeeeek-d7-eee | 13 |
| 617105 | rs7685686 | <0.4 | 2 | 15 | 5 | eekk-d8-kkeee | 14 |

TABLE 7-continued

Selectivity of modified oligonucleotides targeting Huntingtin (HTT) SNPs and/or BMPR1A

| ISIS NO. | SNP | HTT Mut $IC_{50}$ (μM) | BMPR1A $IC_{50}$ (μM) | HTT Selectivity | BMPR1A Selectivity | Motif | SEQ ID NO. |
|---|---|---|---|---|---|---|---|
| 606561 | rs7685686 | <4 | 2.2 | 25 | 25 | ekek-d9-keee | 5 |
| 606562 | rs7685686 | 0.7 | 3.4 | 25 | 8 | eeek-d9-keee | 5 |
| 611714 | rs7685686 (G) | 0.6 | 9.4 | 8 | 16 | eeekk-d7-kke | 15 |
| 611715 | rs7685686 (G) | 0.6 | 9.0 | 9 | 14 | ekek-d9-keke | 16 |
| 611717 | rs7685686 (G) | 0.8 | 10 | 6 | 12 | eeeekk-d7-kke | 17 |
| 611718 | rs7685686 (G) | 0.8 | >10 | 9 | 13 | ekk-d-k-d7-kke | 15 |
| 611719 | rs7685686 (G) | 0.9 | >10 | 4 | 11 | ekkkk-d7-kke | 15 |
| 611720 | rs7685686 (G) | <0.4 | 9.4 | 6 | 23 | ek-d9-kkke | 18 |
| 611721 | rs7685686 (G) | 0.9 | >10 | >11 | 11 | eeeek-d7-keee | 19 |
| 611722 | rs7685686 (G) | 1.5 | >10 | >7 | 7 | eeee-d-k-d7-keee | 16 |
| 611723 | rs7685686 (G) | 2.7 | >10 | 4 | 4 | eeeek-d7-keeee | 20 |
| 617104 | rs6446723 | <0.4 | >10 | 17 | >25 | eeekk-d7-kkeee | 21 |
| 617106 | rs6446723 | <0.4 | >10 | 14 | >25 | eekk-d8-kkeee | 21 |
| 617108 | rs6446723 | <0.4 | >10 | 14 | >25 | ekek-d8-kekee | 21 |
| 617109 | rs6446723 | <0.4 | >10 | 9 | >25 | eekk-d8-kkeee | 22 |
| 623182 | rs7685686 | 0.6 | >10 | 17 | 17 | ek-d8-eeekk | 23 |
| 623202 | rs7685686 | 0.8 | >10 | 4 | 13 | k-d9-eekeke | 24 |
| 623203 | rs7685686 | 0.8 | >10 | 12 | 12 | k-d8-eeekeke | 24 |
| 623205 | rs7685686 | 0.6 | >10 | 3 | 17 | k-d9-eekekee | 25 |
| 623206 | rs7685686 | 0.9 | >10 | 11 | 11 | k-d8-eeekekee | 25 |
| 623212 | rs7685686 | 1.2 | >10 | 8 | 8 | k-d8-keeekee | 24 |
| 623214 | rs7685686 | 1.5 | >10 | 7 | 7 | k-d9-keekeee | 25 |
| 623218 | rs7685686 | 1.4 | >10 | 7 | 7 | eek-d8-eeek | 26 |
| 623220 | rs7685686 | 1.6 | >10 | 4 | 6 | eek-d9-eeke | 27 |
| 623221 | rs7685686 | 1.2 | >10 | 8 | 8 | eek-d8-eeeke | 27 |
| 623224 | rs7685686 | 0.9 | >10 | 11 | 11 | eek-d8-eeekek | 28 |
| 623227 | rs7685686 | 0.9 | 6.9 | 11 | 8 | eek-d8-keee | 26 |
| 623233 | rs7685686 | 0.6 | 5.4 | 16 | 9 | eek-d8-keeeke | 28 |
| 623237 | rs7685686 | 0.6 | 9.8 | 18 | 17 | ek-d7-eeeekeke | 29 |
| 623239 | rs7685686 | 0.5 | 7.7 | 19 | 15 | ek-d8-keeekee | 29 |
| 623242 | rs7685686 | 0.6 | 9.9 | 18 | 18 | ek-d8-eeekek | 30 |
| 623254 | rs7685686 | 1.2 | 4.4 | 5 | 4 | eek-d9-eekek | 31 |
| 623262 | rs7685686 | 1.0 | 4.4 | 10 | 4 | ek-d8-eeekeke | 32 |
| 623490 | rs7685686 | 1.3 | 4.9 | 2 | 4 | k-d9-eekekee | 33 |
| 623494 | rs7685686 | 0.4 | 6.2 | 25 | 15 | ek-d8-eeekeke | 34 |
| 387916 (pos control) | | <0.4 | >10 | 2 | 25 | eeeee-d10-eeeee | 35 |
| 141923 (neg control) | | >10 | >10 | 1 | 1 | eeeee-d10-eeeee | 36 |

[1]$IC_{50}$ measured from average of 2 independent assays
[2]$IC_{50}$ measured from average of 3 independent assays

EXAMPLE 3: MODIFIED OLIGONUCLEOTIDES TARGETING HTT SNP RS7685686 AND BMPR1A

A series of modified oligonucleotides were designed to target SNP positions associated with the HTT gene and BMPR1A. These modified oligonucleotides were evaluated for their ability to selectively inhibit mutant (mut) HTT while leaving the expression of the wild-type (wt) HTT and BMPR1A intact. In the tables, 'k' subscript indicates an (S)-cEt modification; 'e' subscript indicates MOE modification; 'm' before the cytosine residue indicates a 5-methyl cytosine; 'x' before the thymine residue indicates a 2-thiothymine; the number along with 'd' indicates the number of deoxyribose nucleosides; 'o' subscript after the sugar modification subscripts indicates a phosphodiester internucleoside linkage; 's' subscript after the nucleoside indicates a phosphorothioate internucleoside linkage.

The modified oligonucleotides presented in Table 8 were tested in vitro. Selective inhibition of the modified oligonucleotides targeting HTT SNP rs7685686 and BMPR1A was evaluated. Human patient fibroblasts GM04022 cell line was used. Cultured GM04022 cells at a density of 35,000 cells per well were transfected using electroporation at 130V with 0.0, 0.12, 0.37, 1.1, 3.3 and 10 μM concentrations of modified oligonucleotides. After a treatment period of approximately 24 hours, RNA was isolated from the cells. Target message for HTT and BMPR1A were measured by quantitative real-time PCR using ABI assay C_2229297_10 and RTS2623, respectively. The target mRNA levels were adjusted according to total RNA content, as measured by RIBOGREEN and the results are presented in Table 9.

The $IC_{50}$ of each modified oligonucleotide along with HTT and BMPR1A selectivity were calculated in the same manner as described in Example 2. Results are the average of 2 independent assays and are presented in Table 9.

ISIS 141923 and 387916 were included in the study negative and positive control. ISIS 460209 or 572772 was also included in the study for comparison.

TABLE 8

Modified oligonucleotides targeting Huntingtin (HTT) SNP rs7685686 and BMPR1A

| ISIS NO. | SNP | Sequence (5' to 3') | Motif | SEQ ID. NO. |
|---|---|---|---|---|
| 623181 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{es}$ $A_{eo}$ $G_{ks}$ $A_{k}$ | ek-d9-eekk | 23 |
| 623198 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{ks}$ $A_{eo}$ $G_{es}$ $A_{k}$ | ek-d9-keek | 23 |
| 623199 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{es}$ $A_{eo}$ $G_{ks}$ $A_{es}$ $A_{k}$ | k-d9-eekek | 37 |
| 623208 | rs7685686 | $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{ks}$ $A_{eo}$ $G_{es}$ $A_{ks}$ $A_{k}$ | k-d9-keekk | 37 |
| 623230 | rs7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ko}$ $mC_{ko}$ $A_{es}$ $G_{es}$ $A_{k}$ | eek-d8-kkeek | 27 |
| 523232 | re7685686 | $A_{es}$ $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{ks}$ $A_{eo}$ $G_{es}$ $A_{ks}$ $A_{e}$ | eek-d9-keeke | 28 |
| 623235 | rs7685686 | $A_{es}$ $T_{ks}$ $T_{ds}$ $G_{ds}$ $T_{d}$s $mC_{ds}$ $A_{ds}$ $T_{ds}$ $mC_{ds}$ $A_{ds}$ $mC_{ds}$ $mC_{es}$ $A_{eo}$ $G_{ko}$ $A_{es}$ $A_{ks}$ $A_{e}$ | ek-d9-eekeke | 29 |
| 623236 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $mC_{es}$ $mC_{es}$ $A_{eo}$ $G_{ko}$ $A_{es}$ $A_{ks}$ $A_{e}$ | ek-d8-eeekeke | 29 |
| 623238 | rs7685686 | $A_{ts}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{ks}$ $A_{eo}$ $G_{eo}$ $A_{ks}$ $A_{es}$ $A_{e}$ | ek-d9-keekee | 29 |
| 623241 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{eo}$ $A_{eo}$ $G_{ks}$ $A_{es}$ $A_{k}$ | ek-d9-eekek | 30 |
| 623243 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{eo}$ $A_{eo}$ $G_{ks}$ $A_{es}$ $A_{k}$ | ek-d7-eeeekek | 30 |
| 623493 | rs7685686 | $A_{es}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ds}$ $mC_{es}$ $A_{eo}$ $G_{ko}$ $T_{es}$ $A_{ks}$ $A_{e}$ | ek-d9-eekeke | 34 |

TABLE 9

Selectivity of modified oligonucleotides targeting HTT SNP rs7685686 and BMPR1A

| ISIS NO. | SNP | HTT Mut $IC_{50}$ (μM) | BMPR1A $IC_{50}$ (μM) | HTT Selectivity | BMPR1A Selectivity | Motif | SEQ ID NO. |
|---|---|---|---|---|---|---|---|
| 460209[1] | rs7685686 | <0.4 | 1.35 | 5.6 | 3.4 | ekk-d9-kke | 3 |
| 572772[2] | rs7685686 | 0.27 | 2.23 | >37 | 8.3 | eeeekk-d7-kke | 4 |
| 623181 | rs7685686 | 0.35 | 8.9 | 9.3 | 25.4 | ek-d9-keek | 23 |
| 623198 | rs7685686 | 0.4 | 9.25 | 19.5 | 23.1 | k-d9-eekek | 23 |
| 623199 | rs7685686 | 0.35 | 10 | 9.4 | 28.6 | eek-d8-kkeek | 37 |
| 623208 | rs7685686 | 0.3 | 10 | 33.3 | 33.3 | eek-d9-keeke | 37 |
| 623230 | rs7685686 | 0.35 | 4.6 | 28.6 | 13.1 | ek-d9-eekeke | 27 |
| 623232 | rs7685686 | 0.5 | 7.4 | 15.7 | 14.8 | ek-d8-eeekeke | 28 |
| 623235 | rs7685686 | 0.4 | 9.75 | 4.1 | 24.4 | ek-d9-keekee | 29 |
| 623236 | rs7685686 | 0.4 | 8.55 | 21.8 | 21.4 | ek-d9-eekek | 29 |
| 623238 | rs7685686 | 0.35 | 6.05 | 21.4 | 17.3 | ek-d7-eeeekek | 29 |
| 623241 | rs7685686 | 0.4 | 6.85 | 5.5 | 17.1 | ek-d9-eekeke | 30 |
| 623243 | rs7685686 | 0.55 | 10 | 18.2 | 18.2 | ek-d9-keek | 30 |
| 623493 | rs7685686 | 0.45 | 5.45 | 7.3 | 12.1 | k-d9-eekek | 34 |
| 387916 (pos control) | | <0.4 | >10 | 2 | 25 | eeeee-d10-eeeee | 35 |
| 141923 (neg control) | | >10 | >10 | 1 | 1 | eeeee-d10-eeeee | 36 |

[1] $IC_{50}$ measured from average of 2 independent assays

[2] $IC_{50}$ measured from average of 3 independent assays

EXAMPLE 4: TOLERABILITY OF MODIFIED OLIGONUCLEOTIDES TARGETING HTT SNPS AND BMPR1A

BALB/c wild type mice were separated into groups of 4 mice. Each mouse was administered a single 300 µg ICV dose of a modified oligonucleotide or a single ICV dose of PBS. At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after it is lifted; (5) the mouse demonstrates any movement after it is lifted; (6) the mouse responds to a tail pinch; (7) the mouse has a regular respiratory rate. For each of the 7 different criteria, each mouse was given a sub-score of 0 if it met the criteria or 1 if it did not. After each of the 7 criteria were evaluated, the sub-scores were summed for each mouse and then averaged for each group. For example, if a mouse was bright, alert, and responsive 3 hours after the 300 µg ICV dose, and met all other criteria, it would get a summed score of 0. If another mouse was not bright, alert, and responsive 3 hours after the 300 µg ICV dose but met all other criteria, it would receive a score of 1. PBS treated mice generally receive a score of 0. A score of at the top end of the range would be suggestive of acute toxicity.

Each mouse was then evaluated weekly by a trained observer for 8 weeks and examined for adverse events (AEs). Adverse events are defined as any behavior not typical in a naive matched control animal. Animals were evaluated for adverse events including, but not limited to: limb clasping, abnormal limb splay, abnormal gait, tremors, abnormal respiration, paralysis, spasticity, impaired righting reflex, hyperactivity and lethargy. For each group, the number of animals that exhibited any adverse events during any of the 8 weekly observations was calculated. For example, a group of animals where no animals exhibited any adverse events is given a score of 0.

Body weights were also measured throughout the study. Results are presented as the average percent weight change for each group, relative to the average pre-treatment weight for the group.

Animals were sacrificed at 8 weeks. Brain and lumbar sections of the spinal cords were collected from each animal, and RT-PCR was performed. Expression levels of allograft inflammatory factor (AIF1) were determined as a measure of imflammation. Expression levels of glial fibrillary acidic protein (GFAP) were also determined for some samples as a measure of glial cell activation. Cyclophilin levels were determined as a control. After normalization of all samples to cyclophilin, the values of AIF1 and/or GFAP for each treatment group were divided by the normalized value for the PBS control group in order to determine the percent AIF1 or GFAP expression relative to the PBS treated animals. Data shown below represent the mean for each group.

The results of the tolerability studies are presented in Tables 10, 11, and 12.

TABLE 10

Tolerability of modified oligonucleotides targeting HTT SNP rs6446723, HTT SNP rs363064, or HTT SNP rs7685686 and BMPR1A

| Isis No. | Score at 3 hrs | No. of mice with an AE | Body weight at 8 weeks (% change) | AIF1 in spinal cord (% PBS) | AIF1 in cortex (% PBS) |
|---|---|---|---|---|---|
| PBS | 0.00 | 0 | 116 | 100 | 100 |
| 611714 | 2.25 | 1 | 101 | 292 | 153 |
| 611715 | 2.25 | 0 | 104 | 399 | 202 |
| 611717 | 3.75 | 0 | 106 | 353 | 92 |
| 611718 | 2.50 | 4 | 91 | 294 | 155 |
| 611719 | 0.50 | 1 | 105 | 213 | 148 |
| 611720 | 2.00 | 4 | 87 | 1199 | 127 |
| 611721 | 1.50 | 3 | 118 | 216 | 153 |
| 611722 | 1.75 | 3 | 107 | 271 | 150 |
| 611723 | 1.25 | 3 | 110 | 114 | 113 |
| 613581 | 1.50 | 3 | 105 | 95 | 131 |
| 613582 | 0.00 | 4 | 116 | 103 | 118 |
| 613583 | 0.00 | 4 | 115 | 132 | 95 |
| 613584 | 0.00 | 3 | 117 | 97 | 103 |
| 613585 | 0.00 | 3 | 113 | 99 | 103 |
| 613586 | 0.00 | 2 | 115 | 89 | 101 |
| 613588 | 0.25 | 2 | 116 | 81 | 131 |
| 613589 | 0.00 | 2 | 107 | 95 | 122 |
| 617104 | 1.00 | 1 | 112 | 121 | 160 |
| 617105 | 4.00 | 2 | 125 | 124 | 130 |
| 617106 | 0.25 | 3 | 112 | 110 | 116 |
| 617107 | 1.25 | 2 | 111 | 100 | 110 |
| 617108 | 0.25 | 3 | 115 | 97 | 99 |
| 617109 | 0.00 | 3 | 108 | 115 | 105 |
| 617110 | 1.75 | 3 | 115 | 103 | 131 |
| 617111 | 0.00 | 2 | 122 | 116 | 118 |
| 617115 | 0.75 | 3 | 125 | 111 | 141 |
| 617116 | 0.00 | 2 | 112 | 96 | 137 |
| 617117 | 1.25 | 4 | 107 | 105 | 109 |
| 617118 | 0.00 | 2 | 115 | 98 | 117 |
| 617119 | 0.00 | 3 | 120 | 93 | 116 |
| 617425 | 0.00 | 3 | 116 | 101 | 94 |

TABLE 11

Tolerability of modified oligonucleotides targeting HTT SNP rs7685686 and BMPR1A

| Isis No. | Score at 3 hrs | No. of mice with an AE | Body weight at 8 weeks (% change) | AIF1 in spinal cord (% PBS) | AIF1 in cortex (% PBS) | GFAP in spinal cord (% PBS) | GFAP in cortex (% PBS) |
|---|---|---|---|---|---|---|---|
| PBS | 0.00 | 0 | 116 | 100 | 100 | 100 | 100 |
| 623202 | 1.25 | 0 | 122 | 107 | 100 | 82 | 104 |
| 623205 | 0.25 | 0 | 127 | 104 | 116 | 73 | 137 |
| 623206 | 0.50 | 0 | 126 | 72 | 112 | 68 | 178 |
| 623235 | 0.25 | 1 | 129 | 168 | 93 | 130 | 124 |
| 623241 | 1.50 | 0 | 128 | 134 | 116 | 81 | 120 |
| 623242 | 1.25 | 0 | 116 | 81 | 109 | 77 | 108 |

TABLE 12

Tolerability of modified oligonucleotides targeting HTT SNP rs7685686 and BMPR1A

| Isis No. | Score at 3 hrs | No. of mice with an AE | Body weight at 8 weeks (% change) | AIF1 in spinal cord (% PBS) | AIF1 in cortex (% PBS) |
|---|---|---|---|---|---|
| PBS | 0.00 | 0 | 123 | 100 | 100 |
| 623181 | 3.75 | 1 | 126 | 115 | 84 |
| 623182 | 2.50 | 0 | 128 | 94 | 103 |
| 623198 | 1.25 | 1 | 136 | 126 | 103 |
| 623203 | 0.75 | 0 | 127 | 116 | 90 |
| 623208 | 0.75 | 0 | 128 | 117 | 104 |
| 623214 | 0.50 | 2 | 121 | 118 | 76 |
| 623236 | 0.25 | 0 | 121 | 125 | 88 |
| 623237 | 0.25 | 0 | 126 | 161 | 108 |
| 623243 | 0.50 | 0 | 123 | 103 | 80 |

We claim:

1. A oligomeric compound comprising a modified oligonucleotide consisting of a modification motif selected from:

eeek-d7-eeeeeeee,
eek-d7-eeeeeeeee,
ek-d7-eeeeeeeeee,
ek-d8-eeekk,
k-d8-eeekeke,
k-d8-eeekekee,
k-d9-eekek,
ek-d7-eeeekeke,
ek-d8-eeekek,
eek-d9-keeke,
ek-d9-eekek,
ek-d9-keek,
eek-d8-eeekek,
ek-d8-keeekee,
ek-d9-eekeke,
ek-d8-eeekeke, and
ek-d7-eeeekek;

wherein the modified oligonucleotide has a nucleobase sequence complementary to the nucleobase sequence of a target region of a huntingtin transcript, wherein the target region comprises single nucleotide polymorphism (SNP) rs7685686;

wherein the nucleobase sequence of the target region of the huntingtin transcript differs from the nucleobase sequence of at least one non-target nucleic acid by 1-3 differentiating nucleobases; and wherein at least one non-target nucleic acid is bone morphogenetic protein receptor, type IA;

wherein each "e" is a 2'MOE modified nucleoside, each "k" is a cEt modified nucleoside, and each d is an unmodified deoxynucleoside.

2. The oligomeric compound of claim 1, wherein the nucleobase sequence of the target region of the huntingtin transcript differs from the nucleobase sequence of bone morphogenetic protein receptor, type IA by a single differentiating nucleobase.

3. The oligomeric compound of claim 1, wherein the modification motif is selected from:

eeek-d7-eeeeeeee,
eek-d7-eeeeeeeee,
ek-d7-eeeeeeeeee,
ek-d8-eeekk,
k-d8-eeekeke,
k-d8-eeekekee,
k-d9-eekek,
ek-d7-eeeekeke,
ek-d8-eeekek,
eek-d9-keeke,
ek-d9-eekek, and
ek-d9-keek;

wherein each "e" is a 2'MOE modified nucleoside, each "k" is a cEt modified nucleoside, and each "d" is an unmodified deoxynucleoside.

4. The oligomeric compound of claim 2, comprising at least one modified internucleoside linkage.

5. The oligomeric compound of claim 4, wherein each internucleoside linkage is a modified internucleoside linkage.

6. The oligomeric compound of claim 4, comprising at least one phosphorothioate internucleoside linkage.

7. The oligomeric compound of claim 5, wherein each internucleoside linkage is a phosphorothioate internucleoside linkage.

8. The oligomeric compound of claim 6, wherein the 5'-most internucleoside linkage of the 5'-region is a phosphorothioate internucleoside linkage, wherein the 3'-most internucleoside linkage of the 3'-region is a phosphorothioate internucleoside linkage, and wherein each internucleoside linkage of the central region is a phosphorothioate internucleoside linkage.

9. The oligomeric compound of claim 6, wherein the 5'-most internucleoside linkage of the 5'-region is a phosphorothioate internucleoside linkage, wherein the 3'-most internucleoside linkage of the 3'-region is a phosphorothioate internucleoside linkage, wherein each internucleoside linkage of the central region is a phosphorothioate internucleoside linkage, and wherein each remaining internucleoside linkage is a phosphodiester internucleoside linkage.

10. The oligomeric compound of claim 6, wherein the oligomeric compound contains 2 phosphodiester internucleoside linkages.

11. The oligomeric compound of claim 6, wherein the oligomeric compound contains 3 phosphodiester internucleoside linkages.

12. The oligomeric compound of claim 1, wherein the nucleobase sequence of the target region of the huntingtin transcript differs from the nucleobase sequence of bone morphogenetic protein receptor, type IA by two differentiating nucleobases.

* * * * *

SEQUENCE LISTING

<160> NUMBER OF SEQ ID NOS: 39

<210> SEQ ID NO 1
<211> LENGTH: 202001
<212> TYPE: DNA
<213> ORGANISM: Homo sapiens

<400> SEQUENCE: 1
gcccagcagg tgtcagcctc attttacccc gcccctattc aagatgaagt tgttctggtt 60
ccaacgcctc tgacatatta gctgcatcat tttacatttc tttttttttt ttccttttaa 120
atggggtctt gctctgtcac ccaggctgga gtgctgtggt atgatctcgg ctcactgcaa 180
tctccacctc cgaggttcca gcgattctct tgcctcagcc tcccgagtag ctgggactac 240
aggcacccac catcatactg ggctaatttt tgtgttttta gtagagatgg ggtttcccca 300
tgttgcccag gctgatctca aactcctggg cttaagcaat acagccgcgt tggcctccca 360
aagtgttggg attacaagca tgagctaccc cacccagctc attttacatt tccacttgtt 420
aaactgaaaa ctggcccgag aaagcttctg tactgccatc cttgcgtcct tgcagatgaa 480
tcgtaaccta gcatagtagg taggcagact gaaaacctaa cttagcagta ggcttctgta 540
acaacagctg tgtctcagcc agttcctgca gccagacttc aaccactcac aggccgcaaa 600
ctgttcaaac tgtgttcgga gaaggcgaat tcatctggct gttaacgtgc ctcacttctg 660
ctttctgtgg ccactttccc ttttctgtcc ataaatttgc tttgaccaca cagcatccct 720
agagtctccc tgaatctgct gtgattctgg gacctgcacc atttgtgaat tgtttttttt 780
ttccttgatc agctaaactc tgttcaattc aatttgttgg aagtttttaa cataccaatg 840
gtgcaccaag gttccaattt ctccacttcc tcataaataa gtcattttaa atggcttttc 900
agtattccaa tatttggaag tattaatgtt tctaccaatt ttctattttt ggacattgag 960
gttgtttcat tttttttttc ttttttttgag acagagtctc gctccgtcac ccaggctgga 1020
gtgcagtggc ctgatcccgg cccactgcaa cctccacctc cctcctcagc ctcctgagta 1080
gctgggatta caggtgcatg caccaccaca cccagctaat ttttgtattt ttagtagaga 1140
tggggtttca ccatgttggt caggctggtc tcaaactcct gacctcaggt ggtccacctg 1200
ccttggcctc ccaaaatgct gggattacag gcctgagcca ctgcgcctgg cctcatcttc 1260
ttgatattaa tgttgcttta acatctttgt ccctgtgttt tttgtttttt tttttgagac 1320
ggagtctcat tcattctgtc acccaggctg gagttcagtg gcgtgatctc agctcactgc 1380
aacctctgtc tcctgggttc cagtgattct cctgcgtcgg tctcctgagt agctgtgttc 1440

-continued

```
ctgggtcttt cgatggttat ttaatacttc cctacagtaa tgccctgtgc gtacatgcta   1500
agtgtgatga aatggttggc acagttaaat cttttgaaag acattgccaa gtcactcttc   1560
agaaaagtga taggaggtca tagcaatttt aagaagtcct catttctaca tttccttact   1620
aatctcggtt ggtgtctctt caatctttcc tcacactttt cttgggtttt tcctgaatca   1680
tgagtctact acatttacac attttaaagc atctttagaa acaggatctc attttgttgc   1740
ccaggctaga gtttggtggc atgattatag ctcctcatac tcctgggctc aagtgatcct   1800
tccacctctg aaaccccaaa atttgagaaa ggtctcattt aatttagaaa gtttattttg   1860
ccaaggttga gggtgcacac ctgtgatgat atacgagtta aaaagaaatt atttaggcag   1920
atactgaggg taagaaagtc ctcggtaagg ttttcttttc aatgaaaagc agcccccaag   1980
cattttcttt tctaacaaag agcagcctgt aaaatcgagc tgcagacata cacaagcaag   2040
ctggaagctt gcacaggtga atgctggcag ctgtgccaat aagaaaaggc tacctggggc   2100
caggcagatc caacatggcg gctccatctt ccctttcctt gtcaaccatg tgcacagtaa   2160
ggagcaggca acatagtgtc cccgagtag agaccaattt gcataataaa aggtgagggt   2220
agggtgggca gcttctttgc atgctatgta aacattatgc ctggtccaac caatctttgg   2280
gccctgtgta aattagacac cacctcctca agcctgtcta taaaaccctg tccattctgc   2340
cgcaggctgg aagacccact ggggcacccc tctctctcta taggagacag ctattcattt   2400
ttctctttct ttcacctatt aaagctccac tcttaacccc actccgtgtg tatctatgtt   2460
cttgatttcc ttggcatgag gcaatgaacc ttgggtatta ccccagaacc ttgggtatta   2520
tgccacttca gtgacacagc ctcaggaaat cctgatgaca tgttcccaag atggtcgggg   2580
cacagcttgg ttttatacat tttagggaga catgagacgt caattcatat atgtaagaag   2640
tacattggtt ccgtccagaa aggcggggac aacttgaggc agggagagag cttctaggtc   2700
acaggtagac aaatggttgc attcttttga atctccgata agcctttcca aaggaggcaa   2760
tcagaatatg cgtctattga ctgggcgcag tggctcatgc ctgtaatgcc agcactttgg   2820
gaggcggagg tgggtggatc acctgaggtc aggagtttga gagcagcccg gccaacatgg   2880
tgaaaccctg tctctactaa aaatacaaaa aattagctgg gcgtggtggc gggcgcctgt   2940
aatcccagct actcgggagg ctgaggcagg agaatagctt gaacccagaa ggaagaggtt   3000
gcagtgagct gagatggtgc cattgcactc cagcctgggc aacaagagtg aaactccatc   3060
tcagaaaaaa aaaaaaaagg cctgggcaaa gtggctcacg cctgtaatcc cagcactttg   3120
ggaagccgag gcgggcaggt cacaaagtca ggagattgag accatcctgg ctaacatgat   3180
gaaaccccat ctctactaaa aaatacaaaa aactagctgg gtgtggtggc gagcacctgt   3240
agtcccagct actcggcagg ctgaggcagg agaatggcgt gaaccgggga ggcggagctt   3300
gcagtgagcc gagatcacac cactgcactc cagcccggac gacagggcaa gactctatct   3360
caaattaaaa aaaaaaaaaa aaaaaaaaaa aaagagagag agaatatgca tctatctcag   3420
tgagcagaag gatgactttg aatggaatgg gagcagttcc tagcttgaac ttccccttta   3480
gcttcagtga tttgggggct caaggtatgt tcctttcaca tacctcagcc tcccaagtag   3540
ctgggaccac aagtgcatgc caccacacgt ggctaatgtt ttattttttt tgtaggaata   3600
gggtctcact atgtgtccag gctggtctaa aacccctgag ctcaaatggt cctcccgcct   3660
cagcctcccg aaatgctggg attacaggca tgagccagca tgcccggcct agtctacatt   3720
tttataaatt gctaattcaa agttccctct ccaaaacctc atggttttcc ctgttctcat   3780
cccctgcacc ctcccttccc ctggagtact cacctggcct tggaggtctg gtgtgagccc   3840
```

```
ggacttcgat tctaggcaca gcatgtgatg agcgccccca ggtcaaacac ctcccctctg   3900
cggcctgtgc ttcaccgcct tgacagtgag aaaggtctcc cttcggctca ttctcgaagt   3960
ctcaaacttc acttctcctg tgcgctgatt ctgaattcag cccccgtcca aggtcctggc   4020
ccctttctct tctgcttggc gtgttgttca tcaccactgt gcactgctga gggtaagtgc   4080
ggttctctgg acctctgctt tatcattaga acagactctt gcggtttccc acgacattcc   4140
tttcacttct cacttggaag atgagccgtg aggaaatcct gtgttgtgtg gtatgtgggc   4200
tgtgcttctg cttgacttga gggccaagca gcattgcaag ccatggtttt aaataagaaa   4260
gaacatttct aaccttcatc ttctagtaag gaaacaagtg ggctttagag ttcttgctca   4320
ggaaagacct atgtcccagt ccaaccggac cttttactaa agagatcttc ctgatcctcc   4380
tccccaggcc aggggagggg tcctccctgg ggttggagcc tttagtaggg ggtcggagac   4440
acgacgtagc cttcatgaca ttcatagtct agttacacga tccctgtaag ggtcagttga   4500
agtaagtgct acaaaggaag ggaggtgctc agtggagagg gctctctttt atgtattata   4560
tttctttcat ggggagggat atggatcagg gatcagcaga ggtgtttcag tcccgaggga   4620
aagaaagtca gcgtggcttg ggagttggga gcagcaagac agtggctcaa gatatcttaa   4680
gactagtgga gtacaccttg catgttaaaa gccttgctca gggctgcctg gttcttgtag   4740
gacgacagag atggcctagc tctgcatact gcacccccag gggctcagaa cagtgcaaat   4800
gtcagtctat ctgtcagtgg cagagccagc cttggagcag gggtgcaagg aggtctctgc   4860
actggccagg catgcagaac attctgttca gtagcactgg acagaaggcc ccatctagat   4920
gagacagagc tggtggggca ggacaaagac tcctggcagc tcaaacggcc tggcagatgc   4980
ttggagagag gggcttcttt gagacagcac catttctggg aagagagtca cctgggaggg   5040
atgaggccac gctccggctt ggaggtgaag agaggggctg ctgcaagaaa gaattagaga   5100
catgccagcc tttgctgtgt tgcccaggct ggtcatgaac tcttggcctc aagcaatctt   5160
cccacctcag cctccccaag cgctgggatt atagacatga gcccccatgc tggccaataa   5220
aagatgattt tatggagggg atggtggtga aggttgtggg tggtatgaaa tagtaagaaa   5280
tatatattgg tctgcaccca gttcctgcca cagagctcct aaaatcctga gaacttcctg   5340
ggtgagcatc ttttgttcta atgaggtgac tcttggtggc tcctggatag gagtgaatca   5400
ccagaaagat caagccagag ttagaagcag aaagtgctgg ctataacaca ggaaagctgt   5460
aacacaaata ataaagtttt tttttttttt tttgagatgg agcctcactc tgttgcccag   5520
gctggagtgc aatggtgcaa tctcagctca ctacaagctc tgcctcccag gttcaagtga   5580
ttctcctgcc tcagcctcct gagcagttgg gactacaggt gtgtgccacc acatctggct   5640
aatttttgta tttttagcag agacggggtt tcaccatatt aaccaggctg gcctcaaact   5700
ccttaccttg tgatccgcct gcctcagcct cccaaagtgc tgggattaca ggcatgagcc   5760
accgtgcctg gccaaaagac attgttctta aaagaatcaa ctaactaacc aaataaataa   5820
aaatctaacc taattaagaa actaaaaata cacaaaaatt aatttcaagg ggagaaaaat   5880
catgtaaaga gagaaagata atgaatactt tgcagaaatt tatgaacata aacataaaac   5940
ttggatgaaa tgcatttcta ggaaaacata atttatcaaa actaaccaca agtaaaatag   6000
aagcctaaat aggatatttt caagagaaga agtaaagttg tcaaagtgct acccttcaaa   6060
aaaacaccag gctcaaacaa tctgacatgg gaatgttagc acaccttaga gagcaaataa   6120
aactttgaat gggcttgaaa tattccagac tctagaaaaa caaaacttcc caattctttt   6180
```

-continued

```
tataaagcaa gtataaattg ataccaaaat cttataaaga ccttatacaa aacttcatac   6240
caatctcttt tatgaataca aaacccttaa taaagtatta ccagacagaa cccaacaata   6300
cataaaaatg tcacatcata acatagtggg gtttatttca ataatgcatg gatggttcaa   6360
tacaaggaaa ttcagtaaca caatataata gatcatgtga atatacccaa agaaaaaata   6420
gattattttc atagatgctg taaaggcatt tgaccaaatt caacacctac tttttaggtg   6480
gtcaataaaa taaattagtt actccttctt tagcatgata aaatatattt atcagcccag   6540
aaggcatcat tttacccgat aagggcacac gctggaggga ataatgttaa aattaggaat   6600
aagaggatag ctagtttctt tcttcttttt ttttttgag acggagtctt gctctgttgc   6660
caggctggag tgcagtggtg caatgttggc tcactgcacg ccccccgcct cccaggttca   6720
agcgattctc ctgcctcagc ctcccgagta gctgggacta caggcgcgca ccaccatgcc   6780
cggctaattt tttttgtat tttagtagag atggggtttc accatgttgg tcaggctggt   6840
cttgaactcc caacctcacg tactgggatt accggtgtga gccaccacgc cagcccaact   6900
actttcaaca ttatccttaa tactgatgct tattgactta ctatggggtt acctctagat   6960
aaatccataa taagttgaaa atataagtaa aaaatgccct taatacacct aacctaccaa   7020
acatcatagc tgagcccagc ctgccttagc tatgctcaga cactgacgtc agcctacaat   7080
tggcaaaatc acacagcagc acagtctact gcagagcatc tgctgtttgc ccttgtgact   7140
gcgtggctgc ctgggagctt cccagcttca caagacagta ttacgtagca catcactagc   7200
ctggggaaag atcaaagttg aaaatttgaa gtgtggtttc cattgaatgt gtactgcttt   7260
tgcaccatca tcaagtcaaa aaattttagt tgaaccagcc taagtttggg accatcttta   7320
ttttcaggag gaacttccat gtacattgat gacggacgat agaatccgtt tctatcatcc   7380
taatgaacat aatgaataaa tccagacaaa cataaacatt aacagagtaa gcagctttcg   7440
gggctggaag ccagaagagg gtgggagcgc agagagagag gccaaacacc agggctgctt   7500
ctgctttgcg ggtatttgct gatctggaca aggtatctgg aaggctgagc taagcctcct   7560
ttttttttga ggtggcgtct cactctgttg ccaggctgga gtgcaatggt gcgatctcag   7620
ctcactgcaa cctccacctc cctggttcaa gcgattctcc tgcctcagcc tcccgagtag   7680
ctgggattac aggctcccgc cactacaccc agctgatttt tgtaatttta gtagagacgg   7740
ggtttcacca tgttggccag gatggtctcg atctcttgac gtcatgatct gtccacctcg   7800
gcctcccaaa gtgctgggat tataggcgtg acccaccgtg ccccgtctga gctaagcctc   7860
ttgagcatag gggactaaaa atgaaatcta gcgcatgcca agtttagggt cccaggcaat   7920
tcctttccac tttggggtcc actttggggt ccacccccacc caagaagaag gatgacttgg   7980
aagtaaacca gctctgaaat atggatggtc ctctgggacc ataccaatcc cttcatatca   8040
accacatcca gttcctcaaa actggaactt ggattaagat ggcctaggac ttctagtgtc   8100
ccaggagcct ggcattgcaa acaaaaatcc tctccggaag aagataatac cttaagcttc   8160
aaatgactct ctaataaatt tcaaatacaa tgtccagcac acaaacacaa attaccagga   8220
acgtgatatg aggcctgatg gatgggaatt agcagaaact tcaggcatga gaaacatacc   8280
ctcagaggcc tagaatctat ctagtgtcta gataatggag atatgaaata cagacactta   8340
aacaactatg tttcccatgt tcaaagagga aatttgcaaa acttgaaagt gttggcagga   8400
aatcagaaac tataaaatgt gacaacagca tactttagag tcagtataaa ttacggtccc   8460
gaaaactgca gaattccaga acttaatggt aaagcaaggg tttaacagca gaatagaaat   8520
agccagagag aactaggaag taagtcagat gacactaccc agaataaggc actgagaggc   8580
```

-continued

```
caaggaatgg aaaatgcaga agaaaggata tggtgagagg atctaatata catttatttg   8640
gagtaccagg gagagagaga aggagaagaa cagaagccgt gtttcaagga cggtgactga   8700
gaggcttcga aactgatgaa agccatcagt tcacaaattc aaagcccagt gaattccaag   8760
gagaaaaaaa gaaatccata ctgtgaaagc aagtccagac aatgacaaac accatcaaca   8820
atacacagga caggcataag atgcatttaa tggggacact cagaggcaga gggttatcag   8880
aaggaggcac ttctctccca agttctcatc atcccagggc cagggacagc tggtcacacc   8940
ttagggagtt cactaggaga gggatctggc ttcttgtcat tctgggtatt tgtagggaaa   9000
ttggaaggga accgagagca cctagccaat cgcatagcaa tgggagattt caggctgtgg   9060
ggaatgtctt tgctggtgaa aagaacatcc tgaccttaga aatctttcac cgagggggat   9120
ctgcgttcca gaacttctgg agctggtata ggtaaggctt tgagctttcc tactgagcca   9180
gcctgttgct aggttaccaa aggggacctc gagggccatc tggccaacaa gcagacttgt   9240
ctctccttac acccccagac gtatcactgc aaaactacag aaaaccaaag acagagaaaa   9300
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaaattag   9540
tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaaa aaaaaaaaaa aaagggtgac   9720
gaagcttcaa tctcctgaaa ggaagcaact gccgcctttg attcgatacc caccaaaatc   9780
cgtgaagaag gaaggcaaaa taaaaacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatggaa aattcggggg   9960
ccaatttaaa caaaagctga ctgctctaca actgttgtgt ctctatcttt tgtaacatat  10020
atgtgtgtgt agcttttttt tttttttttg tcaagatgga ttctcactct gtcgcccagg  10080
ctacagtgaa atggcacggt ctcggctcac tgcaacctct gccccttggg ctcaaatgat  10140
tctcttgcct cagcctcctg agtagctgag attacaggtg cctggcacaa tgcctggcta  10200
atttttgtat ttttactaga gatgggattt ctccatgttg gccaggctgg tcttgaacac  10260
ctgacctcag gtgatccacc tgcctgggcc tcccaaagtg ctaggattac aggcgcgagc  10320
cactgcatct ggcctatgtg tgtgtttata tggaattaaa acacatggca ataataccct  10380
ccaaattggg agaaaccaaa aatagcattt aaatgttgta agctccctgc ataatcaaga  10440
agagaataga tttacgttag attttgatac ctggaggatg aatgttgtaa tttctagggt  10500
gaccatgaaa agaggagaca acggtgtatg tttttttttt tttgagatgg agtctcactt  10560
tgtcacccag gctggagtgt tgtggtgtga tcttggctca ctgcaacctc ctcctcttgg  10620
gttcaggcca tcctcccacc taggcctcca gagtaggtgg gatcacaggc acctgccacc  10680
acacctggct aatttttttt ttttttttaaa tatttagtag agatggggtt tcaccatgtt  10740
ggccaggctg gtcttgaact cctgacctca ggcgatctgc ctacctctgc ctctcaaagt  10800
gctgggatta caggtgtgag ccatcgcgcc cggccaacag tgatcacttt caaactaaca  10860
gaggttcaaa aataaaatca gacttaacca aaaaccaggt aacagagctg gtaggatata  10920
```

-continued

```
cagaaagact gacctcacgt atatcaacga ttacagttaa tattaatgaa ggaaatgctc  10980
tagtttaaaa acgagggttg tcaaagaccc cacataagaa gctccttacc agcggtgcac  11040
ctagaaccta aggaaacagg acagatgaag gaggacgcgc ccccgccgct gtcctgcgcc  11100
tcagccatcc tatgagacgg gaaaggtttc tgtctgcagc tgggcccgtg ctctttacca  11160
gctcctggct ttcttctctg gaaggttcct gcctgttttg ccctcacacc tgctcctctc  11220
tcagccctct caggggtggg gctggaggcc accaaagagc ctcctctgct ctccagttgc  11280
tcgactgctc ctcatttccc cctggggtct gcgtcagggt ttccttcttt tccagcccca  11340
ccccgcgtgc atcccacctg gtctcgggtc ggggctgctc ccgcttactg ccccctgccc  11400
aggctggtgt gcaccccctc tggctgcttt caaggcctct tctctcttct cggcaggaca  11460
ggcacaggca ggtggccagg tgtcatgctt agctccccgc ccagtgagat tctttcattt  11520
aacaatcttc ccctgaatag ttcatgttca ttgctgaaaa tttgaaaaat atggaaaagc  11580
acaaagatta agatataaac cgccctcaat tcccctgccc agagagagtc actgctatga  11640
cttggtgact aggaacctta tttctctctc gctctttttt ttttttttga gacagagtct  11700
tgctctgtca cccaggctgg agtgcagtgg ctcgatctca gctcactgca acctccgcct  11760
cctgggttca agcgattctc ctgcctcagc ctcttgagta gctgggatta caggcacctg  11820
ccaccatgcc cggctaattt ttgtattttt agttgagaga gggtttcatc ttgttggtca  11880
ggcggacttg aactcctgac ctcaggtgat cagcccacct cggcctccca aagtgctggg  11940
attacaggtg tgagccactg cgccttcatc tctcttctgt gtatgtgtac gctgtttttt  12000
ctttagaatg ggggacgtta tcaggctcta catggtgtgt agtcggctag catgttgtaa  12060
gcctttccct gtgtcacaag tgctcatctg gaacaggatt ctaatgactg cctgtggcta  12120
tgttgggatt cctttaactc agctccttct gcccagcatc tatctttttt ccatcttttg  12180
tcctaagtgt tgctataata aatcattgat cacacatgcc tgactgtttg cataggataa  12240
attacgggaa atgtttttgc tgttcaggga ctgtgcccat ttttaggcct cagagacacc  12300
atgccagact gcccagtatt gatctttact ctttttagat gatgccaaac ttttctgtga  12360
actttaaaaa cctgtgtctt gacagtccat ttctgtaagt ctttcacatt agatttcctg  12420
tcaggatgat agtcaattct aggcagatga tgttttctca gccatggctg aagcagttgt  12480
gatttgttgt ggccatgtaa agtcccgatg atccattgcc tccctggatg ggttggaata  12540
atttggtttg ggagcatata acagaatgac ctggagtcac agcagctcag acggaagtgt  12600
atttctccct tacagatgaa agaattccag gccaggctgg aatgacaact gcacacagtc  12660
atctgggccc cctccttcca gctcccatca ccccaggatg tggcttttat gcagatgatc  12720
caaaatggct gctcaagtcc cagccaacac atcccattcc agggagcagg aaaaaggtgt  12780
gtctttccct tcattttatg tgattccttt ctagaagtac tactcattac ttctgcttgc  12840
atctccctgg ctagcactta cttagttata tggccatagc tagctgaagg aaggacaggg  12900
actgtcatac actagctaag aggcaaactg cttagataaa aaggtctcta aagaaggtca  12960
gagcggctgc tagggtgcaa ctctattact tattgttatg ggacgaactg tgtccctcat  13020
tcaggttgat gtcctaagcc ccagaacctc agaatgggat tgtatttgga gacaggttct  13080
ttaaggaggt aaggaggcta aaatgagatc attagggtgg gccataatcc gactgatgtc  13140
ttacaagaag agattaggac acggacatgc tcagagggac ggccacgtga ggacaccaag  13200
aaaggcagct gtctgcaagt caaggacagg gctcagggga aaccaacctt gccaacacct  13260
tcatctcgga cttctagcct ctaggaccat gagaagatac atttctgttg tttaagctgc  13320
```

```
ccggtctgtg gtactttgtt atggcagccc aagtaaacaa atacagtcat ctgctgctgg  13380
aacaaatcac cccagcactg tggcttggca gcacacatgt ctagtcatag agttatatgt  13440
agttacgtgt agagccatat gtatcgtcac acgttctgtg ggtcaggaat ttggacccag  13500
cttaaccagc tccacttctc gccagggttc agtcaaatac cagctgcctc ccacctgaga  13560
gctcagccgg ggaagggtcc ctttccaatc tcacgtggtg ttggcaggat ccagttcctc  13620
atggcctgct ggactgagaa cctcagttct cactgcctgt tggccagagg ccgcctttat  13680
gtcctcgcca tgtgggcctc tccaacatgg cagctgactt catcagagca tccatgccaa  13740
gaaggcaaca gagagggcca gggagactga agtcataccc ttttgcgacc tagtcatggg  13800
gtgacattcc atcacctttg cccattggtt agaagcaggc caccaggtac agcccaagct  13860
cacggggagg ggtcatacaa gggtgtcaat accaggaggt gaggggtgct ggggccatct  13920
tatgagtctg cccactgagg taactaacaa ccttgaggcc tgacacagtg gacaaaggcc  13980
cttattaaca gcagagaact gggaacttta tttatttatt tatttttgag acagagtctc  14040
actcttgtca cccaggctgg agtgcaatgg catgatcttg gctcactgca acctccacct  14100
cccaggttca agcaattctg cctcagcctc cggaatagct gggactacag gcatgcacca  14160
ctacacccgg ctaattttg tatttttagt agagacaggg tttcgccatg ttggccaggc  14220
tggtctcgaa ctcctgacct ctggtgatct gcctgccttg gcctcccaaa gtgctgggat  14280
tacaggcgtg agccaccgca cctcgctgga acttaatttt tttagagaca gtgtcgctct  14340
atcacccaag ctggagtgca gtggtgcaat cctagctcac ttgcagcctc aaattcctgg  14400
gttcaggtga tcctcccaca tcagcctccc aagaactggg aactaacagc tgtttctctg  14460
ctgtccttct caagaaaagg gaggctactg ctaccccact ggggacaatg ctgggtttcc  14520
ctttaggaca ggctctgaga caaggcggag gtgctgtttg tggccacaga gcaggggact  14580
ctgggttgca ggtgtggcct ggctaaagta ggctttactg ggctcctctc tgcctgcatc  14640
accccccggc tgggcggttg tctctgaggc caaccttact ccctgctggg caggctggac  14700
agctgccctc tccgtttgcc cctctaccac ccaaaaggca ggaggctctg gagaccagga  14760
ccctgcccgc cacggcctgt gtcccaggcg tgagggggtg ccccacagac ctctgctgag  14820
ctgctgctga atgacgcccc ttgggggtcc tgccggaagg tcagagcagg ggtgcactcc  14880
cataaagaaa cgcccccagg tcgggactca ttcctgtggg cggcatcttg tggccatagc  14940
tgcttctcgc tgcactaatc acagtgcctc tgtgggcagc aggcgctgac cacccaggcc  15000
tgccccagac cctctcctcc cttccggggc gctgcgctgg gaccgatggg gggcgccagg  15060
cctgtggaca ccgccctgca ggggcctctc cagctcactg ggggtggggt gggggtcaca  15120
cttggggtcc tcaggtcgtg ccgaccacgc gcattctctg cgctctgcgc aggagctcgc  15180
ccaccctctc cccgtgcaga gagccccgca gctggctccc cgcagggctg tccgggtgag  15240
tatggctctg gccacgggcc agtgtggcgg gagggcaaac cccaaggcca cctcggctca  15300
gagtccacgg ccggctgtcg ccccgctcca ggcgtcggcg ggggatcctt tccgcatggg  15360
cctgcgcccg cgctcggcgc cccctccacg gccccgcccc gtccatggcc ccgtccttca  15420
tgggcgagcc cctccatggc cctgcccctc cgcgccccac ccctccctcg ccccacctct  15480
caccttcctg ccccgccccc agcctcccca cccctcaccg gccagtcccc tcccctatcc  15540
cgctccgccc ctcagccgcc ccgcccctca gccggcctgc ctaatgtccc cgtccccagc  15600
atcgccccgc cccgcccccg tctcgccccg cccctcaggc ggcctccctg ctgtgccccg  15660
```

```
ccccggcctc gccacgcccc tacctcacca cgccccccgc atcgccacgc cccccgcatc  15720
gccacgcctc ccttaccatg cagtcccgcc ccgtcccttc ctcgtcccgc ctcgccgcga  15780
cacttcacac acagcttcgc ctcaccccat tacagtctca ccacgccccg tcccctctcc  15840
gttgagcccc gcgccttcgc ccgggtgggg cgctgcgctg tcagcggcct tgctgtgtga  15900
ggcagaacct gcgggggcag gggcgggctg gttccctggc cagccattgg cagagtccgc  15960
aggctagggc tgtcaatcat gctggccggc gtggccccgc ctccgccggc gcggccccgc  16020
ctccgccggc gcagcgtctg ggacgcaagg cgccgtgggg gctgccggga cgggtccaag  16080
atggacggcc gctcaggttc tgcttttacc tgcggcccag agccccattc attgccccgg  16140
tgctgagcgg cgccgcgagt cggcccgagg cctccgggga ctgccgtgcc gggcgggaga  16200
ccgccatggc gaccctggaa aagctgatga aggccttcga gtccctcaag tccttccagc  16260
agcagcagca gcagcagcag cagcagcagc agcagcagca gcagcagcag cagcaacagc  16320
cgccaccgcc gccgccgccg ccgccgcctc ctcagcttcc tcagccgccg ccgcaggcac  16380
agccgctgct gcctcagccg cagccgcccc cgccgccgcc cccgccgcca cccggcccgg  16440
ctgtggctga ggagccgctg caccgaccgt gagtttgggc ccgctgcagc tccctgtccc  16500
ggcgggtccc aggctacggc ggggatggcg gtaaccctgc agcctgcggg ccggcgacac  16560
gaacccccgg ccccgcagag acagagtgac ccagcaaccc agagcccatg agggacaccc  16620
gccccctcct ggggcgaggc cttcccccac ttcagccccg ctccctcact tgggtcttcc  16680
cttgtcctct cgcgaggga ggcagagcct tgttggggcc tgtcctgaat tcaccgaggg  16740
gagtcacggc ctcagccctc tcgcccttcg caggatgcga agagttgggg cgagaacttg  16800
tttcttttta tttgcgagaa accagggcgg gggttctttt aactgcgttg tgaagagaac  16860
ttggaggagc cgagatttgc tcagtgccac ttccctcttc tagtctgaga gggaagaggg  16920
ctgggggcgc gggacacttc gagaggaggc ggggtttgga gctggagaga tgtgggggca  16980
gtggatgaca taatgctttt aggacgcctc ggcgggagtg gcggggcagg ggggggcgg  17040
ggagtgaggg cgcgtccaat gggagatttc ttttcctagt ggcacttaaa acagcctgag  17100
atttgaggct cttcctacat tgtcaggaca tttcatttag ttcatgatca cggtggtagt  17160
aacacgattt taagcaccac ctaagagatc tgctcatcta agcctaagtt ggtctgcagg  17220
cgtttgaatg agttgtggtt gccaagtaaa gtggtgaact tacgtggtga ttaatgaaat  17280
tatcttaaat attaggaaga gttgattgaa gttttttgcc tatgtgtgtt gggaataaaa  17340
ccaacacgtt gctgatgggg aggttaattg ccgagggatg aatgaggtgt acattttacc  17400
agtattccag tcaggcttgc cagaatacgg ggggtccgca gactccgtgg gcatctcaga  17460
tgtgccagtg aaagggtttc tgtttgcttc attgctgaca gcttgttact ttttggaagc  17520
taggggtttc tgttgcttgt tcttggggag aatttttgaa acaggaaaag agagaccatt  17580
aaaacatcta gcggaacccc aggactttcc ctggaagtct gtgtgtcgag tgtacagtag  17640
gagttaggaa gtactctggt gcagttcagg cctttctctt acctctcagt attctatttc  17700
cgatctggat gtgtcccaga tggcatttgg taagaatatc tctgttaaga ctgattaatt  17760
tttagtaata tttcttgttc tttgtttctg ttatgatcct tgtctcgtct tcaaagttta  17820
attagaaaat gattcggaga gcagtgttag cttatttgtt ggaataaaat ttaggaataa  17880
attattctaa aggatggaaa aactttttgg atatttggag aaattttaaa acaatttggc  17940
ttatctcttc agtaagtaat ttctcatcca gaaatttact gtagtgcttt tctaggaggt  18000
aggtgtcata aaagttcaca cattgcatgt atcttgtgta aacactaaac agggctcctg  18060
```

atgggaagga agacctttct gctgggctgc ttcagacact tgatcattct aaaaatatgc 18120
cttctctttc ttatgctgat ttgacagaac ctgcatttgc ttatcttcaa aatatgggta 18180
tcaagaaatt tcctttgctg ccttgacaaa ggagatagat tttgtttcat tactttaagg 18240
taatatatga ttaccttatt taaaaaattt aatcaggact ggcaaggtgg cttacacctt 18300
taatccgagc actttgggag gcctaggtgg acgaatcacc tgaggtcagg agtttgagac 18360
cagcctggct aacatggtga aaccctgtct ctactaaaaa tacaaaaatt agctggtcat 18420
ggtggcacgt gcctgtaatc caagctacct gggaggctga ggcaggaaaa tcgcttgaac 18480
ccgggaggca gagtctgcag tgagttgaga tcacgccact gcactccagc ctgggtgaca 18540
gagcgagact ctatctcaaa aaaaattttt tttaatgtat tatttttgca taagtaatac 18600
attgacatga tacaaattct gtaattacaa aagggcaata attaaaatat cttccttcca 18660 ccccttttcct ctgagtacct aactttgtcc ccaagaacaa gcactatttc agttcctcat 18720
gtatcctgcc agatataacc tgttcatatt gtaagataga tttaaaatgc tctaaaaaca 18780
aaagtagttt agaataatat atatctatat attttttgag atgtagtctc acattgtcac 18840
ccaggctgga gtgcagtgat acaatctcgg ctcactgcag tctctgcctc ccaggttcaa 18900
atgcttctcc tgcctcagcc ttctgagtag ctgggattac aggcgcccac caccatgtcc 18960
agctaatttt tgtattttta gtagagatgg ggtttcacca tgttggccag gctggtcttg 19020
aactcctgac cttgtgatct gtccacctcg gcctcccaaa gtgctgggat tacaggtgtg 19080
agccaccatg cctggctaga ataataactt ttaaaggttc ttagcatgct ctgaaatcaa 19140
ctgcattagg tttatttata gttttatagt tattttaaat aaaatgcata tttgtcatat 19200
ttctctgtat tttgctgttg agaaaggagg tattcactaa ttttgagtaa caaacactgc 19260
tcacaaagtt tggattttgg cagttctgtt cacgtgcttc agccaaaaaa tcctcttctc 19320
aaagtaagat tgatgaaagc aatttagaaa gtatctgttc tgtttttatg gctcttgctc 19380
tttggtgtgg aactgtggtg tcacgccatg catgggcctc agtttatgag tgtttgtgct 19440
ctgctcagca tacaggatgc aggagttcct tatggggctg gctgcaggct cagcaaatct 19500
agcatgcttg ggagggtcct cacagtaatt aggaggcaat taatacttgc ttctggcagt 19560
ttcttattct ccttcagatt cctatctggt gtttccctga ctttattcat tcatcagtaa 19620
atatttacta aacatgtact atgtgcctgg cactgttata ggtgcagggc tcagcagtga 19680
gcagacaaag ctctgccctc gtgaagcttt cattctaatg aaggacatag acagtaagca 19740
agatagataa gtaaaatata cagtacgtta atacgtggag gaacttcaaa gcagggaagg 19800
ggatagggaa atgtcagggt taatcgagtg ttaacttatt tttattttta aaaaaattgt 19860
taagggcttt ccagcaaaac ccagaaagcc tgctagacaa attccaaaag agctgtagca 19920
ctaagtgttg acatttttat tttattttgt tttgttttgt ttttttgag acagttcttg 19980 ctctatcagc caggctggag tgcactagtg tgatcttggc tcactgcaac ctctgcctct 20040
tgggttcaag tgattctcat gcctcagcct cctgtttagc tgggattata gacatgcact 20100
gccatgcctg ggtaattttt ttttttccc ccgagacgga gtcttgctct gtcgcccagg 20160
ctggagtgca gtggcgcgat ctcagctcac tgcaagctcc gcttcccgag ttcacgccat 20220
tctcctgcct cagtctccca agtagctggg actacaggcg cctgccacca cgtccagcta 20280 attttttgt atttttaata gagacggggt ttcaccgtgt tagccaggat gatcttgatc 20340
tcctgacctc gtcatccgcc gaccttgtga tccgcccacc tcggcctccc aaagtgctgg 20400

-continued

```
gattacaggc atgagccact gtgcccggcc acgcctgggt aatttttgta tttttagtag  20460
agatggggtt ttgccatgat gagcaggctg gtctcgaact cccggcctca tgtgatctgc  20520
ctgccttggc ctcccaaagt gctaggatta caggcatgag ccaccatacc tggccagtgt  20580
tgatatttta aatacggtgt tcagggaagg tccactgaga agacagcttt tttttttttt  20640
tttttgggg ttggggggca aggtcttgct ctttaaccca ggctggaatg cagtatcact  20700
atcgtagctc acttcagcct tgaactcctg ggctcaagtg atcctcccac ctcaacctca  20760
caatgtgttg ggactatagg tgtgagccat cacacctggc cagatgatgg cttttgagta  20820
aagacctcaa gcgagttaag agtctagtgt aagggtgtat gaagtagtgg tattccagat  20880
gggggaaca ggtccaaaat cttcctgttt caggaatagc aaggatgtca ttttagttgg  20940
gtgaattgag tgagggggac atttgtagta agaagtaagg tccaagaggt caagggagtg  21000
ccatatcaga ccaatactac ttgccttgta gatggaataa agatattggc atttatgtga  21060
gtgagatggg atgtcactgg aggattagag cagaggagta gcatgatctg aatttcaatc  21120
ttaagtgaac tctggctgac aacagagtga aggggaacac cggcaaaagc agaaaccagt  21180
taggaagcca ctgcagtgct cagataagca tggtgggttc tgtcagggta ccggctgtcg  21240
gctgtgggca gtgtgaggaa tgactgactg gattttgaat gcggaaccaa ctgcacttgt  21300
tgaactctgc taagtataac aatttagcag tagcttgcgt tatcaggttt gtattcagct  21360
gcaagtaaca gaaaatcctg ctgcaatagc ttaaactggt aacaagcaag agcttatcag  21420
aagacaaaaa taagtctggg gaaattcaac aataagttaa ggaacccagg ctctttcttt  21480
tttttttttt tgaaacggag tttcgctctt gtcacccggg ctggagtgca atgatgtgat  21540
ctcagctcac taaaacctct acctcctggg ttcaagtgat tcttctgcct cagcctccca  21600
agtaactggg attacaggcg tataccacca tgcccagcta atttttgtgt ttttagtaga  21660
gatggggttt caccatgttg gccaggctgg tctcgaactt ctgacctcag gtgatccact  21720
cgcctcagcc tgccaaagtg ctgggattac aggtttgggc cactgcaccc ggtcagaacc  21780
caggctcttt cttatactta ccttgcaaac ccttgttctc attttttccc tttgtatttt  21840
tattgttgaa ttgtaatagt tctttatata ttctggatac tggattctta tcagatagat  21900
gatttgtaaa aactctccct tcctttggat tgtcttttta ctttcttgat agtgtctttt  21960
gaagtgtaaa agtttttaat tttgatgaag tcgagtttat ctattttgtc tttggttgct  22020
gtgcttcaag tgtcatatct aagaaatcat tgtctaatcc aaagtcaaaa aggtttactc  22080
ctatgttttc ttctaagaat tttagagttt tacatttaag tctgatccat tttgagttaa  22140
tttttatata tggttcaggt agaagtccaa ctttattctt ttccatgtgg ttattcagtt  22200
gtcccagcac tgtttgttga agagactatt ctttccccat ggaattatct tagtaccctt  22260
gttgaaaatt aatcgtcctt aattgtataa atttatttct agactgtcag ttctacctgt  22320
tggtctttat gtcgatcctg tgccagtacc atacagtctt gattactgaa gtttgtgtca  22380
cagtttaaat tcatgaaatg tgagttctcc aactttgttc cttttcaaga ttgatttggc  22440
catgctgggt cccttgcatt tccgtacgaa ttgtaggatc agcttgtcag tttcaacaaa  22500
gaagccaagt aggattctga gagggattgt gttgaatctg tagatcaact tggggagtat  22560
tcgcatctta acaatattgt cttccaccta tgaacatggg caaactttgt gtaaatggtc  22620
agattgtaag tatttcgggc tgtgtgggca cagtgtctct gtcacagcta cgcggctctg  22680
ccattgtagc atgaaagtag ccataagcaa tatgtatgag tgtctgtgtt ccaatagaat  22740
tttattaatg acaaggaagt ttgaatttca tataattttc acctgtcatg agatagtatt  22800
```

-continued

```
tgattatttt ggtcaaccat ttaaaaatgt aaaaacattt cttagcttgt gaactagcca  22860
aaaatatgca ggttatagtt ttcccactcc taggttaaaa tatgatagga ccacatttgg  22920
aaagcatttc tttttttttt tttttttttt tttttgagac ggagtttcac tcttgttgcc  22980
caggctggag tgcagtggcg cgatctcggc tcactgcaac ctctgcctcc caggttcaag  23040
acattctcct gcacggcctc cctagtagct gggattacag gcatgcgcca ccacacccag  23100
ctaattttgt atttttagta gagacggggt ttctccatgt tggtcaggct ggtcttgaac  23160
tcctgacctc aggtgatcca cccgcctcag cctcccaaag tgctgggatt acagggtgtg  23220
agccaccaca ccctgctgga aagcatttct tttttggctg tttttgtttt ttttttaaac  23280
tagttttgaa aattataaaa gttacacata tacattataa aaatatcttc aagcagcaca  23340
gatgaaaaac aaagcccttc ttgcaagtct gtcatctttg tctaacttcc taagaacaaa  23400
agtgtttctt gtgtcttctt cccagatttt aatatgcata tacaagcatt taaatgtgtc  23460
attttttgtt tgcttgactg agatcacatt acatatgtat ttttttactt aacaatgtgt  23520
catagatatt gttccatagc agtacctgta attcttatta attgctatgt aatattttag  23580
aatttctttt taaaagagga cttttggaga tgtaaaggca aaggtctcac atttttgtgg  23640
ctgtagaatg tgctggtgac atattctctc taccttgaga agtccccatc cccatcacct  23700
ccatttcctg taaataagtc aaccacttga taaactacct ttgaatggat ccacactcaa  23760
aacatttagt cttattcaga caacaaggag gaaaaataaa ataccttata aagcactgtt  23820
taatattgta ttaaattgga tcaatttggg ggctagaatg tatgttagag acatgatatg  23880
tccataggtc cttgctatca cagtgaggtc tcagggacag tcgtttggta tcatttggga  23940
tctcataagc agactctctc tgcttgacct gacaaatcag agtctgtgtt ttaacaggtt  24000
cagtgagtga cttacatgca cattggagtt tgggaagctc cactgtaggt gcttagacct  24060
tacctttgtt gttgctaata acaatgcaag catttgggag gaagacctgt gttgctcata  24120
tgtgtccagg tgtagctgag gtggccttgc ttatctgctg tagggccgtt gagcatttct  24180
gtagctgtga tgagtgagct gaggtgagcc tgcggagagc tcccagccat tggtagtggg  24240
actcgcttag atgaactgga aggacccttt catctgagca gccactatgg agaaaaacaa  24300
ccgaatgagg ggagagacaa tgtgcaattt tatttagggc acaaaggaga gctgtggtta  24360
gaaggtgaca tttgagtgga aagggggcaa gccatgtgta tagcgggaga agagaggtcc  24420
aggcagagtt aacagaaggc agaaatgctt tccatgtttg agaaccagta aggaggccag  24480
tggctgaagt aaggtgaagg gcagaaataa ggatgaggct gcgagagatg agaggttaga  24540
gacgagcgtc ttgtgcacca agataagctt gtgtggtcaa aacaagtagt ttaatttatg  24600
tttttaaaag atcattttgg ctgggcacaa tggttcatgc ctgtaatacc agtagtttga  24660
gacggtgtgg tgggaggatt gcctgaggcc agacgaccag catagccaac atagcagcac  24720
ctataaggtc tctacaaaaa actttaaaaa attagctggg catagtggtg tgtgcctgta  24780
gtcccagcta ctcaggaggc tgaggaggct ggaggattgc ttgagtccag gagtttgagg  24840
ctgcagtgag ctatgattat gccactacac tacaacctgg gcaagagagt gagaccctgt  24900
ctctaaatat acacacacac acacacacac acacacacac acacacacac acacacacac  24960
acacacatat atatgtatat atatgcattt agatgaaaag atcactttga caataccaca  25020
tgctggtgag gatttagaaa aactaggtca cttattgctg gtgggaatat aatatagtac  25080
ggccactctg gaaaacagtt tggcagtttg tcataaaact gaacataccg ttagtataca  25140
```

-continued

```
gcccagcagc aactacaatc ctgggcatta atcctagaga aatgaaacct taatgttcac  25200
ataaaaacct atactcaagt atgcatagca gctttaccca taatatctaa gaactggaat  25260
cagctcagat gtccttcaac aggtgaatgg ttaaactact cagtaataaa aaggaatgag  25320
ctactgatag catgcaacag tttaggtgaa gttatgctaa tgaaaaaagc caatcccaaa  25380
aggttataca tactgtatga ttctatgttt ttttgcaatg gcacagtttt agggatggag  25440
aatagattag tggttgcctg gggttagaga tggggtagta gagtaggtta gtggtggcag  25500
aggagagaaa agagagggag gtgaatgtgg ttataaaagg acaacacagg ggaatacttg  25560
taatggaaat gctttgtctt tttttttttt tttttttttt tggcgacaga gtcttgctct  25620
gttgcccagg ctggagtgca gtggcatgat cttttctcac tgcaacctct gcctcctggg  25680
ttcaagtgat acttgtgtct cagtctccca tgttcagagt gaaacaaacc agaggtaatg  25740
ttcatccaaa taatccaaca cacatgacat taaaacatca agatcaggtc ggacgtggtg  25800
gctcatgcct gtaatcccag cacttttggg aggccaaggt gggcagatca cttgaggtca  25860
ggagttcgag accagccggg ccaacatgat gaaaccccat cttgactaaa aatacaaaaa  25920
ttagccgggc atggtggtgt gcacctgtag tcccagctac ttgggaggct gaggcaagag  25980
aactgcttga acccgagggg cagaggttgc agtgagctga gagtgcgcca ttgcacttca  26040
gcctgtgtga cagagtaaga ctccatctcc aaaaaaaaaa aaccaagatc aattaaaata  26100
cagcattact gggccgggtg tggtggctca cacctgtaat cccagcactt tgggaggccg  26160
agatgggcag atcacgaggt caggagatcc agaccatccc ggctaacacg gtgaaacccc  26220
gtctctacta aaaaatacaa aaaattagcc gggtatagtg gtgggtgcct gtagtcccag  26280
ctacttggga ggctgaagca ggagaatggt gtgaacccgg gaggcagagc tggcagtgag  26340
ctgagatcgc gccactgcac tccagcctgg gcgacagagc aagactccgt ctcgggggaa  26400
aaaaaaaaat aaataaatag aatgctgtag tgtccttgag tttacatgcc cctccttacg  26460
cttgtgtgcc cgtgcagatt gcttgattac acaattagag gaggctggcg gaggattgtt  26520
ttaatttttt tttttttgag acagtctggc tctgttcccc aggctagagt gcaatggcgc  26580
aatcttggtg cactgcaacc tctgcctcct gggttcaagc agttcttctg ccgcagcctc  26640
ccgagtagct gggattatag gcgcccgcca ccacgcccaa ctattttttg tatttttagt  26700
agagcagcgt ttcaccatgc tggccaggct ggtctcgaac tcctgacctc agatgatctg  26760
ctgccccagc ctcccaaagt gctgggatta caggcgtgag ccacacctgg ccgtttgttt  26820
taattttgaa ggtgaagtga aagtgactac atttaccaaa agtgattgaa aagccaggac  26880
tgttcttacc ctgtttttcc agttcttgct cagagcaagg tggtttcttt ttcacttaat  26940
caccatactt acttttcatg tagaacaagt cagtttgagt tatcagttca tcatcttaac  27000
taaattccat gggggaagga attagtttta gtttcttaaa cttccaggtt tgcttattgg  27060
acaaaatgag atagcaaggc agtgttttta agttagattt tttatttctt tggtaataca  27120
attttctcag aaacttagta gtcttttagt ttagttgttt ttagttggtc ctatgttttg  27180
gatcacccct ctctacttta ttttgatagt gccaactgtg aagacatctg aagccatagg  27240
tttggatggg aaggaggcat ctttagcctg atcatcttcg ccaggctgtt tatctccttt  27300
tgcttggctg agaagtctta ataggaggct tattcccagc tatttgggga catagaagca  27360
gttagccatt gcttatattt tactgaggtc tgtgtggtat gttgattgta gtcagttaac  27420
gattttgaga actgaaggca gcctggtata tatagagtag gtattagact gtgtttcttc  27480
taattgaatt tcccatctct tgtaatctat gccatcatct tctgtactgc tgagaaagaa  27540
```

```
agaaagtttc taatcaaact ataccactgg ttgtaagatg cagtttggct ttagtgatgt  27600
taacacatga ttcaaacgtg aaattgattg agtattggtg aaatacagag gagatttaaa  27660
gccagaagac ctgggtttaa atgctggctg tatgacttca tatctgtgtg atcttgggca  27720
tgtcatggtt ggcacttcaa tttcttctct ctataatggg ggaagtgagg ccagtcatgg  27780
tggctcatac ctataatccc agtgctttgg gaggccaaga tgggaagatc gcttgaggcc  27840
aggagtttga gcaattgggc aacatcgtga ggccccgtct ctacaaaata ttttgaaaaa  27900
attagccagg cccagtggtg cgtgcctgtg gtccgcgcca ctcaggaggc tgagacggga  27960
ggatcctttc agcctaggag tttaaggcta aagtgagcca tgattgtgct atcgtactcc  28020
agcctgggca gcagagcaag atcctgactc taaaaaaaag taaaataaag taaaatgggg  28080
gaaatgaact gctttagtaa catcatctgt tttttctgtg agcagcgtag cttgacagcc  28140
attggtgaac tcgtgccctg tgcttccctg tccagatccc cattctgccc gcaacatgga  28200
gtataacggt ttattcatag tagtcgagaa acactcactg aatgaatgaa tgaggtgtag  28260
aactaagtgg agtgggtaat tcaacacata ttaatttcct tctttttttt atttttagaa  28320
agaaagaact ttcagctacc aagaaagacc gtgtgaatca ttgtctgaca atatgtgaaa  28380
acatagtggc acagtctgtc aggtaattgc actttgaact gtctagagaa aataagaact  28440
ttgtatattt tcagtcttaa tgggctagaa tattctttgt gtcccagcta ttttaaatgg  28500
attcagaaat ccatttaaga tgaagaagga ccctttttccc atatttctgg ctatatacaa  28560
ggatatccag acactgaaat gaataatgtt cccttttttgt aatcttttat gcaaaaaatta  28620
aaaccattat ggtaattgaa caacatgttt atgtttagtt aacaccctta gcaactatag  28680
ttattttaaa accatctatg gtttgatatt tttgcatttg ttgcaatagt aggaacagca  28740
caagacagtt cagtttgtct ctcttatttg ctttttcttg gcagtttgct gtcctattgt  28800
acctctgctc ctagcagtgg ctggagccca ctcctctgtg cttcgggatt agtggggatc  28860
gtggggcatt gactgtaggt cagctttcct tgcttgatct ttctcactgg gatgaactag  28920
cagcaccttc ttttgtagct gctttgcttt tgactatctt tctgaccgtt gttcctagta  28980
gctgtagatg gtaaatatat ttaggcctgt ttccaatggc tcagtaggag acatattcac  29040
ctatgatatc tgaattctgt tacccacatg ggcatgcgtg aaatagttgc cttgccttac  29100
tttcccttgg aataaataat tcatgttatt ctcctggtag aagctagaaa aagcctttat  29160
agtcagtcag aaaaaaattt ttagacaaat aatcttgatt ttagtactga caaaaacgtg  29220
tggtgattct tttttaatt tttttttgag acggagtttc actcttgttg cccaggctgg  29280
agtgcaatgg cgtgatctcg gctcactgca acctctgcct cctgggttca agtgattctc  29340
ctgcctcagc ctcccaagta gctggagtta caggcatgtg ctactgtgcc cagctaattt  29400
tgtattttta gtagagatgt tggtcaggct gatctcgaac tcccaacctt aggtgatctg  29460
cccgcctcag cctcccaaag tgctgggatt acaggcgtga gccagggcgc ccggtgattc  29520
atttgttttt tcaaaaaatt tcctcttggc cattgctttt cacttttgtt tttttttttt  29580
ttttgagacg gagtcacgat ctgtcaccca ggctggagtg cagtggcatg atcttggctt  29640
actgcaagct ctgcctccca ggttcacgcc attctcctgc ttcagcctgg cgagtagctg  29700
ggactacagg tgctcgccac cacacccggc taattttttg tatttttagt agagatgggg  29760
tttcaccgtg gtcttgatct cctgacctca tgacccgctc aactcagcct cccaaagtgc  29820
tgggattaca ggcgtgagcc accgcgcccg gccctctctt gtctttttat tgtggtaaaa  29880
```

-continued

```
tgcacataaa attgactgtc ttaaccattt ttaggggtac agttcagtat atatattcgt  29940
aatgttgtac agccatcact gccatctact tcataagttt ttcttctgtc aaaactgaac  30000
atctgtcttc attaaactcc ctatcatcca ttctttcctg tagtcccttt ctactttctg  30060
tctgtatgag tgtaactgct ctggagacct catgtaagtg gattcctaca ggatttgtgt  30120
tttttttttg gtgatctgct tatttttaat gcctctgtgc atttgtatta tatactttca  30180
aagtgatttc acaaaaccgt ttcattttag gttaactcat ttctgttgtt tgtgaaatac  30240
tgtgtatgat tctgttctgt ttctgtctaa tttgtggaaa tgttgtggga agaaaatgaa  30300
ataacaaatg agcatatgtc ctgaaaaataa aaatataaaa attctaagtt agcatgctat  30360
tgtagaatac aacgctatga taaaagtagg aaaaaaaaag gtttgaattc tatctctgct  30420
acctgtgtaa gctgggtgac tttagataag ctgtaacgtg tttgagcctt actggctcat  30480
ttttgaaatg taatccctag ttacacagtt cttgtgggat cagatggtac atgtgaaaca  30540
ctgtgaaaaa gcaactgcat agatatgttc attagccacc tgagcgggaa gcgtatccca  30600
ttgcgatgcc catcatccaa agctatatgt tatctttact tttttttttt tgagacagag  30660
tcttgctctg ttgcccaggc tagagtgcag tggtgcaatc tcagctcact gcaagctcca  30720
cctcccgggt tcacgctatt ctcctgcccc agcctcccaa gtagctggga ctacaggcac  30780
ccgccaccat gcctggctaa atttttgtat ttttagtaga gatggggttt caccgtgtta  30840
gccaggatgg tcttgatctc ctgacctcgt gatccgcccg cctcggcctc ccaaagtgct  30900
gggattacag gcgtgagcca ctgcccctgg ccatctttac tttttttgtg aaatgacttt  30960
aaatacttgg caaacatttg gtcattgttc atctgatctc caccatccag gtctcagaga  31020
acataatttc tctctgaaag cttattgacc caggaaataa gatctctttc aatctgagtg  31080
cgtcaggctt tattcttgtc attttgtctt ttgataattt tcaaatggaa ttcatggaat  31140
gttggcttat attcatatat tagtaaagta tgttgagaca tcttaagatt gatttgtggt  31200
tctatatgcc atattaaatc aaaataatag ctgttaatgg ttttcacatt agtctgtctc  31260
ttgtttttat ggagtaatgc tgagagttca ttatgcttgt tctacagaag agcatgttaa  31320
aaggagtttt tggagtcaga gaggttattc ttggtttcat aggatacact ctatactttt  31380
tagggatttc agagtatata gctgaaggtg atattttatg taaatatgtt ttatggaaac  31440
ttattgctca tcgctgtttc ctgttaactc tcctaaaata taattaaact tttggaactt  31500
ttttatagct tttgtgctag actaattttt gtctctaatg aggttatata aatggcagct  31560
tctgacgttt tcaatgtagg aagtcattta aaacttcatg tatattgtga aaatgtagtc  31620
tgctttaagc tctctaaagt ggtctaagtt actggttcct aagtatggat gagcatcaaa  31680
atcatctgga aaatttgtta aaaatacagt aatgaaggca cctcactgtc ctttttccca  31740
aacatacttc tgcattctgt ttgagtaggt agggactaca catttttcac aagtatcctc  31800
ttgggaatac ccaggaatgc ttacttgagc aacctcttac taatatgtac cttgataagg  31860
tggctaggta aacataaata tacaaaaatc catagatctc ccatatatta gcataaatca  31920
gctagaaaat ataacgttta aagatctagt tcacagtagc accaatatat cgaactctaa  31980
ggaatcgata aatatgcaaa aactttataa aaacttctgt taatgtttct gaaagatata  32040
ggtgaccact ttctagatag gaagatttta tattactaag ttgaattttc tctaaattaa  32100
cacagaaatt taaaataatc ttgatcaaaa ttctagtaga ggtatttttg aacttgttca  32160
ctgcaagaat aaatacataa ttgcaaagaa tatctcaaaa tcatcaccag gcctggtgtg  32220
gtggcccatg cctgtaatcc cagcactttg ggaggctgag gcaggcagat cacctgaggt  32280
```

caagagtttg agaccagctg gaccagtgcg gtgaaacact gcctctacta aaaatacaaa 32340
aattagctgg gtgtggtggt gcatgcctgt agtcccagct acttgggagg ctgaggcagg 32400
agaattgctt gaacccagga ggtacaggtt gcggtgagcc tagatcgcac cactgcattc 32460
cagcctgggc gacaagagca aaattctgtc tcaagaaaaa agagaaaaaa gaaaaagaaa 32520
tcaacactaa tatggtgaga cttaatgtat gtgacattaa aatagtgatt ggatgttaaa 32580
acaggtatag aacagaaaga agagtgtatg tgtgtatctg tatgaattta tgatgggtgt 32640
aacatatatg tattagggaa atgagggaaa tgatacattt ctctgacttt gggagaacat 32700
tatatctcta cctcatattg caaacaaaca taaagttcag attaattacc taaatgtgaa 32760
aaaatgaaat aatttcttta aaaaatgtaa tcttagtttg aggaaggtta acattataaa 32820
ggaaaaaact gttttgagtg gaatatagtt caatatgtca aaatccacct tcaacaaaat 32880
tgaaagtaaa ttgaacttgg ggaaagtatt gacagcatat agatcaaagg ttactagcct 32940
gtgtaaagag cagttataaa tatcgttaag aaaaacactg tcgacctgtc ggcaccttgt 33000
tctccgactc ccagcctcca gaactgtgac gagtaagtgc ttattgttta aaccacccag 33060
tctgtatgtg gtattttgtt atagaaactc aagctgatta ggacactagt aatcagtaga 33120
ctgaaactga aacaaaaata agaacctttt ttacctgtca aattggcaaa cattaagaat 33180
attcagattt ttgtcagagg tgatacaacc ttctaagaag gcaatttggg aaaatataaa 33240
gctttagatt attatatgtc tgacctagca gttttacctc tagggtgctt accccctagga 33300
aagtgtgtaa tgatattggt gcagtgccct tcatcccatt agaaaattaa aaataacctt 33360
aatggcctac cactaaaagg ggattgaaaa tttaagatat atttatttat gtgtttattg 33420
agatggagtc ttgcactgtc cgcctgggcc agagtgcaat ggtgcgatct cggctcactg 33480
caacctctgc ttcccgggtt catgtgattc tcctgcctca gcctcctgag tagctgggat 33540
tacaggctca caccaccgca cccggctaat tttttgtatt tttagtagag atggggtttc 33600
actgtgttgg ccagactggt ctcgaactcc tgacctcatg atccgcgccc ctcggcctcc 33660
cagtgttggg attacaggtg tgagccactg cgcctggcca gatacattta tacaagagaa 33720
tgttagttaa cattcataga tatttatatt ttgtttactt tttattaaaa aaattttttt 33780
tagagacagg atcttactct gtcacccagg caggatgcag ttgcacaatc atagcccact 33840
gcagcctgaa ctcctgggct taagtgatcc ttctgcctca gccttttgag tacctggggg 33900
actttaggca gtgctactat acctggctaa tttttaaatg ttttatagat gagatcttgc 33960
tgtattgccc aggctggtct agaattcctg ggcccaagtg atcctcccac cttggcctcc 34020
caaagcgctg agattacagg catgagccac cacttctgac caatagatat ttatatttgt 34080
gactggaaaa tatattaaca atgtgttaaa aaattcagtt aaaaaataat gaaagatttt 34140
tgcttctggc taagatagaa taacaaggac agcatttatc ttcttgcctt gaaatagttg 34200
aaaacggaag aaatatatgt aacagtggtt ttcaagttat tgggcatcag gcaaagaaga 34260
atagttatcc caggaaaatg aatgtggaga gccctacaat ttccttacat tactgcctgg 34320
tcatggcaag aggaaaaact gagaggagac tgaggctgag ccagtggttt gctgggttga 34380
ggaggcagag ctgggagtgc agagatgcaa ggtggtgaga gcccatatgg aagaatacca 34440
gggaagagag ctgcagaggg agctccggag acctgcaccc tgccctctca gtaccctgtc 34500
atgtgtgtag ctgagtactg acgagcactt gcttgtgcgg aaatgaccca gggctggagg 34560
tagagccacc tgaaaggatt agaaggaaca gttgctgaaa gtcacacagg gccaggaaga 34620

-continued

```
atttctaatc acaccagttg gagtggaaaa cctcagctct catagagcag gtagggtact  34680
cagaagggtt tgcccaccta gccccagact aagtttcgtt actctgaccc tacctaatat  34740
taaaaagaga ttaattaaat tgttcgcaac aaaaataata tatttcagtg tttgtaacac  34800
gtagaagtga attgtatgac aatagcataa aggctggaag agcagaaatt gacatgtatt  34860
tgcgctgggc agaataatgc tcccctcttt ccccaaaaga tatcaagtcc taatccctgg  34920
agcctgtaaa tattacttta tatggaaaat tgttttatga tgtgattaaa ttcaggatct  34980
tgagatgagg gggctatctt ggatgatctg ggtaggcact aaatgcaatc acatatatat  35040
aaaaaggagg cagagggaga ttttacacac agagagaagg ccctgtgaag atggaacaga  35100
aagatttgaa ggtgctggcc ttgaaaattg gagtgatgaa gctataagcc aaggaatgca  35160
gcagccacca aagctggaag aggcacggag cagttctcat ttagagccta ctccagaggg  35220
aatgtggtgc tgccaattcc tttttttttt ttttttttaa gatatcattt accccttttaa  35280
gttggttttt tttttttttt ttttttttta gtatttattg atcattcttg ggtgtttctt  35340
ggagaggggg atttggcagg gtcataggac aatagtggag ggaaggtcag cagataaaca  35400
tgtaaacaaa ggtctctggt tttcctaggc agagggccct gccacgttct gcagtgtttg  35460
tgtccctggg tacttgagat tagggagtgg tgatgactct taacgagtat gctgccttca  35520
agcatctgtt taacaaagca catcttgcac cgcccttaat ccatttaacc cttagtggac  35580
acagcacatg tttcagagag cacggggttg ggggtaaggt tatagattaa cagcatccca  35640
aggcagaaga atttttctta gtacagaaca aaatggagtg tcctatgtct acttctttct  35700
acgcagacac agtaacaatc tgatctctct ttcttttccc acatttcctc cttttctatt  35760
cgacaaaact gccaccgtca tcatggactg ttctcaatga gctattgggt acacctccca  35820
gatggggtgg cggccgggca gaggggctcc tcacttccca gatggggcgg ccgggcagag  35880
gcgcccccca acctcccaga cggggcggcg gctgggcggg ggctgccccc cacctcccgg  35940
acggggcggg tggccgggcg ggggctgccc accacctccc ggacggggcg gctggccggg  36000
cgggggctgc cccccacctc ccggacgggg cgggtggccg ggcgggggct gccccccacc  36060
tcccggacgg ggcggctggc cgggcggggg ctgcccccca cctcccggac ggagcggctg  36120
ccgggcggag gggctcctca cttcccggac ggggcggctg ctgggcggag gggctcctca  36180
cttctcagac ggggcggctg gtcagagacg ctcctcacct cccagacggg gtggcagtgg  36240
ggcagagaca ttcttaagtt cccagacgga gtcacggccg ggcagaggtg ctcttcacat  36300
ctcagacggg gcggcggggc agaggtgctc cccacttccc agacgatggg cggccgggca  36360
gagatgctcc tcacttccta gatgggatga cagccgggaa gaggcgctcc tcacttccca  36420
gactgggcag ccaggcagag gggctcctca catcccagac gatgggcggc caggcagaaa  36480
cgctcctcac ttcctagacg gggtggcggc tgggcagagg ccgcaatctt ggcactttgg  36540
gaggccaagg caggcggctg ggaggtgaag gttgtagtga cccgagatca cgccactgca  36600
ctccagcctg ggcaacactg agcactgagt gagcgagact ccgtctgcaa tcccggcacc  36660
tcgggaggcc gaggctggca gatcacttgc agtcaggagc tggagaccag cccggccaac  36720
acggcgaaac cccgtctcca ccaaaaaaca cgaaaaccag tcagacatgg cggtgcgtgc  36780
ctgcaatccc aggcacttgg caggctgagg caggagaatc aggtagggag gttgcagtga  36840
gtagagatgg tggcagtaca gtccagcctt ggctcggcat cagagggaga ctgtgcgagg  36900
gcgagggcga gggcgaggga attccttaat ttcagtttag tgatactaat tttggactct  36960
ggcctctaaa actgtgaaag aaaaaatttt ttgtttgttt gtttctttta agccacatag  37020
```

tttgtggtaa tttgttacag cagctgcagg aaactaattt atgctgcatg tgaaatggtg 37080
taataaggta gattgtgatg aagatacata gtataaacaa ttaagcaaca actaaaagca 37140
caacaaggaa ttatagctaa tgaaccaaaa aaggagatta gaataataaa aatggtgaat 37200
cccaaagaag ccagaaatag gggaagaggc aaataaagga aagaaagagc ttgatggtag 37260
atttcaacct aactatgtca aaaaggacat tacatgtaaa aggcagcgat ttttcagatt 37320
gaatggaaaa gtaagactcg gtatatgctg ctgcctgcaa gaaacacatt ctaaatataa 37380
aggcaaaaat aacctacagg taacagaacg gaaagaagtt cactgtgctt acaagaatta 37440
gatgcaagct agactggttc tgttaatatc agacaaagtg gatttcaaag caaaggctct 37500
tgcccaggat gagatggtca tttcataatg atgaagggga ttcgttcatc agcctggcat 37560
agcaagctga aatgtttatg caccggacta cagagctaaa atacatgaag caaagcctga 37620
cagaactaca agtagaaaca gacaaatcca cagtgataga gatttcagta gccgctctca 37680
atgatttgta gaacacgtag ccataatatc tggatctaga acacttgacc aacactgtcc 37740
cctgtgcaac ctcattggca tttacaggac actccaccca gcaccagcag aagagacact 37800
ctctcaagtg ctcacagaat gtttgccaag atagagcaga tgctgggcca taaaacaagt 37860
ctctaaatta aaagcattca aattattcag agtatgtttt ctgacctcag tatcattaag 37920
ttggaatata ttataggaag ataacctgga aaagcctcag atatgtggaa aaacccattt 37980
ccacatggcc catgggtcag aagtgaagtc aaaagggaaa tttgaaagtc ttttggattg 38040
actgatataa aaacaataga tttctaaact tgtggggtgc tgttacagca tagtaaatgg 38100
aaatttctag cattaaatgc ctgttttagg aaagaaagat ttcaaatcaa tgacctcagc 38160
ttctaccttt ggaaacttga aaatgacaag caaatggaat ccagagttac cagaagggcc 38220
aggtacggtg gcttatgcct gcagttctgc cactttggga ggccgaggca ggtggattgt 38280
ttgagactgg cagttgaaga ccagcctggg cagcctaggg agaccccata tctacaaaaa 38340
acaaaaaaat tagccaggtg tggtggcatg tgcctgtagt cccagctaac caggagtcta 38400
aggtgggagg attgcttgag tctgggaggt tgaggctgca gtgaactgtg attgtgccac 38460
tgtgttccat cctgggcaac agaatgagac cctgtctcaa aaacaaaaac agttactaga 38520
agaatggaca tcataaagat aggagcagaa gtcagtaaaa tagaaaacaa aaatacatag 38580
gaaatcaata aaaccaaaag ctggttcatc aagaacatca ataaattggt aaagctgata 38640
ggaaaaacag tgaagtcaca aattagcaat atcaggaatg agggagatga cagtagtata 38700
gattatatag atattaaaag gactgtatga ggcaggtgtg gtggttcacg cctgtaatcc 38760
cagcaccttg ggaggccgag gtggacagat cacctgaggt caggagtttg ggaccagcct 38820
ggccaacatg gtgaaactct gtctctacta aaaatacaaa aattagttgg tcgtggtgct 38880
gtgtgcctgt aatcccagct acttgggagg ctgaggcagg agaattgctt gaacctggga 38940
ggcggaggtt gcagtgagct gagattgtgc cgttgcactc cagcctgggt gacagagcaa 39000
gactccatct caaaacaaat aaataaataa aaaggactat atggtaatat tatgaacaac 39060
tttatgccaa taaatttgac aacttataga tgaaatggat gagttccttg aaagacacag 39120
aaactattaa agctctctca agaagatata gataagctga ttagccctat atctatttta 39180
ttgaatttaa atgtaaaaat caatatttag ttactggaaa acttttaagt gtggttggaa 39240
atggtatacg aactttttca actgaatttt atgaagtcta atcacaggta aaggttttct 39300
gatgaaaatt tagtgtctga attgagatat actgtaaaaa atgttatata tcttaattat 39360
ttcttcacat taattacatg ttgaaataat actttgggtg tattgggtta aattaaatat 39420
tatgaaaatc ttgcctgttt tctttttact tttgatgcgt cagctaggaa atataaaagt 39480
gtagctcaca ttctgtttct gttgacagta ctgctttgga gcacagtgtt tgaatgatct 39540
atcatttcaa agacctttcc tcagttcgtt attcatggct gtctgtattc cacatagata 39600
aggtctgaaa tactgctaag tggcatgttt tgttttatgc ttttataagt ttgttgatca 39660
ttactgatgt ggacttttgg tgcctcttag gctcattgct atcttccaac cattgtttgc 39720
aatttttacc tagagataaa gagaaagaga catttggttt cagagtagtt agattgggat 39780
catgaaagag caacctcatt ttgatgcttc aaaaatagca catcccccgt attactggga 39840
tttgctattc ttgggattac ttcaagaaca tccttgtgtt actggtttgg atgcttctga 39900
atgctgtgaa gtcagtttca tgtacatggc tcatcagttt agctctctct tggctttgtt 39960
tagacagttg gagcatgatg gcctaaacag cttctttcaa ttaaacattt taaaatagtt 40020
tacaaatagt aaacaaactc cagtttttgt gactctttgt ctcgcacaac aaaaacacaa 40080
tctgaccatg atcatctggc atcttagggt gaaatatggt tatactttgg cccataccga 40140
aagcaagatt aaaaaggggc aggagagata gactgctgaa ctgattttca aggttccaag 40200
aatattgtag gttaagagta aaagtaaact tttggtagaa agcagtgggt tgtctaggat 40260
tgaagtatct gaagttttta aacgaaaatt taaaaagaaa aatgagaatt gccttacaag 40320
tacaatctct tctttttaa aaaataaact ttattttgaa atagttttag atttatagaa 40380
aaaaattaga tagggtagga agttttcata taccctacat ccagttaccc cagttattat 40440
catcctaatt tagtgtgaga cattttcatg tttaatgaat caatattgat atgctattaa 40500
cttaagtcca gactttattc agattttctt aatttctatg taatgtcctt tttctgttcc 40560
agaattccat gcaggacacc ggatacctca ttacatttca ttgtcatgtc accttaggct 40620
cctcttgaca gtttctcttc ttttttgct tagaaattct ccagaatttc agaaacttct 40680
gggcatcgct atggaacttt ttctgctgtg cagtgatgac gcagagtcag atgtcaggat 40740
ggtggctgac gaatgcctca acaaagttat caaagtaaga accgtgtgga tgatgttctc 40800
ctcagagcta tcattgttgt aggctgagag aagaagcgat cattgagtgt tcttctgttt 40860
tgagtccctg aggatgtctg cacttttttc ctttctgatg tatggtttgg aggtgctctg 40920
ttgtatggtt tggaggtgct ctgttgtatg gtttggaggt gctctattgt atggtttgga 40980
ggtgctctgt tgtatggttt ggaggtgctc ttgtatggtt tggaggtgct cttgtatggt 41040
ttggaggtgc tctgttgtat ggtttggagg tggtcttgta tggtttgcag gtgctctatt 41100
gcatggtttg caggtgctct attgtatggt ttggaagtgc tcttgtatgg tttggaggtg 41160
ctcttgtatg gtttggagat gctctattgt atggtttgca ggtgctctat tgtatggttt 41220
ggaagtgctc ttgtatggtt tggaggtgct cttgtatggt ttggaggtgc tctgttgtat 41280
ggtttggagg tgctctgttg tatggtttgg aggtgctctt gtatggtttg gaggtgctct 41340
attgtatggt ttggagatgc tctggtatct gcctgcattg cttgccacac ctgcccggtc 41400
agaaggcgct atgttgacaa ttgtgcctgc acggtgccta ggtcaatgaa gggaaccgat 41460
ggtagccact ggatgctcct gggaaaatgt cactacaggc accagagaag ccagagctat 41520
gcccaaattt ctatgagtct cagttttctt aaccataaaa tgggatcaat gtttttgtgg 41580
catgtgtatg agtgtgtgtc tgtgtatgtg tgaggattaa attgtgtatg tgtgaggact 41640
aattgccact actggatcct caaagtggta agaagtgttc ttattaataa tgacatcctt 41700
acactcttac ccagcaagat tgatgggtgt ggcactgctt ctctttttcc atcacatggt 41760

-continued

```
ttccatggta tccttttgcc cagggaatct ttgctttgtg gctagcactt tgttgtttgg  41820
ctaatcacgc tttctgtggt caggacgctg gcttctctgg agccatggga ttctagctcc  41880
ctgtcttgtc cctagagtgg tcactgtctt ctctctccgc ttgcaattcc tgctttgctc  41940
gcatctcact tatgcagtga cgtatatcag tttcaccttg ttctccgtgc ctgctgatca  42000
ttggcaccac ttgcatggtg ccatttaggg cctgcttcca gttaagcttg cttctccaca  42060
ggcctaaata tccttgcttg cttcttttat tctcactggc aggaccaggg cggtctgtct  42120
ttgcatgaga cagggtctcg ctcagtcacc caggctggag tgcagtggct gatcacggct  42180
cattgcagcc ttgagctacc gggctcaagc tatcctcctg gcttggcccc ttgagtagct  42240
gggactacag gcgtgcacca ccatgcccag ctaattttta aaattatttg tagagatggg  42300
atctcgccag gttgcccagg ctggtcttga acgcctgggc tcaagtgatc ctccctcctt  42360
ggtttcccaa agtgctggga tcacaggtgt gagccactgt gcctggccct tgatgtttca  42420
gttcttgata tttgatcctc agagtcagaa aatctaaaaa gagggctatc ccaggttgcc  42480
ttggttcatg gcaaatggga cgttaagagg gcagagagaa tatgaacaga aactgttcta  42540
atattggtca tttaatgtgt aagtattgtt ctttttttaaa cctccttcat tttttttcca  42600
ggaattgctg gacacagtgg cttggtgtgt gtctgaggac tgtaggccat ggccctaggt  42660
tgtggtttta ggtctcaggt gctcttcctg gctgtctcct tgcttctttc ccatgtcctc  42720
ttctttgttt ccagccattt ctcccttatg cttaagtttg gtgcagcagg gtttggctgc  42780
tctcagattc ctgcttcctc agatgctgta gttgtcaggc ccagcgggct ggcagcggga  42840
tcaggatctg gctaggtttg ctctcactgt ggcagagtag gggaggcgt gggagagcac  42900
gtgtgacccc aggccagctg tagggagcat aggcatggtc acgtagcctt caggtcctag  42960
actttgtctt ctcatgagta tggctgtgtg tgtatggtga aaactaggtt ctacttagcc  43020
caagaaaatg ggcacatttt gcatgtggtt tctgtagaga aatgcactgg gtatctgaca  43080
tagcctggca gcatgcctcc ctcaggtagg ttagtctcag gcggtgaagc acgtgtgtcc  43140
agcaagaact tcatatgtgg cataaagtct ccgttctgtg aggtgctggc aaatcaccac  43200
caccgtcaag aggctgaagt gatttttgtc tagggaggca ggaaaggctt cctggagtca  43260
gcagccagta ggtgaaagag tagattggag accttcttaa tcatcaccgc ctcttgtctc  43320
aaggggtgcc aggaagctgt ggaggctgaa cccatcttat gctgccagag agtgggacac  43380
catgagggtc aggtcaaggg gttgtacctt gtttggtaga gaattagggg ctcttgaaga  43440
ctttggatgt ggtcagggga gtgtatcatt taggaagagt gacccggtga ggacgtgggg  43500
tagaggagga caggtgggag ggagtccagg tgggagtgag tagacccagc aggagtgcag  43560
ggcctcgagc caggatggtg gcagggctgt gaggagaggc agccacctgt gtgtctgcgg  43620
aagcaggggc aagagggaag aggccagcag cgtgctgcca tcacccagcg actggcgtag  43680
attgtgagag accattccct gctcttagga ggggctgagt tttagttttc tcttgttata  43740
caataagctt ggtatttgtt tacaaaacat ttgtaaagct aaatcaaggt ttgataaggc  43800
ttctagtttt atttaagaag taatgttgaa ataaatgttt gtccaattcg ctttgctcat  43860
ttaaggactt tcagtacaaa ctgcaacaac aggattagga tttaaacgtt tctgagatgt  43920
ttttactcct cagaatttcc cagaatgtga tctggttttg attttcaagc ttgctgaccc  43980
aataggttaa cccacaagtt ttacgaagac catctcagtc cacttacatc aactgcccat  44040
gccacggtta aagagatcat cgactgatgt ttggcacagc ttcctccctc ttgggtgggc  44100
```

```
aagcatttgg aagagaaggc tcctatgggt gagagtgggg caccaaagtc ttccctgtcc  44160
catcccctag cttgagaagc ccttctctaa tgtggacttt gtgccgttag catcgttact  44220
agcttgaagt tgaccatctg gacgtacttt ctggtttagc ctcacaagtg agcaaggagg  44280
gttgagagat gtgctgtgag gaatgtgggg ccccagctgg cagcaggctc tgggtcaggg  44340
gggcagggac cacgggcata cctgacagtg aggaggggcc acacctgcag aaaaggatgc  44400
aggactccgc cttgggaagt gttctaggcc agagcgaggg tctgtggttt ataagtacac  44460
ccacagtgct cgggaccctg cagatgtcca gggtgccgtc tgagcccgta tcatccaaca  44520
gaatgttctg ctagtgaaga ttaaagattt actccagggg ctttaggatt tattatatat  44580
atataaatcc tatatatata attttttttt tttttttttt tgagatggag tttcgctctt  44640
gttgcccagg ctggagtgca atggcgtgat cttggctcac tgcaacctcc gcctcccggg  44700
ttcaaactat tctcctgcct cagcctctcg agtagctggg attacaggcg cccaccacca  44760
cacccggcta atttttgtat tttttagtag agacggagtt tctccatgtt ggtcaggctg  44820
gtcttgaact cctgacctca ggtgatctgc ccgccttggc ctcccaaagt gctgggatta  44880
caggcatgag ccaccccacc tggccaggat ttattgtatt tgaaccatct accattttaa  44940
ttttgatgtt atgtagtatt tgatgataat gaaagttaaa ttgtttttct ttccattttt  45000
ctgtttaagt gaatgacctg tatctagttt attcagtaac ttcctgcata tatttgtttc  45060
tttcattctt aatgaatata ttcttaattt agttgctatt atgttttgct ttgccccaaa  45120
attgaaatct tagtttcctt ttagctcgtt ttagaactag tgatgggatg tgtcttccat  45180
aaatctcttg tgatttgttg taggctttga tggattctaa tcttccaagg ttacagctcg  45240
agctctataa ggaaattaaa aaggtgggcc ttgcttttct tttttaaaaa tgttttaaat  45300
tttaaatttt tataggtaca cgtattttgt aggtacatgt aaatgtatat atttatgggg  45360
tacatgagat attttgatac aggtatacaa tacataataa tcacaccatg gaaagttgga  45420
tatccatgcc ctcaagcatt tatcctttgt gttacaaaca atccagttac atgctttact  45480
tattttattt tatttttgag acagagtctt gctttcaccc atgctagagt acagtggcat  45540
gaccttggct cactgcaacc tccgcctccc gggttcaacc gaactttggg ctggtctcaa  45600
actcctgacc tcaggtgatc cgcccgcctc ggcctcccaa agtgttggga ttacaggcgt  45660
gagccactgt gccgggcctg attgtacatt ttaaaataac taaaacagtc agggcacagt  45720
ggctcatgcc tgtaatccca gcattttggg aggctgaggc aggtgatcac ctgagatcag  45780
gagttcgaga ccagcctggc caacatggag aaaccctgtc tctactaaaa atacaaaaat  45840
tagccaagtg tggtggcggg cgcctgtaat cctggctact cgggaggctg aggtagggga  45900
atcgcttgaa cctgggggtg gaggttgcag tgagccgaga tcacgccact gcattccagc  45960
ctgagcgaca gagtgagact ttgtctcaaa aaataaaaat gaaataaaat tgggccgggt  46020
gtggtggctc acaccttagt cccagcactt tgggaacctg aggcaggtgg atgcttgaga  46080
ccaggagttt gagaccagca tgggcaacat ggcaaaacgc tgtctgtaca gaaattagct  46140
gggtgtggtg gtgcacaact atagtctcag ctacttggga gattgaggtg ggaggattaa  46200
ttgagcctgg aaggttgaat ctataggtag ctgagattgt gccactgccc ttcagcctgg  46260
gcgaccaagt gagaccctgt ctcaaaagaa aaacaaaaaa acaaaaaaca aaccactatt  46320
atcgactata tattattgtc tatgatccct ctgctgtgct gtcgaatacc aggtcttggg  46380
cccttatttc catcactgag caaacttcac tctgttaagc agcaggtgtg ggatttcatc  46440
gttattcagt aattcacaat gttagaagga aatgctgttt ggtagacgat tgctttactt  46500
```

```
ttcttcaaaa ggttactctt tattagatga gatgagaatt aaaaatggta acttacttta  46560
tatctttata attgaagccc actagacctt aaagtagtta ccagatgttt tatgcattta  46620
aatggccttt tctctaaaat tagaaagtaa caaggaaaga aaatgcttcg tttctatgca  46680
accctcttgg tgactagtat gtgactctta atgcaaccct cattgcaccc cctcagaatg  46740
gtgcccctcg gagtttgcgt gctgccctgt ggaggtttgc tgagctggct cacctggttc  46800
ggcctcagaa atgcaggtaa gttgtacact ctggatgttg gtttttgtcg ggggccagct  46860
gctactgatc ctttatgtct cagctcagat gtcatttcaa aagtctgctc tgccctctcc  46920
aaattgcagt cgaccttgcc ctgtttatgt ttccctcata gcactaatcc atgtcagaaa  46980
ttgtcacgta cagtctatct gtgtgcttgt ttattttcta tcccaccctt ccgcaagaga  47040
cttatgggat gtgtgcccca ggacagcagg ggtcttactg tcttatgctc tgttgcagcc  47100
cagcagcgat aacagtgtct gcacatagta cttgcttaaa agatacttgc caaattgttg  47160
aaggttgagg taccaatttc attattgctg actataggag ttatagcaaa atatccattt  47220
gtctgttaca tgagttaaaa atatggttgt tgcactgtga atagtttggt ttagtcaaaa  47280
cagttgtatc ttaacggatt gagaaacaaa agcaggacca cttttcatca gctccctcct  47340
tctccttaac cagcaataca tgctgatgct gatatcccat agaccctcag ctccatcctg  47400
agtcactggg aatgtggtct aaaccctcac tattaatatg aactgagttt caataagaat  47460
cttatatggg tcgggcatag tggctcatac ctttgatccc agcacttcag gaggccaagg  47520
caggtggatt gcttgaccca gactaggcaa catggtgaaa cgccgcctct acaaaaaata  47580
caaaacttag ccaggcatgg tggtgcgtgc ctgtggtcac agccactcga gaggctgagg  47640
tgggaggatc acttgagcct gggaggtgga ggtcgtgttg agccaagatc gcaccactgc  47700
actccagcct gggcaacaga gtgagacctg tctcaaaaaa accaaaatcc agaaaagaac  47760
ttatatggct gcagaggtat aatcactaag gaaatttcct tttgtataat ctttttttctt  47820
ttactatcat ttaaaaaaat gtgttatatt tctgaagcaa cacatccagg ttctgcacat  47880
agcagccaaa gtgaccttaa agaatataac tgggtcttgt cattccctta tttaaactct  47940
tgtacccatt tcccagtgcc gtttagatag agattccaga ctcgtcaatg gctctgtcac  48000
ctcagacacc ctgcattgac tcattagtct gattagagtc aggtttttct tcctcctgat  48060
ggtttttttt tccccccttag ttctcagcgg aacagtcact tccttaggga ggtttcccca  48120
gccaccctct gaggccgtgc ttgttgccag actctgccac tagagggcag ggctgcacca  48180
ctcctggcac ctcgcacccg gcctgccctg tcactctgtg tgttgggtga attcctgtga  48240
tctgtgactc actgctctgt gtcctacaca ttcggctttt cttctctccc cacaacccca  48300
ttttataatt ctcctttttc aggaaagctt tattcccatt taaaaatttt tgtttttaaa  48360
atggtatttt cttacactta ttttctaatt aaaaatgagt gttttaagaa gtattatgat  48420
ttactgcaaa taatttttaa acccagcctt ttagatcctc tgtgatcata agagaaatga  48480
aggatgtctc ccaacacttg agcttcatcc acatttcatc ctcctgttct ttcagctgag  48540
ttttccccat cccattaggg actgttggaa tataaaactg gcttttccct aacagggaat  48600
gaattgcttc tgtttctcct gaaggagagc tggaagaatg acttgcgttc ttttgcatac  48660
acaggcctta cctggtgaac cttctgccgt gcctgactcg aacaagcaag agacccgaag  48720
aatcagtcca ggagaccttg gctgcagctg ttcccaaaat tatggcttct tttggcaatt  48780
ttgcaaatga caatgaaatt aaggtatgat tgttgcctca ggtcacaaac atgcgagtga  48840
```

-continued

```
tgctgtgagt gagtctgtgg agggtgaggg cttctgaaca gggagtcctg tgggagtgct  48900
tcttggggta tgttgtatgt cgtaatttag actaccatca tttgtgttat ttttgaggca  48960
cctaaggact tctttccact tctcatttct tactgtgggg tgaagagttg aattgggaga  49020
tggtttctag atgcaaattg aaaaggcatt tttccagagc agatttgttt tcggcgtact  49080
agagtgactc tttaacctag ctgcgggaag atgactgtgc caagactgca ggtaggagaa  49140
agctcactga cgaggccttg tgggtctgaa cgtcctgcag ctatcagagc ctgttggctt  49200
cctgttgtgc attccaacaa atcatcttca aacccacttt agtgttttgt ttataatgtc  49260
cagaaatagt gaccctgtca catgctctac agattacagg attcttagcc tcttcctttt  49320
tggtaggtca gtcctgggtt tgagcccaag tgaccctcct gggaggtgat gatacacact  49380
gggtagagtg gaatcagatg gacttggatt agaattctgt cctctttact agttattttc  49440
ctctaggcaa actgcccaac agctctaagc tatttccttc gtattctgaa aaataagcct  49500
taatgggacc catatagggc aactctgaga gtaaaataaa ggaatatgtg ttagagtgta  49560
gcatagtcac ccacgggaag ggcttagatg ttagctgcta ctgctcttat tagctgaatg  49620
atttggaata aactgttagc ctctctcatg tttttctct tgagcttcga agttttcttg  49680
ttaatactaa ggagatattc aaactagtca tggggttttg gaatgacgaa gggagatgat  49740
gaatctaaag aatttagtgt aatatttctt catgctcagt aaatggtagt ttctgctgct  49800
gttattttta ttaccatctc tttggaatgg gagtaggtgc tcctttgtgg tcagaggctg  49860
tgagagctcc acagcgccag tttgcccatc tgtacactgg ggtctgttga aggcagtccc  49920
ctctgtgata tctctggctg tcagagctca gatgatagat ggtatttttg tactcttagt  49980
tctcatcatt ttcatgattt cgatcaccat ttgagtatga tgatgctaac actttgttga  50040
acgtagaatc cgttaattac ttccttcctg aacctttggc attaaaaaaa atctattctg  50100
ctacctctct gctcatttat ggttattcaa atttattatc aagagcctgg tacagtggct  50160
tgtgcctata attgtagcta cttgggaggc tgaggtagga ggattgcttg aggccaggag  50220
tttgagacca gcctgggcaa gatagtgaga ccctatctct aaaaaaactg aaaaaaaatt  50280
agctggacat gatggcatgt gcctgtggtc ctagctactc aggaggctga gacaggaggc  50340
tcggttgagc ccaggagttg gagttcgagg ctacactgag ctgtgattgt gccaccacac  50400
tccagcatgg gtggtaaaac aagatgccat ttcttaaaaa aaaaaaatat atatatatat  50460
attatcaatg aaattcagta gtaccaacag gattataaac aaagatagta gttcccttcc  50520
tactttttct cttaatcctt gtgtctcaca ggcaaacata actcttagta tttcttccaa  50580
tatttacttt catgtttctt tctttctttc tttttttttc tttgagatgg agttttgctc  50640
ttgttgccaa ggctggagtg caatgacgca atcttggctc accacaacct ctgtctcccg  50700
ggttcaagcg attctcctgc ctcagcctcc tagtagctgg gattacaggc atgcatcacc  50760
acgctcggct aattttgtac ttttagtaga gatggggttt ctccgggttg gtcaggctgg  50820
tctcgaactc ctgacctcag gtgatcctcc cacctcagcc tcccaaagtg ctgggattac  50880
aggcgtgagc cactgcgccc agcaacttcc acatttctaa ataacatgct tctactgcta  50940
ttttttttt caattttaga catttttta ctttcactat agttctatca gaattcagtg  51000
tgtacgttat tatgcctaag taaatagtca tggttgctta cgtattatat ttctttgatt  51060
gtgtttctta tttgatgaga aagctgtgtt ttttgctctg ggttgaaact ggagagagga  51120
cctggggagg aggaggagga cagatgaagt tggtgactgt accttcatgg ccatagctgg  51180
gttctcagca cccggggatc tgctgatcac ctactcatag gccaggcccc tatcgaagtt  51240
```

```
ctaggtgacc cagtgctggg gacggggggg ccacctgcaa ggtctaatca tggaggtggg  51300
ggctacagtg ttggcttgtg ctggggccag catccttagg aaggcatctt ggaggtggag  51360
gagacagccg cccacttctt gattggggcc ttcagcagca ccagcttctt gggcaggctg  51420
gtgctggctt tcatcaccat gtcgtgttca atcttcttcc agatcctgac ttctaggttc  51480
agctttcctc agaccctggt tcctttcaga ggccattgct gctgccttgc tctttgctgg  51540
cttgtgcctt gattatatgt ctttgtacaa ctttttgttt tcctggagtt aatcttcaca  51600
tctgttttct tggagttaat cgttacctct atatcgcttg cttattattc tttggccttt  51660
ttgtcttctc acaccttcca acttctttgt aatatgtgtt tagtacaatt tttcatgaca  51720
ggtagtttac tgaatcagtt tttccccagt gtggtcatcc aacttgagtt atccagctct  51780
ctgccccagt ctgggcaggt tgatcttcag gtctgtagta cacttgtatc ctaggacttc  51840
tctttgccat tagcctggaa tttcctttgc agttctcccg ttggatgccc agttcctaga  51900
tgccatatgt ttttctatcg tctagtagct tcctgagaga agatgaatgg gagggaaatt  51960
gtatgaggtt ttgcattcat aaaaatgcca tttttttcc tgtacacttg gctgggtatg  52020
gtgttctggg gtagaaatca ttttccctca gaaatgcaaa gtctttgccc tgttgtctta  52080
aaatctccaa cgtgacccga ttccttaacc tatgaatgta cttttctttg gaagctttcc  52140
atttttgggg aggtgaagtg ctaggtactt agtaggcctt ttaatttgga aacttacatc  52200
ccttcagttc tgggaaaatt ttcttaacat ttctctgaga agttcttgcc ttttattttc  52260
tgtgttctct cctgaaattg gttagttgga tgttggtcct cctagattga ctcacatctt  52320
acctttttct tttcttttc tggtactttt tagatatcca tctcaaactc ttctattcat  52380
tgttatgttt ttaacttctt tcttttcttt gtctcttgat ggggtcttgc cctgttgccc  52440
aggttgtggt gcagtggtgc gatcatagct cactgcagcc tcaaattcct gggctcaagc  52500
agctgttctg cctcaccctc ccaagtagtt gggactacag gtatgcacca ccacgtccag  52560
ctattttctt tacttttttt tttttttttt tgagatggag tcctactctg tcgcccaggc  52620
tagagtgcgg tggtgggatt ttggctcact taagcctctg cctcccaggt tcaagcagtt  52680
ctcctgcctc agcctctcaa gtagctggga ttacaggtgt gcaccaccat gcccggctaa  52740
tttttgtatt tttagtagag ccagagtttc accatgttgg ccaggctggt ctcgaacgcc  52800
tgacctcagg tgatccgcct gccttggcct ccgaaagtgc cgggattaca ggcgtgagcc  52860
catcattaga tctttaaata ccagtatcta taagtctttt cctcttgagt cagctagtat  52920
ccctggaagg aaattactca ttttcctgct tggaggctat aagcttggct atgtttatcc  52980
tgcaaccggg gactggaagg gaggggactg acagtgttgc tggtcagggt gccctcttac  53040
tttttgtttt ctgtgtgcat ctcacgtctg tcctcagcct atgtaaacac ctcttgagat  53100
tatccctctc aatctttgcc ggaggtgggg gaggggctgc ttcctgggct gccttggatt  53160
ggagggaaga cctcaggtga gtgggtggga atttgcccaa ggagccatga gaccagccac  53220
tatttcaccc tctccatccc tccactttca gatgtatgtg gcgcctccaa agcccgagct  53280
cttcttggcg tctgtggctt caataagctt gctttttgct ggtatccctc ctaccctccc  53340
ctgtccccag caaagcttgc atttgaactt cttcctacgg gctaacaaat cagtcagtta  53400
tgtagctctt gttacttttt agcttccgaa gttttgttga cacccgtagt ctgctaatgt  53460
ccctgttctg ttctttctgt tcgtgtaaat atatgcttta tacaacttct ttacatgatt  53520
tttgtggggt ttctgggtag cagagcttca caagttcaat ccagcgtgtt ggattagaaa  53580
```

-continued

```
tctcccaccc tctggtttat tcttattctc aaaattacct gccaaacact gatactccct  53640
tgtttttcct tttcctgaca ggaaatgtac ataccataca ggacagaaat cattagtgta  53700
tcccttggtg aataaccaca aagtgaactt aacccttgta accgccaccc aggtcaagac  53760
agaatattac caagcactca gaagcctctc ccctattccc ccgtcactgc tcctgccttc  53820
ctccccaagg tcatgactgc tggcttctaa ttccagagtc tgtttttaaa ttctgtgtac  53880
atagaccatg gattaagtgt tctttttgtc tggtttattt tggtcgacat taagttcatg  53940
agagtcttct atattatcgt gtgtattagt attcctgtag ttttaggagc ttcatagcat  54000
tccattgtag ggatatacca cagtttattc attgtattat cactgggttg tttctagttc  54060
ttggctattg cgagcagtgc tactgtgacc actcttaggt gtgtcttttg gagtacatgt  54120
gcaggtttcc atcttgcaca gctagaggtg gagttgttgg gtgatagggt gtgtgcatct  54180
cagctgcagt agaaactgcc aaatagcttt ccttgagtgc ttgtaccagc tcaccctttt  54240
gccactgtgt atggggattc caggagctct ggtcctcgct agcacttgga attgctgatg  54300
cttttactct tagccttcct gatgggtgtt ttctggaatc acattatgat tttaatttcc  54360
attccttaaa gtacccttgg ctctgaagtt taatgattca tgcatctctt ccccttttgaa  54420
gtactcttac aggtatgttg tgcatgtgtt gaaaagtggc actatctatt ctaaaataca  54480
gtatgcctcc tctgtgtttg aacagttgta gcgtggcctt ggggcctcct gttagctggc  54540
ttggagaagg gattcttggg attgtagaga ttagacctga ggaggcccct tggagctctc  54600
tgactaaatt ttattcttta ttattccaaa ctatttaagc tcaccgtgtg ctgactcatc  54660
ataataatga gtagctctca ttgtgcttgt ctatttggac tcatacaatg attttttttt  54720
tttctttgag acagagtctt gctctgttgc ctaggctgga gtgcagtggc acaatctcgg  54780
ctcactgcag cctccacctc ccaggttcaa gtgattcttg tgcctcagct tctcaagtag  54840
ctgagactgc aggtgcgtac caccatgcct ggctaatgtt tgtattttta gtagagacgg  54900
ggtttcacca tgttggccag gttggtctca aactcctgac ctcaagtgat ctgccttctt  54960
cagcctccca aagtgctggg attacaggtg tgagccactg agcttggcca aagtagtttt  55020
ttaagatgtt agtatctttt cttgcagcta aaaaagtttg tcagagatga ttctactttg  55080
ttctccaggt gttttctcag ggagaaattg gaggcagtaa gccactgggg gagtcctgtg  55140
gctgggggt ggggtagtcc tgtggctcct tgtcagggag tcctgtggct ggcaaggaga  55200
gaagtcctgt ggctgggttg ggagggagtc ctgtggctgg ggtctcatcc tgtgcctaac  55260
agtgtccaga ggtgccgaga ccagctcagt cggggagacc ctaacccagc agcgctagag  55320
gaattaaaga cacacacaca gaaatataga ggtgtgaagt gggaaatcag gggtctcaca  55380
gcctttagag ctgagagccc tgaacagaga tttacccaca tatttattaa tagcaaacca  55440
gtcattagca ttgtttctat agatgttaaa ttaactaaaa gtatccctta tgggaaacga  55500
ggggatgggc cgaattaaaa gaagaggttg ggctagttaa ccgcagcagg agcatgtcct  55560
taaggcacag atcgctcatg ctattgtttg tggcttaaga atgcctttaa gcggttttcc  55620
accctgggtg ggccaggtgt tccttgccct cattcctgtc aacccacaac cttccagtgt  55680
gggcattagg gccattatga acatgttaca gtgcttcaga gattttgttt atggccagtt  55740
ttggggccag tttatggcca gattttgggg ggcctgctcc caatacagag gtctcgtgta  55800
aattccctgg gaggcgataa gcctctgaga aacagactat gctaaccacg ccatgaaaga  55860
gaaacttatt tataaatcag atgccagtta ctagtttact gcttatttgc ccaggcgtag  55920
ctctgacaga gtccccgact catagtgctt gctcagtgca tgctgaacaa tgattggaat  55980
```

caagtcatgg ctcagagcat agttttgaat aatgggaaat ggatgttctt aagtaacata 56040
gtcaccaaga taatgcgact agctgggtca ccccttttca attttaggat atttttatca 56100
agatttaaat ggccatcatt agagttatag cactttctcc tttggattgt cctagaggcc 56160
catgagaaag tattccctaa tttcttagga gaacagtttg tgggtagtat gcggtcatgt 56220
ccagttaaat tgcagatatt tccgatcgaa gatgttccag tcctgagaac ttcgtgacat 56280
tagcaggact tctacaagcc atctcttagg gtggggcatt tactgcagtt ggctagtact 56340
cttttctcct taactttgtc atttgttgat ttttttttaa ctgtccccaa atactgtggg 56400
cagagtgtat ctagaattga ggcctccacc attgcggaga ggacatggat gctgagcagt 56460
cccctgagtg aaggttataa agaagcaaat agactacaca tgtctgtaaa ctgctcttga 56520
gtgtcccaaa tttggggtac ttcagttcag ctgtaggaaa agcctcaaac tgtttatact 56580
ttgcaagaat tggaaacttc taattcacgt taagttttat gtaatacatg ataagcttca 56640
taggagcttc atcttttatc tacttggact tttgcttccg taggttttgt taaaggcctt 56700
catagcgaac ctgaagtcaa gctcccccac cattcggcgg acagcggctg gatcagcagt 56760
gagcatctgc cagcactcaa gaaggacaca atatttctat agttggctac taaatgtgct 56820
cttaggtaag gtggaggcat atgagtggaa gagtctccag catgtactca agatagacct 56880
ttgaaataaa taaaaccaga tgatccctca gcttctagac caggctattt ggcactggtt 56940
gattgaatgt gaactgcact ggggctgctg tgagcccgca tgggtctctg tgaccctgca 57000
gatgcagccg tgcccaggga ctgggcagtg ggtgtgggct ggtgtgagcc ctgtctgcca 57060
cccagggcct ggccctctgt ctgtgtcggc catgactatg gtgagtcttg taggcttgag 57120
actgtgcctc gggttcctgc gggttctctg taggtcagtt gacagtttct cctgttgttt 57180
gggtaactgt ggaaacgaac actggcaagt gctgaagcga gcatgtggac gtgcgatatg 57240
aaataacgac ctggctttca aaggcagtga ggctctctgg aaaggacctt gctgagctag 57300
ggatgtgggt gtgtagccat tcccagtggg cctcatggcg tactcgttca tgatcatgtt 57360
tgtgccatct tgatctctca ggatctcttc ttttttaaca gattaagccg ggaatctcca 57420
aacagtgagt cagatgttaa gatgtcttgc ttccaccccc acaggcttac tcgttcctgt 57480
cgaggatgaa cactccactc tgctgattct tggcgtgctg ctcaccctga ggtatttggt 57540
gcccttgctg cagcagcagg tcaaggacac aagcctgaaa ggcagcttcg gagtgacaag 57600
gaaagaaatg gaagtctctc cttctgcaga gcagcttgtc caggtaggag cacagggttt 57660
actctaggcc ctgcatgtga atgactgaca ttcaaagaac cgattaattt ggaagagaag 57720
cggcagaacc gagagttaga ggtgtggact ctggagctgc gctgctcgtt tccaacccta 57780
ggtgctgacc tctagctgtc ttccctctgt atgtccctgt caccgtgagt caaatgcggg 57840
tgatgcctcc tcaggtgccg tgttacctaa gcctctcaga gaccactgct accctgtttc 57900
taaaaccaga ggtcacgata tgtgttcatc cacccagtaa atactgattg agcacccact 57960
gtgtgctagg ctctgggata ggggctgggt atacaatggt gagtatttca gctgcagctt 58020
ctgccccgtg gaggctgtgg cctagcacac tggtctaggc acggtggtat atgctcactc 58080
aaggagatag ggacgtggtc gtttggggtg tcggaacaaa atgtcggaac ttctctttcc 58140
aatgcagaga aaccttgcag taattctaat gtactgtgat tggcagttga cttcagttct 58200
ttgtagcacg cttactcagg ttatttcact aactatgtaa ccatgcagcc tcattttaag 58260
caattggatt ttttgaactt tacttaaaat gttatgtcag ggtttttatt gtgcttaatg 58320

```
tgtgccattt agctaagttt tgtaggatac gaaattgtaa gtggcttaaa atgattctta  58380
atagaatcat gaattgaaga taatgctaat aatttaagca ctgagttagg tagtgtttgt  58440
aaaatgctta gaatgcttcc tggcacatgt taaggccatg taagtgctgc gtgttgataa  58500
acagctgagc aaaagtggac tcttaagaaa gtattggggc tgagagttct gttccaacca  58560
gctgcccttt ggttattttt cagaataaaa gcagagtctc atgggatatg acatttatat  58620
ttccttcaca aaaaacactg ctgagtgttt tgttgagtaa aaagggtgta gccatggtaa  58680
taatacattt aaaatatagt ttatttcatc tttaccttgc cttgtttttt ttttaagcta  58740
gctttttatt gagaattcca cacatacaaa agtatcaact catgaccagt tatatttcat  58800
ttataatcct acttctccct ttttttatta tttgaaagca aaccccaatt atcctcttat  58860
ttcatctata agtatttcag tatctctata gatgaggact cttctttatt tttaaaactt  58920
tatttttaaa atgatggtca gatgcagtgt tcatgcctgt aatcccagaa ctttgggagg  58980
ccaagctggg cggatcactt gaacctggga gtttgagacc agcccgggaa acatggcgaa  59040
accccatgtc ttaaagaaaa aaatcagcca agtgtggtga tgcatgcctg tagtcccagc  59100
tacttgggag gctgagatgg gagggtcaca tgagcctgga agatcaaggc tgcagtgatc  59160
catgattgta ccactgcact ccatcctggg tgatggagca agattctgtc tcaaaaaaac  59220
aaaactgcaa aacaacgtca caaaacagtg ccattgttag acctgaaaat attaaacatt  59280
tcctacatca aatacccacc aactcattat caatttttct ctctactctt ttggaatcag  59340
catctaaata aaattggtcg ataaggattg taaatctctt tgatgaactg gttcccctcc  59400
atcccagttt ttttccctta gagttcattt attgagaaac cagattgttt gtcttctaag  59460
ttttcctgtg gtctgatata ctgcttccat ctccactgtg taaattaaca ccttttttctc  59520
ttctctgtat ttcctgtaaa tcaataattg gaggaaaagc cttgtcagat ttagtgtata  59580
ttttatatct gagtccagta tttcttatat aatattttaa gataagtgta ctcttttaaa  59640
aagtattgaa actatatgct caattttttt taactgatgc ttttaagaag gctgcttgat  59700
cataaaagtt tagagatcat tggtctgatg ggaaaagcaa ataattacta aaccgtttag  59760
caaggttgag gtgcacatgg tggggcctgg agaagttcag tcatgagccg tcacttatgg  59820
gcacgtggaa tctgacccgg cacagagttg ggagaagaca ggagctttat agacagaaaa  59880
tgtggtcttt gctaagtccc aggagtgaaa gggtgagaca gtgctcacag cacacgagtg  59940
tgggtgcgta gacagagcaa gggtgggtcc tgaaaaggcc tgcaggcttt ctcatagatt  60000
agcaagagtg ctggttacgg aggtttctaa catttgtgaa cagatcgaaa ctgtgttaaa  60060
ttgggattgc agtaatcctg gaaggacagg gatagagggt gaaggggaaa aaagggtatg  60120
gatgtgagac ttaattgctg attttcttaa gacctttctc caaagtaaat aaatgatgtg  60180
gcacattttt gaactggcaa attctaaact ctagatatga ttatctctat aacatatctt  60240
actccatctt cttttgacta aaaactgttc ttaattaaat taccatgaga cgttcaattc  60300
agcaaatgta gtttggctaa ccatatttaa ttagaattta atataatcct aggcctggcc  60360
aaactattaa gcaagtgtgg gcaaaatatt gataatttta gatatgcagg aacttagttt  60420
gctttccatg tgtgcttttc gaaaaaggaa taaattgaaa aatagaggaa gccctgaaat  60480
ccaagaagca aactctctca cctaggcatg cagtaaaagc aattctagga tgattgctgt  60540
ttggcgcgta gttcgtatta gaaaccattc ttcttgaata aatagtatgt ttaagaagct  60600
gggcagaggg aaggcatatg catatattat caacaaggag ggagaaaaag gcaattagta  60660
accatccata ggagggtcag caagatttat aaaggaaatt tgtgatccaa gtatgaagca  60720
```

aaataaggtg cagaataaat tttaagcaag taatagatta gagtaagaga acccatttga 60780
ccattaacct tgggacattc tctttcaaat gacatggagt agtactgaaa tctttctttc 60840
tttctgagtc taggttattg tgactggact cagaaagaaa tatttcatta ttgcagtgaa 60900
taacatttgt gaacattatt gttcataaat tatgcagtga ataacattta tgaacacgtg 60960
atgtgtaaga tacatactgt ttatttttag ttaagttttt tggctcaact tctaggcaga 61020
gaacattaaa tgtaaatagt gttacctagg agcatgtaaa tggaaatctc catagtatga 61080
aagcagtgct gttgctaaca gaatttagga gggggcagat gaggtgaagg aaatgtgggt 61140
gctgatttcc ttattacatt gagaggagcc aggagattct ttgttcaaaa tggatggctt 61200
aagaagtcaa agtataagct gattacgtag agcaggtacc caaaaatgtt ttgtgtaagg 61260
ggccagatag taaatatttt cagtcttgca ggccatccca agtctgtggc agctactcaa 61320
cactaccttt gtagcatgaa agcagccaca ggcagcccat aaatgtggct ctgttccggt 61380
gaaactttag gtacaaaagc aggtgcaggc cagacctgac ctgtgcactg tggtttgctg 61440
acctgggatt caggggtata gaagttacca tcagaagagc taaaagtgag actttttact 61500
ttatactctt ctacactgtc tgattttgaa aaaaagaaac atgtatttta taatattaaa 61560
gatagggttg gcaaatagca aataaaaata cagaatacca gtgaaatttg aacttcagat 61620
acattatgag taattttatg gtgtaagtat attccaaatc atgtgggaca tacttacact 61680
acaaaattat ttgttgtttg tttacagttt aaatttgagt gccttgtatt ttatctggca 61740
actgtaatta aagggaaaaa gaataaattc attatgttca tataatgtga tatagcaggg 61800
gtccccaacc cccaggctgc agagtggtac tggtccatgg gtccccaacc cccaggctgc 61860
agagcggtat tggtccatgg cctgttagga accaggctgc ccagcaggaa gtgagcagca 61920
ggtgagctgg cattcccacc tgagcaccgc ctcctgtcag atcagtggca gcattagatt 61980
cccataggag tgcaaaccct attgtgaact gcacatgtga ggggtctagg ttgtgcgctc 62040
cttatgagaa tctaatgcct gatgatctga ggtggaacag tctcgtcttg aaaccatccc 62100
ctggccctgt ggaaaaattg tctcccatga aaccagtctc tggtgccaga aaggttgggt 62160
agcactgtga tatagtatta aaagtgctaa taaatatggc atactgcctt taaaatgtct 62220
ggtagctctt tctcagtggc actcataata gtgtttttg atttttaaat gtgtgtcaag 62280
ctgactctcc cctccgtgta tgctgggctt tattttccct ttcctagtca ccagttttgg 62340
gaaatagaga tcttcattct catgctgctc ctctagtgca agtgctccat ttatttttaa 62400
ggaattaata taacaaaaaa tcatgggaat ttagaaaaca acatggaagc taatgatcac 62460
attggtggaa gtgataggga aatatttagg gggagaagtt aaggtataaa ctttgtcaat 62520
gaagtcctat taaaaacaac aaaaaagtga agcttaggat gcattttata aactctgacc 62580
agaacacctg tgtttctctg tttctaggtt tatgaactga cgttacatca tacacagcac 62640
caagaccaca atgttgtgac cggagccctg gagctgttgc agcagctctt cagaacgcct 62700
ccacccgagc ttctgcaaac cctgaccgca gtcgggggca ttgggcagct caccgctgct 62760
aaggaggagt ctggtggccg aagccgtagt gggagtattg tggaacttat aggcaagtta 62820
ttagcaaggt ctactcttac aattaacttt gcagtaatac tagttacact ctattgatta 62880
tgggcctgcc ctgtgctaag cagtctgcat tccatcttcc ttgccaaaac ttataataca 62940
aatttcatct ttattttata aataggggag ttgggctggg tgtggtggct cacgcctgta 63000
atttcagcac tttggaagga tcgcttcagc ccaggagttt gagacaacct ggccaagtga 63060

-continued

```
gaccctgtct ctacaaaaaa aaaaaaaaaa aaaaaattag ctgggcatgg tggcacatgc  63120
ctgtagtccc agctgctttg gaggctgagg tggtaggatt gcttaagccc aagaggttga  63180
ggctgcagtg aatcttgatg gcagctgcac tgagcctggt gacagagcaa gatgctgtct  63240
caaaataaat ttaaaaataa aataagagaa ttaaagttta gcaggttggg tggcaaaatg  63300
aggccacaca tttaaagccc ctcctcctga ttcttttctc tgccttggct gcctcctgtg  63360
gcattttagg tgctgagaaa tgaaaacagt agggaaaata gttccaggat cctcatgtta  63420
atttgccaga aatggcatct tcaagtcgtc agagggatct gagagttcct tcctggcctg  63480
acttgagaaa atccgtctgt ccccagctct gcgtctgcct ccactgccca gtcacctcct  63540
ctccatgctc ttggggctgg gccctacccc accatgcagt gctgccctgg agcagtgagc  63600
ttggtgggtc ctgtctggca tgagagctgc ctttgggagc tggatcccag cctctaccac  63660
tgggtctggt gcctagcagg ctatggataa acttctgctg actccggcct ctcctaagcc  63720
actgcaacgt ggtcggtgta gtgcacagtg tgtgtgcagc gtggccttac tcacagcctc  63780
cacattagag agaatctgac tgaagtctta ctgctgcctc gtgtgaacat aaatgtttgc  63840
cagaaccatg agcaggaaat gttaatctgc cttgtttcct gtcctttaca cggaagaatt  63900
tttttctgta tggaatgcgt gccttacaaa taatgagtgg aaataccat cgctaatgaa  63960
aagttatact tgactgttag tcagctaaat aatctgagat ttctaatact tttaatttgg  64020
cttttacaat gcaatttatc ttagcttttt tgatttctta ggtcatatct ttagaactat  64080
atatttgaat gttaatgtaa ttttcatatt gaaattaaaa tgttgaactg cgatgttaag  64140
tgtttcctgt ggaaaaacgt tcacattttc tctagtttta aagttgaatc aagctgtttg  64200
aagattttca catttcttct agattttatc agcttgttac tttatctgtc actttctgtg  64260
atttgcagct ggaggggggtt cctcatgcag ccctgtcctt tcaagaaaac aaaaaggtga  64320
ttatttcaga aatcagagtc ttgtgttgaa tcttactgat tttcttgtat ttctgtaatg  64380
taatgtatct tgtatttctt gtaatactgt attggactct gtgtatatct cttctcagat  64440
gagtgattat atgtgtgaat gttgctggaa tctgataacc aggcctgaat agttttgtag  64500
ggtggctttt aaaaattact ttcatatcag aattgctttg tcataaattt tgaacgcatc  64560
ataaatttct aatgttcggg gtcagcagac ttttttgta aagggacaga gtgtaaacat  64620
cttagcttta tgggccatat ggtctctttt gcaacattca gctctgccct gtgacaggaa  64680
tgcagttgta aagacatgag ctactggcca gctatgttcc agtagaactt tacttacaga  64740
aacagacagg ctgtagtttg ccaatacctg ccttagggaa tgtgttgtta tattttgtga  64800
gttaccttct cagtaaattt tatttagtat tagtcaggaa tattattaag tagcttcttt  64860
tccagcctgg tcaacatagt gagacccggt ctctaccaaa acaaaaacaaa acaaaaaaac  64920
agccacgcat gtggcatgtg cctgtagcct cagctgctgc tcagggggct gaggcaagag  64980
gattgtttga gcccaggagt ttgaggtcac agtgagctgt agtcatgcca ctgcactcca  65040
gcctaggcaa cagaatgaga ccttgtgtct taaaaaaaaa aagtttcctt tgttgggtta  65100
ttttaatttg gacctggtta tcatttttca gccatattta actttgtaca tatcagaatg  65160
ttctgataaa acttaacttt tattaaagtg tttgtgatat aatctgctag ttttggtaca  65220
cattatcttt tgcaatgcca gttattttct tttccagtgt gggtttgcat aggaaaagaa  65280
ttgctgtcac tttctatttt gaaatcttaa aagactgatc ctttttgtg tcatgatttg  65340
agtatttaat tgagagccta atgcctaata ttatttgcag tattaaatgg gatcttaaca  65400
ggaatagcat tctagccttc attgaattaa gtaaacattt cttaagagaa cttggaatct  65460
```

```
ataatatttg cgtcatcata gtatgagata cttaatcaag tttgagattt tagtgaaaca  65520
ttgtttagaa gccaaaagga ttctaggaaa aattaatgtc tatattcttg aattaggaga  65580
gattttggga cgtgtgacta agttacgctg acacttgttt gtttcttagt cgctttttcc  65640
agtggcggtg agaacgaaga tgactgattc acattgctca gatgagttta tcctcttctg  65700
gctgggacat gggatatatc ctgtctcttt taagcctttt tggtattttt cccccattga  65760
gagctgtgtc ttcaaactct tctgttatag ctggaaaatc ctttttaagt gaaatctgcc  65820
caaattataa gacagatgaa ggtagagttg tgttggatat aggattaggg tgaaagtagt  65880
gggggtgtcc tggagcctct cttctggtgg cagcctagct cttgtgcctt tgaggaaatt  65940
accctgggga cggctctgtg gaacatattt gcaaaccact gatttggaag atagagatgg  66000
cttttgttaa gatctgaatt caccttttttg gcattttatt tgatttctca aggtaaagaa  66060
cttattttgt aataaagttt cctattattt agtagatagg ccaagttgct gtgttaattc  66120
catgtagatt ttgggtttcc tttgctcatt ttttcactct taatctcaca tcattgtaag  66180
tttatggaag ttatcatact tctgactttt tctttgaaga gcagaaatta gaaattccca  66240
ataattattt tgatagtgtc atttaatgac actcacatgt gatgtagcca caaagattta  66300
atgagttcag ttttaaatca tattaagact gttggtttca tttgttctca ttaatgtaat  66360
tctgaagatg aacaataaaa tgtattttta gaactttcaa atgaaatatt atttcatcct  66420
tccagatcat ataatgctta agttctgatt gttaatcata aagtctagaa aattaaaaga  66480
taataaaatg aaagtgactt ttaggtatta gagttttatt ataaattctg gtgtgtcatt  66540
ggagctatga catgaatatt tcaaaggcca atagcattgg atctttacag ttataactta  66600
ccatttttaa gtttaagtag taatatagat tatttaataa tcaaaatcaa taaatattaa  66660
ttattaaaat gttttgtggt atagtttgag aatcattgct tttaactttt tccatatagg  66720
tttattgact ttaatagcat tctaaacata acatctctac attctttgtg tttaatactg  66780
tggaggtata aaaatactta tatatgatga taaactatat tagagtaaat taaatattct  66840
tatgagtttc attttagagt gcatttactt aattttgaag tccttatttt tagcaaacta  66900
aaaggaatgt tggtacatta tttactaggc aaagtgctct taggagaaga agaagccttg  66960
gaggatgact ctgaatcgag atcggatgtc agcagctctg ccttaacagg tagttctcac  67020
tagttagccg ctggtgtgga ccttcactgt ctgccttcca cccccttgccc ttcctgctcg  67080
tccccctgca cctggtggac agcacgactg ggggcagcag tggagccagg ttgcttaaat  67140
ggggcatatt cgggcttctt ttataatact tactctgaag cttgtgtgtc tgtggtgttt  67200
gcatcatata tttgttgttt tccatggttt aggctgtttt aaaattaggt ttatggcttg  67260
agcatagggc tttgtgagta ggggatggca ggtcgaaaca tctcatgagt tggatgggtt  67320
atgctggggg ttgggaaatg ggatgaaaaa ttatgggatg aaaaattgcc tatggatagt  67380
ttaacttgaa agaatctgcc tttgtttaca gatagttatc tttttctttt tttgagatag  67440
agtctcacac tgtcacccag tgcagatacc cagtgtcact ggagtgcagt ggtgtgctct  67500
tggtgcactg cagcctccgc cttctgggtt ccagcgattc tcctgcctca gcctcccaag  67560
tagctgggac tacaggtgcc cgccaccacg cttggctaat ttttgtattt ttttgtggag  67620
acgggttttt gccatgttgg tcaggctggt cttgaactcc tgacctcaag tgatctgcct  67680
gcctcagcct cccacagtgc cgggattaca ggagtgagcc actgtgcccg gccagttaca  67740
gatacttatc taatgaaatt ctctgtgtac tttataaaag atgaggatta actgaaggta  67800
```

ctaataactg gattatatga gggtggtttt ggttgtataa tcctatctaa aagaatattt 67860
tagctataac tgaaagtaag acttaaatat ttagagagga aaatctgaat aattctagta 67920
gtaattattt atttacaaaa taaaaataga tttttttttg attacacaaa ttaaacaaca 67980
ataaaacatc acagcaatcc ggatactata aagctcacat gcttaccgac ccaactgccc 68040
caggagtgac cactgccaac agcttcatgt cgaccttttt gccataattt ttatatagcc 68100 tttttgttt ttaaatggta atttagaaag tcaactagga aaatgtgtta caggtttatc 68160
ttccaggaga ataggactgg agtcgagatc ttgaatgtgg cttggaagaa ggcaagccca 68220
ccccagagag atgagttgac agttgtttct gaccactgct tgcttagagg gcctgcgtgt 68280
ctgtgaccgc ctagctttgc gcccctgact aggctgcccc ttaattacaa atgtctttat 68340
atattgctcc agctaaggct tggagtagtc ggttaagaac ttgaacttcg gtttttgcag 68400
tgaaacagca tttgagaata tcaccttctg ataagcctta ttttataagg tgggtactgt 68460
agtgggaggc agtgtgagag atgcttgaag gatgcactgc tgtcctgcat ttcagcatct 68520
tcaggatgct gtgcagctga aacatttgat aacggtggaa ctgttcgtta ttttgcaagc 68580
ctgtgattcc ctattgaatg ttttctctcg ccatttgaca aatgagtgtt tctctgtctt 68640
cagcctcagt gaaggatgag atcagtggag agctggctgc ttcttcaggg gtttccactc 68700
cagggtcagc aggtcatgac atcatcacag aacagccacg gtcacagcac acactgcagg 68760
cggactcagt ggatctggcc agctgtgact tgacaagctc tgccactgat ggggatgagg 68820
aggatatctt gagccacagc tccagccagg tcagcgccgt cccatctgac cctgccatgg 68880
acctgaatga tgggacccag gcctcgtcgc ccatcagcga cagctcccag accaccaccg 68940
aagggcctga ttcagctgtt acccccttcag acagttctga aattgtaagt gggcagaggg 69000
gcctgacatc ttttttttta tttttattt gagacagagt ctcactccat agtgcagtgg 69060
aggccgggca caggggctca tgcctgtaat cccagcactt tgggagactg aggcaggcgg 69120
atcacttgag gtcaggagtt cgagaccagc ctggccaaca tggtgaaacc ctgtctctac 69180
taaaaataca aaaattagtt gggcgtggtg gcacatgtct gtagtcccag ctgttaggga 69240
ggctgaggca ggagaattgc ttgagcctgg gaggcagagg ttgcaatgag ccgagatcgt 69300
gacactgcac tccagcccgg gcaacagagc aagactccat ttcaaaaaaa ataaaaaaat 69360
aaagtgcagt ggctcgttct cagcccactg caacttctgc ctcccaggct cgagcgattc 69420
tcccgcctca gcctcctgag taggtgggat tacaggtggg caccaccaca ctcagctaat 69480
gtttgtattt tcagtagaga cagggtttca ccatgttggc caggctggtc tcaaactcct 69540
gaccttagat gatccaccca ccttggcctc ctaaagtatt gggattatag ttgtgagcca 69600
ccatgcccgg ccctgccacc tgccatcttt tgagttcttc cctggagacc tagacctgaa 69660
ccctcctgct tgttctcttg ttatctaata cccctattga cagcgcagct tagatcatta 69720
atggagagct tgacctcatc tgataccttc actgaaggaa acaacttagt gtcttttgtg 69780
ttgaacactg aggtaaaaaa ttggaatagt tgattatatg aactctgcta aaattgagtg 69840
cattttacat tttttaaggc cttgttgggc cctggttaaa taattatttt taaaaatcct 69900
taaggagcct attataaaca gatctgtggt cttaatgaaa tgtgattaat actgtgcatt 69960
attttaagaa cttttgactt ttcaaaaaac ttttacaaca tttcccattt gatagcggca 70020
taggtttaag cacttctcat ctctaagtta gtggacaaaa aaccctcatg gatagtctaa 70080
taatgtttgc tacaagtcca tgttgagttt tatactccat tttattttca gtttttaaaaa 70140 ctgtggttaa atatgtgtaa cataaaattt atgttcttaa ccattttttg cgtatacagt 70200
tcgctggtat taaatacatt taaataatgt catggaatca ttgctaccac ccatctctgt 70260 aacctttga tcatgtaaca ctgaagctct gttcccattg aactctattc ctcctttccc 70320
gccaagtccc tggcaaccac gattcttctt tctgtcttct gaatttgact actttgggtt 70380
ctcatatact ttaggagtca cacagtattt gttttactta gcataatgtc cccaaagctc 70440
atgcatgttg tagcctatgt tagaacttcc taatgtttca ggccaaatac tattccattg 70500
tatggatagg ccacatttg cttttccatt cctctgtcca tggacacttg tattgcttca 70560
tgttttagcc attgtgaatc atgctgttat gaacgtgggt gtacagatag ctcctggaga 70620
ctctgctttc catttttttg gctaaatacc cagaaatgga gttgctttta cattccaatt 70680
ttaatttaaa acattcatat cattgagtgt tttacttaat agtatagtag ttaacaaact 70740
taataaaata gtattttggt aataatttgc tggtagtcca ttgttcagtt tttttaggta 70800
aattacacag gacatttcaa gtggacatga aacatcttgt gatgtggaat catgccccaa 70860
gctgatggct aaacatatga aataccatac cctaaattta gtagatttag tctttgcaat 70920
ttaggagata acctgttata ttgttaggtt tttgtcgaaa agctttgtcc tcatatttcc 70980
aacttgctgt aaaatttgtt tgtgaagaca aatattttg tatgggtttt ttcttttca 71040 tattaaaaag aaatgtccac attggaattt ttttggagtt tttagagcta atagagcttt 71100
tcataatgta gtgggaatga gtgatcagta agctcttagc agtttccatg cgtgcatttc 71160
tgtgccttga aataaatgac agatgagtac atttgtgttc tgtgtgtaaa atgtgctctt 71220
tcctcattgc acttccatgt tggagggctt gtctcttggt gatcacactt caaaattctc 71280
acagcccccc ttgaaccgtt taggtgttag acggtaccga caaccagtat ttgggcctgc 71340
agattggaca gccccaggat gaagatgagg aagccacagg tattcttcct gatgaagcct 71400
cggaggcctt caggaactct tccatgggta tgtggactac aggtgatgcg ctacaaagtg 71460
gtttgtattc agacctggac atcttaatta tatctttgct tccaagaaga agtcctttga 71520
tactgttttc tgagttctga atagctgatg aaaatgacca attgaggaat aatcatactt 71580
tttcttgatc taaatcttat acttttgagt tatcttagca taaatgtata attgtatttt 71640
aagtggaaat ttgtcactta atcttgattt ctctgttttt aaagcccttc aacaggcaca 71700
tttattgaaa aacatgagtc actgcaggca gccttctgac agcagtgttg ataaatttgt 71760
gttgagagat gaagctactg aaccgggtga tcaagaaaac aaggtgaggg acataggctt 71820
gagacgactt ggtgtttctg agcttgtgtg aggatttaaa atcgccctgg ctactgtcta 71880
ctttattgct ttcccatccc tggccttta aatttcccct ttaaatacca gctcttccca 71940
ggcctgttgt tttctgcctt tccaggtact acccacagcc ttgagaattg cctgagttct 72000
gcctcctttg agagtgtgcc ccagacaaat ctattctgta ctgaatgttt ccttgtctga 72060
tttcttggat cattcatttg atggttgcgt atggcctgca acgtttcttg ttttggttct 72120
actgaactgt tctaaaagtc tctcttcata ttatcttttt acatgtaaat gtaactgtct 72180
tcacttttaa ttcctcaagg acaaggaata gcgtttcaca gttcgtccca tcaatcagaa 72240
ttatagcctt tggcatctcc ctatctacca ggcccacttc ctcttagatt tgggcttccc 72300
caggctgttg cctttcccca agtagcttct gcttgtcctg tagaagacct ttcatgcttt 72360
gcttctgcag cagccgttcc tgaatgccta gtgtcaactg ccttcttacc acgcccaccc 72420
tccctgcatg ctgcatttat cccctgccac agccctgtga ccctgtgtcc tgctgcctct 72480
gacttgtctg tttctgcttg gccatggtct ctgtgaggtc aggtgtgcat atgggcacaa 72540

-continued

```
accagggcat ctctttatcc ccagcacctg gcttaagtgc tgctctggaa ctatctgttg  72600
aatgaactaa tgcatgaatg tattgttgag tatgagacaa acaagtgtca ttgtctcctt  72660
tctagccttg ccgcatcaaa ggtgacattg gacagtccac tgatgatgac tctgcacctc  72720
ttgtccattg tgtccgcctt ttatctgctt cgtttttgct aacaggggga aaaaatggtg  72780
agtacaaaag gggatgtgca cagttgaagg aaataactag gtttcagagg tcagcttggt  72840
ggcctgtttt tgccttgcgt gcagcagagg aagtagaatc tgaggatgag tttggttttc  72900
actagccgag gggagggagg aaatgatggg agcaggtagg ttattgggtc tggttttgtt  72960
catttgaaaa caatctgttg tttgaggctg aaggtggctt gggtgatttc ttggcagtgc  73020
tggttccgga cagggatgtg agggtcagcg tgaaggccct ggccctcagc tgtgtgggag  73080
cagctgtggc cctccacccg gaatctttct tcagcaaact ctataaagtt cctcttgaca  73140
ccacggaata ccctggtatg ttaaaagttc acatcttatt ttctcagatt taatcattat  73200
tgtaaaaact atttcagtat tgactatttt agttttagag cagtaagtgt tttgagttca  73260
tttgggatat ttgacctgcg ttgtagctct tcagaaaaca catgaatagt gaagttcttt  73320
gtttcatggg ttccctttag atgaaaccca tagaggagaa aagtagaaac ctcagcacgt  73380
aagagccaac atatatacac atcggattta aacctaaagc acaaattgtg cctggtcgca  73440
gtggcgctga gtcgcactca gccaggccag gcattcacac tcagggtgag tgggaaccag  73500
gactggctga ggcagcagtg gacccaagtc tccatcgcgc ccatgcttac tatggagcct  73560
tctcgttctc tctttttctt tgggtgagag ggtacacttg tgtttttgaa tttatatgag  73620
gtaagtgtgt aatagggttt tttctaatct tttttaagtg gaatctggaa ttttaatcag  73680
atttattatc tgacaaccta gaattataat ccagaaagtc tgtggtattg aggacatatt  73740
ggcaatatga tgaatctcta attcttaaat cctgaaactt tttttttttt aatcacttag  73800
ggttattata gtgaagtcat ttctgaattt ggatcttctc ttcacacctc tttttctctt  73860
tcctgagaat taagcttttg tttcgagtta gaaagttgat agtagggaat tgttccatgg  73920
ctgagcaatt tatctccaca gaggaacagt atgtctcaga catcttgaac tacatcgatc  73980
atggagaccc acaggttcga ggagccactg ccattctctg tgggaccctc atctgctcca  74040
tcctcagcag gtcccgcttc cacgtgggag attggatggg caccattaga accctcacag  74100
gtaacggcca gtttttcagc tgtgtttttt ctagttatgc ttactaaggt ttaagtttag  74160
atgatgatgt ttgttgcttg ttcttctggt taggaaatac attttctttg gcggattgca  74220
ttcctttgct gcggaaaaca ctgaaggatg agtcttctgt tacttgcaag ttagcttgta  74280
cagctgtgag ggtgagcata atcttctgtg gaaccatttc ttcacttagt ggacatttta  74340
tcattgctac aattaaaatt ggagcttaat aggaaatatt tccatgcact ctaaagctgt  74400
aaccagtaat acccaccatg tatccatctc tcagctttag aaagaaaacg ttgccagtaa  74460
agttaatgct tcataaactt cagtttaagt tctaattctc agaatatttg tttgaaatag  74520
acctcttcct aaaggatata tttagaaata acctatcatt aagtgtaaag tctgttgaat  74580
atgctgggca cggtgactca cacctgtaat ctgaccactt tgggaggcca aggtggaagg  74640
attgcttgag cccaggagtt caagactatg ggcaacatag ttgaccctgt ccctacagaa  74700
aattaaaaaa aaaaaaaaaa aaagtagctg ggtatggtgg tgcatacctg tagtctcagc  74760
tactcgggaa gctgaggtgg aggggggatt gcttgagccc cagagatcaa ggctgcagta  74820
aggcgtggtt acaccactgc cctctagcct gggcaacaga gtgagactgt ctcaaaaata  74880
atagtaataa taatcagttg aattaaaaaa aaaaaaaaaa aaaccactgt gctaggccca  74940
```

tagtatggta agagttaaag tgagccttag ggattattta ctcaacctct gtttctgtat 75000
aaagtggaat aggctcaatt ctttaagtga tagcatgttg aacctttcca taccaactgg 75060
ctcataagtc acaactggcc agtcaacaag agtaaaaatt aactggtaaa aatcaaagca 75120
aaaaacctac aattgtcaaa tttgtgggat aactccccct tttaaaatgt catgcctgac 75180
agtaatttct ctctagtttc caggttttca gtcagttgtg tctttttga gcagaaggaa 75240 gcatgctaag agctcaatct tgtggctagc tgggggtctt tgtgtcagcc atgcatgtga 75300
tggtgcccct gggtgcttgg ggctgcaggg gaggggtaca gcagtagggg cctgttctgt 75360
tctctcgtgc tgtggagtac atagtgacat agtggggtgg tccttggtgt aggtcccttg 75420
ttcctacccc tgggtctgag atttatttag aagtggtgtt ggggctgtgc ggcaggcccc 75480
tctgtaactg atcaatgttt gtgaagttgc tgtttgagag ttgaaaccat gacataagca 75540
gaaatggaag gaagaaagaa ccagttatgt gaaagggaca catttacttt taagcttgta 75600
tttactgaga taaagtattc ttaatcaatg ttcttgagag gtgtgggaaa aatgcaacat 75660
cctggttgca gttaaaccca gaacattgtg tgttgaagag tgacggttct caaaccgtca 75720
agacgcgggt actgagtggg actaacctgc tgtcctcttg ccttggacct tgtgttccag 75780
aactgtgtca tgagtctctg cagcagcagc tacagtgagt taggactgca gctgatcatc 75840
gatgtgctga ctctgaggaa cagttcctat tggctggtga ggacagagct tctggaaacc 75900
cttgcagaga ttgacttcag gtaagtgagt cacatccatt agatttcatg aactaagctc 75960
aattgaaagt tctgggatca cttgatgcaa ggaatgatgt tatcaagtac cctgtccatc 76020
agaaatccga gtggtttagg tagatgacag tgattttctc ctcccagtgg ctttttgctg 76080
aactttgccc tatgcttgga attttatttt attttattat ttatttagag acaagatctt 76140
gctctgtcgc ccaggcttga atgcagtagc acaatcatag ctcactgaag ctttgaactc 76200
taggactcaa gtggtcctcc tgcctcagcc tcccgattag ctaggagaat aggtgtgtgc 76260
cgtcacactg gctaatattt tttgtagaaa tggggtcttg ctatgttgcc caggctggtc 76320
tcaaactcct gggcttgatt gatcctccat cttggcctcc caaagtgctg ggattacagg 76380
catgagccac tgtgcctggc ctagaatttt aaaatataag tagaagagta gattttttt 76440 tttggtagtc ctcgtcattt aagtattctg gatagtggga ataaaagagc ttagaatttt 76500
tcatctttgt cttaaacttt taaaaaaatg tagcttatat taattctgct tgtttaaaaa 76560
gaatatactc ttcattatac tgaacctagg taagacagct ggtttatatt ttgttgcaat 76620
taaaaaacgt gagctgtggt tgcagtgagc caagattgtg gccattgcac ttcagcctgg 76680
caacagagtg agacttggcc tcaaaaaaaa aaaaataaca tgagctgtgt tggcactttc 76740
attttctaag agtagtttg gctggagaag ttttctttca gtactttctt ttagaaggga 76800
aattttcctt tataatttag ggtttgtttt ttttttttcc aagccacctt ttatagagcc 76860
cttgtgggtt atttcattta atccttagaa tgtttataaa tctgggcttg ttctcggctc 76920
cacccacaga tagggacgct gagcgtgcat gagtgggcag caagatagca ggttatggag 76980
ggcccagctc accccttctg tggcttgagc caattttata gggcacttac agagtctttt 77040
gaaatagtat ttattttgaa gaaaaagaaa aacagtttac tgagtactgt cttattgagt 77100
ctggaattgt gagaggaatg ccacctctat ttatttaaag ccattggcct tttttgttgt 77160
tttgagtaag tgctgcccaa ggtccttcca gggcacctgg atgagcctgc tctggagcaa 77220
gctggcggta agtgtttact gagtaactaa atgatttcat tgttaaatgt gctcttttgt 77280

-continued

```
taggctggtg agctttttgg aggcaaaagc agaaaactta cacagagggg ctcatcatta  77340
tacaggggta agcggtttat ttttgtgaga tgctgtttta ccttcaagaa ggtgaaagtg  77400
aggctttcct tgtggaattt ctctaaatgc attcgtcatg ttttagatgt ttatttcaca  77460
gtttatatca tgaaagttat aatcttgtca tatggattta agtctagtaa tgttgagttc  77520
tttctcacta gctttccaaa atatcttacc taaaatttag tcaaatacaa gattatgttt  77580
atttttatta tccttctctc taaagctttt aaaactgcaa gaacgagtgc tcaataatgt  77640
tgtcatccat ttgcttggag atgaagaccc cagggtgcga catgttgccg cagcatcact  77700
aattaggtat ttaccaatat tttatctctt ttcctttttt ggttgaagta ctaaaagata  77760
cgagaatgga aagagaggga agaattcaaa ggatgtagag cagtattcct gaatctgagc  77820
tcatttcagc cattctattc ttaaactata atgaaaaaaa aatccaaaaa agtctaaaat  77880
tataattaaa aaaacaacaa aatactaact gtccattgta aaaagtaatg cactttcatt  77940
gtaaaaattt tggactatag agaatagtac taagaagaaa aaaaaaatca ccttcaattc  78000
tgctgccacc tggaggtaat cactgttaat attttgctat atactctatg agtttcttgt  78060
tcaaaatcag gtcaaaatta catgcaattt tgtaatctga caatttccac ttaatatttt  78120
attagcattt tcctgttatg aaacagtaat tttagttatg ggtcgttgtt ttgctatgcg  78180
gttgggataa aattttatat actttttttg gcaattactt attatacata aatgtttgtg  78240
tatagtttc tttttctgag aattcctgga agttgagtta ccaggcccgg ctttgaattt  78300
tttttttat ttttttttg agacagagtc ctgctctatt gtccaggtgc tatctcggct  78360
cactgcaacc tctgtctccc tggttcaagc gattctcctg cctcagcctc ccgagtagct  78420
gggattacag gggcacacca ccacgcccaa ttaatttttg tatttttagt agagacaggg  78480
tttcacgata ttggccaggc tggtctcgaa cttctgaccc cgtgatccac ctgcattggc  78540
ctcccaaagt gctgggatta caggcgtgag ccatggcgcc tggccaggct ttaaatttaa  78600
aacaaatctt ctaatagctt tatggaggtt ataatttaca tttcttgaaa tgtactcact  78660
ttgagtgtat agtaaactcc aattttatca catttctgtc accccaaatg tatccttgtg  78720
cccatttgct gtaacctccg gttcctgccc caactcctag gcagccactc atctattttc  78780
tgtcccttaa gatttgtgtt ttcgccaggc gctcatgcct gtaatcccag cactttggga  78840
ggccgaggtt ggtggatcac ttgaggtcag gagttcgaga ccagcctggc caacatggtg  78900
aaaccttgtc tctactaaaa atacaaaaat tagtcggatg tggtggcaca cgcctgtaat  78960
cccagctact cgggaggctg aggcaggaga atcacttgaa cctgggaggc ggaggttgca  79020
gtgagcagag atcgcgccac tgccttccaa cctgggcaac agagagagac tgtctcaaaa  79080
caaacaaaga tttgtatttt ctggacattt tatagtactg gggtcatagt atagatggac  79140
ttttgcattt ggcttctttt acttaattgt gagattggtt cttgttgtag catgtatcag  79200
tagtttgttc atttttattg gcgaaagtat tctattatat gaataatacc atattttatc  79260
tatccatcag atggatatta tagagttcat gttttggcta atttatgaat tatggtactg  79320
tgaacatttg cctgcaagat tttgtgtaga catgtcttca tttctcttga gtagatcacc  79380
tagaagtgga tttttaaata attttggtac ttactgtgaa actgctcttc aaaaacatac  79440
cattgttcct tccttccttc cttccttcct tccttccttc tttccttcct cccttcctcc  79500
ctcccttccc tacttccctc tccctttccc tttcccttcc ccttttccct tccccttccc  79560
gcctgcctgc ctgcctgcct tccttccttc cttccttcgt ttctttctac atatacacat  79620
ttttttaaat ttcaatggtt tttggggtac aagtggtttt tggttacatg gctgaatttt  79680
```

```
ggttacatgg tgaagtctga gattttagta cacctgtcac ccgagtagtg taccttgtac  79740
ccaatatgta gtttttgtc cctcaccttc cagccttccg ccttgtgagt ctccaatgtc  79800
cattatacca cactgtatgc ccttgcgtac ccacagctca gctcccactt ctgagaacat  79860
atagcagaaa catgccaaag tatactccca ctaccagaat gtgattgtgc ctgattcttc  79920
tcaccagtac aaatatttca aaaaaagtta aatatgtatc agtttttgg gcagaagttg  79980
atacttctct ttatttattt atttttttg agatagggtc tcattctatg atgcccaggc  80040
tggagtgtgg tggtgcgatc tcggctcact gcagtctctg cctcccaggt tcaagtgatt  80100
cccacgtcag cctcccagga agctggaatt acaggcgagg gccaccactg ccagctaatt  80160
tttgtatttt ttggtagaga tggggtttca ccatgttggc cagactggtc tcaagctcct  80220
gacctcaagt gatccacctg ccttggcctt ccaaagtgct gggattacag gcgtgagcta  80280
ccacacccgg ctgatatttc tttttaaaat aacttacctt cttttgaaag taatacatgt  80340
ttaatgaaca gaatttaagg aaaatataaa aaaacgaaat aatctttgta atcaaactac  80400
tgaaaagaaa accaaagtta cattttggtg catattcttt ttcattttca tcattgtaat  80460
ttgcatttct ttgattactt gtgagacact cctttcattt acttaatagg tttatatgac  80520
ttgcctattc agagatttg cagctttacc attttctgca aatgatagca acttcttttt  80580
gtttgtttgt ttgtggagac agagtctcgc tctgtcactc aggcaggaat gcagtggtgg  80640
aatcttggct cattgcaact attgcctcct gggttcaagc gattttcctg cctcagcctc  80700
ccaagtagct gggattacag gagtgtgcca ccatgcccgg ctaatttttg tatctttagt  80760
agagatgggg ttttgccatg ttggccgggc tgatcttgaa ctcctggcct caagcggtcc  80820
ccctgtctcg gcctcccaaa gtgctgggat tacaggcgtg agccaccgta cccagccagt  80880
agttacttct tatattctag aaaaaattct actcatgatc aagtctccat gaggaaagag  80940
actttaattg aagatcatgg ggcttgcaga ccaatatgat aaaatagttc attgtttcta  81000
aaagtattac tgagtgttga tggcagatat gaacccttt gtttttgtag gaaaatgtta  81060
cccgtattct ccatttgaat tcagtttaga tttgttagga atcgcagctt aagctttgcc  81120
atctgggagt gtttgggaca gttttgcaga caaaattgca aaagtgccta aggaatgcag  81180
ctggcattca gacctgctct gtgctcagta ctctgtggac agacactgtt cagcacttgt  81240
tgatcagaag gtttagaaag agaactttca aagttggttt ttaattaaag catttaatag  81300
tgtaaataga aagggattaa attttatgac agacaaaaga aagtacagca cccagctggg  81360
cgtgggggct cacgcctgta atccagcact atggggggct gaggtgggtg gatcacgagg  81420
tcaggagttc aagagttcaa gaacagcctg gccaaggtga tgaaaccctg tctctactaa  81480
aactacaaaa attagccggg cgcggtggca ggcgcctgta atcccagcta ctcaggaggc  81540
tgaggcagga gaatcacttg aacctggacg gcagaggttg cagtgagcca agattgcacc  81600
attgtactcc ggcctgggcc acagagtgac attctgtctc aaaaaaaaaa aaaaaagaaa  81660
aaaagaaagt acagcaccca gttatgtccg agtgggtgca tgagagtgac cctgagattg  81720
gagacaacgc tgtcacgtgc ttgaagaacg ccacctgaga aagggggcga gaagtggtgt  81780
ccgctggtaa ccagaggtgt tggcttagcc atctgcaggg aggagggtgg tctatcacag  81840
gtgagtttca tctactttct taagcaaatt aaccttactt ttgtgttagg cttgtcccaa  81900
agctgtttta taaatgtgac caaggacaag ctgatccagt agtggccgtg gcaagagatc  81960
aaagcagtgt ttacctgaaa cttctcatgc atgagacgca gcctccatct catttctccg  82020
```

tcagcacaat aaccaggtat gctgacccag tggcatcttc acattgtcgg gaaaatgccc 82080
tttcctgatg cctttcttta ggctttaatt gaaaacattt tattttctag aaaaaagctt 82140
cagctcagga tgtttgagtg taggtcagtc ctttgatagg atattatcat tttgaggatt 82200
gaccacacca cctctgtatt taagctctgc cacaatcact cagctgtgac actgtaaatc 82260
tcttaatagt ttattacatt ccatgtgctg acagttgtat ttttgtttgt gacacttacg 82320
tattatctgt taaaacattt tcactttagt tgtgttacct ttaaagagga ttgtattcta 82380
tcatgcctgt tgattttttg gtgagcgggc tattaaagtc agtgttattt agggttatcc 82440
actagttcag tgatttgcga gattatcatt cacatttatt gtggagcttt tgaatatcgt 82500
gtcaaatggc cacatatatc ccattcttat ctgcttctta ggtgagtggg acacagtgct 82560
ttaatgaagc tataatcttc agaattctag cttgcagaga agattgcaga agtgataaga 82620
cttgtgcttt ttaattttgt cttttaaatg ttattttaaa aattggcttt atatgatact 82680
cttttttttct gctgagtaac agtgttttac aaaacttgga ctaaatgact tctaagctta 82740
aatgatcact tgatgctttt tttctgaatt aggaactcag cttatcaaat atcaaagtca 82800
taattcctga ataaataacg tcttttttca tgtaaagact gctttaaaaa acacatggaa 82860
ggctgggtgc ggtggctcac gcctgtaatc ctaacacttt gggaggccca ggtgggcagg 82920
tcgcttgagc tcaggggttc aagaccaccc agggcaacat ggcaaaaccc acctctactc 82980
aaatacaaaa aattagccag gcgtggtggc gggcccctgt aatcccagct actcgggagg 83040
ctgagggatg agaatcactt gagccccgga ggcagaggtt gcagtgagcc aagattgtgc 83100
cattgcactc ccagcttggg ctacagagtg agactctgtc tcaaaaaaag acacacacac 83160
aaacaaaaaa aacatggaga catttttttg gccaccttaa tatttcccct cagataattt 83220
cctttgttta aactcagaac tggcattttc tctcttggag aagattcagg acaaatactc 83280
ctttaagata agtagaagca gtgaaagagg atttgattat caggaatttg ataagcttag 83340
aataaattgt tgcttcttaa tgtcatttca gaagatgaat atttattaat agatgccaac 83400
tgagatatca ttaaaattga ttactaacta ctacttggaa aagtctccca gttccaaact 83460
tcagcaggcc tcttgacaat tcagctgtgg tcaattgggt cttgcgtgat agatacaatg 83520
accaattgtg cagcagagtg tgctgcttag ctgcctattc tgttagcatt catgtgttaa 83580
cttaaaatca taatctcctt agttttgttg agtgtctccg tggacaagac actgtgaggg 83640
atacaaaatc agattggctt tattcaaacc actggggtat tataattcat ttataattta 83700
ttttattttt tgcctttttt ccatgtgttc taaaggaatt agagtttgta tataactata 83760
atgggggata gaaattgaca tgtgccatga agggaatgca aaaaagtgcc gtgggagatg 83820
agaagtggag aaaggaattt cttttttctt ggaagcagga ataacttcat gaagcatgta 83880
tttcaactta aacagatagt aggcaacgct gtaaggggag tatggctgca gcaaaagtgt 83940
tcggggcaga ctgggaggaa gggagggaat aaattcagcc attgttatgg aataatgatc 84000
aaaatttatt ttcagcccgt ttcacttaaa agttgagact gcttaacttt ttttaatctt 84060
taatcttaaa cttttaaatg ccatttgatc tttaaaaata tatgttttaa tagtgtattt 84120
taagtctcta tatttttgtt attagaatat atagaggcta taacctacta ccaagcataa 84180
cagacgtcac tatggaaaat aacctttcaa gagttattgc agcagtttct catgaactaa 84240
tcacatcaac caccagagca ctcacagtaa gtctctttct tgatcggtct tactgacatt 84300
gtaatagttt ttggtagctt gtatggccag ttagttgtat ggtcatctta cggtgaggtg 84360
cttgtcttac agctcttact tatccatgag gcttgctaag aaattgtgct tctgtgaaaa 84420
gaatctcagc ttactccagg aatgtaaatg actatgtttt ttctgattat taaagtaata 84480
cacgcccaaa ataaaaaaat tcagccaatt taggaagaca caacaattaa aataagccag 84540
gcatggtggc tcatgcctgt aatcccagca ctttgggagg ccaaggttgg gggctcactt 84600
gaggtcagga gtcggatacc agcctggcca acgtggtgaa accccatctc tactaaaaat 84660
acaaaaatta gctgggcgtg gtggcgggcg cctgtaatcc cagctactca ggaggctgag 84720
gcaggagaat cgcttgaacc tgggaggtag aggttgcagt gagctgaggt caagccactg 84780
cactccagcc tgtgcaatag agcgagactc tgtctcaaaa aaaaaaaaaa aaaaagaaaa 84840
gaaaaaagta aactactgtc acctgcattg gtaatgtatc agaagtttaa aatgtctaga 84900
ttataattaa ctcagtgacc tggtaatata tactaaggga aaaatattta taatttacat 84960
ttttacattt ttattttttt aattttatta tttttttttt gagacagagt tttgctcttg 85020
ttgcccaggc tggagtgcaa tggcatgatc tcagctcacc acaacctcca cctcccgggt 85080
tcaagcaatt ctcctgcctc agcctcctga gtagctggga ttacaggcat gcaccaccat 85140
gcccggctaa ttttgtattt ttagtagaga cagggtttct ccatgttggt caggctggtc 85200
tcaaactccc aacctcaggt gatccgccct cctcgacccc ccaaagtgct gggattacag 85260
gtgtgagcca ccatgcctgg ccttacattt ttataataag aatttatgtt gctgacatta 85320
gaaaagaacc ataatatcca agaatccaag aataattaaa ttatgtacat atgctagtat 85380
atagtgtgat gctttggaga atttttaaca atatggagat gtataatctg gattgtaata 85440
ttgagtgaaa aaaggcagaa tacaaacctg gtgggggtat agtcggattt cagttaagaa 85500
aaataatatt tacatatata catttctcac actggcagat aatcaccaag ataaattttg 85560
ggattgtgga tgattttttt cttctttata tttttcagat attctcaaat tttctaaaat 85620
gagcaagtat aacttttgtt atcagaaaaa aataatatac aaaagtaatg ttaatttgct 85680
ggtgaccagg ttaaaccttt ttatttttat tttttgagat ggaatctcac tctgttgccc 85740
aggctagagc acagtggcat gatcttggct cactgcagcc tccgcttcct gggttcaaat 85800
gattctctgg ccccagcctc ctgagtggct ggaattacag gcgtgtggca ccacacctgg 85860
ctaattttttg tatttttagt agaggtaggg tttcaccagg ttggtcaggc tggtctcgaa 85920
ctcctgacct cgtgatccac ccacctcggc ctcccaaagt gctgggatta caggcgtgag 85980
ctactgcgcc cagccagacc tttttatttt atttgacaaa agaaatactt ccatgttata 86040
gaagactaaa tattgtttgg gctgtctgca gtatggtctt cccttgattt gttcaaaata 86100
tcgtaaactt tgcttattta tttttattgt ggccgactgt gtcgggcact gttgtaggct 86160
tgggatggaa aaacaggatt cctgccctta gggtttctgc aggctggtca gggagacgat 86220
gtggtaagct ggagctcagc tcctaaggat gtgcaggggc agttgagagg cggaagggtg 86280
ggagatcatt ccagggtgtg ggcagcacag gaacctctct tcattgggat ataattgcca 86340
ttctgataac acgtgtttga ggtgtctaaa gtaggaagtt gtaccatggt gggacagata 86400
tcctgtggtt atcatacaca gatctcagtt ttcttctcat tgtttgtact ttttataaag 86460
ggtaacagga gatataattc aataaacctt tgtggtgttt gggtgtgatt ttattgtttc 86520
tttcttctca gtttggatgc tgtgaagctt tgtgtcttct ttccactgcc ttcccagttt 86580
gcatttggag tttaggttgg cactgtgggt atgtattttc ctcagtatat attaatagtt 86640
gtctacaaca gtatgacata aacatagtta ttaggatgcc ctttttcttt ctttttaagt 86700
cttttatcaa tttggctttt tggaaaaata tctgatggaa tacttgtttc tgctatatta 86760
gctgtgtgag actagtgaca ggagctgtgg gaaatgaatg ccaaatgttc ttaggcattg 86820
atgggaattt cagggtgtgg tcttcaagtt catttaaggg aattttcata tgctggcaaa 86880
aggcttttct cattagcttg actctttcca aaattatttg ctgtgaatta gaagtttagg 86940
aacctttttt cacttaattg tgacctagca tacgaaatgg tgatgattta ggaactactg 87000
ttcttgtatt aacagctttt atttaaaaat gattttcctc cagtagatgg ccctactagc 87060
atctgggaaa taatttcaag tcttctccag cattcaggaa taggctttca ttttgtgtat 87120
caattactga gaatgatttt ggtgactcac atcacatttg agaagtaaac ctgcagattt 87180
cttgtgtgtg tcagcaaatg accaactgat atttgcttga agtggattac attatctgct 87240
ctagaatgat tgctttccca ccttcctcac atacagactg agcagctacg gtttctaatc 87300
ataggtctgg cactagactt cacttctggg caactttggc attggagtaa aatgtattaa 87360
tttaaagaaa gttaaaaatc cgttcaagta aacatacagt tctaatactt tttacaattt 87420
aaaatataga tttaaatgat aaaataaaaa agaaaatatg ggtagacacc ataatcctcg 87480
tttctgcatc tgttcacaag gggttgatat ttatgagttc tattctccat atccattcta 87540
tgttctctta atgctcagtc agcacctcag gtggttggag ttcaatgctt ggtagtttga 87600
cttacactgt cttttctagg ggattgagcc ctgggtagtc ctgcttattt gaggttgcaa 87660
tttgtctttc aataactttt actacaagat atggcgtgtt aaaggatacc attggggaac 87720
caacataata atatcaggaa aactaaccac gtcagacctg ccccattgtg tatcaagtac 87780
actatttttc catagtaata aagagttcac cccagccaat tctcttttat tttgtgcctg 87840
tttactcaat ggcattaaca tgcccaaatg tctgggtagc tgtctcatct ccagttcagc 87900
agaaccattg tcatatgccc tagtaaaagc attccttcat tggacactta ggccccaata 87960
ctttcattca gatctactac ctgatttcat ttctcaaatg atttttatgg agctctgatt 88020
tataggaaag atgttagttg attaaaaata aaacaatttc tgagctggta taaaatgtat 88080
tgtgacatgc cttcctcttg gaattgcaag agaaaggaag actgttgttt gcttaaaaat 88140
tgtctataat ttgactttgc aaatgtctgc ttccagagtg cctccactga gtgcctcaga 88200
tgagtctagg aagagctgta ccgttgggat ggccacaatg attctgaccc tgctctcgtc 88260
agcttggttc ccattggatc tctcagccca tcaagatgct ttgattttgg ccggaaactt 88320
gcttgcaggt actggtactg agttgaaaca gggactccag gacttggatt ttgatttcct 88380
tagggggaat gggggtggtg agcatatgag gggaaaatac tataaggtca ttgccagtga 88440
tggcttgtcc ctttagtcaa atttcagatg ttacctatat gcataaacac atgcagttgg 88500
cagctgttct gtgctgagta ttttaaagta gcctcttccc aatatagccc ctcagttaac 88560
tacaagtaaa ctcatttga atttcatttt aatgggcacc atatgccagt actccctcgg 88620
gcactgggat gttaagaaag tataatgtat ggacttcatt ctcaagttag ttttagatta 88680
gagggggata cacgtaaaca aaagtgcagt ggtcacacag agtggcccta atcactctcc 88740
ttgggcagat ttatgggctg gtaggaaaga gcacaacacg gagagggtgt agcaccttgg 88800
cgatgataat ggaggatgtg gccagcaagg aagacggagt ccattgaaat tgattttggg 88860
agaagttgcc aatctccatg aaagaattgg ggcctgtgct atttgcttca gggggctata 88920
ggagagtttc gtgaaaggga ctaaaagatg agtattttaa taagatcatt catccaactt 88980
gaacatgggc tggaggagaa ggtagggaga ctcaggagat taatgttgat gctaaggcaa 89040
gataatggct ttgggactgt agggaagaca ctgattgtaa gagaatgaag gaggcagaat 89100
tgccaggcct ggttcaccaa ctgaacttcg gttgtgaaga caaagaaacc tgggatgact 89160
tcacatcctg ggcaggtgtg tggtggtgac agtcatggaa attgggaaca cagatttgtg 89220
cgggaaacat cagtttcagt ttgagtttgg cttatcagtt gaatatcagg cacagatgtc 89280
tggccaactc tcaacatagg gtcttaaatg acttcagttc cccaagcaat ttgtccttcc 89340
catgctattg ggtggagag gtaatgtctg tgcccatatc acagccagtg ctcccaaatc 89400
tctgagaagt tcatgggcct ctgaagaaga agccaaccca gcagccacca agcaagagga 89460
ggtctggcca gccctggggg accgggccct ggtgcccatg gtggagcagc tcttctctca 89520
cctgctgaag gtgattaaca tttgtgccca cgtcctggat gacgtggctc ctggacccgc 89580
aataaaggta atgtcccact tgggtgctgg attcatacag ccttaatgac tatgggtttc 89640
cagactacct ttgtttagta atctgtccct tctttattct ctttttgctt taaatgaaca 89700
aaattgctca gattgtgaca ctaaatttaa catcaaaatg tgaccatgtg gatgggtgca 89760
gtggctcgtg cctgttattc cagcactttg ggagactgag gcaagtggat cacttgaggc 89820
caagagttcg agaccagcct gggcaacatc acgaaacccc ctctctacta aaaatacaaa 89880
aaattagatg ggttgggccg ggcgtggtgg ctcaagcctg taatcccagc actttgggag 89940
gccgaggtgg gcggatcacg aggtcaagag atcaagacca tcctggctaa cacagtgaaa 90000
ccccgtctct actaaaaata caaaaaaatt atctgagcat ggtggcgggc gcctgtagtc 90060
ccagctgctc gggaggctga ggcaggagaa tggcgtgaat ccgggaggcg gagcttgcag 90120
tgagccgaga tcgtgccact gcactccagc ctgggtgaca gagcgagact ccgtctcaaa 90180
aaaaaaatta gatgggcatg gtggtgcgtg cctgtaatcc cagctacttg ggaggctgag 90240
gcaagagagt tgcttgaacc tgggaggcgg agtttgcagt aagccttgat tgtgccgctg 90300
cactccagcc tgggtgacag agtcagactc tttccaaaag aagaaaaaaa tgtgaccatg 90360
tgttttatag ctcttttagt atcatcagtc actgttatcc ctaagaggga aatacctagc 90420
tttagtttta ggtttccagc attagccaag aaagctcaga attgatgttc ctggccaagt 90480
acctcattgc tgtctcctta aatcttggtt aatggctact gtcctggcta gcatagttat 90540
ggagcatttc catggttgta gaatgttctg ccaatctcag ggacagtttt gcttttctgt 90600
gaagcaataa aatcaacttc aaaacaaatg ttaactattt gtacaatgga tttaagatag 90660
accagttcac atactttttt tttttttttt ttttgagatg gagtttcatt cttgttgcct 90720
gggctggagt gcaatggtgt gatctcagct cactgcaact tctgcctcct gggttcaaac 90780
gattcttctg cctcagcctc tcgaggcaga ttacagctgg gattacaggc atgcaccacc 90840
acacccagct aatttttttg tagttttagt agagacgggg tttcaccatg ttggtcaggt 90900
tggtctcaaa ctcctgacct gaagtgatct atccgcttcg gcctcccaaa gtgttgggat 90960
tacgggcatg agccaccacg cccagcctaa gatagaccag ttcacttact gtttatatct 91020
gattactctc tctttgcctt gtcttctacc tttaaaaatc tccctactaa cttcccattc 91080
tcctttagct gccatcagtc ttctcccttc tctgcaaaca tctctggaga gtcccagcct 91140
cagcccacag agcttcccac tgctctgagg tggaccttgt ttgcaaggct tctttggctc 91200
tcttggcctg gaccctgtct actacttcag ccatccttcc ttaacccctg ctggtggttt 91260
ctgttgccac actccatagc agcgtttccc gcccagatca tgtctttaca tctctgggca 91320
ctgctctggt cctgcctgcc tttccctctt tgtatcctgc aggctgctac ccccatcttg 91380
agtgtcctct tcagttggct ttcagagggc ctcctgggtg ttcccttacc cacttgccac 91440
tccccagtca ctgggttcag tccttcctgc ccaccagcac atgctttcta ggctctgtcc 91500
taggccgtct tctctctttg tagtctctgg gccagtgctg ttctagagag tggcagaatt 91560
ttctataacc atggcagtgc tccatagcta tgccaggcaa gacagtagcc actaaacaca 91620
tatagctgtt gagcccttga aatgcagcta gtgtgactga agaactgaac cccgattcgg 91680
tttaattttc attaaattta aatttaaata accttatgtg ggtagtggct ccagtattgg 91740
gcagggcagc ctgagagtcg gggctgttct cctgtcttca gtgtctagat gagggacctc 91800
agaggacctg tctctggagc tgcagttcaa tgtagccagc tgccccgtga cacttacata 91860
tagctgattt gtggatatgt cagacacggt gtgatgagct cagctttctg tcctcctccc 91920
cacatctgcc cctgccccat ttaccccact ttgtgtctta tcaagctaga aacaggtcac 91980
cacaagtctt catttccact caccaagtct tttgtttccc ctactaaata ttttgcgaga 92040
agaaagtgtg tacctttgta ttcacataca tgtacatgca catatacatg cacatatgca 92100
ggggtcccca acctctgtta aaaaccggac tgcaggccgt gcgtggtggc tcacgcctgt 92160
aattccagaa ctttgggagg ccgagaccag tgcatcacaa ggtcaggaga tcgagaccat 92220
tccggctcac acggtgaaac cccgtctcta ctaaaaatac aaaaaaaaat tagccgggtg 92280
tggtggcggg cgcccatagt cccagctacc tgggaggctg atgcaggaga acggcgtgaa 92340
cctgggaggc ggagcttgca gtgagccgag attgtgccat tgcactccag cctgggcgac 92400
agagcgagac tctgtctcaa aaacaaaaca aaacaaaaaa aaaaaaaacc aggctgcaca 92460
ggaagaagtg agcaagcatt accatctgag ctctatctcc tctcaggcca gtggtggcat 92520
tagattctca taggagcgtg tatgagttcg ttctcacact tctgtaaaga catacctgag 92580
acatataaag aaaagaggtt taattggctc acagttctgc aggctgtaca ggcttctgtt 92640
tctgggaagg cctcaggaaa cttgcagtca tggcagaagg tgaaggggaa gtaggcacat 92700
cttcacatgg cccacaggaa aaagagagaa ggagagagag agagagacag agagagagag 92760
agaaaaagaa agattgagag ggagagagga gggagaaagg agagtgcctg taggggggagt 92820
tgctacacaa aggagcacca gggggatggt gctcaaccat tagaaactac cccatgatc 92880
caatcacctc ccaccaggcc ccacctccga cactggagat tacaattcag catgagattt 92940
gggtggggac acagagccaa accatatcag agcatgaacc ctattgtgaa ctgcacattt 93000
gagggatcta ggttgcatgc tccttatgag aatctaatgc ctgatgatga tttgaggtgg 93060
aacagtttca tcccgaaacc atcccccgcc aaccctggtt tgtggaaaaa ttgtcttcca 93120
cagaaccggt ccctggtgcc aaaaagtttg gggacctctg cacatatgca tgcacctgta 93180
catggacaca taatacatgt acatatgcat actttatatt ctctgccact tctggtccag 93240
actgatatac tatctcattt ggattactgc actagccttt tgttttggaa acagcatttt 93300
ttaaaaaatt taatttaatt tttttgagat agggtgtcat tctgttgccc agcttggagt 93360
gcagtgtcat gatcatagct cactgcggcc tcgatctccc aggctcaagt gatccttctg 93420
cctcagcctt ctcagtagtt gggactacag gcatacccac catgcccagc taattttttg 93480
attttttttt ttttttgaga cagagtctca gcctgtcgcc caggctggag tgggttggcg 93540
cgatctcagc tcactgcaac ttctgcctcc caggttcaag tgattctcct gcctcagcct 93600
cccgagtagt tgggattaca ggcgcctgcc accacaccca gctaactttt tgtattttta 93660
gtagagacgg ggtttcacca tgttggccag gctggtctcg aacttgtgac ctcgtgatta 93720
gcccgcctcg gcctcccaaa gtgctgggat tacaggcgtg agctaccgct cccagccagg 93780
aaacagcatt cttgagataa ttcatataat tcacccattt aaagtatata attcattctc 93840
tttagtatgc ccacagagtt gtacagccat caccagaatc agttttagaa cccataaagg 93900
aactctgtac tctttaccca aaacctccat gcctccagct gcaggcagcc actaacctgc 93960
cttctgtctc tgtgactcta cgtcttctgg acattactgt ggatgggctc atacagtcag 94020
tgagcttgtg actggtgcct tctaccaagc agggttttca gtgtagcagc ctctctgttt 94080
ttcttttttt tttaaattgt gacggaactt ctgcctcccg ggttcaagcg attctcctgc 94140
ctcagcctcc cgagtggctg ggactacagg cccatgtcac catgcctggc taattttttt 94200
tttttttttt tttagtagag atgggtttca acatgttagc cagggtggtc tcgatctcct 94260
gacttcatga tccgcctgcc tcggcctccc aaagtgctgg gattacaggc gtgagccacc 94320
atgcccggct aacctttcat ttactgtctg catttcttcc ctgatgcctt ccagtccatg 94380
cacccgattg tagccattca tcctattatg gtttaaggtg actgtcttag tcagcatggg 94440
ttgccataac aaaataccat agcctgggtg gcttcaacaa cagaatttac ttctcacact 94500
tctggaggtt gggaagtcca agatccagga ctttcgcctt gccctcatgt ggtgaggggg 94560
tgaggaagct ctgtggggcc tcttatatat ggatgctaat ctcattcatg aggggtctgc 94620
cctcatgacc cagtcacctc ccaaaggccc cacctcctaa taccatcacc ctggtaatta 94680
agtttcagtg tataaatttg gggactata gacattgaaa ccataacaag cacttttcta 94740
agatcaggga gtgagtaagt agcagagcta ggacctcaat tccacatgtc agtcatcttg 94800
ccttcactct gctccatgat ggctgcctcc tagagcattg ggagtctcga tgttctatat 94860
gctctcatgt gttgtgtatt ggagatagtt gaggctttat gaatacatct ggatttgttg 94920
acttctagct ttgctggtaa ccagctgtga ccttgaataa gttacttcat ctctgagcct 94980
gtttcctctt ttagaaacag gagtttaaaa tgctgctttg ggttgggcac ggtggctcat 95040
gcctgtaatt ccagcacttt gggaggctga gatgggagga tcactggagc ttggagttcg 95100
agaccagcct gggcatcata gtgtgagatc ctgtctcctc aagaaattaa aaaattagct 95160
gggtgatgtg gcgtgtgcct gtggtcccat ctactctgga ggctgaggtg ggaggattgc 95220
ttgagcccag gaggttgagg ctacaatgaa atatgattgc accccatcct gggtgacgag 95280
tgagaccctg tctcaaaaaa gaaaaaaaaa atgctgcttt gtaccccttt catgtcatgg 95340
cgtcatggcc aacatagaat gccctggttg tttgctgttg gagggcatgg gcctgggggc 95400
tccctgaggg ctccttccat cttcaactca ttctctgtgc acctgttagg aagttgtggg 95460
ccagtcccta ccatgtatca ttgtgtgggt aaaagtaaat aaaatgtgta cagtgtctga 95520
actgtacata tcagggtcca agaacaaaat gagtgacatg ggttagctct ttttaataaa 95580
tggtaaaacc aaatattcta attttcagtt ttgttatact tccatcacat gtttttgttt 95640
ttttgttttt tgtttttgtt tttctatttt aggcagcctt gccttctcta acaaaccccc 95700
cttctctaag tcccatccga cgaaagggga aggagaaaga accaggagaa caagcatctg 95760
taccgttgag tcccaagaaa ggcagtgagg ccagtgcagg taggaaacag cgtggggaag 95820
ggagggacat gagtgcagca tctgtcatgt agaaacatag gatttaagta acttggtgtt 95880
ttagagaaat aaatataata cacatcagta aagtgagaga aagtttctcc aggtgcggtt 95940
caagatatta gaaactaatg actgatgtac acagaccacc ttttggtctg aagcatttct 96000
aagtgccact ggctgacatg cagcccctac agcctccagg cttccagccc tagcatggag 96060
catcactctc ctatgcttcc ctggttgcag gtgatggctg gagaggcctc ctgattttca 96120
gtaagggaag tggtgtagat gcttaggaat agatgtagtg agtgaaaaaa ctgattctga 96180
tatgtcaaaa attctgattg gaaatggaat atttacattt ggaagagcta aaggcgagag 96240

```
aaagtgggga taaagtcatc tgagttggag gagcttaaac cattcacaag tttggaggac  96300
ctttttttac ccatgaaaag gtcagaacag aaggggctag gatttaggtg tgactgcagt  96360
ttattgaatt cccatccata ctgctctcgg tgggcagtgg caggggcagg agaggagcct  96420
ggcaaagcat gaagtgactg ctgctgcctc tgctatctgg gacgcctggc cacctgtctg  96480
tacagtctcc ctccagaccc attctcacgc tgtctcttgg cacccagggg ccagtgatgg  96540
ttctcccatt tgttttgtgt atatagcatt tatatcaagg ctatttattt atttatttat  96600
tttatttatt tattttttg agacagagtc tcactctgtc acccaggctg gagtgcagtg  96660
gtgcaatctc ggctcagtgc aagctctgcc tcctgggttc aagcaattct cctgcctcag  96720
cctcctgagt agctgggact acaggtgtgc accaccacac ctggctaatt ttttgtattt  96780
tttattagtg gagacggggt ttcaccttgt tggccaggat ggtcttgatc tcctgacctc  96840
gtgatccgtc cacctcagcc tctcaaagtg ctgggattac aggcatgagt cactgtaccc  96900
ggcctattta tttattttta attgacaaaa ttgtatatat ctgtaatata caacatgatg  96960
tttgaaatat gtgtacattg gccaggcgtg gtggctcaca cctgtaatcc cagcactttg  97020
ggaggctgag gtgggcggat cacgaggtcg ggagttcaag accaaactgg ccagcatggt  97080
gaaatcctgt ctctactaaa aataccacaa aaaaaaaaaa aaaaaaaaaa agccgggcat  97140
ggtggctcgc gccagtcgtc ccagctactt gggaggctga ggcaggagaa ttgcttgaat  97200
ctggcaggtg gaggttgcag tgagctgagt tcatgccact gcactctagc ctgggcgata  97260
gagcgagact ccgtctcaaa aaaaaaaaaa aaagaagaaa tacatatgca ttgtggaatg  97320
gctaattaac ctgtgcatca cctcacgtat cattgttttg tggtgagaac acttaaaatc  97380
tactctttca gtgattttct tgcatatggt acattgctat taactgcagt caccatgcta  97440
tacagtagat ctcttgaact cattcctcct gtctataaat gaaattttgt atccttgacc  97500
aacacattca aggtttttt tgagatggag tcttcttcac ccaggctgga gtaccatggc  97560
acgatctcat ctcactgcaa cctccgcctc ccaggttcaa gcaattctcc tgcctcagcc  97620
tcctgagtag ctgggattac aggcacatgc tactgcacct ggctaatttt tgtattttta  97680
gtagaagtgg agtttcacca tgttggccag gctggtctcg aactcctgac ctcaagtgat  97740
ccgcctgcct tggcctgcca aagtgctggg attacaggtg tgagccactg cacccggcct  97800
caagcgtttt aaaagatgct cttttctaag gattgactgt agtacaggag gaagattgac  97860
ctgttgaaaa gcctcagcct ttacaagtgt aaaattatca gtatattact atcatctttc  97920
tgatgaatta aataaactaa ggactccaag tcaaaagtct tcaaactgaa gtagaatagt  97980
tgtatatagt gcttggcact ttaatattta gtatcggttt aatgataatg tttgtgcctt  98040
tgccgtcttt aaaacatttt tacatcatcc ctgtttgatt acttggtgtg ctcatgaagt  98100
tgttggccac taaggaatct taggctcaga gaggttctgg aattggccag tggtccttga  98160
atcagctgct cctatgattc tctaactgat ttctcacaaa gcaaacaagc aatcataaca  98220
aaacaactgt gcacactgct cttcttattt tgttatttaa aaagtactta ggctctactt  98280
atgtttgtta gtcaatttct cattacttct agttaatcaa aaggtcagag gaaatacttg  98340
aatattttca tactagaata ctttaaaaaa tcatgatttc cagtaatctc tttaaaactt  98400
ggcaagttat tttgatctaa aagtttatct tttgtgtgca tatttttaaa gcttctagac  98460
aatctgatac ctcaggtcct gttacaacaa gtaaatcctc atcactgggg agtttctatc  98520
atcttccttc atacctcaaa ctgcatgatg tcctgaaagc tacacacgct aactacaagg  98580
tatgggcctc tgcatctttt aaaaatatat atgcacacat acttacgtct aatggatagt  98640
```

tgatgttttt cttatgattt gtaggatgta taagcccttt gagatatgag ttacatttag 98700
ttttttcaag tttgtttgtc tttcagcttt gtttatgata gcttctatca tacaggtgtt 98760
ttggattttc atattgtttg tactcacagc taagattgat tacagtgaca gagctaggat 98820
gtgcagccag gttatagggg gaagtggccc tggtggagtc tggagggatc cgtgtacagg 98880
cttccttccc tcccgtgagg ctcacacaaa aatacagcaa catgctggtc ctgcaggtac 98940
cctctgccta acatgagcca caattccaga ctcacagaag aaaagcaggt gttcggcata 99000
aaccatgtgt ttcaaatagt ctgggcatgg tgagccactt gttatcagct agggaaagtt 99060
tatgtcagcg taagaaactg ttcaccagat acccccaaga gccagccttt ctgtctaggg 99120
atgttttagt tttttagttc attttttttt ttaactttaa aattttctgt tcatctgcaa 99180
tttgttagat atgaagtatg tgtctaattt aatttttgtt tttggttgtc cccaataatg 99240
tttacagaag aatttttctg cactaattgg cttgagttac ttacattctc atagttctct 99300
agtttcagta gtttcattta ttattttgtt atatcaatct atctgtctgc tcatctatta 99360
gaagcatcct tgtttttttt ttttcttttt tagacagagt cttgctctgt ccccaggttg 99420
gagtgcagtg gtgcaaccat gcctccctgc agtctcaggg ctcaagtgat cctcccacct 99480
cagctcctga gtacctggga ctaccggcat gtgccaccac acccagctaa tttttacatt 99540
ttttgtagag acagggtctc cctaagttgc ctgggctggt ctcaagctcc tggcttaagt 99600
aatcctccct ccttggcctc ccaaagtgct gggattacag gtgtgagcaa ctgcacccgg 99660
ctacaagtat acttcttaat tattgtagct taatggtatt tatgagggga tcagttcccc 99720
tgttgttctt tagaattttc tggatattct tctttattga ttttgggatg tgaacaatag 99780
aatcaacttc tacttgtaga ttgatttagg gagaacttat acctcagatg ttaagtcacc 99840
ctgtccagaa tgtgggatgc tttcctattt gttcagaact ttttaaatta cctcagaagc 99900
acatgaaatt taaaggattt taaaaaaaac ttaaagatta tttcacatag ctcttgcaca 99960
tttcttgata aatgaatcct caggtattcc tctgtttttg ttactaatag ttacttctta 100020
tgggtttttt ttcccctgaa aatcatttat caaacgtatg tggcttattt tctgaaggat 100080
gtttgataat tttggaagat atgaaagtct tcatatttta caaggtttga ggtctcttta 100140
agctgcatgg ttctcatgtc agctcccaaa gcagaagacg gcatgttgaa aaatgccgta 100200
gagaagatac ttcttttcca cctgttttca actcatatca tcttgaattt cagggcacct 100260
ttccatgctc ctagtgcttg ctatctgttt attattttcc ttcctgaata ccctgaactc 100320
cagcatgttc tgctgtaatt ctggcctccc tggcatcttg gactcctgtt tcctttgctc 100380
tgtcatcccc gcggtcagct cctgctgcgc agcttctcag ctgaagtgcg tttggagtgc 100440
ctggcgtgtc ttgctggatc tttgagtatt gcctctggtt tccttggttc cttctgctga 100500
gttgctcagc gtctccactc cccatttctt gtgtggccct tcctgcactc ctctgattcc 100560
ttttgtcttc cctggtttct tgctttggtt tcgagtctcc acagaacttt tgcagctctt 100620
ctgaagacct ggaagctttt tcatcttaat tctcatctca tgacctcttt tcccttcttt 100680
gagagctaga acttcccatg gtgaacttct ctttccagaa ttccatgcct tcttttccct 100740
cccacttacc tgttgtccag gagaggtcag attgctgtgc atattggagg agaacccttt 100800
cttccctggg ctcttcatct cacatgacat caccacatca cctcgttcct tggaccctca 100860
gtggtgtcac tgctggattt ttctttcctt tggctggcct tagggcacac ccaggttgac 100920
tagcgtagtc atggtattta gatccactca cattttcagt ttctgtgtct gtctcttgcc 100980

-continued tgcttctgac ttcgcccaga gaaagcttct ctttcacaag ggttcttaga tttatgttca 101040
ctgagcacct tcttttctga ggcagtgttt taccaatatt tattttccta gtcagtctcg 101100
ccttaccttt cttgttatgc atgtctttgg tcctgaccca ttctctgagt ctgtaaaata 101160
gaattgctgt ataatttaat tacatgaaat cctttagaat cttaacacat cttacacctg 101220
atttaatatt ttattgtatc caaattgaac caaccctatg tgaatttgac agtgatttct 101280
cccagggatc ctagtgtata aggaatagga cttagtattt tctatttttt gatataccac 101340
ataccagata ctgattatga tggacattta accctttttt ctcattatga aagaaagtta 101400
ggaattattt cttccagtag cgccagtgta acctgaaagc ctttgaaaga gtagtttttg 101460
tatagctatc tgaaaggaat ttctttccaa aatatttttc cagtgctgac aacaaacacg 101520
cagacacacc ctgcaaggtg agtgtacggc gccgcacagt ggaggcatct gctgcagccg 101580
tcgatgtttg tgtctttggt tgtacattat gagatcgtga cagggccagt aaccgtgtgt 101640
tctctccttc accttcccaa ggtcacgctg gatcttcaga acagcacgga aaagtttgga 101700
gggtttctcc gctcagcctt ggatgttctt tctcagatac tagagctggc cacactgcag 101760
gacattggga aggtttgtgt cttgtttttt ctccttgggt tgtggctggc acacttgatg 101820
tgcgtcttct gggctgagtt catctaggat ggagcctggt tctccagggt gcctccggga 101880
gactcctccc tgccccacgt gcttgcgtca caggacccaa gtctgactct gccttagcca 101940
tgaagtttag ggggaagttt ctatttgtat tctatttttg tctgttatca tgtattagct 102000
tagacccagt ttagtttgga aaatcagtgg gtttcaaaat gtgtttgtag agtcctttat 102060
ttcttaactt gaccttttca agtggaaagg ggcaaaacag acgggtaagg gggcggggcg 102120
ggaggtgtga cttgctcttt tgtgcctgag gaagtaacag agctggggtt gacagtcata 102180
ttctctgaca cagatagtct ctgacttatc tcacagaaag tcagcggcag agcctgagtt 102240
aaaagtctcg tagattttct ttttcttttt tttggtggct aatttcagtt ttatttatat 102300
ttgtttattt atttattata ctttaagttc tgggttacat gtgcagaatg tgcagttttg 102360
ttacataggt atacacgtgc catgatggtt tgctgcaccc atcaacccat cacctacatt 102420
aggtatttct cctaatgtta tccctccccc agtcccctca ctccccatgg gccccggtgt 102480
gtgatgttct cctccctgtg cccatgtgtt ctcattgttc aatttccact tgtgagtgag 102540
aacatgcggt gtttggtttt ctgatcttgt gatagtttgc tgagaatgat ggtttccagc 102600
atcatccatg tgcctgcaaa ggacatgaac tcatcctttt ttatggctgt atagtattcc 102660
atggtgtata tgtgccacat tttcttaatc cagtctatca ttgatggaca ttcgggttgg 102720
ttccaagtct ttgctattgt gactagtgcc acaataaaca tacatgtgca tgtgtcttta 102780
tcgtagaatg atttataatc ctttgggtat atgcccagta atgggattgc tgggtcaaat 102840
ggtatttcta gttctagacc tttgaggaat cgccagactg tcttccacaa tagttgaact 102900
aatttacact cccaccaaca gtgtaaaagt gttcctattt ttccacaacc tctccagcat 102960
ctgttgtttc gtgacttttt aacgatcgcc atcctaactg gcgtgagatg gtatctcatt 103020
gtgattttga tctgcatttc tctaatgacc agtggtgatg agcatttttt cgtatgtctg 103080
ttggctgcat aaatgtcttc ttttgcgaag tgtctgttca tatcctttgt ccattttttg 103140
atggggttgt ttgctttttt ttcgtaaatt tgtttaagtt ctttgtagat tctggatgtt 103200
aatcttttgt cagatgggta gattgcaaaa attttatccc attctgtagg ttgcctgttc 103260
actctgatga tagtttcttt tgctatgcag aagctcttta gtttaattag atcccgtttg 103320
tcaattttgg cttttgttgc cattgctttt ggtgttttag acatgaagtc tttgcctatg 103380
cctatgtcct gaatgttatg gcccaggttt tcttctagga tttttatggt cctaggtctt 103440
atgtttaagt ctttgatcca tcttgagttg atttttgtgt aaggtataag gaaggggtcc 103500
agtttcagtt ttctgcatgt ggctagccag ttttcccaac accatttatt aaatagggaa 103560
tcttttcccc attgcttatg tgtgtcaggt ttgtcaaaga tcagatgatt gtagatgtgt 103620
ggtggtattt ctgaggcctc tgttctgttc cattggtcta tatatctgtt ttggtaccag 103680
taccatgcag ttttggttac tgtagtgttg tagtatagtt tgaagtcagg tagtgtgatg 103740
cctccagctt tgttcttcta gcccaggatt gtcttggcta tgcaggctct tttttggttc 103800
catatgaagt ttaaaatagt tttttccaat tctgtgaaga aagtcagtga tagcttgatg 103860
gggggatagc attgaatcta taaattactt tgggcagcaa ggccattttc acgatattga 103920
ttcgtcctat ccatgaacat ggaatgtttt tctatttgtt tgtgtcctct cttatttcct 103980
tgagcagtgg tttgtagttc tccttgaaga ggtccttcac atcccttgta agttgtcttc 104040
ctaggtgttt cattccctta gtagcatttg tgaatgggag ttcactcatg atttggctct 104100
ctgtttgtct gttattggtg tataggaatg cttgtgattt ttgcacattg attttgtatc 104160
ctgagacttt gctgaagttg ctaatcagct taaggagatt ttgagctgaa ccaatagggt 104220
tttctaaata tacaatcatg tcatctgcaa acagggacag ttttacttcc tctcttccta 104280
tttgaatacc ctttattgct ttctcttgcc tgattgcgct ggccagaact tccaatacta 104340
tgttgaatag gagtggtgag agagggcatc cttgtcttgt gccggttttc gaagggaatg 104400
cttccagttt ttgcccattc agtatgatat tagctgtggg tttgtcataa atagctctta 104460
ctatgttgag atacgttcca tcgataccta gtttattgag agtttttagc atgaaaggct 104520
gttgaatttt gtcaaaggcc ttttctgcat ctgttgagat aatcatatgg tttttgttgt 104580
tggttctgtt tatgtgatgg attacgttta ttgatttgcg tatgttgaac cagccttgca 104640
ttccagggat gaagctgact tgattgtggt ggataagctt tttgatgtgc tgctggattc 104700
agtttgccag tattttattg aggattttca catcgatgtt catcagggat attggcctaa 104760
aattctcttt ttttgttgtg tctctgccag gctttggtat caggatgatg ctggcctcat 104820
aaaatgagtt agggaggatt ctctcttttt ctattgattg gaatagtttc agaaggaatg 104880
gtaccatctc ctctttgtac ctctggtaga attcggctgt gaatccatcc tggacttttt 104940
ttggttagta ggctattaac tattgcctca agtttagaac ctgttatcag tctattcaga 105000
gattcagctt ttttctggtt tagtcttggg agggtgtatg tgtccaggaa tttatccatt 105060
tcttctagat tttctagttt atttgggtag agatgtttat agtattctct gatggtagtt 105120
tgtatttctg tgggatcggt ggtgatatcc cctttatcgt ttttattgag tctatttgat 105180
tcttctctct tttcttcttt attagtcttg ctagcggtct acctatttta ttgatctttt 105240
caaaaaacca gcacctggat tcattgattt tttttggagg gttttttttc gtgtctctat 105300
ctccttcagt tctgctctga tcttagttat tttttgtctt ctgctagctt ttgaatttgt 105360
ttgctcttgc ttttctagtt cttttaattg tgatgttagg gtgttaattt tagatctttt 105420
ctgctttctc ttgtgggcat ttagtgctat aaatttccct ctacacactg ctttaaatgt 105480
gtcccagaga ttctggtatg ttgtgtcttc gttctcattg gtttccaaga aaatttttat 105540
ttctgccttc atttcgttat ttacccagta gtcattcaag agcaggttgt tcagtttcca 105600
tgtagttgtg tggttttgag tgagattctc aatcctgagt tctaatttga ttgcactgtg 105660
gtctgacaga cagtttgttg tgatttctgt tcttttacat ttgctgagga gtgttttact 105720
tccaactatg tggtcagttt tagaataagt gcaatgtggt gctgagaaga atgtatgttc 105780
tgttgatttg gggtgcagag ttctgtagat gtctattagg tccgcttggt ccagtgctga 105840
gttcaagtcc tggatatcct tgttaatttt ctggctcatt gatctgccta atattgacag 105900
tggggtgtta aagtctccca ctattaccgg gtgggagtct ctttgtaggt ctctaagaac 105960
ttgcttcatg aatctgggtg ctcctgtatt gggggcgtgt atatttagga tagttagctc 106020
ttcttgttga attgatccct ttaccattat gtaatggcct tctttgtctc ctttgaactt 106080
tgttgattta aagtctgttt tatcagagac taggattgca atccctgctt ttttttgct 106140
ttccatttgc ttgttagatc ttcctccatc cctttatttt gagccaatga gtgtctttgc 106200
atgtgagatg ggtctcctga atacagcaca ccaatgggtc ttgactcttt atccaatttg 106260
ccagtctgtg tcttttaatt ggggcattta gcccatttac atttaaggtt aatattgcta 106320
tgtgtgaatt tgatcctgtc attatgatcc tagttggtta ttttgcccgt taactgatgc 106380
agtttcttca tagcgtcagt agtctttaca atttggcatg tttttgcagt ggctggtact 106440
ggttgttcct ttccatgttt agtgcttcct tcaggagctc ttgtaaggca ggcctggtgg 106500
tgacaaaatc tctgcatttg cttgtctgta aaggatttta tttctcgttc acttatgaag 106560
cttagtttgg ctggatatga aattctgggt tgaaaatact ttttttaaag aatgttgaat 106620
attggctccc actcttttct ggcttgtagg atttctgcag agagatctgc tgttagtctg 106680
atgggcttcc ctttgtgggt aacccgacct ttctctctgg ctgccctttc cttcatttca 106740
atcttggtgg atctgatgat tatgtgtctt ggggttgctc ttctcgagga gtatctttgt 106800
ggtgttctct gtatttcctg aatttgaatg ttggtctgcc ttgctaggtt ggggaagttc 106860
tcctggataa tatcctgaag agtgttttct aacttggttc tattctcccc atcactttca 106920
ggtacaccaa tcaaacgtag atttggtctt ttcacatagt cccatatttc ttggaggctt 106980
ggttcatttc ttttcactct tttttctcta atcttgtctt ctcgctttat ttcattaatt 107040
tgatcttcaa tcactgatat cctttcttct gcttgattga atcggctgtc gaagcttgtg 107100
tatacttcac aaaattctcg ttctgtggtt tttagctcca tcaggtcatt taagctcttc 107160
tctacactgg ttattctagc cattagtcta acattttttt caaggttttt agcttccttg 107220
tgatgggtta gaacatgctc ctttagctcg gagaagtttg ttattaccga ccttctgaag 107280
cctacttctg tcaattcatc aaactcattc tccatccagt tttgttccct tgctggtgag 107340
gagttgtgat cctttggagg agaagaggtg ttctggtttt tggaattttc agcctttctg 107400
ctatggtttc tccccatcat tgtggtttta tctacctttg gtctttgatg ttggtgacct 107460
acggatgggg ttttggtgtg ggtgtccttt ttgttgatgt tgatgctatt cctttctgtt 107520
tgttagtttt ccttctaaca gacaggcccc tcagctgcag gtctgttgga gtttgctgga 107580
ggtccactcc aggccctgtt tgcctgggca tcaccagcag aggctgcaga acagcaaata 107640
ttgctgcctg atccttcctc tggaaacatc gtcccagagc acgaaggtgt ctgcctgtat 107700
gaggtgtttg ttggccccta ctgggaggtg tctcccagtc aggctacatg gggggtcaggg 107760
acccacttga ggcagtctgt tcattatcgg agcttgaatg ccgtaccggg agaaccactg 107820
ctctcttcag agctgtcagg cacgtatgtt taaatctgga gaagctgtct gctgcctttt 107880
gttcagatgt gcccttcccc cagaggtgga atctagagag gcagtaggcc ttgctgagct 107940
gcagtgggct ctgcccagtt cgagcttccc tgctgctttg tttacactgt gagcatagaa 108000
ccacctactc tagcctcagc agtggtggac acccctcccc cagccaagct cctgcatccc 108060
aggtcgattt cagagtgctg cgctagcagt gagcaaggcc ccatgggcgt gggacccgct 108120

-continued gagccaggca caggagagaa tctcctggtc tgctggttgt gaagactgtg ggaaaagtgc 108180
agtatttggg caggagtgta ctgctccttc aggtacagtc actcatggct tcctttggct 108240
tggaaaggga agtcccccga ccccttgtgc ttcccaggtg aggcaacacc ccgccctgct 108300
tcggcttgcc ctccgtgggc tgcacccact gtccagcaag tcccagtgag atgaactagg 108360
tacctcagtt ggaaatgcag aaatcacctg tcttctgtgt cgatctcact gggagctgta 108420
gactggagct gttcctattc ggccattttg gaagcatccc ttgtttttttg aggtggagtc 108480 ttgctctgtc gcccaggctg acgtgcatcg gcacaatctc ggcccactgc aacctttgcc 108540
tcctggtttc aagcgattct cctacctcag cctccggagt agctgggatt acaggcacct 108600
gccaccatgc ctggctaatt ttttgtattt ttagtggaga tggggtttca ccacattggc 108660
caggctagtc tcgaactcct gaccttgtga tccacccacc tcagcctcct agagtgctgg 108720
gatcacaggt gtcagccacc acgcccagcc atattttcag atctccctct ctttgcccta 108780
aaccactgtg cttaataagt agtttttagt ggccagcagt ctccatgtat aacacatttt 108840
agcaaaatgg aaaatactat atgttttaaa tttgaacgtg agattatact gaaataaaaa 108900
tcatctaact gggattcttt aaatagtaag attttctttt ttgtatgtgg gttttttttt 108960
aaccttatta ttatgactgt catatataga aatggctgtt tttcagttac agtcagtgaa 109020
tgtatcaaat gctgccttat ccaaataata aaagtaaatt attaataagt cacaatttaa 109080
tgaagattga tgttagttga tctttatatt cttgaaatca gccatatggt tgtgtgtgta 109140
tgtatatatt tttaaaggta cataaagata ataagctcat ctctgaaaat ttttacattt 109200
ggcataagaa taactggata attaagcatc ttattctctg gcctgtgtct ttacagttaa 109260
aggtagattt actcacctct cctttttgt ttttctaagt tcatcttttt tgctgtttca 109320
agacagaggc ccattttagc tttctcgcat atccttttgt ttgtactttg gaagcctcac 109380
ctgcttaatt gttgagtttt tatccgtggt cttttagagg gggatatgta gggtagaagc 109440
tttcacaggt tcttgtttgc acttggcccc tgactgtttt gaggaatctc cctcactgac 109500
tcacagcatg gcaaggtttc agatctcttt ctgccacaca gcagttctga ggcagctgga 109560
aagatatcca gatgcttaga ttgtcaggcc aggcttgaga tatacaaact attgagcctt 109620
atctgtgacc ttgcttaggt gaaggcatca gagcccctgc accaacatgc ataggcctct 109680
gcatgtgtgc ggggctgggt gttgaggtct gagcacaagt gtagctggag aggtgagctt 109740
gatgtggcga cgggtatgag caggttttct tcagacttct gtgagtttac ctagttccag 109800
gatttaaagg cacagagact ttagaattaa aatagaatca ttttcttttt ctaaatagca 109860
acactaggaa taaaaaataa taattccaca ttcttgacag gtaatgtttt ttcttgtctt 109920
ctaatcctta tttattccat actcattttt atacataatt gaaatgtatt atgcattgga 109980
tttttctttt gcattatatt atagacgatt tttcatgtaa ctccttactg ttccatttta 110040
tatgttttgt ctggtttaag actttatctg caaaccggga aactgtctct acaaaaagaa 110100
aaacaaaaat agttggccgc agtggcatgc gtctgtggtc ccagctactc ggggctgagg 110160
tgggaggatt gcttgagcct tgggaggttg aggctgcaaa gagccatgat catgccattg 110220
cactccagca tgggtgacag actttatact gtctgttttg ggtgatttga taatgatatg 110280
ccctgatgta gttttttat atcttgtgtt tcttgtgcct gggtttattg aggttgggtc 110340
tgtggcttca tagtattttt aaagtttgga aaattttagg ccattctttc tttctttctt 110400
tctttttttt ttttttgaga cagtgtctcg ctctgtcgcc tgcgttggag tgcagtgaca 110460

-continued ctatcttggc tcactgcaag ctctgcctcc tgggttcacg ccattctcct gcctcagcct 110520
cctgagtagc tgggactaca ggcgcctgcc accacgcctg gctaattttt tgtattttta 110580
gtagagacga ggtttcactg tgttagccag gatggtctca atctcctgac ctcgtgatct 110640
gcccgcctgg gcctcccaaa gtgctgggat tacaggcgtg agccactgca cccagctagg 110700
ccattatttc ttcaaagatt ttttttctgc cctgcctccc tccttttttc cctctcttaa 110760
aggggctgtg atttcctgaa tgattgctta gtgttgtccc atagcttact gatgctcttt 110820
tcagtgtttg attgttttat gtgttttctg ttttgtatag tttctattat tgtgttttca 110880
agttctctga tcttttcttc tacagtgtct actctgttgt taatctgtta atctgttgtt 110940
aatcctgtcc agcgtatttt ttttttgtt tttgaaacag tctcactctg ttgcccaggc 111000
tggagtttag tggtgcgata tcagctcact gcaacctcca cctcccaggc tcaagcaatt 111060
cttctgcctc agcctcccga gtagctggga ctataggcac gtgccaccac acctggctaa 111120
tttgtgtatt tttattagag atggggtttc accatgttgg ccaaactggc cttgaactcc 111180
tgacctcagg tgattcatcc gcctcggtct cccaaagtgt tgggattata ggcatgagcc 111240
accgtgtctg gcccctgttc agtgtatatc actaattttg tttttatctc tagaagtttg 111300
atttaggtct tttaaaaatg tctccctgtg tttctgttta gctttgtgaa cacaattgta 111360
ataactgttt taatatcctt ctctgctagt tctaagatct tctaataact tcccagttct 111420
tggtgtttct cattggttga ttgatactcc tcgttttggg ttgtattttc ctgcctcttt 111480
gtatggctgc caatttttta ttggatgccc aaccttgtga attttacttt gttggatgct 111540
atatattttt gtgttcccat agatcttctt gagctttgtt ctgaggttag ttgagttaca 111600
tatagatggt ttactctttt gggtcttgct ttataatttg tcagatgggt tggagcagtg 111660
cttagtttag gactaatttt ttttttggac taattattcc tctttaggaa taattaggta 111720
ccatgcttag gaggcaagac catcctgagt actctaccta atgaaccaga aagtttgggt 111780
tttccagtcc gcctgctgag aacagtgact ttctagccct gtgtgagcgc tgagctctgc 111840
tccttctaat cctttccaat gcttctttcc ctggcctcag ggagttttct cacacacata 111900
tctctgctga gtactcgaga gggaccttcc ccagatctcc agagctctct ctgtcttgtt 111960
ttctcttctc tggtgctctg tcttatgaac tgtggctgtc ttggtctcct tagattctca 112020
gcacctcttc aattcagagg gttgcctgtc cctcctcctt gtgccacagc ctaggaactc 112080
tctcaaagca gcgagttggg gcagccatag ggctgactta gtctctcgtc tcccagggat 112140
cactgtcctt cattgctcat gtccagtgtc ttgaggactc tgggttttgt ctgttttgtt 112200
ttttggtttg ctttggttgt ctcaggcagg agggtaaacc cagtccctca ccctcattgt 112260
gctcagtagt ggaagtctca ctctattaca ttagatatta gtatttgtag cagagccctg 112320
gttccctggt acttggggag ctcttgaaag gccagaaaca gcatgctttc tcaccttttc 112380
cagggcttca gtttctggtg cacatcaagc attccataca catttgttaa agtcctttgt 112440
tagacaagta gtgattcaca ggttctattt gtaatttttt cagttaacat gtattgggta 112500
tctgctggga gctagtaaaa acaaaaagtg gtgtgtgaca aattcaattc tgacaagaac 112560
aaccttaaac acttagaata tactttgagc atatcagaat tttaaaaatg tgtggccctt 112620
gagtatttga aaccaacaag aatctattgc ttattagtag aggatatttt gttaaacaag 112680
tggagagaga ggcattttca gtctaattgg tgttggcttt tagcagctga tggaaaccag 112740
ttcgtgatta gccaggcagt ggtgaaacag gctgtgcatt ctgaatgcct aggtatctag 112800
gcattcagaa tggtggcgct ctttgagtta gcatcttctt ctttcttgat tctttttttt 112860
ttttttttga gatggacttt cgctcttgtt gcccaggtaa caactccagt gcaatggcgc 112920
catctcggct cactgtaacc tctgcctccc tggttcaagc gattctcctg cctcagcctc 112980
tcaagtagct gggattacag gtgtgcgcca ccacgcctgg ctaattttgt atttttggta 113040
gagatggggt ttcactatat tggtcaggct ggtcttgaac tcctgacctc aagtgatgca 113100
cctgcctcga tctcccaaaa tgctgggatt acaggcgtga gccaccactc ccagcccctt 113160
cttgattctt gaaaaggaca ttgggtgctg tacatctcgt tatagatgtt gataaaaatg 113220
cttgtgagaa gagtaacatt aaggtagtta tttggtcatt tttgcagatt attttaagac 113280
aattctagga ctgatttgtg gtaaatcaca cattgctgta tcatagttgt gttcactgaa 113340
catattcagg ggctctacag atgcagggct cttagctgct ttgcacactt ctgaattcct 113400
gccctgcgaa caggactgga tacctaatag acaacaggta cttgataaca gtttattgaa 113460
ttaatgagtg aatgaacaga tacataaatg catgaaagaa tggttgtaat gtatataact 113520
tggatttcaa gactttttac tgactgttca aaataagaaa ttgaaaactt tcctctgatt 113580
ttcctctact atttacacaa tttaaatgga agttatcttg taccttcaat ttctgtctag 113640
gattcgtaca ataacgggtc atctctgagt cgcttaatgt ctcacttgtc tttctacagt 113700
gtgttgaaga gatcctagga tacctgaaat cctgctttag tcgagaacca atgatggcaa 113760
ctgtttgtgt tcaacaagta agagcttcat tcttttcctc ttctgttaag acgttcgggt 113820
atgacagcaa aacgctgcta ctccttaaga ggcaggcgct gttggcataa tcagctggga 113880
ggattgtggg gtccagcgca gcactttttg gctcagtcca tgattgagcc aagaggccat 113940
ccttcccttc actccccagg aggacgaggt ctgtcactgt ggagggcaga ggacaccaga 114000
agctcctctg caacctcgct agttaacttc cagtccctcg gagtttctgt ttagaatgct 114060
caatctcatt tagaattgca aggaaaccca aaacgcctat ttaaggtaca aacagcactt 114120
catacaatat ctcatgaggt attaatagtg attcacagga agaatttcac gctgtgagtc 114180
tttgctaaca tatccagtta tttacagatg gatttgatat ttgtgtggga gattcttaaa 114240
agtgttgttc acgccacatt gttgatgcct catttttttc actgtagttg ttgaagactc 114300
tctttggcac aaacttggcc tcccagtttg atggcttatc ttccaacccc agcaagtcac 114360
aaggccgagc acagcgcctt ggctcctcca gtgtgaggcc aggcttgtac cactactgct 114420
tcatggcccc gtacacccac ttcacccagg ccctcgctga cgccagcctg aggaacatgg 114480
tgcaggcgga gcaggagaac gacacctcgg ggtaacagtt gtggcaagaa tgctgtcgtt 114540
ggtggaagca cgaaagagca agcaggaaat actttgtaaa agaataaaaa cgaaaaatgt 114600
tagcgaacat cttctaatag tctgctgtat tcagagaact ctaggagata tatatggttg 114660
atgcaaagat gatttaaggc atagcccggc cttccaagaa gtgtgtggcc agtgagtgag 114720
atgggcttgg gacttacaca tctcagaggt gggggtagag gaggaggaac actgagtggg 114780
ctgagaagca gccagctctc attgccaaag tgtgtcagca aaccagaatg cagttcataa 114840
tgtccccacc cattcaaagc acaggacctg tagagtggtg tggcatgtgt tggtggcact 114900
tttcaggcct gtaacaagga tgaaagaaca gcttcatagc agcacagtag tgctggtgtt 114960
cagaggtgtg tgaaggccat agaagcatct tggatatatt accttgtgtt ttgtcagctt 115020
tatgactaga agtctctttt cacttaaatt tgtttttttt ttttttgaga cggagtcttg 115080
ctctgtcgcc caggctggag tgcagtggtg caatctcagc tcactgcaag ctctgcatcc 115140
tgggttcatg ccattctcct gcctcagcct cccgagtagc tgggactaca ggcgcctgcc 115200

-continued atcacgcctg gctaactttt ttttgtattt ttagtagaga cggggtttca ccatgttagc 115260
caggatggtc tcgatctcct gacctcgtga tctgcccgtc ccggcctccc aaagtgctgg 115320
gattacaggc gtgagccacc gcgcccggcc tcttttcact taaatttatg tttgtgtttt 115380
taatgcctag tatacaggac ttcttaaatt gccttaagta tgaacaggta tttgagttgc 115440
taatctgtat agtagcaata atagaatccc ttgtttttcc ttttataaat ttagcgatta 115500
aatagctaca attaaaacac tagagtcagg agtcaaggaa aatacccatg ttccaggctg 115560
tatgttagtg atgtacttac tatatattgg agtttcagga gtaagtctgt ttcaatgctt 115620
tctgtaacca tttggggtat taataagcat gtgagtgtgt gcatgtttgg gttaatttca 115680
tatatgtttc ttagaaggga tatcattgat gtaaatattt taaaggcttg tcctccaaaa 115740
aaatcatgta atttcttcta aattactgat cttttaaatg accttcacct ttctctcaaa 115800
tctcacttaa gactgggctg agtagtcagt ttcctgtagc agaaaaaagc tcagacttga 115860
gtagccttct gcgagtgagg agacttgatg gctgtcaggc agctgtaaac tctaaataga 115920
gtgtcattat ctgaagaggg cgatgctgcc acactgagtg gcctttcaag ttgtttctca 115980
atctgacacg ttctgatcgt gtgaatgtga aattggtttg agcaggagta tatctgagtg 116040
cagaggagat tatttaaaga tattctcatt ctctgcttcc cttttattcc catttggcag 116100
atggtttgat gtcctccaga aagtgtctac ccagttgaag acaaacctca cgagtgtcac 116160
aaagaaccgt gcagataagg taaatggtgc cgtttgtggc atgtgaactc aggcgtgtca 116220
gtgctagaga ggaaactgga gctgagactt tccaggtatt ttgcttgaag cttttagttg 116280
aaggcttact tatggattct ttctttcttt ttttcttttt tatagaatgc tattcataat 116340
cacattcgtt tgtttgaacc tcttgttata aaagctttaa aacagtacac gactacaaca 116400
tgtgtgcagt tacagaagca ggttttagat ttgctggcgc agctggttca gttacgggtt 116460
aattactgtc ttctggattc agatcaggtt tgtcactttt atctttcatc catcatacct 116520
gttcctaatt tagtacaaat taccctaaaa gacactgaaa tctactttaa agaaatgtgg 116580
tctgcatgtt tccctcatca gttgctgctg cttatctttt tcatgcacct agctggtgca 116640
gaaggcctgg ggcatagcca gcctcagcaa gtcagcatcc ttgccccagc tccctggact 116700
caaggctaac ctggggttgg ctgttaggga tttccaaagg tttgtcccat ccacttgcct 116760
cccctccaaa ataagtttga atttaaattg tgagatacaa ttaagattta ttgtttgggg 116820
aacatttttg caaaatctag agttagttta aacagattat caattattac cataattgat 116880
catctgcagt ttcaagctat ctaacaggtt cacttacctc tttaaaaagg aatggaattt 116940
agcaggacag taactgagac ccgtgctcct ggagtccatg tgggagctgt gtggctctgc 117000
acaagcattt gcacgcttcc cctcttgact gcattacctt cctcctatag ttgctgtggg 117060
caccagattc tggctagtcc tgtcccttca tgatgcacat tttcctcaag attcgtccca 117120
gttaaatcac tgcagatgaa actgcctttt catcgtcaaa atttaactgt catttttgag 117180
ccgtgatctt gggctacttt cttatgtggg gtaggaatat ttgtgagtta gaaatattac 117240
acttctctat ttccttctag acgtaaatct gttaatcctg tcagcactgt tactcacctg 117300
aaagggtctg tttccctagg agaactgagg gcactcggtc aacactgatt ttccacagtg 117360
ggtattgggg tggtatctgc ttgttttttt tgttgttgtt gtttgttttt ttttgttttt 117420
tttttgagat ggagtctcgc tctgtcaccc aggctggagt gcaggggtgc gatctcggct 117480
cactgccagc tccgcctcag aggttcacgc cattctcctg cctcagcctc ccgagtagct 117540
gggactacag gcacccacca ctacgccagg ctaatttttt gtatttttag tagagacgag 117600
gtttcactgt gttagccagg atggtctcca tctcctgacc tcgtgatctg cccgcctcgg 117660
cctcccaaag tgctgggatg acaggcgtga gccaccgcgc ccggcctggg gtctgctttt 117720
aatgaaggag gcatcaaggg gtgggctttg cgttggcctg atgctttcat ctttctttca 117780
caaaacctgt ccgaagaaaa tccgtctaaa tgggccattg ctctcctcag gaaatagtca 117840
ttgggaactt cttttccttt cctttgacac taggaggctg actggggaga agccctggtc 117900
tatggctgtg ggcagcaggg gctgagagga gcaggctctc agggggcac gggtacccca 117960 agggaagcca gagccctgat ttgttccatt ctagtaagaa caaagactgc tctggtttca 118020
tgtttgttct gattgccttt catcaaccgg tccccttct cccagttctt aagattcagt 118080
acagtgacag ttttatgaac aagaatagaa cactagaaca gacaaaccat tgaactctat 118140
gctgataaag atttattgag ctcctgctgt atgtttgcat tctgcccaga ggctctgaga 118200
aaaccaggcc atatgctcca tgctttatcc atggaagctc cccgtcaggt tgggaaagct 118260
gacagctgca gggaatacag tgtgacacaa aactggctcc catgcagccc ttacgtgtcg 118320
cctctcagat ggttggggga cgaaggtcga ctcctttggg tatcttatta ctaaaccagt 118380
ttcagggaat ctgtgccacc ctatctgcca ttaacgtgaa cagatgagtc cccaaggtgt 118440
aattttgggt attgtctgat gtctcttgga atttattatt tgtttttcca atgagatttc 118500
acctcagggt atagtaaagt tgttgagggg attcctggat gtgttctgca attatctagg 118560
ctgatttcag aatagagtta tgcttatagt caaatttatc agctgtcaag aattttattt 118620
aaaatttatg cagataagca ggaggaaaag aagcctggtt tttacatttt aatcctatta 118680
ttgatgtgaa attttatttt ccttcctgta ggtgtttatt ggctttgtat tgaaacagtt 118740
tgaatacatt gaagtgggcc agttcaggta atagcatttt attattttag atttttttct 118800
tcttcttgtg tacttacatg taatttaggt tattaagtga atgtttaaac tactgttagg 118860
catttttgct gttttcttta aatggaaatc tgactaacat actgtgcatt tttgcttctc 118920
ttaaaaatta atgtatatct caagacttgt ttggaagtag ttatgtatct gaaaattcca 118980
tatgttgtca gtattcattg cacatttcaa agcatttaat tgtgttgaca gatggtggaa 119040
tgaaatcttg tggtggagca ctagttttta aatcttctta gagaaagcag ttttatataa 119100
tgttgtcttt agtaattatt atgcatttgt attctctgca gctttttctt gctagatgtt 119160
gaggttttaa tacttcttgc tagtccatta caggtttata attattaaaa gttaaaattc 119220
ttttagtacc taaaatgctt aataaacatt gtaattagga aaatttagtg cagaaggaaa 119280
gtgttcccag attccctggg gtctggaaac atagtgttta ttctaattac atgacacctc 119340
cactgtgttt tggggcaagt tactgtttct cttttgagtt tcaatttctt caagagcaaa 119400
gaggcagagg agagctagga agatcgtagc tgctgtgccc ctgtgccgtc gggtgccttc 119460
tacctgctgc ctccgaacct ttacacatgt ccctgctctg cgcgagggca cagatgggat 119520
gcactgtggc aggggtgggg ttagagtaga tcacggacac ctgttagctt gatgtgtgct 119580
tgctgtcaag gttgaatcat gaattatttt atgttgctta tattgatatg tatcttaatt 119640
ttaaaagaaa ggtctaaatg gatgtttttg tttttaggga atcagaggca atcattccaa 119700
acatcttttt cttcttggta ttactatctt atgaacgcta tcattcaaaa cagatcattg 119760
gaattcctaa aatcattcag ctctgtgatg gcatcatggc cagtggaagg aaggctgtga 119820
cacatggtaa cgggacacac ctttcactgt cgtcttcggt gtcgtgatgt gcttggcagt 119880
gttcgttttc atatacccac tttgaacgtt gtcagtggca gccatgtgct tctcaggctc 119940

-continued

```
tgcatgtgtg tctgtgtatg tgaaggtact ggttagagac gtttcaaaag agaagagagc 120000
atattcttta ctctcagcaa tttgtaatct tctcagggaa aaaaattcaa gaaacagtaa 120060
gataacctaa ggtacagata gattctgaat ataaagttcc tgttcattca catgaaacgc 120120
taaaagttct tcacttgatc ttagccaaaa ggccaagaag cgatgcaaca ctaaaaattc 120180
ttaaatcgaa cttgccgtga attaaatttt gatctctcat ccagtggtat tggagatata 120240
gtttgacttg ggttcagggc tttctgtttt gcctgatgat tttgctggag cttaaataag 120300
gaacccagga gatggccagc tgtgcaagcc cccagcctgt ggaaggagct agtgtggttt 120360
tatgaatgag ttgcaaatct ttctttgagc tttttgaact gatcttccag cattgcccta 120420
ttgacccctc cctgactcct ttgctggaat ctgtaggctt ttgaactttg acagggacac 120480
atcctaagac ccttgcaaac tcccagatgt gagaatggca ctactactta gagtcttttc 120540
gactcagcgt gtgtgcagaa gagcatcaac cgggctgtgt tgcgaggcag ggccttggct 120600
gacctctcag tgtttacata gctaagccag ttagtgtttg ccacggcctc acaagggctt 120660
cagattcaca cagccaaagt atagattatt aaaggcatag gtgtttggtt tcctggactt 120720
ggagggtctt tggacagaaa atcagtaggc aaccacaccc agtactttgt gctgggaagc 120780
ttggtcatct gtgagagggt cagagagtat acccatgcgt gcatgccacc gaagggtcag 120840
tgagtattcc tgtgtgtgca tgtctcaggg ccggagagag tatgtgtcac tgagaggtca 120900
gagtgtttgt gtgtgtgtca aagagggttg cattgtgccc ttcactgagg ggtcagaggg 120960
tgcctcgcgt gtgtgtgtgt gtacgtgtgt gtgtgtcact gaggggtcag agtgtgcctg 121020
tgtgtgtgct tgtgtgtgcg tacatgtcac tgaggggtca gagtgtgcct ctgtgtgtgt 121080
gctcatgtgt gtgcatacgt gtcactgagg ggtcagagtg tgcctctgtg tgtgctcatt 121140
tgtgagcgta tgtgtcactg agggggtcag agtgtgcctc tgtgtgtgtg ctcatgtgtg 121200
agcgtatgtg tcactgaggg ggtcagagtg tgcctctgtg tgtgtgctca tgtgtgagcg 121260
tatgtgtcac tgaggggtca gtgttcctat gtgctcatga cattgagggt cagagtgtgc 121320
ctgtgtgcca atgaaaggca tttcttatat ttttttatat gtggtcatag tagaccagtt 121380
aatttatttt gactcctgtg ttagaccaaa ataagacttg gggaaaagtc ccttatctat 121440
ctaatgacag agtgagttta cttaaaaaag cataataatc cagtggcttt gactaaatgt 121500
attatgtgga agtctttatt gtcttttcag atgaatcaag tagattattc ttgagaccag 121560
gaatgttgct gttttggtta tttggaaagt tttatcattt tcaaattgac ttttgaattt 121620
gagtcacctt ttttcagaag tggtgttaaa ttataggagc cctaggtttt ttttcttttt 121680
ttagaagtca tcacaaaatg atcagtgttc agaggaagag ctttgacctt ccacatggta 121740
taatgattga taaccttaat tcatctctta ccataaacca agtatgtgta agggtttttct 121800
ttatttcttg aaagcatttt gtagatgttg agagcagttt tccaaatgta atttccatga 121860
aatgcctgat aagggtaccc ttttgtcccc acagccatac cggctctgca gcccatagtc 121920
cacgacctct ttgtattaag aggaacaaat aaagctgatg caggaaaaga gcttgaaacc 121980
caaaaagagg tggtggtgtc aatgttactg agactcatcc agtaccatca ggtaagagga 122040
atgtatgttg gaactgtcgt ggatacttta ttgacccgtg cagatggaag gaagtgccat 122100
gtggtaacgc tcactgttaa ctgtgttact ttgaaccagg tttgggcttt ctggggcctg 122160
ggtagatgcc ggtgcagggg gatggggagg gaggcggggg gtgggggggt gtggtggagt 122220
tggggaggtg cagtggcagg aggtgttgtt ggtgtgtatc cttttttttt ttttgagatg 122280
gagtctctct ccgtcgccca ggctggagtg tggtggcacg atcttggctc attgcaagct 122340
```

-continued ccacctcccg ggtttaagca attctcctgc ctccacctcc cgagtagctg ggattacagg 122400
catgcaccac catgcccagc aaattttttt ttttgtattt ttagtagaga tggggtttca 122460
ccatgatggc caagctgttt cgaactcctg acctcaagtg atcctcctgc cttggcctcc 122520
caaagtgcta ggattacagg cgtgagccac catgcccagc ctggtgttta tctttaaagt 122580
gggcacagcc acaggagttc acctgactcc tggtctgaga gtcacgagat cgttcaagat 122640
agtgaggccc tcttttccaa aacgaggacc aaaaatcaat tgacagtgtt ggtcaagatg 122700
gtagaaacct taaaatgata gaaatctcaa ctctgaaata aaaactttat ttgtatattt 122760
atttaccact attttgacat agggctaagg tctttttctt tgagctgatt tctggttttg 122820
ttttcttaaa gtggcataag aattcaaaga cattttgagg aaggctgagt gcagaaatct 122880
ctctttttaa atgacttctc ctttctttta acttgcactg ttgtctagcc ctcacttatt 122940
ttgtcaattc tttttagctg tttgtctttg aatcttcata aagccatagc ttttctcata 123000
agaagcagca ctttctttgt tcattcatat tttaatgaac ccctgtagta tttaattaaa 123060
tacttaatgc ctaattaaat cacataattg caatgcaaaa gtacatgtat cataaagagg 123120
tctgaaaatg agcaactggc aagcaggtgg tggcaggcag agctgcttgg gtgggtgggt 123180
gtcatggaga ggagttcatc agccacatgt tcagtgagct ctggatatgt ctgtttagaa 123240
atgatcacta ataaacttgt gctcaaccat gtatacctct gggaagcagg tgctcttcag 123300
tagattgcct ctgcagagaa cacagaattg aagtgaatgt ccacaaaggc aatgagccac 123360
ctgcagaata gtttagtcaa ggctgtgttt gaagtttgcc aaagattaat atacatttga 123420
ttttcatgtt gtgccttttc tctgattgtg aaatattaca aattctatac aaataacaat 123480
gatggcaaat cctcctgagc aaagtgtgca ccttgtatgt gccctagagg aacttgtgtt 123540
tcgttctgat tcccctacat ttctcatgtc atagagtggg ggttgcatta gtgtcccccct 123600 gtcctcgctg ggatcacatc tgtttggatc ctagagtctt ccagctgaac tgggacaagt 123660
ataacagacg gacacgtagg ggtggaaagg cgtctcttgg cagcagactt tctaattgtg 123720
cacgctctta taggtgttgg agatgttcat tcttgtcctg cagcagtgcc acaaggagaa 123780
tgaagacaag tggaagcgac tgtctcgaca gatagctgac atcatcctcc caatgttagc 123840
caaacagcag gtttgtcccc gcagccttgg cttgttgttg catagtgatg gtagcttaag 123900
gtccttgtga aaggtgggtg gctggaatca gctcttcctt cagtcctaat ctgtgccttg 123960
atagcagttc tccgtgctag tcatgggaca gctgacttca tttcttctca caatgccatc 124020
tcaggttggt attgcccacc tactttacag gggggatccc acagctccga gaggttatgg 124080
aggtgatcag gcagcacaca gctttagagt gctggggtga gggcgggcca aggctaactc 124140
taaagcccga acccttacct cctacactgc ctcctgcatt ctggtcaacc cagtgtttta 124200
tttggtggtt agatttttgt ttttgttacc ttactgcttg taatttagca gttttccttt 124260
cctttccctt cctttccttt ccgacagggt ctcactctgt cacccaggct agagtgcagt 124320
cgtgtaatct cactgcaaca acctctgcct cccaggttca accaattctc ccacctcagc 124380
ctcctgagta gcaaggacca caggtgtgca ccactacgcc tggctagttt tttgtatttt 124440
tagtagagat gaggtctcgc tgtgttgccc aggctggttt taaactcctg ggcgcaagtg 124500
atccaccaac cttggcctgc caaagtgctg gcattacagg tgtgagccac ctcgcctggc 124560
ctattcatca ctaatcagaa tttctatgat caaatgacat gaatcattgt ttccacaact 124620
gcagtggaag gaaatggcct ggcagtgcca gtttcagaag cagcctgccc ccagtcaggc 124680

-continued acaggccact gtgcccccag tgtagcagca cctctgtagc tcacagagaa gggtggtggg 124740
gacctccttg aggcagctct gccagaaaat ctcatgagct gcctggcaca gcttgaggtt 124800
gccttttaag tggactcagc aaatacatgt ttgttcatct tgattataca caataaacaa 124860
ctactctgta tagtacgagt agtccgtggt ttttggcatt tgatttaaac ttagaggcat 124920
gtgatattga tgttactgcc ttcatgactg cacccccatt ctgatttcat aatggaatgt 124980
tatcttgaga ccagttagac aacaggacag ggatcttggc ttctggtgag attgacagca 125040
gttttagtgt ggtcagggtc tccctgccta cagatggttt tagaatggtg ccctggaagc 125100
tttatcccat tcttttctgt gcgtaatctg agtagagtgg agatcgaagg cctgaataca 125160
tagtaaatac ctgacttaat atctgccgca atggaaattg tgtgatacaa catttatgaa 125220
acgcttagtg cagcacctgc caggtagctc accacaggtg catgttgcat tcagaagtag 125280
tgctagatac tatcctgtta ctggcagtgc atacatcagt gatcaaagca gattaaagaa 125340
agaccccctg ccttcttgga gtgaagattt tgttgggatg cgggtaaggg gacagacaat 125400
agaaaagcaa gtgagtgaag tctataccat ggcggctgat caggaacacc gtacagaaga 125460
atccaggagg gaagagagtt aggtggtgtc tgcggtggga gtggcattgt tcagctggtg 125520
atgagaagaa gctttggtga tctggtgaca tttgagtgaa tttgcagaaa ggaaagatac 125580
aagcctagga gatacctggg gaaggaacat tccaggcaga gcaaatagca gtgcaaaggc 125640
cctggcgggg ggcggacatg ctgttagggt acaagcaatg agggtggagg agtggggcag 125700
ccatggggag ggaagggagt gaggcctggt ggggtgaggc cagtgtggag gagccttgag 125760
agggtttgcg ctgatgtggt gtaggtttta gcaggatcat tcttattcct gagttgagaa 125820
tagccttgag gggaggtgga gggcagagca gggccaccca tgtgagaccc ggcactggag 125880
tggaatggcc caagtcagca tcccttggca gcatgaaagc aaaaccagca aggtttgctg 125940
gtggcttaga tgtggcatgt gagagagagc agggctttgg gggtgatttc agggtgagga 126000
cagggtggct gtggacaagg tagggcagac attgggggca gcaggaggtc agagcctgtc 126060
tggatgtagc agttgagacc ccataggtgc ctaatgaggt gaggccagca tcaggtgtat 126120
gagcctggag ttgtcgagag actgtggggc agggggtcag catctgagat gtccactcac 126180
agtggaccca gactggctgg agaggaggag gagcttgaat accgagcctg ctgagtccca 126240
gctccaaggt caggtaggtg aggggagcca gtgctggggc agggggagta ggcaggtgtg 126300
gggttcctaa agccaagatt ttttttaagg cattttgtgc aggagggcga catctgctgt 126360
cagcaccttg ggaacttggc ccaggtttgg cagcaccgag ggcactgatg agtgcttttg 126420
gaggagcaaa gggagccaaa ccctaatggg aatgtgttcc tgaaaggaca ggagagagac 126480
ttgggaaaag gttttacttg aagagggaac ggagaaatag ggcagtagcc agaggaggag 126540
aggagtcggc aatgggttaa gttggcagaa atgaaggcct gtttacgcac tgagggcaga 126600
agcaacaggg aggatcagtt catgacacag gagacacaaa tcgccgttgt ggtgttcaca 126660
gacatgggtt aggattggct gcatggatga cagagcactg tgggttctcc cagagttgct 126720
ggggaggagg cagagttggt gagcacaggc gagggtccag gatgcaggaa tcctggagct 126780
caagtcagtt gttcccttgt tgtaagatgt ggccagtgtt gtgagcttca catctgtgcc 126840
ttgaaaaaca ccacatctgt ttgcagagtt gtttactatg tatacacact cagtagaaac 126900
aaaaattgga aacagtcagt gcccaccatc aataagtaat ggttgaacac actgtggtat 126960
aagcttagac tattttagct tgggctattt tgcatgatta aaaatgttct ggccaggtgt 127020
ggtggctcat gcctgtaatc ccagcacttt gggaggccaa ggcaggcaga ttgcttgagc 127080
tcaggagttt gagaccagcc tgggcaacat ggtgaaaccc tgtctctact agaaatacaa 127140
aaagtagctg ggtgtggtgg tgtgcgcctg tagtcctggc taactcagga ggctgaggtg 127200
ggaggatcac ttgagcccat tcgtgcgcca ctgcactcct ggggcacaga gtgagactct 127260
gttagaaaga gagagagaga aagaagagag agggagggag gaaggaagga aggaaataaa 127320
tggaagaaat ggaagggagg aaggggaggg aggaaggaag aaaggaagtt cagccagttg 127380
ccttgggagt tctccattgc actgggttaa gtgagaagag cagagacgtt tatgattttt 127440
caaaacaact aaaacaaaac ctctgtgggt gagggggcaa ggatatggct ataggaacat 127500
ggggcagatt aagaaaggga tatacacaca ccacttagca tttgttacaa ctgttgtggg 127560
agggatggag tgcagaaaaa gaaaaaaaaa agtgcacacc atcccatgta tgtgtataca 127620
aagggacgct tggaagactg gtccccaaaa tgttggtaat gattgtgtca gggtgctgca 127680
gtgctagttg atttttttc acacttttgt atatttgagt cttttacaga aagcatttat 127740
tatttatgta ataaaaatct aaatgacaag atttctgtta tgggaaaaat gtagctatac 127800
agtgttgttg taaaaatgtt tgcttggttc accactgaac ttaaaatgct tttaaatgag 127860
ggaaggtgac gatgagatga ttatgatgat ttgcccttga gttacatagc tggtgtacag 127920
gaagctgtcg tttcttttgg cttacgtaga aatgtttgtg gtgtctaatt ccacagatgc 127980
acattgactc tcatgaagcc cttggagtgt taaatacatt atttgagatt ttggcccctt 128040
cctccctccg tccggtagac atgcttttac ggagtatgtt cgtcactcca aacacaatgg 128100
tgagtctctc gcctggctca gcagatgaat ctggacggct tgttcaggct ctgattactg 128160
ggaccacccc cagaatgtct gagtcagtca gtttgggtag ggcttcttga gagtttgctt 128220
tttttttttt tttttttttt ggtgtggggg tggtgcggaa cagagtctca ctctgtcgcc 128280
caggctggag tacagtgtca tgatctcggc tcactgcaag ctctgccttc cagcttcaca 128340
ccattctcct gcctcagcct cccgagttgc tgggactaca agcgcccacc accacgcccg 128400
gctaattttt ttgtattttt agtagagatg gggtttcacc gtgttagcca ggatggtctt 128460
gatctcctga cctcgtgacc cgcccatctc agcctcccaa agtgctggga ttacaggcgt 128520
gagccaccgc acccggcctt tttatttttt ttggagatgg agccttgctc tgtcacccag 128580
gctggagtac agtggcgcta cctcgactca ctgcaacctc cgcctcccgg gttcaagcaa 128640
ttttcctgcc tcagcctccc gagtagctgg gactacaggt gcgtgccact gtgcccggct 128700 aatttttgt atttttagta gagacggggt ttcactgtgt tagccaggat ggtcgcgatc 128760
tcctgacctt gtgatccgcc cgcctcggcc tcccaaagtg ttgggattac aggtggctct 128820
cgcaccaagc caagagtttg catttttagc aaattcccag gtgaaactaa tgcctgcttt 128880
tctgggagca cactttggga ctcagtgata gagaggttta ttggtaggat agtaaaatag 128940
gagttatttt ctttcacaaa attggcaatt gggggaaatt taatcttcct tttttcttca 129000
gctgtgactt atgtattatg tttattttag gcgtccgtga gcactgttca actgtggata 129060
tcgggaattc tggccatttt gagggttctg atttcccagt caactgaaga tattgttctt 129120
tctcgtattc aggagctctc cttctctccg tatttaatct cctgtacagt aattaatagg 129180
ttaagagatg gggacagtac ttcaacgcta gaagaacaca gtgaagggaa acaaataaag 129240
aatttgccag aagaaacatt ttcaaggtat gctttctatc tgagcctata actaacccat 129300
gccttttggg aagtcacgtg atgtttcaca gtcagtaagt ctggaataat acctggtctt 129360
gcttcacttc tgagttgggt aaagaagtct gtatcagtgt aattttctaa tccgtcctgc 129420
attatctatg gctcttggtt catacctgtc ttgaagttct gtcatgttct gtctcttgtc 129480
ctcagtagag atgctacagc agtggctcgc ctcaggcagg gcagggcagt ggggtggctg 129540
tcctgggggc aggcagtagg ggcacgctga cgtcagggaa gttgaaaccc aagagaagcc 129600
agtaaaagtg agtctcagat tgtcaccatg tgctggcagt tttacacgct gtcagtaata 129660
aaagtcttct ccctgcaggg cagcctgcct ccaataaata cgtgtagtat caaatcctgt 129720
cttccctcat aaattgtttg gaagctcccc aaggacagtg atgaggcact cgtaagtgct 129780
tgctgcctag atgggtccct ctccaccttt gctagattct gagcattcac tgagttagag 129840
ctgcttctgc aaatgtgctg cttctgctaa gtggctgtga cttcatgcag ccttcacttg 129900
gtttgtcatc agtggagatg ccctgtgttg tcgaaggaga taagcccagt aagcctgctg 129960
ggcacctttt ggtttgcagg ttcagcaggc agcccatggc tttccctgtg tcgcattgaa 130020
gcagctggct aaaattgatg atacattaaa ttcctgtgac agatgatcag cttgtatttg 130080
tgtaatggtg tacagttcac aaagcttaaa aaaatgctac ctgccatttc atcctcagtg 130140
aggaaggtga tacacagaga gaccaagtga ctgtgtccac ggcgacggcg ctctgcattt 130200
cactttagcg gttaatgtac tctacctata tttttacttt atatttacca tatatctttt 130260
catgtatact tggcgtaagt gctttatagt agtcacctaa ttcactgtca tctttttttgt 130320 ttcttggaag gtttctatta caactggttg gtattctttt agaagacatt gttacaaaac 130380
agctgaaggt ggaaatgagt gagcagcaac atactttcta ttgccaggaa ctaggcacac 130440
tgctaatgtg tctgatccac atcttcaagt ctggtaggtg aatcacatta gtcttcctgg 130500
agtgtctcgt tccccattct gcactataca ctctcagagt gtaggagctg tgctgcccgg 130560
tagaaactct gccttgccca gtgtgccagt tgaaaatatt tgttgctgta agagtacacc 130620
tgataccatg tgacccagca gttccactct tgggtatata cccaaaagaa tggaaagcag 130680
ggtggtgaaa agatatttgc atgccagcat tcatagcagc attattcacg atagctaaaa 130740
tgtggaacca actgaagtgt ccctcgatgg atgaatggat aagcaaaatc tggtgtatat 130800
ttacagtgga atattattca gccttaaaaa aaggacattc tgacacatgc tacaacatgg 130860
gtgaccctta aggacattat gctaaatgaa ataagccagt cacaaaagga caaatactat 130920
gtgattccac ttacatgagg gacctggagt agttaattca tagatataga aagtagaatg 130980
gtggttgcca ggggctgcag gggaggggag ttatttttac aagatgaaga gagttattct 131040
agaaatgaat ggtggtgatg gttgtataac attatgaatg tacttaatgc tactgaactg 131100
tacagttaaa aatagttaag aggaccaggt gtcatggctc atgcctgaaa tccaagcact 131160
ttgagaggcc aaggcaggag gattgcttga gccaaggagt ttgagaccag cctcagcaac 131220
atggtaggac cccatctgta caaacaaact agccggggat agtggtgtgc atgtggtccc 131280
agctactcag gagactgagg ctggaggatc gcttgagccc aggaggttaa gtctctagtg 131340
agatgtgttc atgccactgc actccagcct cggctataga gtaagaccct gcctcaaaaa 131400
aacaaaacaa aacaagacaa gagccaaaaa tggttaagat gggccaatca cagtggctta 131460
tgcctgtaat cccaacactt tgggaggtca aggtaaaagg atcacttgaa gccaggagct 131520
tgggaccagc ctgagcaaca tatcgagacc cctatctcta caaagaaaat caaaaactag 131580
ctagatatgg tgggcacatg cctgtagtcc cagctacttg ggaggctgag gtgggaggat 131640
ctcttgagct caggagttcg aggctgcagg gagctattat tgcactccag cctgggctac 131700
agaatgatac cctgcctctt attaaaaaaa aatccaaaaa aaaaaaaaag taaacctgag 131760
agcttcctcc tcctgtgtta aatttggagg ccaagatgtt tttgttactt ttacaaatga 131820
tcaaggacgg tgaaggttgg gcatggtagc tcacacctga aatcccagca ctttgggagg 131880
ctgaggcggg gtgatcgctt gagcttgaga ccagcctgga caacatagca agagacccca 131940
tctccacaaa aataaaaaaa taaaaaaaaa tagccaggag tagtggcatg agcctgagcc 132000
caggaggtca agctgtagtg agccatgatc atgccactgc actccagcct gggcgagatc 132060
gagaccatgt ctctagagaa agaaaatgac aaggacagtg aacccaagaa agtcataaga 132120
tgccagctgt gcagcaagca tggaaagcag ccagtccaaa ttaggacagt gtgttttcca 132180
agaagaacga tcgtttgtaa tgagaatgct ttgctttaaa taaatgacta aatagctaga 132240
agcctagttc taggggatag gcacgtcttt cttctctcaa gaaaatagaa aggcaattct 132300
aatttctagt aacagcaaac agcattaagt catggtccaa atatgaggca aaccaaaatg 132360
tggcttgatt gttcagcagt tgatctgttg gaagcccttg atattaaaaa ggttctcctt 132420
taagcggctt aggagtcacg atcaaagacc tatagaaaga gatgccatcc ttctaggatc 132480
cttggctctc ttgggaacta gattcagata gtcataatgt aaatactgct tgagctttct 132540
ttctttcttt ctttctttct tttttttttt gagacagagt ttcactcttg ttgcccatcc 132600
tggagtgcaa tggtgccatc tcggctcacc gcaacctctg cctcccaggt tcaagcaatt 132660
ctcctgcctc agcctcccga gtagctggga ttacgggcat gcaccaccac gcctggctaa 132720
tttttgtat ttttagtaga gacagggttt ctccatgttg aggctggtct cgaactcctg 132780
acctcaggtg atccacccgc ctcggcctcc caaagtgctg ggattacagg tgtgagccac 132840
cgcacccggc ccgagctttc atttttgaaa tcaatgtatg actgaaacac tgaagactta 132900
ctgacttaat tatggtttca gaacagaatg aaaatgtctt cggttctgat gaatataaaa 132960
ggaaaactaa ccaagttaat ttggcaagta gatggtagag atagaggtgg ggagtggaag 133020
gggaactaaa atcttcacct agcattgttg ggattatatg gttacatcat ctgaagttga 133080
cagaccaaaa tatagaggct tcagaggtct ccaaatagaa ctaaacatgt aattcagatt 133140
gttaggaggt agtataaatg agctaaatct catctttatt acggtagagt taatgggtga 133200
tgtctaaagt tgtctgaagt ctataaatca tgacaaatta tgatgtggtg attgtattca 133260
acagtctttc agttgcaggg ataaaacccc agtttaaact agagtaagag aaagaatgtg 133320
ttggtttaag ctcctggaaa gtgcaggcaa gggtagttgg taggactgca tctagtgttg 133380
taattctgtg gtctgcattg tatatttatg catctcagct ctgctttctt cttttcattt 133440
atataatttt taaattttat tttaaagata gggtctcact ttgtcgccta ggctgaagtg 133500
cagtggcatg aagtgcagtg cgaggctcac tctagcctcg aactcctggg ctctagagtt 133560
cttcctgcct cagccttcta agtagctgag acaataggca tgtaccaaca tgcctggata 133620
ggttttaaaa tttttttgta gaaatggaag tcttgctgtg ttgcccaggc gggtctttaa 133680
ctcttagctt caggcgatcc tcctgcctct gcctcccaaa atgctgaggt tataggtgtc 133740
acccaccacg cccagtctca tctctgcttc ctgtgttagt tttgttctct ggtgggctgt 133800
tttcacatga ccgaagatga cctctagcag gctgtgttct cagcccctca agtaggccta 133860
tgtgattggc cttgcatgag taatatgggt gaccataaac ccctgaatgc tctggtccac 133920
atgggccaaa tgggagactg gacagcattc cattgatgag gaggtggggc tggtctccgg 133980
gagtaaggga gaggagcaca tgcagtaact gatggtctgc tgcaagggat agcagcacag 134040
cagttagaat tttggaggta actaccagaa ctgaaaacag aaatgataac aagtagttgc 134100
cttaaaaagg gatgggagca gggtgctttt gtgatcaaag ctcctttctc ttactggatt 134160

-continued

```
tttgtacaca ttttgcatac atatcttaga gtaaaagata gcattttcag ccttggtcca 134220
tttgaggata ctcttggcgt ggcccgcctc catgctagca ggctctggtt gtgccaagtt 134280
cagttgagca tcctggctct tgcctgcacg gaacttccag tcagtgcgtc agtatcacaa 134340
gtcttgatat ttcctatgaa gaagaacagt agtgcagtga cagacgaaat gggtgggcag 134400
gcagaggcag gatttctgag ggagagaagt agctagcttt ttgcagagaa gagttccggc 134460
acccaagaga gcagctgaga gtacaggcag gcaggcagga tgccggtagg gcccggccgc 134520
acggcgccac agaatcctgg agaaaggggc ctcttcatgg cctctgcatt cagctgctgt 134580
caccctccgc acaggccatg gccaaaattt aattttcata gtggactcta gtttttgagc 134640
cttacttgct attattgaaa taattttctt gtttcttttt aaagatcttc ggattatgct 134700
tcactgacca ctgtaataag tttaaagttg agaaaatatg gcttgttaat gaatgatagg 134760
tcaattttag tatgttggtc attttaatat tttgccacca gttggtttgg atttgatgcc 134820
aggaggagac agcctcattt ctaaggacta gtcttgcctt tgtgggataa gggtggtgtg 134880
ttctgtgtcc ttctacatgt ccgagcgatc tctgtgcagc tcaaatgtgg tcactgtctt 134940
attgcgctga tttcctctcc ttccatctca caattgaggc aaaatattgt tactgttgaa 135000
gtgttgtcca ataggacttc cagcagagac aggatgtctg cactgtctaa tttagttgcc 135060
tttagccaca tgtggtgttc tgtacctgaa atgtggctgg tctgattgga tagcttaatt 135120
tataatttta tttaatttta attaacttaa atttaaacag ctctgtgtgg atagtggctc 135180
ctgtatgaga cagtgcaggt ctgttgagaa gcagctttac tggtgggagt ggagggcttg 135240
gagagggcac gtgggtttcc tgctggtatc ttttgacctt atttaatctg cccaacattt 135300
gcaagtaagt tgtgtgtgtg tgtatatata aatgtgtgtt tctgtcttct tgtttccttt 135360
gactgcattt atttgaaaga cactaggtgg cagaattact gtatttgatt ggtttcaaga 135420
taagagttga aataattcat ctcgtgtttt tatataagta aggtgtgttt agcatgtaaa 135480
attggtaata tgtattcacg tactgcttaa acaaaggcta tgaattccac ccataaaccg 135540
aaaatgaaga cctttaaatt tgtccatttc aggcgtgggt acttcttaaa taatacctgg 135600
ttcaggaact agtcagaatg gcacccttga ctttttgttt cctgcttttc ctcttgttgg 135660
gagaggaggg tattcatccc aaagtggttt gcctatttca cattccatct aggataagca 135720
gaatagccaa gaaagatagc tgtcctcctg tttacaacat ttggggtaac cagcatccct 135780
ctcttttggt ccaagataga ctggtttaga aacagatgat ggcaccagag gcccaggagg 135840
tggaaacatc agctttgttt gttgtccatg tggctgaatt agagctgtct ggccttgtag 135900
cctcaacacg gccttccagc tttgctcacc gtgattttca aggacacatc ttgtgctctt 135960
ccctgcctgc catccagact atacccagtc agggtggcag gagctgctgc cccttcctcc 136020
ctgagtcctg gtcgtgggtg gtggagatgt gccatgacgc tcacggaggc atgctcaccc 136080
cttcctctgt ggcagagggg atggctgcac gacagctctt ccctgtcctt tccaaagcgt 136140
ctgtggttcc actttttggg gcaaagcagg aatactggaa gagagagaaa gtggtccttt 136200
ctatagtaat aaagttgaca ttgattcaag ttcatgcttg gggaaaggac agggctacta 136260
acaattataa tgctgggagc aatggaattt tctcatgggt atgtggtagg tttaatttta 136320
attatcccag ttaattctta gaactgctct gtgaagtatt tcccgctttg tgcttaagtt 136380
ctaaaagatc ctgtgccaaa accaagaatg aaaacccaag cattctttct tgcccatcga 136440
tctttctctc atcaggccac ttcttgggtt gatagtggtg agtgtagccg ctgccacttt 136500
cagaataccc accatgggcc ccagtcactg tgtggcgtgg agaagagatg gttctctctg 136560
```

-continued tgtcatagct gaacaagccc agcccagaga ggtttctgcc ctaggagctc tcgatggtgg 136620
aattgggatg cgatcccaca tcctgcctgt tttgaaaaca gcattcttta tttccaattc 136680
ctgcttccat tgttcctttt aatatttctt tgtttagctc acaaaaacac ggcttgcgga 136740
gctgctgcgt gcagctgtag ctgtttctct gggtgcagcc tgcatccgcc ttcctgcccg 136800
cctcctttcc tgcactgcca tcgtggtctc cgggcacttg gtccctttct cttcccctga 136860
gtccctttgg ctcccctgtg ccacccttgt gatccacagg ctctgccttc tttctgtctc 136920
agactgctgc tcatcactac tcgggaccct aggaagggag gttccaccga gaagcatctt 136980
ctcatctcag ccacgttctc agtgccactg ttgtctttgt taggtaatgg tagctactgt 137040
aacaaataaa ccaacatttc catggcttca caccagagaa ggttgtttct tggttttatg 137100
acaatgtatt gagggtgttc ttggttcacg gatggttttc ctccatgtgg gaattcgggg 137160
acccaggctc ctttccttct tttggttctg ttctccaggc cttcacatcc tctgtgtctg 137220
gttggggaca aggagaggga aggtaaagaa ggctttgtgg ccttggataa gtgacaggca 137280
tgcctttgct ggtgttctct cgtggtgaca ggtcacagcc ccaccctgta aaaggggact 137340
gagagacgtc gtcctgctgc ttcccagcag cagcactgtg gtctctgatg tgttttctgt 137400
gaggataaaa acaggtgatt ccaggatgag gaaagtcagg gaaacccttg gaaggagggg 137460
accaggcggg tgtcaccatg ggattagtgg tggcttcaga atgagctgca gcgagtgcca 137520
tgccttctaa agcttttgct attctgatat gcccacacca tgcccagcag gtgtctgcct 137580
tgctctccgc agagagagtg atgaatcctt ctcatgagcc tctgtccagt tgttcctccc 137640
tccacctgga agggaccctg ggttcctcat aacatcccag cggaacaggg gaccttctat 137700
cctgtcccca agttcatcct catcctcctg ccggcttcct ggcccctctt atgtctgctt 137760
cctgacgcca catccttctg gattctctgg aattgaattt tgcctttgat gcttatttaa 137820
aaatatccat tgcaggccag gtgtggtggc tcacacctgt aatcctgtgc actttgggaa 137880
gccaaggtgg gcagattgct tgagcccagg agtttgagat tagcctgagc aacatgttga 137940
aatcctgttt ctatagaaaa tacaaaaatt agctgggcat ggtggcgcac acctatactc 138000
ccagctactc aggaacctga gacaggagga tcaattgagc cccggaggcc aaagctacag 138060
tgggctgtga tcgtgccact gtactccagt ctggtcaaac agagtgagac cctgtctgaa 138120
aaaaaaaaaa aaatccattg catacttcac cgtagcgaaa catgtatgtc ttacctttcc 138180
tttcctgcct gtagctgctc ttttacactt aacagccaca ctaagccagc cttaaatgaa 138240
aaacaaacca gcacttcctg tgccctcctg cttccttcat gaggggtccc tccctctgtg 138300
tacactccat tctcattgcc catggtggtt tgtttccctc ttgtttctca agccatggca 138360
gcctgcctct tgccctcttt actaaaaagg cctttgcaga ggctgcctgt gttctttctt 138420
tctaggtctc tctcatccta ggccctccag cttgattctg tggagctgcc ctcttgtcac 138480
tcagtagctt gtggggtctt ctctgtctag ccacttaatt gattgtgttc ctcgagttgc 138540
tgtccatggt ctctcgttac tgttttctct gtgtttctgc ctctctcctt ggccttggta 138600
ggtccatccc ctttgtgacc ttggctgttg ctctcatgga caactttctc ttgctggtcc 138660
ttgtagtcct ggcatccagc ttctcgacac gggacttgtc ctgccagtac ctcagacttg 138720
cacttaaaat tgaactagca ccactgtcac tctccagggc ctcttcttgt taattagatc 138780
attagggatg ttcagaatcc cagcatcata gtatgttcct cctcccgcta ccccaggaac 138840
cctaacctta cctcctcctc tctatctact aggaggtggc cctcagagtc cgtctcatct 138900
tccacctgaa cttccctaat aggctccagc agctgccacc ccgggggctg agtacttcct 138960
ccatgccttg tgcagtgctg agccctttac ctgggttctc ctgtttgctc cttattacag 139020
ccctgcgaac agatactgct cttaattcca tcttacacct aaggaagctg aggccccagg 139080
taaggtgcat ccaaggtcac ccaggtagta gacagtagag ccacgatctg aaccaggcag 139140
tctgattcag agcctgtgtt gacactcagc cacctagaac acagcttgga ttgtgggttt 139200
ctattacctg ttcaaaaccc ctacatcccg ggtctgtccc tgcacgtgct ctgtggcctg 139260
gctgcatctt ccttgaaggc agtgcatgcc tcttcactca gggggcccat gcaggaacag 139320
agggccccac agaaggatga ggccagtgca gaatgggctg gaggggacaa tgctgaccag 139380
gaagcaagtg tagagaaatc ccaggaaacc tggaggagcc agagacaagg cattagaact 139440
cctcgtcgtg acctggtctg cattctctga gtgtgctgct tctgttagct cgcttccttg 139500
gtctcaggtt atagtttaag gcattgtgga gccctaaaaa gcctgtactc tgtttttacc 139560
tgttttagga ccctttcact ttggggatgt gttgattttt tttttttttt tttttttttt 139620
tttgagatag agtctcgctc cattgcccag gctagagtgc agtggcacga tcttggccac 139680
tgctgcccct gcctcctggg ttcaagcaat tcttgtgctc ccgcctccca aatacctggg 139740
attacaggca cccgccacca cactcggcca atttttgtat ttttagtgga gacagggttt 139800
taccatgttg gtcaggctgg tctcgaactc ctgacctcaa gtgatctgcc caccttggcc 139860
tcccaaagtg ctgtgattat aggcgtgagc caccacaccc ggcctgaaat ttaaatcaga 139920
aataaaattt tgatcccaac agtgatgcca ggcagcccag atctggggga gagggtggcc 139980
ttggccagct gggcctttct ctgtttccca agtcttgctg cctctccctg ctgggctttg 140040
cagcctgtgc atgtctctgt gcctttgacc ttgtttatcc aaaggagagg atagaatgaa 140100
gtcatgattc ctggagccct gagaaggatg ctgtggagaa atttgccggt agaatctagc 140160
tgagtgtgtt gctgaggtgc cagcattgtg tgtggggagg ctgaccgctt ggcctgccta 140220
ggcccaggat gctccatggc cgggcacaga ggccacttgg ctgtcaggtg tcaggagcct 140280
gcagagggca cacagagcct ggaccgcagg ggggtcctgc tttctcacct ggcctccttc 140340
agcatttctg tccctcagtc cttagcaagc ccaggagctg ttgagtttgg caggtgccga 140400
gtgctgttcc tgcctgtgta gctgtggctc agtcctgtgg gggccccgct gtggcccgag 140460
tgcagtgatt cgaggcgctg agtgttccct gactccttct ccaggagctg tgttcagact 140520
ttcgcagctc ttggcttgga gctcctggag ggcttggcat tgccgaccaa tgtggaggtc 140580
gacagtgaga gaggaggaat gctagctttc ttgaccagtc cattaaataa gtgggatatt 140640
ggccaggcac ggcggctcac gccttaatcc cagcactttg ggaggctgag gcgggtggat 140700
cacgagctca ggagttcaag accagcctgg ccaacatggt gaaacccct ctatactaaa 140760 aatacaaata ttagctgggc gtggtggcag gcgcctgtaa tcctagctac ttgggaggct 140820
gaggcaggag aacagcttga aaccggaagg tggagtttgc agtgagccaa gattgcgcca 140880
ctgcactcca acctgggcaa caagagcaaa actctatctc aaaaaaaaaa aaaaaagtag 140940
gatatctgtt tctgcttaga aaaatcagaa ttttctaaat gccaggtgtt ctgaatacgt 141000
aagtatggga gacgactcag cctgtttcat ttttatgtaa aatcttcgcg tagccatgtg 141060
gcactggacc gagatgaaag caaagacatt tctccttaac tttgtttcta ggaatgttcc 141120
ggagaatcac agcagctgcc actaggctgt tccgcagtga tggctgtggc ggcagtttct 141180
acaccctgga cagcttgaac ttgcgggctc gttccatgat caccacccac ccggccctgg 141240
tgctgctctg gtgtcagata ctgctgcttg tcaaccacac cgactaccgc tggtgggcag 141300

-continued aagtgcagca gaccccgaag taggttcata atgccccaca gcccagggcg ccagcccagc 141360
accctgtcct gagactccca gtaacctgag ctttggccac cgttaaagca ttttcatttt 141420
ccattttttg tgagggcttg tgaaatttct gctgcatatt aatattcctt tcatggacag 141480
catattattg ggacaaacat gcggtccagc taaaggcatt caaaatagca gttgctttct 141540
aaatgcgatt ttctttggca ggttctttga caccattgca tcttgtggga tatgcttgtc 141600
atgctctgtg gctcctacta agttctagtc cttaaattgg ttccatagcc agacatgttg 141660
caatgtctta acctcattat aaagtaaatg tggttctggt tatccttaga taatgaagta 141720
acagtgtagc aaatttcaaa acctcttgga aatgttattt taccattcaa aaaggcttac 141780
taaggttctc gttatgggtg gccctctttt tgcaaaaggt tttcaggctt aagctccatt 141840
tctaggtgct ccaacactcc attatttgta tatgtatgga aataaaagct gtgaccaccc 141900
ccaaccctgg cccccgccca gctgaatcct cagcacagta tttctggaag gctcaagatc 141960
ccacgctggg gaaaagaagt tctggagaca aaagagggca ggtgctgccg tgcctctctg 142020
ctcagtatgg atactggacc ttgtgctgcc agggctccca gtagggccag ttcatggcac 142080
tcagctggaa agtccactgt tgggaggcat tcttaaccat ccactctgtg ccgtatgtag 142140
tggggtctgg tcattctgtt ggaggagaca gaccagtgac gacatttgaa atgcttggtg 142200
gatgtcttag gcctgttacg atgactgagc actgtggggg caggagacag aaagtcagtg 142260
tctcctagtt ctgtgctgct ttaacgtgca tagaaatcag ctgcggattc agcagatcac 142320
tccttttctg acagatgggc ctgcttactc tgatgttata tcagaaagct ctgaatctgg 142380
gaattgtgtc ccctgaattg gagtaacaga aatgcttaga tgatgagtgt ttaaaagaaa 142440
taaaccaaag gtaaatttag tttggaattc agcaagcgtc ttcattcagc cctctgaggg 142500
caaactacag ctttttgtaa atgtaggtaa attctgtgac tgtttcgtga ccccctctga 142560
tccagttttc ctttataacc ttctgtattg ttccttctat tatcctgaaa taacattaat 142620
agattaggct gggcgtggtg gctcatgcct ataatcccag caccttggga agccaaggcg 142680
ggcagatcac ctgaggccag gacttcgaga ccagcctggc caacatgatg aaatgctgtc 142740
tctactgaaa ataacaaaaa ttagccgagc atggtgacag gtgcctgtag tccctgctac 142800
tcagaaggct gaggcgggag aatcgcttga acctaggagg aaaaggttgc agtgagctga 142860
gatcgcgcca ctgcactcta gcctgggtga cagagtgaga ctccatctca aaaaaaaaaa 142920
aaaaaaaaaa aaattaatgg atcaatggat ttttaaccta ataattaaat ttcaaaaaat 142980
atcgttcttt aatggtaatg taaaggtaaa attaagataa tatgtaacaa gcatgtgagt 143040
gtctaaggtg tccccgtggt ggaaggaaaa aataaatccc cataagtgtc caagatgccc 143100
atagagagca gagctgttct ggtttaaacc cctgctctta gcactgtgtt tttccagctg 143160
tgggtggtgg gggatgagta tctttttatt tccatgagat gagaaaaatg aattactaga 143220
agtgtgaaat acaaaacaca gctgctcttt ttttagccat agactcagca gccataaaat 143280
tgctgtatcc agttgcagaa attcctgctg cttactcttg accctctctc ggtttgtgtg 143340
catctcctct caggctggct cccagatggg agctggctcc aggcgacact gggtgctctg 143400
ctccaggagg tccttatgtg ggtcctgccc tagcctagcc cctctcttat ggactctgtc 143460
actgtgggtt tatgattcac tctcaatctg tcttacctct tggtgaactg ttagagtcct 143520
gcctatactt tggcgcttgt gggtgtgttg tggtacacat gatgtgttgg tcacttccca 143580
gctcatcttg ttctgagtca ccctagattt gggacattca ttcgccacca gtaccgggcg 143640

-continued gtgtatggcc tgagatttgg gggggcttgt gctgctacaa attggggctg aatttgagtt 143700
gacagtggac cttctttatg tctactgctc atatttgaat tgcaaatact gcctcttctc 143760
tttcagaggc tcattaccct atagctgtat tattgcaaag tgcacaatta cagcttgagt 143820
gtaagtcaca ctgcgctggc aggacggccc actgagaaag ggcacgtttc ctgttcgtta 143880
gttttcacat tgacacataa tttacaatac agtaaaatgt acttttctat caactgtagt 143940
cagtaacagc ccccctcccc caaccacatc aagatataga ggagtgctgt cacttcaaac 144000
agttccctct tcctctgcca catcctgccc ctccccaggt ctaaccacca atccgtgctc 144060
tgtccctctg ttcagcccat tgcagaaggc catagaaata gaatctatag gctaggtgtg 144120
gtggctcatg cctgtaatcc cagtattttg agaggctgaa gtgggaggat gacttgaggc 144180
tgggagttca agactagcct gggctgccta gcaagacccc atctccagaa aaaaaaaatt 144240
taaaaattac aatcacgtcc ctgtagttca gctgcttggg aggctgaggc aggaggatca 144300
cttgagctca ggagttagag gttacagtga gctatgatcg tgccactgtg ctccagccta 144360
ggtgacacag caagacgttg tctctgggga aaaaagaaag aaacggaacc acgcggtgtg 144420
cagccttctg agtctggccc ctttcggtga gcagtgtcta aagttctgtc gcgtgttgcc 144480
cacgcgtcgg tggctcgctc cttgcaactg ctgagcattg tatggctagg ctgtagtttg 144540
ttttcacttc accagttggg aaacagagaa aaggcacttt ttaaaaagtt taaatctgta 144600
gaattttggt ttttaccagt tctcttctaa atcctgaggg attacaggaa aagttgttgt 144660
atttcagaat attcttagct tgatgtgacc tctgtccccg ttaaggccct ttgccgcaat 144720
gggaaggacg tcgctcggtc agaccctgaa ggtcagaggg gcagtttggg agtgtgtcaa 144780
cattttaact gtatggacta gagccaagag tctcaaggtt tataattccc acgtattcaa 144840
aaagaaaaaa acaataaagt gagaagtcag tgtagagtga aataacctgt gttagtgggg 144900
aagaagtgtt tttaaacagg atttccataa cgtataacat caacatgttt agagtggtga 144960
tgtttcattg ggaaacgaac agtaaaacat gaaagcaggg aggttttcat tctggcagtt 145020
ggcaactttc acggcagatg gagaatttca aaagcaattg ctcaattatc aaacatagcc 145080
agtgtgagtt ctgaaataaa ggtgctgatt gaatgtgcag ctttatggtg gattttgcta 145140
ttcaggcaag cattttaatt ttctgcctgt taaattctgt tttctttagt ttttcatatg 145200
tggtttattg tagcttagga atagataact gagagtatat attacacata caacattctg 145260
atatggcaat atttaaaaca acttgtctgt tttagaacta gaattaaaca taatcatctt 145320
cagtattttg caaataagct cactgccatc cagaaacatt gtcaatgcat ctgttgctcc 145380
ttctagaaga cacagtctgt ccagcacaaa gttacttagt ccccagatgt ctggagaaga 145440
ggaggattct gacttggcag ccaaacttgg aatgtgcaat agagaaatag tacgaagagg 145500
ggctctcatt ctcttctgtg attatgtcgt aagtttgaaa tgcctgtaaa cggggttgag 145560
ggaggtgggg accaggagaa catcctgtgt agatgacact tgcatggacc ctctggaacc 145620
cagaccgccc ggtgtcctgc caagctccat cgaaactaaa tctagaatga atgtttactt 145680
ctgctgtgac atataattgg agaccaggcc tggccttcca gtcactggat tctaagttgg 145740
actgtgagag tttttgcagc tgactcattt atcaaatgcc cggctattgg ctcacgccta 145800
catgatgctg ggtatgtttg ttaatttgag ggaagcaatg gaataataat aactaatgat 145860
ttaaaaaaca aagtaagtgc attgactgta gtggggttct gattttaaat ttttttaaaa 145920
attaatacca ggagcagtgg cttatgccta aattccagca actcgagagg ctgaggtagg 145980
aagatcactt gagcccagga gtttgagaca agcctgggct atggtgtgag acacccatct 146040

-continued ctaaaaaaat aaaaaataaa aaattatcca agtgtggtgg ctcgtgcctg taatcacagc 146100
tctttgagaa gctgagggcg gaggatggct tgagcctggg agttcgagac cagcctggca 146160
acacagagaa accctgcctc taccaaaaaa agaaagagag gaagaaagaa aaattagcct 146220
ggcgtggtgg tgcatgcctg tggtcccagc cacctgagag actgagaagg gaggattgct 146280
tgagcccaga agtttgaggc tgcagtgagc tgtgactgtg tcactgcact ccggcctggg 146340
tgacaaggcg agacccctgc tctaaaataa tttttttaag ttaatttgta gaaaaggtgt 146400
tagatgttct ttgtcacatt ttatgatgga ttcctgttta aatgccgttc tctttaaaga 146460
aaaaaaaata acttgtggga gtttttaacc ataaaactag catcacatat ttaccatgga 146520
gaatttacaa aaaaacaaat aaacggagga aaataaaacc tcctgtaatc atactactca 146580
gagataactt gctgttagat tttggtctag atttaatact ttttctatat ttatattaaa 146640
aatatttaaa acatatgcat ttctttgtca caaacatggt atcttataga tactactgtc 146700
acatagcaaa acagtgttaa atattctgaa tcagaaaagg aagccgactc tccaactgaa 146760
agaggtgtta tcctagagac tttttctggt gatgacaatt tattaatagt cactttttgc 146820
tttactttct ctattgaagt agtttttcta ttttgttcta cttttaagga taatataatt 146880
tataatgctg tttttcacag aaatataaga aaaaagatac taattttata agttaataaa 146940
gtttgatcat cccaaatcca aaaatctgaa atccaaaatg ctccaaattc tgaagctttt 147000
tgagtgctga cattatgttc aaaggaaatg ttcattggaa ggtttcagat tttcggattt 147060
agggagctca acaaataagt ataatgcaca tatttcaaaa cctgaaaaaa atcctaaatt 147120
cagaatactt ctgatcccaa acatttcaga taagggttat tcaacctgta ctgtcagatg 147180
atcccaaatg aaaaatatta atcgttaacc aaatatcaag gaattgatca cattttacag 147240
tttctgccta ggattatgaa tcaagatgaa aaggctctgc atgtttaaaa atatatattt 147300
ttattttctt ataaatctta aatatctaca cttaagattt atttgatatg tgggatccat 147360
tcatattttg gattcaacag ttctgtcaaa actgtggcag tgatagggga ttcttttttt 147420
cccactgaac tatcacaaaa ttggaaaaag agtaattgga gaaccccact ggcttagccg 147480
gcccgaagcc cgggagaggg caggcagtgc tgtggatggg gtcatcccag cgcaacgctg 147540
cccctgctac ctgcggatct cgctgaggcc tgcctttgtc ctttgaccct tggccatttg 147600
ttagtgtctc tgagagctgg actgctgtac cctacttccc caggggggcct aacttcacac 147660
agcctctgcc gcagtgcgtg gttggaggtg acggccttgg taaatcgagt ttcctacctc 147720
ctcaattatt tgtgctcata cactgtatat ttttagtgag gtttatattt gggatgtgtt 147780
ttctccttct taccctttct ggcctttcta tggcattaat acctggtctc ttcttgtgta 147840
cttgaaaatg aatctctcat catatttttc cttagtgtca gaacctccat gactccgagc 147900
acttaacgtg gctcattgta aatcacattc aagatctgat cagcctttcc cacgagcctc 147960
cagtacagga cttcatcagt gccgttcatc ggaactctgc tgccagcggc ctgttcatcc 148020
aggcaattca gtctcgttgt gaaaaccttt caactgtacg tcttcatcct gccgactatt 148080
gccagttgca gttttccctg ccttaaaaat ggagtattga aatttttaac tttaatttct 148140
gatttgcaaa atagtcatct tttgttcttt tccttcttgc tgttagccaa ccatgctgaa 148200
gaaaactctt cagtgcttgg aggggatcca tctcagccag tcgggagctg tgctcacgct 148260
gtatgtggac aggcttctgt gcaccccttt ccgtgtgctg gctcgcatgg tcgacatcct 148320
tgcttgtcgc cgggtagaaa tgcttctggc tgcaaattta caggtattgg gaagagaaac 148380
cctgatattg atttatattg aaaatttagc aggccaagca aaacaggtgg ctggcttttt 148440
cctccgtaag tatggtcttg acatggtcac cgatagaaac atggaaacat ctgcaaactt 148500
gccgttactc gtgtgtccga tctgactgtt tcttgtattt ttttctagtc tgcccttact 148560
aggatgaact gtacacatca gttcatcctt tttaaatgag catgaggtta ttttgggttg 148620
ttaggtgtta caaacacact aatgtgtttt tgtctattag agcagcatgg cccagttgcc 148680
aatggaagaa ctcaacagaa tccaggaata ccttcagagc agcgggctcg ctcagaggta 148740
atgctggaaa cacaggtcgt ccttgtgtta ggacaaccca ggatataaag gatatagatt 148800
tgtacgggaa taaattcaca ggacaagaaa tcgatgtgcc ttataggtgg gtttactgca 148860
gaagtgccat aatagaacct tcctactttt aaaacaacca gatctcactt tctaaagagt 148920
aaaggatgac cggcaggatc acgtctgtga cgtgagtgga ggcagtttgc actcctggtg 148980
gctgtttgag aggtagcatt tagaatgcct gtattcactg tcctgtgatg agtgggaaaa 149040
taggttatca ggtttatctt agcaaaatca aagcatgtca tctaattgct aaacaagagt 149100
tggcaaatct gagagacatt actcaatcct tggcatgcag gacttacatc tgcatcctgt 149160
tgccatttta tgtcttcaaa gcatttaatc atttagttgt gtttgcaaag tctttgagaa 149220
gcctttgtca gaaatcccta catctcctat gtgagtgtat ttccatgact gcagaataag 149280
ttaaactttt accttttttcc ttcccttgcg gggcggggtg gggggcaggg attgtgtgtg 149340
tgagagggag agagagacag cagagaagga gaatataatt atcatgctgt gtactttgag 149400
ctgaaactgc aaaaaaggaa aaacacacaa aaattattat gcttttcagt ctttagagta 149460
ccttgtctat tatgcttttc agtctttaga gtaccttgtt gatggtgttt ttaaatggga 149520
ttgggcacaa ttaggtggac agtttgggat gatttttcag tctgtagggc caagctcttt 149580
tgtaatttgc attatgaagt tgtcactctc atagcagatg gcgggagata aactattatt 149640
actttttgac cctagactta gtcttcagtc cagatgaggg agattaaaag attataaata 149700
tcttgtgcca gatgaggtga ttttattttg aaatgaccat gaattcctat cagttgtctt 149760
actgggatat ttgatagtgg aatttgtgca tttgagtctt agatgatctg ttttacattt 149820
attaagaaag cctttattag cttttatact gtgtattgcc tgttgcagtg tttgagtata 149880
aatgaaattt ctggaaaata ttaatggagt acaaactgtg atacttaaaa gtaaactagg 149940
gcctgcattt gtatcatgac ctgtttgagt attgatgaga agatagctgt gaagaaaaag 150000
gtttaaacaa gtgtattttc ctttaagaag ccactaatag tgcatctcct tagagtgtat 150060
atttctagaa tcctagtgtg cagagtttag actaagacta aaaaaaaaaa aaaacaaatt 150120
atactgtaat ttcattttta tttgtatttt agacaccaaa ggctctattc cctgctggac 150180
aggtttcgtc tctccaccat gcaagactca cttagtccct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480
gggacccttt tggtaggagt gtggggtgag tagttagtgg gtgaatcaag gaatagtcgg 150540
ccgtggcctg caggcccctg actgcacagg ccttcaagca catgtcaatg ccgttagcct 150600
ccctccatct cctcatacct tctggccacc tgtgagttgc actgccactg ccagccattc 150660
tggtatgttg tcagcacctc cactgctcat acctcatggt tagggaccac ctggagcctt 150720
ggtagagcct tggtagagcc ttggtactct actttcctgg acaaagttca gcttatgaat 150780
atgaatttag atttcaaaaa ccagcagccc aagtataaga aagcgaaggt tcagtcctgc 150840
cttcttaggc tctattcgct aagcacctgc cctgccctgg ttgctgggga gagatgagta 150900
aagcagacaa cccaggagag gatggcaaag gggccgctaa cccttagtgg tttagctata 150960
tttggaaggc ctattggaag ttcaccaggt gaagggggag gctgtgaggg tgcccaggca 151020
ggtaacagaa gtccaaaggg gaaaacctgt ggtgtggtga gccgtatagc cacagcctgc 151080
cggccggcag ccctctcagc ctagtgcggt gttcccaagc actggcctag gcctgtagct 151140
ccagggatgt gaagtcccct tgaacgccgc ccatcatgtt ccccttatcc attttttct 151200
tcccaggact ggtacgttca tcttgtcaaa tcccagtgtt ggaccaggtc agattctgca 151260
ctgctggaag gtgcagagct ggtgaatcgg attcctgctg aagatatgaa tgccttcatg 151320
atgaactcgg tacgggggga gcagtggagg caaggaatcc tcagcttttc ttgtgacttc 151380
caagtgggat ttgtctcatc atcatgtgac ccacttgttg acaacacatg ttggggactc 151440
cagtctgggc agggacggga tgtcggagag actccactct gaatggggcc gggaagtggg 151500
gaggactcca tttcagatgg ggtcgggaca tgggggttat gctgatcgag acagaaaagc 151560
acattgtttc agccacatta gaatccacgg aggtgttgtt ttgaaatcca gctggcccca 151620
aggctgggtg tatggtttgg gatgagaact atctggcctc cactggagga acaaacacag 151680
gatgttatca tctaagctcc atggccaaga cagaatggaa gtcaaggttg cgtatttgcc 151740
gtagacttca acacagtgtc gtaatgcgtg acgtcaataa cttgtttcta gtgtcttgga 151800
agttgatctt tagtcgtaaa agagaccctt ggatgcagcg agatttcctc tactcacacc 151860
tctgttagat gtagtgaggt tcttcacccc ccaaccccag atgtcagagg gcaccctgcg 151920
cagagctagg aggccatgca aagccttggt gtccctgtcc ctcacccgtg ggcaggtcct 151980
gtgagcagtg ggggggccac ctcttgggta tggtgcagcc atggcccaag cagggcttct 152040
tctcagacct actaggacgg gagaaacctc ctggtgcttt agccctgcgt tgatatgcag 152100
caaatgggag ggaagtgggc acctgggagg acaaatgcct gtagaggccg ggagtgacgg 152160
caggtgttca tgaaaagaga ccttgtgggg agggcaacac aacagtgtgt tctgatgtac 152220
tgaagagctc aactgaaaac aacaggagaa ttagcccaaa atccatttac taaaattgtt 152280
tatctttttt tttttttttg agacaaagtc tcgctgttgt cccccaggct ggagtgcaat 152340
ggcgctatct tggctcactg caacctccgc ctcctgggtt catacgattc tcctgcctca 152400
gcctcccaaa tagctggtat taacaggcat gcaccaccac gcccggctaa tttttgtatt 152460
tttagtagag acgggatttc accatgttgg ccaggctggt ctcaaactcc tgacctcagg 152520
tgatccgccc acctcggcct cccaaagtgc tgggattata ggcctgagcc accacgcccg 152580
gcctaaaatt gtttatctta agattcatgc agtgaaagct aacttactga gtgataaatt 152640
tgcttagtga tctgtttatt aggttttcca aatttgctaa ttgggctttg aacagctgta 152700
aaagttctga ctgtaaaaga aagcttcaac ttttggcatt catgatgctt ttctgagtat 152760
taaactaaga tagatgtttt acctgaagga tcggccacca atctttaaat ggctaaacaa 152820
aagggttgct aaaacataat ccaaattgac ataagaaata ccatttttcc aaccaaaatt 152880
ttggcattca tatggctact tttacgtatt tcagctgcat ttgaacatct ttttcaaact 152940
ttagggtggt tggtgtatca ctgaggtctt ggatgacact ttagctttga ttttgttttt 153000
atgaattaaa attgtcatac caaaattttt atttcaagca aatccaagag cataaaaaat 153060
taaaatatta cttaaaatac taagagagaa cagatatata ttttactaag catatgttga 153120

-continued atgaaattgt tcaaatattt ataacaggca tagagtagaa ttttcttaaa aatatttttg 153180
atggtatacc aatttgtatt ttctcagaaa catttgcctt attctttttt ctgttgtgtt 153240
tttcttacct gattgaaagc tcataatctg ttgttattgt ttgttaacct ttaatgctct 153300
gatttcagga gttcaaccta agcctgctag ctccatgctt aagcctaggg atgagtgaaa 153360
tttctggtgg ccagaagagt gccctttttg aagcagcccg tgaggtgact ctggcccgtg 153420
tgagcggcac cgtgcagcag ctccctgctg tccatcatgt cttccagccc gagctgcctg 153480
cagagccggc ggcctactgg agcaagttga atgatctgtt tggtaattaa aattaaaatt 153540
tatcttattt ttaaaaagca ttccagggcc agtatagtac tttgcaccaa gtaaatgtac 153600
aataaaggca gtggatctaa tacattgaaa gcgtttacag aggtagctaa agagcagcac 153660
gggtgtcctc ggctcagaat ttcttcctgt gtgtttgcca ctttgccatt cattgacatg 153720
gtcatggaca tagggctcta agcccttgag gaaggctggg ccagacctca ggggagatgc 153780
agccccaaac cacgtgcagt cctgtggacg gatgtgtaga tgtgccactg aggaacaatg 153840
tcttgagctt tcatcagatt ctcagagaat tgcttgactg cctttcgaag ttgatgcatc 153900
tgtgctcacg tttgcaccca cccacgaggt ccttctgttt caggggatgc tgcactgtat 153960
cagtccctgc ccactctggc ccgggccctg gcacagtacc tggtggtggt ctccaaactg 154020
cccagtcatt tgcaccttcc tcctgagaaa gagaaggaca ttgtgaaatt cgtggtggca 154080
acccttgagg taagaggcag ctcgggagct cagtgttgct gtggggaggg ggcatggggc 154140
tgacactgaa gagggtaaag cagttttatt tgaaaagcaa gatctctgac cagtccagtc 154200
acttttccat ctcagcctgg cagtaagtct tgtcaccgtc aagttattgt agccatcctt 154260
caccctcacc tcgccactcc tcatggtggc ctgtgaggtc agccaggtcc ccttctcatc 154320
tgcacctacc atgttaggtg gatcctaatt ttagagacat gaaaaataat catctggaag 154380
tactttatgt cttaagttgg cctggacatg tcagccaagg aatacttact tggtttgtgt 154440
tagtgcttgt aattcgcccc cagaatgtgt acacgttctg gatgcattaa agtctggcct 154500
gtatccttaa agggccatcg ctgtgctgcc tgccctcagc aaggacacac tttgcagacc 154560
cacagaggct ccgcctccac ctcacaccaa agaaagggag gagtccaaag ggcatcagtg 154620
ccattactca caaaatgata aatacaccct tattctgaac cacgtggagt catatggttt 154680
gtgatccctg tccttcaggt ttcagcttag tggggaagtg ggaaagtcag cgtgtgatca 154740
cagcacaggg tgattgctgc tgattatatt atgtgcctgc tgtatgcagg atgaaatact 154800
ttatatgcgt catcttattt gactctcaca accccctgtg agataggctc tgttactccc 154860
atttgacagg tgaggaaagc aaggcttaga gaatttcagt gacttgccca ggtcctctga 154920
gctaggaagt agccattctg gcatttgaac ccaaggcctg ctatccctag aacccacgct 154980
ctcaaattca acctatgaca gaggcaagcc ctggtgctgt gggagcccca aggaagagcc 155040
tctggcctgg tggccacgta gcccaggaga gatttctaca ggagcccaca gcgctgaagg 155100
agagagaggc agcagagtaa gggggctttg tggcagagag gggactggca ctttggggaa 155160
taggtgggtc aggactgaat gtaatggagc catgtcagag ctgtccttct ggaagggcaa 155220
gggcacctgg acgcgctgcc cctcagtgct ttggacggtt ccacaactgt gattcacacg 155280
gcttccccaa acgaaggtac acgagtgggc attctgtgac tcggtacttc cctttaggcc 155340
ctgtcctggc atttgatcca tgagcagatc ccgctgagtc tggatctcca ggcagggctg 155400
gactgctgct gcctggccct gcagctgcct ggcctctgga gcgtggtctc ctccacagag 155460
tttgtgaccc acgcctgctc cctcatctac tgtgtgcact tcatcctgga ggccggtgag 155520
tccccgtcca tgaacggtgg gttcctatca tagttcctgt ctgcttcacc atgtttttat 155580
tttgtgctgc ctgtttgcca ggtactaagc taggaattgg ggatggagag gtagataaaa 155640
tatgcatcag gaagggctgg gccccatctc ttactctcca atatattgga gtctacactg 155700
gaatttaact ggaatttgct tttttagtca ttttatttag attttgaagt ttcagctttc 155760
atcaaaaata cctctaaact ttatgtctct gtgatctttg gtcttagctg ttttatgtat 155820
ttagtcttat atgatcataa gattaataac attacattca gaagattatt tgttttctgt 155880
cagagttaaa atgtttgttt ttatactgca ttgtaatatt aacgtactgt aaaataaaag 155940
tggcttgttc ttttcaagga acagtatcct caacaagggt cattagccac aatttttaaa 156000
aaattggacg tcatagttta catgttagag ggcgttttga agctttgtat ttttaaatta 156060
aatgttatag agtgatgttt tcatgtttca taattgtttt catctgtgca tttgtagcca 156120
acttgaaaac aaagatccag ggattactac ttaaaagcca gacttcttgg aggttatagt 156180
gatgattttg atagtatctt gagccgtctc ataataacct cagggtgaga gatggccaac 156240
aggagacagt cgagggactt agaaatctga atgaaatctg aagttcaaat cttcagacat 156300
ataccactaa ccaagagatt ggtacctcag tctagtattg tctgtttgtc taaaattggt 156360
tctaaggaat ctaggctagt ctgtctatcc ctttcaactt ttgtgaggct gcacaaatgt 156420
aaaatgttga ataaaaagca ctgatggaag tgtgtagaaa ttcttctctt tgttctgttg 156480
taattttagt tgcagtgcag cctggagagc agcttcttag tccagaaaga aggacaaata 156540
ccccaaaagc catcagcgag gaggaggagg aagtagatcc aaacacacag agtaagtctc 156600
aggacccatt tttttcttac atgttgttcc tccaggactt aaaaatcatt cacagagacg 156660
tgcaccgcgg tgagtgtgga ctcctggaag cgcaccgtag ctccgctgtg tcctgctgct 156720
cctccctagc tgtcagggag gctgtagtcc attgctttgc cagctctttt gtttccgagt 156780
gaacacctta tccgtacaca tgcggctgtc tctgacccta cagaccagct gggatgccac 156840
tgggggagcg ctcccttccc cccgcacttc ccacactctg cagttattct gagatccttg 156900
agggcaggga acaggtttgt cttctttgtg ttctcagaaa ttaatgctcg gcctctggtc 156960
agcaagcaac aaccttttgt tgagtgataa tgaataaata aatgtttccc acatgagtat 157020
tcagtaacct cagtgtcagg ttcagccatc tgttttggtg gatatttaaa agaaaattcc 157080
gcttttccta cagaaaaaaa aaaaaatcca aatcccagtg atttaagcca gttatagact 157140
tagacatata ctacggcttt tcatgcactt tcctcccaat tctagagtag gtattttact 157200
aggaaaatgg tggcagtgcc tgttgggagg aagattcttt ggccaagtgt cttttgttct 157260
tgccagggcc cctaggctgc tggggtgctt cagcttcttt agcccagtgt ctggtgggga 157320
atggcccctg ttgcctgtcc cacagaggtg gggtgcctc acctggagcc tgtccacaca 157380
ttttacacag cacgcttacc tggagcatca ggcatctttt ccatgctctg tggctcagga 157440
aacacgcctt ttcaatcatg agtgcaccag tgcttttggg ctttttctcc ccgcttttgt 157500
gcaatcctgg ttgtggatgg agttttcctg tctttagtct tctgcatagt actttctct 157560 tctggttccc ggttcaaggt tttgtaatta gagaatgacc cagaagcaat ggcattttaa 157620
tgcacagcca aggacttctc tgaatttgta tctcaaacct ctgtgggtcc ttcaggcttc 157680
agtttgtgat ttcatgattt cttgttgcta cctaaggaat atgaaaacac ccacctccct 157740
actctgcatc ttccagccga gtggcacctc aggctgtgga tcctgtgctt ctgtggtgag 157800
gataagaata gtgccaaccg tgtggattga aatcaatcag ttaatccctc catgtaaagc 157860
acctggaacg gatgacagtc ttgttatgaa tactcaacaa atgctatcat gatttttagt 157920
tagatttcca ttgctttaaa acagttgaga catcttggcg gtttgagtta gagcaacggg 157980
ccctgaagtg ggttctgttt gggtgaagat gattatgctt attccccatg gccctcttta 158040
ggcaagagtg ggaagctttc tttgtttttt taatcacctc gataggacgt tacttcttaa 158100
aggtcatcca ataaatatta ataggccggg cgcggtggct cacgcctgta atcccagcac 158160
tttgggaggc cgaggcgggc ggatcacgag gtcaggagat cgagaccatc ccagctaaaa 158220
cggtgaaacc ccgtctctac taaaaataca aaaaattagc cgggcgtagt ggcgggcgcc 158280
tgtagtccca gctacttggg aggctgaggc aggagaatgg cgtgaacccg ggaggcggag 158340
cttgcagtga gccgagatcc cgccactgca ctccagcctg ggcgacagag caagactccg 158400
tctcaaaaaa aaaaaaaaat attaataaag ccaactcgtt agcgtggggc ttaattgctt 158460
aagtccaatg agaagtcctt ctctatccta ggaagttgcc caaactgtag aatctcgtgg 158520
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gccctttgat actagctgag 158760
ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgcccccac tggtgagtct gctcgttcct tgcagaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggccctacat ccctaagaga ttagtgttag acctgattct agagcaacta 159600
gaccactttg cttaatagca gaccagaaac cacacccccct cgagtgagtg agattttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
tactcaggag actgagacag gagaatcgct tgaacccagg aggcgaaggt tgcagtaagc 159960
cgagatcgcg ccactgcact ctagcctggg caacagagca agactccgtc tcaaaaaaaa 160020
aaaaggtagg tgttattgat cagaaccctt gtttcagata acatgaggag cttagcttga 160080
ggagagtgag ggttgatgga gggggactga cttctgccca gtgaaatggc atcatctccc 160140
accagcccgc tgaaataaga tgatggggcc tgttccttag ggcctgcagc atcctcaggc 160200
aggaaagaaa ggccgacctg gcagggtgtg agccagcagg tgtaggtcag ggagaatgga 160260
gccaggtccc agggaagagg cttgtggctg cctgagaagg gtgcgtgcct gcctgtgtgt 160320
gtgtgtgcac gtgtgtgtat gtatgctgga gagtctaggg aggcttgctc caaggacgca 160380
gtattgtttg atcctgagag ataaggattc tgccgcaggg aatgaaggta ttccagatgg 160440
cgggcttatt ccgaagaaga ggccagtgcc tggcggtgct ggaagcagtt gcagaacagg 160500
gagttgtagg ctttcctggg aagagagcag caggggtgct ggagaagcag gccacacttg 160560
ctgcatgggg ttgctctcgg ccccactctt ggtgcacagc gagtcactgt gggttcatta 160620
gcatctggtt atgagacagt aactgctcct ttggaggggc tcgtggagac catgcaggag 160680
ggcacggtct tgaggtcatg ccgtccagag cacacctgag gataggccag gacgggctgc 160740
acgctgtagg taaaattcct ccagcaagct cttcactggc attgaggagt tccctgagtg 160800
cggtcatctg gaaggcagct gtaacaggca ctgcagtctc tccctgggtg ggtaccagag 160860
aggagcatag gggagcataa ccgatttaaa gagagggctt tcctgtggtg aggtaagaga 160920
ttagctggtc attatcatag agccccctct gcctttgtgc agatgggctg tgggaatcct 160980
ggggttccgt tgggtccttt gtcacctcac tgaaggcatg taagctgagc tggccagacc 161040
gtgagctgat cctgccactt gaacagcatc aagcctgcct ctggattctt ctgtgcatgg 161100
cacttgtctg agcacctcac gcacagagaa ctggacttca gagtttacag aaataagctg 161160
tatggttcat tttcatgcct gcttgccaat aaacatatct gagctgaacc tcattgaacg 161220
cctgccttta ttctagcaca gcacctgctg tttgtgggcg aggggtgctg tctctaactc 161280
ctgcctgctt ctcccagcac tccctgagtg gggtgtgcca gcagcctcag gatgaggaca 161340
ggaagtggga gggcagagca gatttgggag ggccacttga tggggaagga agtcccagga 161400
agcagttgga gctgttttct gggggagaag gtgccagctc tgggacagtg ttggggtagt 161460
gaggagggag cccagtggag agaagtcggg cttcctgctt cctcacagta tgtctgtcct 161520
gactcaactc ggatgatgtc acttcctttt catcttctca ggtgtggaag cttggatggt 161580
cacccaaacc gggaggggat tttggcacag cattccctga gatccccgtg gagttcctcc 161640
aggaaaagga agtctttaag gagttcatct accgcatcaa cacactaggt actcttgggg 161700
cctctccttc aggtcaccat tgtcggacat ctaccgggag gaaatccaga gcccccagta 161760
ctgggatctt ctcatttgac tccagaaaag atttaagcat gataataata caaacctatg 161820
tgaatacatt ttgcagtgtt ggcaaaactc cttttatact gagaaaatag atcccagttc 161880
ctgtgttttg tggcttgaat cccagctttg tgtattccgg gcttgtttga agtcaggaaa 161940
ggttcatgtg tagtggacaa cgtgagacca aattctgcct tagattttgc atttaggcta 162000
aacagtggca gcacttgtct cagaatgttt tcttgtgttc accagtctga tcctgttgtg 162060
tctcagtggt ccattttctc atatgggaac aagcagacgg gagcagatgg agtcaggttt 162120
cttggcactc gccttcccca gagcctagag gcagcatggg gagaaagcag gcttggggct 162180
cagacagtcc tggtctgctt ccagccctcc tacctgagca gcgcagggca agtccgtcta 162240
acctctagag accctcagtt ttgtcatatg taaaatgggg gtcgtgtcta tttcatagaa 162300
ttgttgcaga tttagaaatt acatttctaa acaaatgtta ccccttattt ctaaataagt 162360
gtctaaatga ataagtcacc acttttgccc ctatttgatg gcaagaggtg tgatcttgtg 162420
gtgggactgt aatcagtcag ttctcagtga ctgtgccctg ctgtggtgtt tcctggaatg 162480
ttcctgtctt gtcctagaaa gtctggcagg ggcaccctga ctccactgtc cagtcctctc 162540
cccagtccct cgggcttctg cagatttgag gcttgtttgg atcccagaag gttgtggcag 162600

-continued gagacacctt gcctctactt tcccctttat aattcaatgt ccaaagagag ccctgagcag 162660
gtacctcacg ccagctgcct cacggagctc ctcctcttcc tggctgtgag gatcggtatc 162720
agtggcctcc tgctctctcc cccttgccta acacgagcac ctttgcttac ttgggtgccc 162780
ttgctcttga actgcccatc ggacgtgcgt gacccaagac tgtgccgcag tccttgcctt 162840
gtctgtgctc attttctttg ttcatttttt tccctgtaac gtaaattgtt atatttgtct 162900
gtatctgtgt ctgaatcagt cctgcacgct ctccttctct ctgtctcttg ttctttcttt 162960
accccgttta tcacggggac cccgatgtcc attgctctag ttctcctgtc ctaagcaccc 163020
catcccgtct ctctggcctt accacaagtg gcgtggctgc ctcagacatc atgatgggga 163080
catgaagcac agctgtcaga aacaactgtt cgttagatac actcgaatgc agctcatcaa 163140
tagggatgga gggtctgtcg gatgtatttt cactgaatcc ccgttcctac cttgatacac 163200
tctttttaat ctattcttct agacaggtca gaggaaccat tactttgact tttaaatttt 163260
tagcagcttt attgaggtag aattcacata ctacagattt cacccactct aagcggacag 163320
cttggtggcc attagtttta tccacagagt tgtgcagcca gctgcacagt ctcagggctg 163380
gactccaggg aagattttag cccatttagt gagtggggca gaagtggccc tggccctgca 163440
cgaggttgcc tgcatgggcg tccctgccct gtccctgtgt ctgctccact ggggggttgac 163500 caggctgcca gggccgactt gggcctgtgc cacctgcctc tcatgtgtct cggacagtgc 163560
agccgatgtc tatacttcgg tttcctcaat gatgaaatgg aggggatagt gttccccgca 163620
tcatagaact gtgtgaggtt taagggactc actgcccttg gcgtggagcc ttctccaggg 163680
gccgtgctgt gtcggcgtag ctgtcagctc tccgttacag gcttgagaag ggttgacact 163740
ctctcatgta acatttatat ttctaggctg gaccagtcgt actcagtttg aagaaacttg 163800
ggccaccctc cttggtgtcc tggtgacgca gcccctcgtg atggagcagg aggagagccc 163860
accagaagta aggccacacc ctgtgctggt tggcacatgg gcagttatgg ccgcttgcag 163920
gcctttggtg gggaataaaa taaggcagca agctggtgtt ctttttttct cttaccttat 163980
ttttgaaaga gtagctgaat ggtgtcttga ctgatattcc agagcaggga caaagcctgc 164040
tgaggtctgg gggctgcgat taccaatggc tggaatgcat tttattacgg tgcattccat 164100
gttaaggatc aatacgattg tgccctttct ggaaaatatc ttttagttta tcaatattca 164160
gaggagtgta ggttgaatta aaatgaaaag gcactttata aaggccatga gtagtacctg 164220
gtttcatttt tctaatgtct tgcagagatt ttatcaggct tcttgaagtg ttcacgtaca 164280
ttacgctaac acgatattaa taataactgt gctctggtac agcggagcca gcagaatggg 164340
aagttgtgga atgcaggccc ttgattctga tagaaggtgt ggtttgaact cacagaaatg 164400
acagtttgga gggtagacat atgtcacaag tcatcaagat tgtctttaaa ttcatgcata 164460
gaagctaaca gggtgtcata agcaaggcct gtaaaatgta tgagggaatt caaagataat 164520
ttattaaaaa gtaattcatg tttggagttt tgtgcccaaa ggagtccttg atttgaaaaa 164580
tgggcttttg cccatcagat tgtttcaggg cccgtgtgtg cggaggccct gccttgtgcc 164640
ccgtgagctc agcctgacag aaatcctttg gtagcactta aggctcctct tcctcccatt 164700
gaggcaggga agactctggg ttctgcaggc agaggtggtt gtgggtgtct tgctgctctt 164760
gttgacatgt gggctctcct tccaggaaga cacagagagg acccagatca acgtcctggc 164820
cgtgcaggcc atcacctcac tggtgctcag tgcaatgact gtgcctgtgg ccggcaaccc 164880
agctgtaagc tgcttggagc agcagccccg gaacaagcct ctgaaagctc tcgacaccag 164940
gtttgcttga gttcccacgt gtctctggga catagcaggt gctggggaca gtgggttccc 165000
cgctgaagcg tccagcagct tcaaccaggc cgttttcctt cattgctaga attgaaaaca 165060
ccgtccgtgt ggcctgtgca ggagatgcag acccaaaggt ggcctcctgg tcagtgagaa 165120
gctggaaacg tgacaggaac tgacgtgggg ttattgagca tttaggggaa gacgttagca 165180
gagcaggaat gagcaggcaa ctagtagaac acccacttaa gggctcacgg acaggtgctc 165240
acttaggaag tgagtttcat ttggtattac accaggttcc tttaggcaaa gcggagggaa 165300
agttctggtg tttttcactt gtaagatttt gaaggaaaca aaacactctt tacctttttt 165360
ctaaaatgta ggtttgggag gaagctgagc attatcagag ggattgtgga gcaagagatt 165420
caagcaatgg tttcaaagag agagaatatt gccacccatc atttatatca ggcatgggat 165480
cctgtccctt ctctgtctcc ggctactaca ggtacctgag ggaaagggtg cgggggagcg 165540
gttgtacttg ggctagaatg agagaagact ggcatgctca ccacaccagt gatgcgggaa 165600
gacctgagtg tggtctgagt tggaggctgt ggtgctaaat acgctgcccc tttcataagc 165660
aggagtctta gtcaggccca gggaggaagt aaaatctgga aatgaatgag aagcattctc 165720
tcctgccagt caagaaatga gaagcgaaag aattctcacg ggctgtaaga ccagcaggat 165780
ttaaaagttg aattagttgc ttatgttaag aactcaacca agttcatcta cacaagctga 165840
atctccagct tttcctaaga aaccatgtgt ggcagtggct gcagggcagg gcacagctgg 165900
gcctgagcac cccgctccct gcacctctcc cctccctggg ccctgcctgt cactgcccac 165960
tctcccacca agccttccgg ttgtgtgcct gccctatcac aggcatcgga gcttgtcacc 166020
tggtttaaaa gaagagagtt gtgtggggat ttgggatgca cgtttttcac tcaaaagtat 166080
tttagcgtag agctctgtga ttccgtagct atttaggagt ttaagcacct tgaaggcttt 166140
aattgcagaa agttctatgt ggacgtgcaa tgtgttatac gcagtgtcta tgagactcaa 166200
atgtttatta gggcgttgaa gtaaactgag cacttggagg gccatggatc cagccttcaa 166260
ggagctcata agtcaggagg acccaggagc aatgacctgt catagaaggc agaaaagagg 166320
ggcacagagg tgggtgggag gcatacacag gcagctcctg gagctccaag gggagcaagt 166380
gcttccaggg aagggggcgt ggaggcccct ttggaggagg caagttgatc tggggtctgg 166440
cagagggtta gctggggaca tttagcggga ggctggtgcc cgggaattgg ggggatgccc 166500
agcagaaaga catgaggagg ctggcctggg gcgtgggggg gtgtgaaagg ttaagtgggg 166560
gcattatcct gctcccgctc ctgccggctg tatctggtca gcctgggcac cgaggtgggg 166620
ttctggaagg cactgttcac caaaatgctt atctgggtcc cccagagagc ttgcctgcct 166680
ggactgtcgg ctcgcctgca actgctgact cctaagcttt tgcagctcag cccacaacca 166740
gttcctattc acagaggtgg gagctgaggg gtgacaagtg actgctgcag tcttatttgt 166800
catagagaaa aagtgacaga gtccagcttg cccactggcc ctgccagctt aactggttat 166860
aaagtgacaa atccccaaga cccacagggc tctgcacaac ctgggccctc ctgccagtgg 166920
cggcgagggc aggtggctca cggctgggtg cctgtctggg caggagctgg gctggtatgg 166980
ggtgggcctg cggccctgcc cccctgtgca gatcaagact cagggtgctg gtgttcacag 167040
gtgccctcat cagccacgag aagctgctgc tacagatcaa ccccgagcgg gagctgggga 167100
gcatgagcta caaactcggc caggtcagtc tcgcgccccc gccgcctggc ctctgtccgt 167160
ttctgtcctc agactttggc gcttgacaca cccaggagaa aagctcagtg cactttttaa 167220
atgaaaggaa gttttccttt tttttaaaaa aaaatttaat gttcattgtt tttatctgtt 167280
ttattcctag gtcccgcaag cagaggaagc attagttttg tttttattta tgttctgtat 167340
tccagaaagt agttaagaga cctcacatgt agcgatagag atgtgtgtaa gagacagtga 167400
gagggcgtga cttggactta agcaaggacc gtgagacaca aaaagggggg tgaggacaga 167460
gtggagtcag ctgaaatgct caggaggaag tagacgccat gaagggccat ggtatggggg 167520
gccgcaggcg tggccgtgag tgtccctggg gccagctctt ggggggctcc ctgagtgtcc 167580
ctgtccctgt ggccagttct gggtgggagc cccgtgtgca ggcagacagc tcggccactt 167640
cctagcaggt cacattggtc tgtgcttctg tttcctcctc agataagtga agggattcaa 167700
gggtctgggt gtggtggcta acacctgtaa tctataacat tttaggaggc tgaggcagga 167760
ggcttacctg agctcaggag gttgaggctg cagtgagcca tgattgcacc actgcactcc 167820
agcctgggca acagaccagt actctgtccc ttaaaaaaaa atgtaaacag aaacgtaggg 167880
ccatttgcat atgatggcac atggcgtgga gccctacagg tgtatgctgg gcggggcccg 167940
gctgtgctgg ccgacttgca cctttccctc caccccggtg ctgtgtcttt cgctcaccgg 168000
gttcctgatt tagtgaaagc agttgtgcag gacagttctc tttgtagctt ttgtttctgt 168060
ggaaatgggt cagaatatgg tgtttagaaa cacttatgag ctctgagagt ttcctcttct 168120
gagttcctgg cctgcagcct tcacagcaga aaccctgtga tgtcacaagc ctgtttctgt 168180
tccctgctct ctgcctgtac tgtcctgttt tgtgcctgcc ggtttcagtg acaggaagca 168240
gggagctact ggaccagcct gtatttttct agacatagtt ggaaaaagaa gtcccactct 168300
tctgtccttt cacctttgac agatgtttcc accccaagat aagtgaaaat gaccaatagg 168360
atgcactgta tttttcatga aagtgtttct gaagggcagg ctgagagtga gaggcctggg 168420
gctcactggg tgcctctggc cttgtcctgg gcccagggac actggtctgt gcccgaggta 168480
ttccctatcc ccccaacccc gctgcatttg gccacatcct tcaatgtttg cgttgtgtcc 168540
agcgtccgca aaccaactgt catgggatca tactggggct gaagtacggt cccacccctg 168600
ccctgtctgg ggctgaagta cagtgccacc cctgccctgt ctggggctga aggacagtgc 168660
caccccctgcc ctgtctgggg ctgaagtaca gtgccacccc tgccctgtct ggggctgaag 168720
gacagtgcca ccccttccct gtctggggct gaaggacagt gccacccctg ccctgtctgg 168780
ggctgaagga cagtgccacc cctgccctgt ctggggctga aggacagtgc cacccctgcc 168840
ctgtctgggg ctgaaggaca gtgccacccc tgccctgtct ggggctgaag gacagtgcca 168900
cccctgccct gtctggggct gaaggacagt gccacccctg ccctgtctgg ggctgaagga 168960
cagtgccacc cctgccctgt ctggggctga aggacagtgc cacccctgcc ctgtctgggg 169020
ctgaaggaca gtgccacccc tgccctgtct ggggctgaag gacagtgcca cccctgccct 169080
gtctggggct gaaggacagt gccacccctg ccctgtctgg ggctgaagga cagtgccacc 169140
cctgccctgt ctggggctga aggacagtgc cacccctgcc ctgtctgggg ctgaaggaca 169200
gtgccacccc tgccctgtct gggatgttta gcccctagat gccactggac tgagccgcta 169260
cttgcttttg ggaaagaggg gtgggggtta ggggtctggg cgaggggagt gcaggggctc 169320
ctccttggcc tgagagctgt tcatacagac tcctcgccca ctccctgcag ggtgctgggt 169380
cccagggggg aaatggccct tggtgccaag aacgtgagtt ggggctagtg ccagtgatga 169440
tggagaacag ctttttatgg gcacacagcc cacagcactg tgccaagtgc tcgaggcttc 169500
ccgagaacca ggcagaaagg aggacagtcg aggtgtgctg actgcgtggt ggctgcgtga 169560
tctagagcgc gggtcacaaa ggcgcgaggg agctctggcc ttgggtttac cgcaatgact 169620
gccagtgcgg gagactggaa aaggaatctc acgtattggt tccgtgtttt ggggactcca 169680
ttcagatgtc acttaggagt gaaagcatcc cttcgtagag cctctttctg tgtcaccctc 169740
ctcagctgct cctggggttg actggcccct gattcatgcc tttagcatgt gctggagctt 169800
cccagcagct gtccagcccc tgccccaccc tctctgtggg ctcccttgcc cgtaacctgg 169860
ggtgtctgaa cgacccttgc taaggggcag actgttagac ggtaggcatg tgctgagtcc 169920
cagtggccac acccacccac caggagcctg gcactgtggc cgcagcactg agcagtgccc 169980
cgtttctgtg gcaggtgtcc atacactccg tgtggctggg gaacagcatc acacccctga 170040
gggaggagga atgggacgag gaagaggagg aggaggccga cgcccctgca ccttcgtcac 170100
cacccacgtc tccagtcaac tccaggtttt ccaatggcct ttttcttttt aacagaaatt 170160
tgaaatttct tatcagtcat ttgatttgtt tgaggtgctt cttgaaatga gcctctcatc 170220
tcatgtactt ggaaaatacc catctcgcat attccacagg aaacaccggg ctggagttga 170280
catccactcc tgttcgcagt ttttgcttga gttgtacagc cgctggatcc tgccgtccag 170340
ctcagccagg aggaccccgg ccatcctgat cagtgaggtg gtcagatccg taagtgagcc 170400
ttcccattcc cctcacacct gcacgtgcca cacgcaccac acacgccaca caccccacac 170460
acacacaccg cccacacaca tgccacttgc acacacaccc ctcatgcatg caacacacac 170520
acaggccaca cgcaccatag acaccacaca cacatgccac atgcacacac atacacggca 170580
tgcaccatac acacaacaca cacagcacac atgccacaca cacacgccac accacatgca 170640
ccacacacat gccacatgca cacacactcc acatgcatgc accacacaca cacacacaca 170700
ccacacacac cacatgcacc acaccacaca ggttacatgc acacaacaca cacatgccac 170760
gtgcacacac cccacacacc acatgtatgt gccacacaca gcacacaacc acacacatgc 170820
accacacaca tgccacatgt gcatgcacca gacacatggc acacactaca cacacgccac 170880
gtgcacacac cccacacaca tgtacgcacc acacacatgc cacacacaca tgcaccacac 170940
acatgccaca tgtacacaca tgtatataca caccccacac cacacacaca ccacttgcac 171000
accacgcaca cacaccacat gcgcacacac acaccacata cgccacatgt acacaccata 171060
cacacaccat acatgcacca cgtgtaccac gcacccacac agacacagca cacgcataca 171120
ccacacacac acgcacacat gcgtcccgca cagtaatgtc tcttgggtgt aagaacacga 171180
cttgccagta gtagcgttct ggatgcgttg cctggattct aacagcgcga ttctcccctt 171240
gccctcctgg ttttccacat ctccagcttc tagtggtctc agacttgttc accgagcgca 171300
accagtttga gctgatgtat gtgacgctga cagaactgcg aagggtgcac ccttcagaag 171360
acgagatcct cgctcagtac ctggtgcctg ccacctgcaa ggcagctgcc gtccttggga 171420
tggtaagtga caggtggcac agaggtttct gtgctgaagc cacgggggcc catctgcctt 171480
gggacctggt gttggccaga ggtgccgggt gcggctgcct ccttccaaga gttgacccga 171540
accggactcc acggcccacg tgagctgcag tgcttctcag atggaggggg ttcagcgacg 171600
gtcagtgcca ttcacaggtc actgtgatgt gggttgtggc ggccaagcca tggtttgggg 171660
tcccgtatcc ctgggcttat gacatcattg tagtagccca tccccacaga accacggtgt 171720
gtggtggcgc tgaggcatcg tagatggtgg aaatgctact ggcttcccca tgctctgccc 171780
tgaggcctga ctgcctcact ccccttctca gttatgttcc aggccccccg agcttcctgg 171840
ctggacagct tctctcctgg gggccgtttt gtcacagtga ccctgtgttt ctagtcccaa 171900
atctgggtgc tatagtctct ttttagcgtg gtggttgtct tagtcttttt tggctgctac 171960
cacaagttac cttagactgg gtaatttata aacagtggaa atttacttct caccgttctg 172020
ggggctggaa gttttcatgg tcaaggtgcc agcagatttg gtgtgtgatg agggctgctc 172080

-continued

```
tctgcttcat agatggcatc ttctggctgg gtcctcacgg tggaaggagt gaacaagctc 172140
cctcaggcct tttagaaggg ccccaatcca caagggctct cccatcatga cctcatcacc 172200
tcccaaggcc ccaccttctt gtactgtggc actgcaaatt aggtgtcagt gtaggagttt 172260
caggagggat agaaacattc agaccatccc agcggtcaag tgttcatcct cttgagttcc 172320
tccttattct gcttctggtt tatcaggatt cagccagtgc agcatggtac ctgtattctg 172380
tggcacatca ccacatggta tttgccaagt atccatcacc tgcacacgtg aaatcattgc 172440
ccgtgggtcc cgacatctgg cgaagcatat tcaaggatgg cagaactgtc agagctggca 172500
cctctggttc cttgtcatgt ggcattacct agtaatccat tttatgatag caatggaaac 172560
tcatttcttc aacaaacacc tgagtggctg ccgtgtgcca gccgtctggg gcccttggtg 172620
agaatggcat ggtggtgccc atcagggcct gcctagcccg tgctctggac gggctcctgt 172680
gtgtcaggaa cgacaatgct gtcatgacgg tgaatgattt tttttttgc catcactcca 172740
gccgctaaca tttgcggagc tcttcctccc gcacccccac ctgacaaggc caagggtgac 172800
cttggcccca ccctaggcgg ccaaggtcag aggttagctg gcttgtctgg gtcacacaaa 172860
atgcagcaga ggttgaggtg agcacatgtc cgtgacctgg agcctgactc cctctctgcg 172920
agtcttgact gctcttgcct agactctgtc ctccccgagc ccaaacgcca gtcatcttcc 172980
cttgtgggtg tccttcagcc tggtgccatg ctggtgactc agcagccgtc cagggagtgg 173040
aaacaattga gtgtgtgggt tccctgtgtg ggcatctctc ttcacggcga acaccctctg 173100
ggtgttgccc acacgatgtc aaagcggctc ttggaagggg tccttctcct ttgtgggaag 173160
tttcagctgc tgggctaact tgaattgtaa ctgtggtttt gtgctcaggc ccagatcccc 173220
ctaggcaagt gttgtgccat cagtaatcaa atgagaaata atcattttga aaagcagatc 173280
ctaaggcagg atggtcatgg acactcactc ccagctcttt gtgcactcat gctttctgga 173340
agatggccat cctctgtgaa ggttttcagc gcgtcatgct tggtacccac gtatccagag 173400
catgtcgttt tgaggtattt gcccaccgtt gtgaaatccg tgccacccga gagcaggtcc 173460
tgatgtgggg ctttcagaag tgggacctgg ggccgtacgc agtccttagg gaggggccgt 173520
gtggcgttgt gcgtgtgagg ggatagcaca gggtgaggtg ggggcccaag aaggaagtga 173580
cccacaaaga acagcctcct cttttggtcc ttgttcctgg gatggctggg agtggcttct 173640
gtgtcgtccg gccatttccc ctgcggagag gctcctacca ctgccgagaa cctcatcatt 173700
ccacaaaaac aagaggccgc ctggccatcc agcgctccat gggaattctg tgtccccata 173760
gtcttgggct gaaggagggt gacattcctt gctgacttct gcaggggtct cctcactgtt 173820
aaagagcaga ttgaaagtga agaacgtggg ctaagtgttt aggtcgatat ttaaccctgc 173880
taggttttgg atactaagtg aaattgaggc cattttggtt gaagttgaca gaaaccacta 173940
tcagggatcc ccaagactac cccaggcttt tctagaaaga ctctcagcta agatgtgtta 174000
tggtaaaagc acacaaaaca aaatcagcaa agaaaattag caagggcaga ggcccatggg 174060
gcgatgtccc gaggacacca ggcttgagct tccagaatcc tctcccagcg gggtcgtgca 174120
ggacgcactt aactccccgc acagtgagcc gtgacagcgc gtgtgcagtg tcgtcgccag 174180
gaaagcacac tagagactcg gtgccagggt ttttactggg ggctgggcac atgggcaccc 174240
tctgcctgcc tcgtgcccag actctggact cccggaggga aggcaagttc tcagcaccaa 174300
ccctggtgcc cacacaagca gctgagcaca gggagcccct cctcagtgag gatggtgggc 174360
accgtcccaa caccagccag gggccagcct tgcacacagg cctctcagga tggtctccgg 174420
cctgctgtgt agtctcttct gcacacaagc gtgagggcag cgcccccgcc tcggctgtgg 174480
```

ggaggagcca ctgggacgtg agctctggtg gcatgcagca gcttttgtct gtgtgtgcct 174540
aggacaaggc cgtggcggag cctgtcagcc gcctgctgga gagcacgctc aggagcagcc 174600
acctgcccag cagggttgga gccctgcacg gcgtcctcta tgtgctggag tgcgacctgc 174660
tggacgacac tgccaagcag ctcatcccgg tcatcagcga ctatctcctc tccaacctga 174720
aagggatcgc ccagtgagtg ggagcctggc tggggctggg gcgggggtct cagaatgagc 174780
tgtgaaggaa gcagcatcac cctctccaag tgcccaggct cctggccaga tggcaggcca 174840
ggtatcagtg ggaacccagg tgggtgccat ggctgaggtc agtgagacgc aagagcacag 174900
gtgcgtccta gaggcttcct cgggcacctc cagcgagctg gagctctcgc ctctgctgct 174960
gtctcatgtg gcgcttagca cactctccca cgtgcccatt cctgactctg ctctcgaggc 175020
catcggctct cattctctgc tcccagaacc ctgttattac ccaggctagc ctcctctctg 175080
caccttcccc gccctggccc agtacctccc tcttgtttcc actgtgattc cgacctcacc 175140
ttatcttaaa gctgctggac ggcaggttct gtacacacgt gtccttgaca aagcacggct 175200
ggtgccgcaa cccctcagcg agcaagtcaa gctcttcaca gcgatgtctt acaagcgcag 175260
agggctctgt gacaccctgg tctcaccgcc actcttccaa agtcgcagag gctttagcag 175320
agatgggccc agcctctctg agtcataggc ttctgcacac gggagctgtc tttagaggga 175380
gggtggaatt tcatcagcca cccacatggg ggagttgagg gcaagaatta ggagcaaaga 175440
tgggaagggg tctgggagga atggccagtg atcccctttg acaagtgggc aggaaacggg 175500
ggctaggtca aagttgagtg gaagacctgg agggagacgg gaaggtctct gtaggcacag 175560
ttcagacagg agggaggtgt gagccagggc acatgccggt ggccgtctgg caggatttgg 175620
gacatgctgg agcagggaca gcggctcatc aggggccatt gccctcatcc aggccagagt 175680
gtcacaagcc cgtggggagg cccttctcgc ctgtcatcct tgctgggcag tgggtgctgt 175740
gctagcagga caggcggacg gctggcaact gtctctgcat ccctggagcc tggcataggg 175800
ccaagtcaca cggggcacag gcctgcaaat caggcacata tgttggtgca gtgacgtgat 175860
tttgggggc agccccagaa caggccccag acacaggcca aagccctgcc tgtgctggtg 175920
tgttgggctg ttctatggct cttgctgtgg gcatggagga ctcagggaag gagagttgag 175980
gtggtccagg agttgcgttt gggatgcaga gagcttgtgg catccaggta gaaatggtgc 176040
gtggggctga cctcagcacc atgggcagag gggccgtgtc acgtgcctcc gaggtggagg 176100
tgggaccacg tggtgacaga tatacgcatc actgggcacg tttttgtggg tgttgggggg 176160
catcgtattg gctcctctgt tcacagtggc cactcattca gtccctggct accaggtcct 176220
cactgtgcca tggggaaggc cggcgctgtc gggggatcac agaaggcagc acgtcatgat 176280
ggcatgtgcc atgaaggaaa agcacagggc actcaggaag tagaggggac tggcctgggg 176340
tgtgggaatc tagggcctcg ttgagggaca gagagaggaa gtgtgtggtg gccagcatgg 176400
aggtggccac aggggaggct gagttaggcc gagagggcag ggcgttgggg aggtagacgg 176460
gctcagccac tcagggagtg gtcaagcaga ggctgaaggg tcaggccagg ttgcaggggc 176520
ctgggggagc cactcagggt aggcgctccc gggagcccgc ctggcccata gctctacact 176580
cccgcgtggg gccggacatg ctgtgaagcc ctctccacgt tggatggggg tggctgagcc 176640
tggatgctgt ctcccgtttt cagctgcgtg aacattcaca gccagcagca cgtactggtc 176700
atgtgtgcca ctgcgtttta cctcattgag aactatcctc tggacgtagg gccggaattt 176760
tcagcatcaa taatacaggt gagtgggccc tggctgtctt cctctgcaca cggggagtgg 176820
gcttcccttc tcttttcctt gcaggatcat accagtgggc cagttttgac ttggtcggga 176880
ggaggcatga acacctgaga ctgtgcagcg attctttgac acagaggcct ttctccctgt 176940
gcagatgtgt ggggtgatgc tgtctggaag tgaggagtcc accccctcca tcatttacca 177000
ctgtgccctc agaggcctgg agcgcctcct gctctctgag cagctctccc gcctggatgc 177060
agaatcgctg gtcaagctga gtgtggacag agtgaacgtg cacagcccgc accgggccat 177120
ggcggctctg ggcctgatgc tcacctgcat gtacacaggt gagcatgtac acggtgccca 177180
taaggccagc ccaagtcctg ttcaagggag gcaggagcat gctcactcaa gggacctcga 177240
ctaggtgccc tctgatttca cacttctggt gttgccccaa gccggcccca tcaccttgca 177300
agaaaggctc tggagccccc agggctggag tacctggtca gggttgaccg tccctgtggt 177360
cactcatccc atgtggctga gctgggctgg gtcctgggca agcaaggggc tgatatcacc 177420
tgctttcaga tctccaggga ctcactggac ccctgtgtac aaagcactgt ctacagagcc 177480
tattgggttg tatagaggta accttcgtac tgaacacttt tgttacagga aaggagaaag 177540
tcagtccggg tagaacttca gaccctaatc ctgcagcccc cgacagcgag tcagtgattg 177600
ttgctatgga gcgggtatct gttctttttg ataggtaaga agcgaagccc catccctcag 177660
ccgttagctt ccctagaact ttggcctgaa gctgtgcttt tgtgtgtgtc tgctgatccc 177720
ctggcgctgt tgctggagtc ctgccagtga ttccccacca cagcctgacc atgggctgcc 177780
ttggctcagg gttccactgg cgagctggtg gtccttggac cccagcactc aggtgtagcg 177840
ttgaccagtt ccaaggttgt cccagtgcct gcccatctct cctgagggct cagggacagt 177900
acctggcagt tgggggtgtg gcagggggca ggaatgacca gcctctggga gggtggggca 177960
gaagcctgta cagtgaggag gagctggctc agcctggctg cctatcgtga gaggggagcc 178020
cacggggctg tgggaggggg gccgtggtgc ctgtgagcag ggtgaggagc agcggcagga 178080
ggatgaaggt ggaacccaca catgcatctt tgagacccgt gtggtcagtg gcttctgccc 178140
cccaccaccc cccactgctg tgcgtgcata gaattggctt ccctcacctg ctctggaagt 178200
gggttaggag cttggtaggg ctttttctca aggacaaggg cccctgattt gctctcaggc 178260
ctcagtcctg gcgacatggt ggatctggag ccttgttgca ctgccttgcc tgtgctctcc 178320
aatcagggtg gccagtgggg agccatttgg cttttctcaa gagcatactc aggtggacct 178380
tgctccactg tttgaccaga tgaggcattc tgaacagcca agcctgtgct ggtctgtttt 178440
catgttgatt tttttttttc ttttcttttt gagatggagt tttcccttg tcacccaggc 178500
tggagtgcaa tggtgtgatc tcggctcact gcaacctccg cctcccgggt tcaagtgatt 178560
ctcctgcctc agcctcccta gtagctggga ttacaggcac acaccaccat gcccagctaa 178620
tttttgtgtt tttagtagag acggggtttc accgtgttgg ctgggctggt ctcgaactcc 178680
tgaactcaag tgatccaccc tccttggcct cccaaagtgc tgggattgca ggcgtgagcc 178740
actgcgcccg gcccccatgt cgatttttaa atgcacctct gcatcgttct tcagtcccca 178800
tatgctcact gagcaccact gcgactggca gacgggcaca gggaggcgcc acgaccagtc 178860
ctggccttca aggggcttgt ggtctagtgg gcccaatgct aggtggcgag tgctccaaag 178920
agtgtggtgc acgccttccg cttgaccgct ctccagacgc cacagggagg cacctcgcag 178980
ctgaccacag atttctctct gtggagcagt gtcttcagag cggctgccat gccactgctg 179040
ggcgagggtc tgcgggcggg tagagccagg agcacctgtg aggaagtgca ctgccatttt 179100
cgtagctgct tcccgtgtgt ctcagttaca cacggctggc atgtgtgcac tgatgagacg 179160
ggaacgtgat ggttgctttt cagcactgaa agggatactg ctcagggggc gtgtttcagg 179220
atctggttag ggaagaagca gcgagagcac agatggggcc ctgtgtggta acaagaaaaa 179280
agtcctggtt gacaacagtg ccacgaagcg ttagaacaca tagggatgtt tgtggagcat 179340
ttgcatgtgg aaagcagcaa aaacataatg ggaacgggtt cttttgttat gatttttaaa 179400
aatctctttt gtaacatcct tcccgctgcg ccgtttctgc atattccttt atgtagcttt 179460
caaactcctc ttaggagttc tggtccctac agggcgtggg agcccaggct ttacgtagct 179520
ttcaaactcc tcttaggagt tctggtccct acagggtgtg ggagcccagg gcctgtgccg 179580
agcagcctgc ctccacgagc tagacagagg aagggctggg gttttgcctt tttagtctca 179640
aaattcgtac tccagttgct taggctctga ctttccccac ttggaaagtc cctcacggcc 179700
gagggtccct cccagccctg atttcacatc ggcattttcc ccagtattag agccaaggcc 179760
ctccgcgggc aggtggggca gctgtgggag ctggtgccag tctctgacct gcgtccctcc 179820
tcccaggatc aggaaaggct ttccttgtga agccagagtg gtggccagga tcctgcccca 179880
gtttctagac gacttcttcc caccccagga catcatgaac aaagtcatcg gagagtttct 179940
gtccaaccag cagccatacc cccagttcat ggccaccgtg gtgtataagg tgaggttgca 180000
tgtgggatgg ggatggagtg ggaaagcctg gaggtggagt tgcctccgac ttcccagcag 180060
attcgccagc agagcccagc tcctccgctt taaagcagca atgcctctgg cccccacccc 180120
acccccgcca cccaggcgca gcaggtgctt cccgtccccc cagccctgac actcaggcac 180180
ctgcttgctc cttgcaggtg tttcagactc tgcacagcac cgggcagtcg tccatggtcc 180240
gggactgggt catgctgtcc ctctccaact tcacgcagag ggccccggtc gccatggcca 180300
cgtggagcct ctcctgcttc tttgtcagcg cgtccaccag cccgtgggtc gcggcgatgt 180360
atcctctctg ggtccctggt gctggccccg tttcccttgt caacaccgag gctcatgttt 180420
catgataagg ttttgaaacc taacctttgc aaaaaacccca cagatgccag ggtgacaggc 180480
cctcagcccc agggaagtaa aatgctgaca ggggtacaga aaggagcacg tccagacatt 180540
tgctgaccag ggcctctcag aggggccggt gtatggcagg agggtcgcag ctgaggggcc 180600
tttctgtgga gggcctgggt gaggggagcg agggtgggcg gtggtctctg cagacgtccc 180660
gcccactcgc gggctctgtg tggctgggct tctcctgaca ctgcttctca ttagctttgg 180720
tcattgtgcc tcgatcgccc tctcggggaa aggcttaagt aaagatccag ttcccacccc 180780
cagatgctgg ctgccaggag tttccctttc cacagccctt ccccaagaca gaccacaaga 180840
gcctccaagc agcacagttg tcctggtgct gacagcacag ccttgcccgg cgtgcctggc 180900
acggctctgc cctcactgca ttggagcagg gctagtggag gccagcggaa gcaccggcca 180960
ccagcgctgc acaggagcca ggccaggtga gtgctgccga gtgggtgccc tgcctgcagg 181020
gcatccagcc agccaagggt tgcaggaatg gaggtggagg cgctgatgca gctggaggca 181080
tccaggtggc ccttccgggg ctctgctcgc tctccaggct ccctggaccc ctttgtagac 181140
tgtttcagga gaggaactcc caggtgagga cagggaggca gcattcccct catttgccgg 181200 ccttttcct taactcctgc accagcctcc cacatgtcat cagcaggatg ggcaagctgg 181260
agcaggtgga cgtgaacctt ttctgcctgg tcgccacaga cttctacaga caccagatag 181320
aggaggagct cgaccgcagg gccttccagt ctgtgcttga ggtggttgca gccccaggaa 181380
gcccatatca ccggctgctg acttgtttac gaaatgtcca caaggtcacc acctgctgag 181440
cgccatggtg ggagagactg tgaggcggca gctggggccg gagcctttgg aagtctgcgc 181500
ccttgtgccc tgcctccacc gagccagctt ggtccctatg ggcttccgca catgccgcgg 181560
gcggccaggc aacgtgcgtg tctctgccat gtggcagaag tgctctttgt ggcagtggcc 181620
aggcagggag tgtctgcagt cctggtgggg ctgagcctga ggccttccag aaagcaggag 181680
cagctgtgct gcaccccatg tgggtgacca ggtcctttct cctgatagtc acctgctggt 181740
tgttgccagg ttgcagctgc tcttgcatct gggccagaag tcctccctcc tgcaggctgg 181800
ctgttggccc ctctgctgtc ctgcagtaga aggtgccgtg agcaggcttt gggaacactg 181860
gcctgggtct ccctggtggg gtgtgcatgc cacgccccgt gtctggatgc acagatgcca 181920
tggcctgtgc tgggccagtg gctgggggtg ctagacaccc ggcaccattc tcccttctct 181980
cttttcttct caggatttaa aatttaatta tatcagtaaa gagattaatt ttaacgtaac 182040
tctttctatg cccgtgtaaa gtatgtgaat cgcaaggcct gtgctgcatg cgacagcgtc 182100
cggggtggtg gacagggccc ccggccacgc tccctctcct gtagccactg gcatagccct 182160
cctgagcacc cgctgacatt tccgttgtac atgttcctgt ttatgcattc acaaggtgac 182220
tgggatgtag agaggcgtta gtgggcaggt ggccacagca ggactgagga caggccccca 182280
ttatcctagg ggtgcgctca cctgcagccc ctcctcctcg ggcacagacg actgtcgttc 182340
tccacccacc agtcagggac agcagcctcc ctgtcactca gctgagaagg ccagccctcc 182400
ctggctgtga gcagcctcca ctgtgtccag agacatgggc ctcccactcc tgttccttgc 182460
tagccctggg gtggcgtctg cctaggagct ggctggcagg tgttgggacc tgctgctcca 182520
tggatgcatg ccctaagagt gtcactgagc tgtgttttgt ctgagcctct ctcggtcaac 182580
agcaaagctt ggtgtcttgg cactgttagt gacagagccc agcatccctt ctgcccccgt 182640
tccagctgac atcttgcacg gtgacccctt ttagtcagga gagtgcagat ctgtgctcat 182700
cggagactgc cccacggccc tgtcagagcc gccactccta tccccaggcc aggtccctgg 182760
accagcctcc tgtttgcagg cccagaggag ccaagtcatt aaaatggaag tggattctgg 182820
atggccgggc tgctgctgat gtaggagctg gatttgggag ctctgcttgc cgactggctg 182880
tgagacgagg caggggctct gcttcctcag ccctagaggc gagccaggca aggttggcga 182940
ctgtcatgtg gcttggtttg gtcatgcccg tcgatgtttt gggtattgaa tgtggtaagt 183000
ggaggaaatg ttggaactct gtgcaggtgc tgccttgaga cccccaagct tccacctgtc 183060
cctctcctat gtggcagctg gggagcagct gagatgtgga cttgtatgct gcccacatac 183120
gtgaggggga gctgaaaggg agcccctcct ctgagcagcc tctgccaggc ctgtatgagg 183180
cttttcccac cagctcccaa cagaggcctc ccccagccag gaccacctcg tcctcgtggc 183240
ggggcagcag gagcggtaga aaggggtccg atgtttgagg aggcccttaa gggaagctac 183300
tgaattataa cacgtaagaa aatcaccatt ccgtattggt tgggggctcc tgtttctcat 183360
cctagctttt tcctggaaag cccgctagaa ggtttgggaa cgaggggaaa gttctcagaa 183420
ctgttggctg ctccccaccc gcctcccgcc tccccgcag gttatgtcag cagctctgag 183480
acagcagtat cacaggccag atgttgttcc tggctagatg tttacatttg taagaaataa 183540
cactgtgaat gtaaaacaga gccattccct tggaatgcat atcgctgggc tcaacataga 183600
gtttgtcttc ctcttgttta cgacgtgatc taaaccagtc cttagcaagg ggctcagaac 183660
accccgctct ggcagtaggt gtcccccacc cccaaagacc tgcctgtgtg ctccggagat 183720
gaatatgagc tcattagtaa aaatgacttc acccacgcat atacataaag tatccatgca 183780
tgtgcatata gacacatcta taattttaca cacacacctc tcaagacgga gatgcatggc 183840
ctctaagagt gcccgtgtcg gttcttcctg gaagttgact ttccttagac ccgccaggtc 183900
aagttagccg cgtgacggac atccaggcgt gggacgtggt cagggcaggg ctcattcatt 183960
gcccactagg atcccactgg cgaagatggt ctccatatca gctctctgca gaagggagga 184020
agactttatc atgttcctaa aaatctgtgg caagcaccca tcgtattatc caaattttgt 184080
tgcaaatgtg attaatttgg ttgtcaagtt ttgggggtgg gctgtgggga gattgctttt 184140
gttttcctgc tggtaatatc gggaaagatt ttaatgaaac cagggtagaa ttgtttggca 184200
atgcactgaa gcgtgtttct ttcccaaaat gtgcctccct tccgctgcgg gcccagctga 184260
gtctatgtag gtgatgtttc cagctgccaa gtgctctttg ttactgtcca ccctcatttc 184320
tgccagcgca tgtgtccttt caaggggaaa atgtgaagct gaaccccctc cagacaccca 184380
gaatgtagca tctgagaagg ccctgtgccc taaaggacac ccctcgcccc catcttcatg 184440
gagggggtca tttcagagcc ctcggagcca atgaacagct cctcctcttg gagctgagat 184500
gagccccacg tggagctcgg gacggatagt agacagcaat aactcggtgt gtggccgcct 184560
ggcaggtgga acttcctccc gttgcggggt ggagtgaggt tagttctgtg tgtctggtgg 184620
gtggagtcag gcttctcttg ctacctgtga gcatccttcc cagcagacat cctcatcggg 184680
ctttgtccct cccccgcttc ctccctctgc ggggaggacc cgggaccaca gctgctggcc 184740
agggtagact tggagctgtc ctccagaggg gtcacgtgta ggagtgagaa gaaggaagat 184800
cttgagagct gctgagggac cttggagagc tcaggatggc tcagacgagg acactcgctt 184860
gccgggcctg ggcctcctgg gaaggaggga gctgctcaga atgccgcatg acaactgaag 184920
gcaacctgga aggttcaggg gccgctcttc ccccatgtgc ctgtcacgct ctggtgcagt 184980
caaaggaacg ccttcccctc agttgtttct aagagcagag tctcccgctg caatctgggt 185040
ggtaactgcc agccttggag gatcgtggcc aacgtggacc tgcctacgga gggtgggctc 185100
tgacccaagt ggggcctcct tgtccaggtc tcactgcttt gcaccgtggt cagagggact 185160
gtcagctgag cttgagctcc cctggagcca gcagggctgt gatgggcgag tcccggagcc 185220
ccacccagac ctgaatgctt ctgagagcaa agggaaggac tgacgagaga tgtatattta 185280
attttttaac tgctgcaaac attgtacatc caaattaaag gaaaaaaatg gaaaccatca 185340
gttgttgctg tgtgaggctt gctttgcttc atgagaacct agaccttgct gagctggagt 185400
cttaggaagc agtctcctaa gtgcttctcc agcaggggca gaaactgtcc caccagctaa 185460
catctggcat tatggagggt cccccaggca gctgccagca gggacaggcc ccgtgttttc 185520
tgtagccagg gatgaggaag tggccccagg gcatgggcct ggctgggtgc ttctgcaagg 185580
gccttcccaa accacagtac aggtggtctt cctgccctgc agatgggagc tgtgggagct 185640
gctggagctg ctggagcctt catggtcaag tgacatcata agcttatatg acatacacaa 185700
gcctcaggac ttggcccatg gcactgaagc aggtcatcag gcccagcaca gagactagag 185760
ctgtgttctc acagggccca ccacccttcc acctccttgg ccattgacac ctgcgtccct 185820
ggcccagctg ctcccaggta acccccaaag cagctggcac atcccacctc tggtgtggcc 185880
ggggctgctg tgtgtccgca gggcctgccc cgtctattct agcttgtttg tcctgtctga 185940
accagcgcct actccaagaa gcctctgctc agcccagcgg ggatgcttct aagctccgga 186000
cgagcctctc ggaagccttg gtgattggtg gtgtagtcat cttgggatgc agatgtctta 186060
ccaacctgca agaacaaaaa ccctgtggct tcctctggtg cagggtattt agtcaatgtt 186120
tgctgaggtc ccgtctggtt ctggctaatt ggcaggggtc gtccacccat tctttccctg 186180
ctctgctgtc tgtgccagga gagacggggg ccagtcggcc aaggggccag ctcctgctgc 186240
ctgctcctct tgggcacgtg cgggggcccc ctttctctga gcagggatag ggatcagtct 186300

-continued

```
gccggaggga tgtggtggac aggcctaaag catttggggc ggggcatgcc acttgagctc 186360
cctaaatctg tctcctcata ggtgacaccg ctccagggcc ccccagtggc ctctcctttc 186420
agagctacct aaattctggt cacttcagag aaatggagca ccccccttctc cctggtccag 186480
gtgtggacag cctggcacac tgagcacacc tggcatggct ggtaatttca gaaagaagag 186540
gggccggggt ccagtgggaa gcagcggtga acccctcgtg agtgggcttt gcagtccctc 186600
cccatgccac ggcagagctg ccctcaacac agccttcctc ttcctcatcg gagagcacac 186660
cctgtcccct tgccgagctg tgccctgtgc cttcggtggt atttgatttt ggctgctact 186720
ggctttgttg ggatctggaa gtcgcttccc ctgcgtggtg cgtggagcac tgtaagtcag 186780
atgagggaag tagccagggt gaggtgagta ccgggtggag ccgccactga agggactggg 186840
tagggggggcc ttgcctctac atgatgtgac acagccaacc gaggacagag gaagccccgt 186900
tcctgggggt gtggggtgca cccctcaggg aagcctgcag tggggcctga ggaaaggcat 186960
cctccgcgag cccacgagtc tggtccatga gcaccgtgac agtgtctgtg ggtagaggtg 187020
gacccggcct tgtgtcatca ccaggacctc ttttgggaaa ccatgtggac atcgcttgcg 187080
ggtcccccag gctctgcagc cccagcagcc tggctgcctt ttgggcaagt ggcttgagcc 187140
acagaggacc cagtcctgtt gcagccacat cctctggggg ggcccgccag tgtggccggc 187200
tttctccacc ctacaccagg cctccaggtg tcctggtcgg gggtgtctgg gccctgggtg 187260
ggccctgtgg acctgtgagg tcagggtcag ggcatcactg gaggcagagg gctgaagttg 187320
tgggtctggg ttccccttgt gtgcacaggc ccctgccctc catgcttggt caggcagcta 187380
cccccaaaac tgctaggaca ggctggtcct gaggtggatc ctggcccctg taccctctgg 187440
acagcccacc cgcccaacct tctaccctgc cccagcggcg gcagtgttgg ccacatcctt 187500
cccctcctgg ccccaattgc tctggggaag tccaggctcc ggagcctgcc caggggcccc 187560
ccgtgatttg ggcccaggac tccacgtggt tctctgcctt cacccaagcc ctgaactcct 187620
cagctgccaa atccccaccc atctgcacag gctgtgctca ccactgctgc tcctggaagg 187680
tgcccctcag tgggacgccc acctcctctc tgggcttctg tgtttgggag ccctgctgcc 187740
cccacccttg gtcagtcccc atgtcctgct ggcctgtcag gcagggcaga aaatccaccc 187800
agaaatgctg agcaggatga gagtctagtt gggcccagcc tcattattta gaagggatgg 187860
aggcctaggg agcatgcttc tagcctgagc ccagcagggc cccgcccatg tcccaggtct 187920
gcaccaggga cagctcctgc cgaggcctga cctgcccctt ctccctcagg tgctgctggt 187980
tgaccagcct ctggccctag gagaccccgt agcgactgag ggtcccagca ggccatgcag 188040
ctttgccaag gtacgagccc ctccccagca ggggacagat gtggggaccc tcccaggcag 188100
gagcagctgg gtgcctggtg ctgccatctg ctgcctgcct ggttcttgtc ctcacattgg 188160
aggtcagtgt gagggctctg cctcgggaaa ggccatggag cttgccctgt ccagggcctc 188220
ccatgtgcac tgagcctggg aagagagggt tggagttgag ccttttaccc tgggaatgct 188280
gcctggagga tggtgcgggt gtggggtggc accctgccag gcagggccct gcctccctgc 188340
gcccactgga actcgggcag gcaggggtgt aggtgcctcc tctagagccg tccggtgggg 188400
gcccccggca gtggtggtgg tgtccactgg ccagcagctg cccccttcagc caggacagta 188460
ggcctgacgc tgtccccagc agctccaagg tggatttgtg gaagggggta gagggcacgt 188520
agaggcccca tgacctcccc agggttctgg gagggctgtg cccccttagc cagcaccatg 188580
ctgggtgata tagtcagatc ctgttacccc tgttgtggag gtgaggaaac aggttagtgg 188640
ggaggacatg actaaggtcc atgctgagtc gctagagctg cacccagaac cactgctggg 188700
```

accccatgcc tttctgctta ccccttgtgc cgggagatgc caagagatgc tgggagccag 188760
ccccacctct gcccttggag tcatggctac ggaaagggca ttcggaccgg tccctgacct 188820
caccggggag ggccgaaccc tgttcctgag gagccagggc ttcctagagg aggtaggcct 188880
tctagtcact ccttcatctg caggcactcc acagagctct ctgtgccagc cccagcacg 188940
gagggctgac cttagtcgag tggagatgcc ccagtgccag gcagtaggga tgatgtctcc 189000
tgaggcccag atggaaggga ctggactagt ctcatggggc tgatggtggg gccaggcctt 189060
gaccagggac ccagtgtagg gggtgcagag acccctctga gttcctcaca catccctggg 189120
gccctcccca tacacttcct atcctgactg cgggcaagag ggagccccag ttcgccttcc 189180
ctatgctggg cacccacagt ggggctgggc acccccgcca tgcccctgcc ctgtccttcc 189240
cctgagagcc tcggtcccac ctccaaggtg cctcagagga cagcaggggc agcgggcaga 189300
ggccgagatg cctcctcatt ccaggctcag ctgcccttct tggggcagcc cacacctgag 189360
agtctcctgc agttggtcag gcctgaggag ggcagggggg tgcctgctgt ccctctgctg 189420
accacagtgg catttagcct gggcaccgcg cccagcacag tccatgctgc acaggtgccg 189480
tgggctccac agagccctgc ctgacatgca tgtgttacgt ttcgggtgcc gatgcccttg 189540
ggcggcactt ctccgggcag aacccccagg ccaccgctcc ggttccggtt ccgctgcatc 189600
tggggctctc ggcaggctgt ggtcctccgg ccagcctggg ggcatctcag tccctcagcc 189660
ccacaggggc ctgccccgca gcctgggcct cgagccccgt ctccgcacgc tgtgccgaat 189720
ctggctgccc atcagctccc tgcgtaccca gactgtgccc tgccatgccc gtggctcttc 189780
ccaggagtgc cctgtggcct ccccctggct tgctgggctg attccctcct gtgtctcaaa 189840
cagagctcac ctttgccatc actgctgtcc tcaccggccg gtgccagagg cccgtgtctg 189900
tgtaccctgt gtctgcacct ctgggcaggg cctggctctg accaacccgg gcttccagtg 189960
tccacagacc taaggcccag ggcgcctggg ggctggagca agagaagcaa aaggagccaa 190020
gggtgggggt ttggggttct tgtgagggcc cagccccagg accccaggac caggacaccc 190080
aggagcccca gggcccagcc ccagttcaga aggcaggggc cttctgaggg agcttaaggg 190140
tcccacagcc caggaccccc accagggcca gtggccagcg ttgggggact cagcctcctc 190200
gtcgctcgtc ctctctgttt ctcccacctt ttgccccctt tctccttgcc tgttcccacc 190260
cgaggccccc tcttggcctg cgtgagccgg ggcggcactg aactgggggc cgatccgcct 190320
gggcggcggt gagaggcagg gccgggagcc gggccgctgg gtttgggcct ggcccgctcg 190380
ccgcaatatt gatggcccgt cagtgcagcc ctgattcctg tgctttcagt taaaaggttt 190440
ctgttgttgt agcttatgca gttgctctgt tgctatggaa acgtgacatc aaaatgacgt 190500
ttcccgttta aaagctttta actaaattcc tgcctgtcag atgtaggccc cattttgagc 190560
gtggagctgc cttcgagcga gcgtgagcgg cgcctcccgc ccatggtgcg tggggccggg 190620
ccggggccct cgctgagcgc gctctctcac cccacaggcg cctccggcat ggcggcggcc 190680
gaggggcccg gctacctcgt gtctccccag gcggagaagc accggcgggc ccgcaactgg 190740
acggacgccg agatgcgcgg cctcatgctg gtctgggagg agttcttcga cgagctcaag 190800
cagaccaagc gcaacgccaa ggtgtacgag aagatggcca gcaagctctt cgagatgacc 190860
ggcgagcgca ggctgggcga ggagatcaag atcaagatca ccaacatgac cttccagtac 190920
aggtgggcga gcgggcagtg tgggccccac caggacgggc gggcccgggc gtggcgggcc 190980
gctcctgact ttcttggagc tctgagtcgg gacgatgtgt gggtcgtggc ctgcctgtcg 191040

-continued gtctcctctg gccgggtatg ggcagaaccc cacggggtga gacggggccc acggaaaccg 191100
tgtgtgcagc cttccattgg ggaagtgggg aaactgaggc ccagcaaggg caggaaacca 191160
gtctaagagc tgaggggtag caggggtggg gctggtgctg ggcagaggcc aggatggctc 191220
ccaggacgta tgggcggtct gggcactgtc cctcggaggc agcaacactc atggtggtgc 191280
ccactgacct cacaccctgc tcccccatag ggaggcggcg gctgccagtg ccctccccac 191340
caccaagctc ccaagctcag caggggtttc aggggcctac tgcgtcattg gggaaattga 191400
gactgcaagt gagaaggagg ctcagtgctc tgcgacttgg agcatccact gagcctctgc 191460
catgagccgg tgagccccac tggggctggc cctagggtca cggtggggta tttccagaaa 191520
tcaccaggtg aggtgcagga ccagccagcg catgggtggg gcttacggtg cgaagaagaa 191580
agaggtggag gcctgccctg gcccaggact cccagcgtgg gggctcccgg cctggcccca 191640
cctctgctcc tgctacatgg caggtgggcc cttcctgccc tggcaacctg cagggaaggc 191700
cggaggggac cacccagcca gggagatgtt ggcgtctagg aggggacagg tgtggtccca 191760
cacacccagc atcttaaagt gcgtgggtcc ccagcccatt aggacagggt cccgggtggg 191820
caggggtcat ggtggggtga aggtctcagg cacaggcaag gtcacaggtg cggtgagggt 191880
cttgcagggt gtgaaggtca taggtgtgcg gtgaaggtca caggtgtggg gtgatggttt 191940
tgggtgtggg gagggtcttg cacggagcga gggtggcagc aagagctgga agctgcaggg 192000
ggagaatggc agcagagagc acccggccct gtgggcggcc tggacagggc tgggcctggg 192060
gctgccggag agcctgtcag cttccaggat gggagtggcc tcactcagct gctccacctc 192120
cgggtcaggc aggtgagcct ggggcagaga ggctgagagc acctgagcca cttgtgggag 192180
aggccacccc cactgccccc ctcaggcgag gagccggcct ccagcacagc agaagggaac 192240
ccccagtccc cagccctagt gggagtgggg aagaggccca gcaaggcccc ggacagaccg 192300
ccagcctgtg aggtctccgc tttcagttgc gttgatttga ttttttctga gccttgaagg 192360
aggggtccgg ggcctggccc tgcccaaagg cccctaggca ggccccaaag ccgggaccta 192420
gggtgctgag catgacggat gttgggtttg agcggctggc ttgcgacgtg agggctgagg 192480
tgtgagcctg ggtatcttca gaggttcggt ggacacaggc agctgcccgc ggccccactg 192540
ttcccgtggc ctcctagtcc tgctcaggca cctggtgagg aagggacgca gagggcagtg 192600
ggaggtggcc acgactgttc cagcaggctc ccctctgact caggaattca cgggcaccac 192660
ctccctggct ggctctggtt ggtgtctggc caggttattc attatttatg ctgaaagcct 192720
cttcagagtc ccaggggagg gtttctgtct ccattcctgg aggctgagag atgagggtgc 192780
agcagagtgg gggcctccac tccagaccct gcagtctggg ctggccaagg gctgcaccgg 192840
tgcactgcac gtcatggctg atgaagcact tccacaccgc agcccctcag agctgccaca 192900
gtcagcctta gttcaccgag ggggaagctg aggcccagag catgagaggg acttgcccag 192960
ggccacatag tccttagcag aggaagctgt ggctgggtga ctcgatcttt gtccttttc 193020 tttatacccg cagtctcccc atagcagagg cttttctttt ttttttcttt ttctttttt 193080 ttttttaca agaactcttt atatattaag gctgttgggc tgaagaagcc tgagagggtg 193140
gctggttctg tggagcatgg tttgttgaag tacagtttgg gggcctccta cactgagaat 193200
aggccttttc tcgtttctcc aaagagtggg ctggctcaag tagggcagag agagaagcct 193260
ggggcagagg ttagggatgg gcacccagcg cctgccctca cacgctctgt gctggtgtct 193320
tcacagccac gtgccaccct gggcagcatc ccctgctcac catctggctg tgcctgtttg 193380
ctgggggcac ctcattcaga atccagctta ttgtttccaa cggccaatgg ccacaccctg 193440
gcaggtagca agagtaggag agaggagaca cccactccga gcacaggttg ggtttggagc 193500
ccggccttgg ggcactctgt cactcaaagg cagagtgggg agtgggcact gggccttagg 193560
aggtactggg tccagtgagg cagagatgcc cctgccccac ccccaccttg tggcttcttc 193620
cctggcctgg ccagagctgt ctggccgcca tggggccctg tgtctcctgc cttgacctcc 193680
cagagggcag ccgaggccca ggggaggcct ggggacttag cctctcaggg caggacctgt 193740
ctgcaggagt aggtgggtgc tgggggtccc agtggtaatg aggcatcagg cagtgtggga 193800
aggggcccat ccggcccacc ccagggcctc tgggcaggtt gcaggttgta gcgctggatc 193860
taggctcctg cccagactgt aggttcaacc aagaatggca tgggagccca gcctgctgtt 193920
tgctttatta aatctgccct gtagctgggg gaggggctta ctttgatcat cactatgtca 193980
ttgatataaa aatagaggct cagagaggtg aatgaacctg cccaaagtca cacagcaaag 194040
tgtggagatg agatactgac tcagggctgt ggacactgaa gcctgtgctc taacgccagt 194100
ggctgtcgct ccctgaggca ttctctcccg aacaacacag ttattatatt acaaaatatt 194160
atcactatat ttatatatct tataatacct tattattaca ataaaacctt attactctac 194220
ctttcaaaat gaattattta aaaagcagta tttgctcatt gcagagagtc tagaaactat 194280
agaaaagcaa gggaaaagca ataggaccag ccccaaggtc ccagcatgca cagataacct 194340
tagtaatact gggacgtgtg cttccttttt aacatctgag cccgtgtagg tcctgaagcc 194400
cagcttcttt ctaagtccat tgtcatcttg accctggagc ctggccgatt ttgctgggga 194460
ggcccttgcc agccgagagc ggctcctgcc tgtgccggcg tggcgcgccc ctctgctgag 194520
gctgggcagg acaggggctg ggccagctct gtttctcacc cttggctctt gtgtctctcg 194580
tttcaggaaa ttaaaatgca tgacagatag cgagtccgcc ccgcccgact ggccctatta 194640
cctagccatt gatgggattc tggccaaggt ccccgagtcc tgtgatggca aactgccgga 194700
cagccagccg ccggggccct ccacgtccca gaccgaggcg tccctgtcgc cgcccgctaa 194760
gtccacccct ctgtacttcc cgtataacca gtgctcctac gaaggccgct tcgaggatga 194820
tcgctccgac agctcctcca gcttactgtc ccttaagttc aggtagtgtg tctgcttgtc 194880
cttcccctgc cctggggtat ctcagccccc accatttaga gaaagggact gggagtggca 194940
aggccggcgg cggcggccac agtggttgca gaggccgtgg ctgcgggcag cgcctccagg 195000
gacaggcggc ctcagaccag ggagggcttt agtgtccaca ggcagaccga gtttgtctcc 195060
cagctccatc acttttgagc tgcacggaaa gttccttgac ttctctggcc tcagtctccc 195120
tcctataaaa tgggggtaaa tcagtacctt tctcagaggg tggctgggag catcacagga 195180
gagaagacgc agcatggggc ccggcacacg gagggagacc aagccccaga ccccagaatg 195240
cgccccctgg cctcccttag cccacacaga ccccaccctc acaggctagc tgccctctca 195300
gcactgggga gggtgtcggg ctgcacctca tcacgtgttg ccgtgggcat gacccgtccc 195360
ctctgccatc catcccacac ctcagacccg tcccgtgctg gccacgtgac tgtgcctgca 195420
agatgctcac agggcagccg ggagccaggc agcatgcagg acagacacct gcggggtggg 195480
cctggggagc ccagagaagg tgcttttgag gaggggacat ttggggtggg ctttcaaggt 195540
aaaatagaag ttggccattt ggaggcaaga acaggaagat tgtggatttg agtcacagct 195600
tctcccctgc cctggtcttc aagtctttct gacaggaggt gtcagaaaag tatctttagt 195660
agagaaggcg tctccgagga gggtccctct catgccgggg gccgctgctt gactcaggat 195720
ttctcattga agacctgaga caaaaacgct tttgctggca gctagaagga accagcagga 195780

-continued ggcctgagat ttgtggctgt tgttcccgtg gactgagccc agttctcaga ctcagctgcc 195840
tggggccttg cacaggactg gggcgtgggg gctgccctcc ctgatcaggc ccaaagcgcg 195900
gatctcacgc ccctgaggtt ggctgtaccc tctcagctca gagcagagtg tgggccaggg 195960
atgagcaggc actggagcag ggccctgggg tctgtgggtt ttggcagctc cctgcccttc 196020
agggaggtct gctgagacca cgggtggccc ctaccccagc agcagagctc tcaggaggcg 196080
cccacagggc tggactgcct ttactcacca cctctaccag agctctgagg tcctggggag 196140
agagcccagg cctcttgtgg gccccacacc ctctaggtgc ctgtccttct gcctctctac 196200
caaggtgtgc cggccccatt tctaggccgc cgggagataa gggggctcac atctcaggcc 196260
cttccttctg ggacctcagt ttccccatct gcctaaggcc gggtggggct ggtggtcttg 196320
gcttccctac aggggtcctg agtactctgc actacccagc accccccacc cctgccttca 196380
tctctccctg gggtggtctc ctccacccct ggcccccaac tggggctgag cccccacctg 196440
cccagtttgg tgggtgaagg gtgctccctg gcaggatatg cccctctgca gcccagaaca 196500
tcccaccctt tccagaccga aggggtgtgg attgtcctgg gaccctggtc attggggtca 196560
tccgctagtc gcaaaggacg gcaatgcctg tggcctctct ttctttcttt ttcttttttt 196620
tttttttga gacggagtct cgctcttgtg cagagagcag tggcgcgatc ttggctcact 196680
gcaacctccg cctcgtgggt tcaagcgatt ctcctgcctc agcctcccga gtagctggga 196740
ttacaggcac ccgccacaac gcctggctaa tttttgtatt tttagtagag atggggtttc 196800
accatgttgg ccaggctggt cttgaactcc tgacctcagg tgatccacct gcctctgcct 196860
cccaaagtgc tgggattaca ggcataagcc tccacacccg gccacccctg ttactttctg 196920
tcaaaggcgg tgggttctgg cccctccttt gcacatggaa tatgagaccc tgagtaagtg 196980
acctgactcc ctggggcctc agtttcccca tttgcccagt aggattgtcg ggagggtccg 197040
gtgaggcccc tggtgtgccc aggctctgtg gccagcacgt ccacagccgg cactgtcctt 197100
ccaggtcgga ggagcggccg gtgaagaagc gcaaggtgca gagctgccac ctgcagaaga 197160
agcagctgcg gctgctggag gccatggtgg aggagcagcg ccggctgagc cgcgccgtgg 197220
aggagacctg ccgcgaggtg cgccgcgtgc tggaccagca gcacatcctg caggtgcaga 197280
gcctgcagct gcaggagcgc atgatgagtc tgctggagag gatcatcacc aagtccagcg 197340
tctaggccag caggcggcgg cggcggcggg gccgggcggc tggtggtact gctcaggcca 197400
cccagggcag gccactcagg ccaggcgggc aagggggccg ccccgcgagc ggagaccgcc 197460
ttccacctgg cctctggcag gatgtccctt ctgaggggta ttttgaggaa cccccaggcc 197520
ctggggaccg tgaggctcca gtctccagca tgaatgccct tcctcggaca caggccaggg 197580
cctctggggt tcactccgag taagaacgtc ctagagccac tctccagtgt cgttactatc 197640
aatgatactt gacgtggctt tgatattaaa cgtatacttt ttcattcttg cctggaacgc 197700
acagtttgct gttgctggct tggtgaggat gccctgattg atggatcccg aaaatgaaag 197760
cagatggaaa cgggttgggg caggctggag ctgggggagc tctctcctga agggaaccct 197820
gtgtcctccc tcaccaggac ctctgcgtct ctccttaaat ggcctctgac gcctgatgaa 197880
aaccccagcg accttccagg aggcttttat tcagctctgt ttggagcatc aggtgtttcc 197940
actgcctcct tagcaatgac actaataaaa gtcgtaacac ctgttcacat gcacagccct 198000
gttgagtgtt ctgggtgctg gagatatcat ggtggatgac acaaaggccc tggcctcttg 198060
gagcttatgc tcccatgcgg ggaagacaca tgggtcagta gagaaatggt tgcaggttgt 198120
gataagtgct ggaagggagg ggttggcctg aggacacgga ggcagacata cgtggagctg 198180
ggaacagtgg ccacacaggg aacggccagt gcgaaggccc agaggcagag gacactggag 198240
caagcccagg agcagctagg aggctggtgg ccagcagcca ggccacggaa gcccgtgcag 198300
cccgtgggga ggagtgttca tgcttttcaa gcttagtggg agtcttttgg ccagtgcagc 198360
tctgggtctg acatcggtgg gggacagagg ggtggtggag cggccacagc tgcaagctca 198420
cctcactgcc ggcccttcca ccagtttcaa actctttcta gaagctccag ctttcccaaa 198480
gctgaattct ctatgagcct ccttggccgg gactcgggcg tctggttgcc ctggctgcaa 198540
aggaggctgg ggccaggtgt gtttgagtca cctcctggaa ttaggcaagt tgctgcccaa 198600
atagaaggtt gttggcaggt gggtcagcag gtgaacagca tggtttgact cagggttcag 198660
aaaaatctcc ctctggctgc caagcgagca ggccgtggag acaggtgcag aggcaggtgt 198720
ggcagcaggc atcctgccag gcagtgctgc agtcatcctg cgacaagcag cagcagctca 198780
tcctaccctc tagggggtct tgaggtcagc caggcaagag agcagcttgg actccactgg 198840
gtgtgggacc agcctgtgga ccatggtggt gtggagggtg ccctcggcct gcctgtgtga 198900
aggagaggcc ggcgtgttct gtggagccca aaggggagct gggcaagcag gattcacttc 198960
actctgaggg tcctggagct cccaccctcc tcagccatct ccccagagcc tgtgtgccga 199020
ggactcggcc catgttgctg tgggatgaga ggcagagtgt cgtgagggtg taaggagcgg 199080
cggcagtggt gggaggaggg agcagcagcc agcgctacgg tgccagtttc cagctgccag 199140
atgacgccgc tgaccctgtg gttgagaaga gatgcacaga gccagctctt gcaagccagt 199200
gtggctgcca tagcacctgc cgagaagcag aaggaagggt ggccccagga ggacagagga 199260
tgcgggcaca tctgatgcgg gcctgagttt tgggagcttt tgctctagcc agtttccagc 199320
tccgggaccc acccgcctcg taggcaagac accacccaag aaatcatttg cttaacaaac 199380
acactgggct ccaactggac acctgtgcca ccctagatgc tgggaaccca gccatgacac 199440
aggcacctgc ccccagctgc tgaccactga ggctggctag cagctcccat ggggccagtg 199500
tggggttccc cagcctccta acagggagcc agtcacaagc cctcgagagg gaagggtgcc 199560
cgcggccctg gcaggaaggt taggctggac gctcccacaa gacataacag atggaggttc 199620
taaatgatgt agcaacttct tcaccctgaa actgctgtag agtcagccat gacgcaccgg 199680
tacttcagta actgccaggc atccgggaca gcacaccgcg agtcgctgct gtgcttgggt 199740
tagaagtggt ttggtctgtt ttcttctcgc cctctctaat cagagtcagt gattcatgcc 199800
cttccatcac cttagagaag gggcaggcgc tgcccgacct tctccaggct ggagcagcat 199860
cgcctcatgt cagcagaact cagctgtaga atatcgtggg gttggtgcct ttcatcagca 199920
gcatgtcctt aacaactttc tgatttcttc cttagttgtt ggtccattaa ggagaaaaaa 199980
aatgatctca gccattgcta aaatatttga taagattcag caaagcagca tgttaacatt 200040
gaaaactaga atcaggagcc aggcagatgt gcttgctttt cacctgtagt atttcatgtt 200100
gttttgacgt ttttagctaa tgcattaaga taaataaaca aaagccgggc acggtggttc 200160
acgcctgtaa tcccagcact ttgggaggct gaggcgggag gatcctctga ggtcaggagt 200220
tcaagaccag cctgaccaac atggagaaac ctcgtcatta ctaaaaatac aaaattagct 200280
gggcgtggtg gtgcatgcct gtaatcccag ctacttggga ggctgaggca ggagaatcgc 200340
ttgaacccgg gaggcggagg ttgcagtgag ctgagattgc accactgcac tccagcctgg 200400
gtgacagtga aactcggtct caaaaaaaaa aaaaaattaa aaaaagataa ataaaataag 200460
caggataaga aatgaagaaa gtagagttac ctttgttttc agatttcatt tttgtatacc 200520

```
cagaaagcca aatgtacaaa agactgggag ctctttaaac cagcttaaac ttgttgaaaa 200580

tgaggatgaa gaaatatccc attcagagtt ggaatgaatt taacccagaa ggaacaggac 200640

ctctactgaa gagaactatg cagtcttact gaaaaatcta aataatacct gagcgctgga 200700

gaaacttcgc acactcctga aagctccaaa gtcaatgtca tcattttatt aatgtcattc 200760

caaacatagt ctcaataata tcacttcttg gttttgacat ggacgcgatg atgtttaaat 200820

tcatatgaaa aaagaacggg gccaaaagtc caaggccagt cagcgtgaga agaccgctcg 200880

gcctccctcg gagtcgggga gttggaaccg cagactgaga tcatgtggct gctggaggcc 200940

aggacgaacg tcgggaaatg gagactcctg cgttgctggt gggatgtggt gcagccgctt 201000

ccaggagcaa tttggtgtcc cgtcctaaag ctgaagaaac gcatttcctc tggtcagtgc 201060

cactcctaga caggccaccc tgcggcagcc gtcctcaaac tggtctgagg acccctcaac 201120

gctcttaaaa atcattaaaa gtgggccagg tgcggtggct cacacctgta atcccagcac 201180

tttgggaggc caagacaggc ggatcacgag gtcaggacat tgagatcatc ctggctaaca 201240

cggtgaaacc ccgtctctac taaaaataca aaaaattagc cgggcgtggt ggcgggcgcc 201300

tgtagtccca gctacttggg aggctgagcc aggagaatgg cgtgaaccca ggaggtggag 201360

cttgcagtga gctgagatca ctccactgca ctccagcctg ggcagcagag cgagactctg 201420

tctcaaaaaa aaataataaa taaataaata aaaataaaat aaaataaaat tcattaaaag 201480

tgccaaagaa cttttgctta tgtgagttct aatgaccaat attaatacac attagaatat 201540

cttattagaa attaaacctg agacctttag aaaacatgta ttcatttcaa aatagcaata 201600

aacccatgac atattaacat aaataacaat tgtatgaaaa atatattttc caaaacaaaa 201660

agttttcggg agaagtgtgg catagtttta catggtcgta aatctctggc ttaagagaag 201720

cccactggcc tctcagcagg ctctgggtcc gtccactttg ggggtgtttt ggttgtgaag 201780

tataggagtg aatggagaag ctcattctta cccagatgtg tatttgaaaa gaaaaggaac 201840

attttaataa cctttgcaaa taatcggtat attcttccgt gatcctattc caacactgga 201900

caggtggtgg tttgtttttt ttttttggag acggagtccc gctctgtcac tcaggctgga 201960

gtgcagtggc gcgatttcag ctcactgcaa gctccgcctc c                    202001
```

```
<210> SEQ ID NO 2
<211> LENGTH: 13481
<212> TYPE: DNA
<213> ORGANISM: Homo sapiens
<220> FEATURE:
<221> NAME/KEY: CDS
<222> LOCATION: (146)..(9580)

<400> SEQUENCE: 2

gctgccggga cgggtccaag atggacggcc gctcaggttc tgcttttacc tgcggcccag     60

agccccattc attgccccgg tgctgagcgg cgccgcgagt cggcccgagg cctccgggga    120

ctgccgtgcc gggcgggaga ccgcc atg gcg acc ctg gaa aag ctg atg aag      172
                            Met Ala Thr Leu Glu Lys Leu Met Lys
                            1               5

gcc ttc gag tcc ctc aag tcc ttc cag cag cag cag cag cag cag cag      220
Ala Phe Glu Ser Leu Lys Ser Phe Gln Gln Gln Gln Gln Gln Gln Gln
10                  15                  20                  25

cag cag cag cag cag cag cag cag cag cag cag cag cag caa cag ccg      268
Gln Gln Gln Gln Gln Gln Gln Gln Gln Gln Gln Gln Gln Gln Gln Pro
                30                  35                  40

cca ccg ccg ccg ccg ccg ccg ccg cct cct cag ctt cct cag ccg ccg      316
Pro Pro Pro Pro Pro Pro Pro Pro Pro Pro Gln Leu Pro Gln Pro Pro
```

-continued

```
            45                  50                  55

ccg cag gca cag ccg ctg ctg cct cag ccg cag ccg ccc ccg ccg ccg      364
Pro Gln Ala Gln Pro Leu Leu Pro Gln Pro Gln Pro Pro Pro Pro Pro
        60                  65                  70

ccc ccg ccg cca ccc ggc ccg gct gtg gct gag gag ccg ctg cac cga      412
Pro Pro Pro Pro Pro Gly Pro Ala Val Ala Glu Glu Pro Leu His Arg
    75                  80                  85

cca aag aaa gaa ctt tca gct acc aag aaa gac cgt gtg aat cat tgt      460
Pro Lys Lys Glu Leu Ser Ala Thr Lys Lys Asp Arg Val Asn His Cys
90                  95                  100                 105

ctg aca ata tgt gaa aac ata gtg gca cag tct gtc aga aat tct cca      508
Leu Thr Ile Cys Glu Asn Ile Val Ala Gln Ser Val Arg Asn Ser Pro
                110                 115                 120

gaa ttt cag aaa ctt ctg ggc atc gct atg gaa ctt ttt ctg ctg tgc      556
Glu Phe Gln Lys Leu Leu Gly Ile Ala Met Glu Leu Phe Leu Leu Cys
            125                 130                 135

agt gat gac gca gag tca gat gtc agg atg gtg gct gac gaa tgc ctc      604
Ser Asp Asp Ala Glu Ser Asp Val Arg Met Val Ala Asp Glu Cys Leu
        140                 145                 150

aac aaa gtt atc aaa gct ttg atg gat tct aat ctt cca agg tta cag      652
Asn Lys Val Ile Lys Ala Leu Met Asp Ser Asn Leu Pro Arg Leu Gln
    155                 160                 165

ctc gag ctc tat aag gaa att aaa aag aat ggt gcc cct cgg agt ttg      700
Leu Glu Leu Tyr Lys Glu Ile Lys Lys Asn Gly Ala Pro Arg Ser Leu
170                 175                 180                 185

cgt gct gcc ctg tgg agg ttt gct gag ctg gct cac ctg gtt cgg cct      748
Arg Ala Ala Leu Trp Arg Phe Ala Glu Leu Ala His Leu Val Arg Pro
                190                 195                 200

cag aaa tgc agg cct tac ctg gtg aac ctt ctg ccg tgc ctg act cga      796
Gln Lys Cys Arg Pro Tyr Leu Val Asn Leu Leu Pro Cys Leu Thr Arg
            205                 210                 215

aca agc aag aga ccc gaa gaa tca gtc cag gag acc ttg gct gca gct      844
Thr Ser Lys Arg Pro Glu Glu Ser Val Gln Glu Thr Leu Ala Ala Ala
        220                 225                 230

gtt ccc aaa att atg gct tct ttt ggc aat ttt gca aat gac aat gaa      892
Val Pro Lys Ile Met Ala Ser Phe Gly Asn Phe Ala Asn Asp Asn Glu
    235                 240                 245

att aag gtt ttg tta aag gcc ttc ata gcg aac ctg aag tca agc tcc      940
Ile Lys Val Leu Leu Lys Ala Phe Ile Ala Asn Leu Lys Ser Ser Ser
250                 255                 260                 265

ccc acc att cgg cgg aca gcg gct gga tca gca gtg agc atc tgc cag      988
Pro Thr Ile Arg Arg Thr Ala Ala Gly Ser Ala Val Ser Ile Cys Gln
                270                 275                 280

cac tca aga agg aca caa tat ttc tat agt tgg cta cta aat gtg ctc     1036
His Ser Arg Arg Thr Gln Tyr Phe Tyr Ser Trp Leu Leu Asn Val Leu
            285                 290                 295

tta ggc tta ctc gtt cct gtc gag gat gaa cac tcc act ctg ctg att     1084
Leu Gly Leu Leu Val Pro Val Glu Asp Glu His Ser Thr Leu Leu Ile
        300                 305                 310

ctt ggc gtg ctg ctc acc ctg agg tat ttg gtg ccc ttg ctg cag cag     1132
Leu Gly Val Leu Leu Thr Leu Arg Tyr Leu Val Pro Leu Leu Gln Gln
    315                 320                 325

cag gtc aag gac aca agc ctg aaa ggc agc ttc gga gtg aca agg aaa     1180
Gln Val Lys Asp Thr Ser Leu Lys Gly Ser Phe Gly Val Thr Arg Lys
330                 335                 340                 345

gaa atg gaa gtc tct cct tct gca gag cag ctt gtc cag gtt tat gaa     1228
Glu Met Glu Val Ser Pro Ser Ala Glu Gln Leu Val Gln Val Tyr Glu
                350                 355                 360

ctg acg tta cat cat aca cag cac caa gac cac aat gtt gtg acc gga     1276
```

-continued

```
Leu Thr Leu His His Thr Gln His Gln Asp His Asn Val Val Thr Gly
            365                 370                 375

gcc ctg gag ctg ttg cag cag ctc ttc aga acg cct cca ccc gag ctt      1324
Ala Leu Glu Leu Leu Gln Gln Leu Phe Arg Thr Pro Pro Pro Glu Leu
        380                 385                 390

ctg caa acc ctg acc gca gtc ggg ggc att ggg cag ctc acc gct gct      1372
Leu Gln Thr Leu Thr Ala Val Gly Gly Ile Gly Gln Leu Thr Ala Ala
    395                 400                 405

aag gag gag tct ggt ggc cga agc cgt agt ggg agt att gtg gaa ctt      1420
Lys Glu Glu Ser Gly Gly Arg Ser Arg Ser Gly Ser Ile Val Glu Leu
410                 415                 420                 425

ata gct gga ggg ggt tcc tca tgc agc cct gtc ctt tca aga aaa caa      1468
Ile Ala Gly Gly Gly Ser Ser Cys Ser Pro Val Leu Ser Arg Lys Gln
                430                 435                 440

aaa ggc aaa gtg ctc tta gga gaa gaa gaa gcc ttg gag gat gac tct      1516
Lys Gly Lys Val Leu Leu Gly Glu Glu Glu Ala Leu Glu Asp Asp Ser
            445                 450                 455

gaa tcg aga tcg gat gtc agc agc tct gcc tta aca gcc tca gtg aag      1564
Glu Ser Arg Ser Asp Val Ser Ser Ser Ala Leu Thr Ala Ser Val Lys
        460                 465                 470

gat gag atc agt gga gag ctg gct gct tct tca ggg gtt tcc act cca      1612
Asp Glu Ile Ser Gly Glu Leu Ala Ala Ser Ser Gly Val Ser Thr Pro
    475                 480                 485

ggg tca gca ggt cat gac atc atc aca gaa cag cca cgg tca cag cac      1660
Gly Ser Ala Gly His Asp Ile Ile Thr Glu Gln Pro Arg Ser Gln His
490                 495                 500                 505

aca ctg cag gcg gac tca gtg gat ctg gcc agc tgt gac ttg aca agc      1708
Thr Leu Gln Ala Asp Ser Val Asp Leu Ala Ser Cys Asp Leu Thr Ser
                510                 515                 520

tct gcc act gat ggg gat gag gag gat atc ttg agc cac agc tcc agc      1756
Ser Ala Thr Asp Gly Asp Glu Glu Asp Ile Leu Ser His Ser Ser Ser
            525                 530                 535

cag gtc agc gcc gtc cca tct gac cct gcc atg gac ctg aat gat ggg      1804
Gln Val Ser Ala Val Pro Ser Asp Pro Ala Met Asp Leu Asn Asp Gly
        540                 545                 550

acc cag gcc tcg tcg ccc atc agc gac agc tcc cag acc acc acc gaa      1852
Thr Gln Ala Ser Ser Pro Ile Ser Asp Ser Ser Gln Thr Thr Thr Glu
    555                 560                 565

ggg cct gat tca gct gtt acc cct tca gac agt tct gaa att gtg tta      1900
Gly Pro Asp Ser Ala Val Thr Pro Ser Asp Ser Ser Glu Ile Val Leu
570                 575                 580                 585

gac ggt acc gac aac cag tat ttg ggc ctg cag att gga cag ccc cag      1948
Asp Gly Thr Asp Asn Gln Tyr Leu Gly Leu Gln Ile Gly Gln Pro Gln
                590                 595                 600

gat gaa gat gag gaa gcc aca ggt att ctt cct gat gaa gcc tcg gag      1996
Asp Glu Asp Glu Glu Ala Thr Gly Ile Leu Pro Asp Glu Ala Ser Glu
            605                 610                 615

gcc ttc agg aac tct tcc atg gcc ctt caa cag gca cat tta ttg aaa      2044
Ala Phe Arg Asn Ser Ser Met Ala Leu Gln Gln Ala His Leu Leu Lys
        620                 625                 630

aac atg agt cac tgc agg cag cct tct gac agc agt gtt gat aaa ttt      2092
Asn Met Ser His Cys Arg Gln Pro Ser Asp Ser Ser Val Asp Lys Phe
    635                 640                 645

gtg ttg aga gat gaa gct act gaa ccg ggt gat caa gaa aac aag cct      2140
Val Leu Arg Asp Glu Ala Thr Glu Pro Gly Asp Gln Glu Asn Lys Pro
650                 655                 660                 665

tgc cgc atc aaa ggt gac att gga cag tcc act gat gat gac tct gca      2188
Cys Arg Ile Lys Gly Asp Ile Gly Gln Ser Thr Asp Asp Asp Ser Ala
                670                 675                 680
```

```
cct ctt gtc cat tgt gtc cgc ctt tta tct gct tcg ttt ttg cta aca      2236
Pro Leu Val His Cys Val Arg Leu Leu Ser Ala Ser Phe Leu Leu Thr
            685                 690                 695

ggg gga aaa aat gtg ctg gtt ccg gac agg gat gtg agg gtc agc gtg      2284
Gly Gly Lys Asn Val Leu Val Pro Asp Arg Asp Val Arg Val Ser Val
        700                 705                 710

aag gcc ctg gcc ctc agc tgt gtg gga gca gct gtg gcc ctc cac ccg      2332
Lys Ala Leu Ala Leu Ser Cys Val Gly Ala Ala Val Ala Leu His Pro
    715                 720                 725

gaa tct ttc ttc agc aaa ctc tat aaa gtt cct ctt gac acc acg gaa      2380
Glu Ser Phe Phe Ser Lys Leu Tyr Lys Val Pro Leu Asp Thr Thr Glu
730                 735                 740                 745

tac cct gag gaa cag tat gtc tca gac atc ttg aac tac atc gat cat      2428
Tyr Pro Glu Glu Gln Tyr Val Ser Asp Ile Leu Asn Tyr Ile Asp His
                750                 755                 760

gga gac cca cag gtt cga gga gcc act gcc att ctc tgt ggg acc ctc      2476
Gly Asp Pro Gln Val Arg Gly Ala Thr Ala Ile Leu Cys Gly Thr Leu
            765                 770                 775

atc tgc tcc atc ctc agc agg tcc cgc ttc cac gtg gga gat tgg atg      2524
Ile Cys Ser Ile Leu Ser Arg Ser Arg Phe His Val Gly Asp Trp Met
        780                 785                 790

ggc acc att aga acc ctc aca gga aat aca ttt tct ttg gcg gat tgc      2572
Gly Thr Ile Arg Thr Leu Thr Gly Asn Thr Phe Ser Leu Ala Asp Cys
    795                 800                 805

att cct ttg ctg cgg aaa aca ctg aag gat gag tct tct gtt act tgc      2620
Ile Pro Leu Leu Arg Lys Thr Leu Lys Asp Glu Ser Ser Val Thr Cys
810                 815                 820                 825

aag tta gct tgt aca gct gtg agg aac tgt gtc atg agt ctc tgc agc      2668
Lys Leu Ala Cys Thr Ala Val Arg Asn Cys Val Met Ser Leu Cys Ser
                830                 835                 840

agc agc tac agt gag tta gga ctg cag ctg atc atc gat gtg ctg act      2716
Ser Ser Tyr Ser Glu Leu Gly Leu Gln Leu Ile Ile Asp Val Leu Thr
            845                 850                 855

ctg agg aac agt tcc tat tgg ctg gtg agg aca gag ctt ctg gaa acc      2764
Leu Arg Asn Ser Ser Tyr Trp Leu Val Arg Thr Glu Leu Leu Glu Thr
        860                 865                 870

ctt gca gag att gac ttc agg ctg gtg agc ttt ttg gag gca aaa gca      2812
Leu Ala Glu Ile Asp Phe Arg Leu Val Ser Phe Leu Glu Ala Lys Ala
    875                 880                 885

gaa aac tta cac aga ggg gct cat cat tat aca ggg ctt tta aaa ctg      2860
Glu Asn Leu His Arg Gly Ala His His Tyr Thr Gly Leu Leu Lys Leu
890                 895                 900                 905

caa gaa cga gtg ctc aat aat gtt gtc atc cat ttg ctt gga gat gaa      2908
Gln Glu Arg Val Leu Asn Asn Val Val Ile His Leu Leu Gly Asp Glu
                910                 915                 920

gac ccc agg gtg cga cat gtt gcc gca gca tca cta att agg ctt gtc      2956
Asp Pro Arg Val Arg His Val Ala Ala Ala Ser Leu Ile Arg Leu Val
            925                 930                 935

cca aag ctg ttt tat aaa tgt gac caa gga caa gct gat cca gta gtg      3004
Pro Lys Leu Phe Tyr Lys Cys Asp Gln Gly Gln Ala Asp Pro Val Val
        940                 945                 950

gcc gtg gca aga gat caa agc agt gtt tac ctg aaa ctt ctc atg cat      3052
Ala Val Ala Arg Asp Gln Ser Ser Val Tyr Leu Lys Leu Leu Met His
    955                 960                 965

gag acg cag cct cca tct cat ttc tcc gtc agc aca ata acc aga ata      3100
Glu Thr Gln Pro Pro Ser His Phe Ser Val Ser Thr Ile Thr Arg Ile
970                 975                 980                 985

tat aga ggc tat aac cta cta cca agc ata aca gac gtc act atg  gaa     3148
Tyr Arg Gly Tyr Asn Leu Leu Pro Ser Ile Thr Asp Val Thr Met  Glu
                990                 995                 1000
```

```
aat aac ctt tca  aga gtt att gca gca  gtt tct cat gaa cta  atc      3193
Asn Asn Leu Ser  Arg Val Ile Ala Ala  Val Ser His Glu Leu  Ile
            1005                 1010                 1015

aca tca acc acc  aga gca ctc aca ttt  gga tgc tgt gaa gct  ttg      3238
Thr Ser Thr Thr  Arg Ala Leu Thr Phe  Gly Cys Cys Glu Ala  Leu
            1020                 1025                 1030

tgt ctt ctt tcc  act gcc ttc cca gtt  tgc att tgg agt tta  ggt      3283
Cys Leu Leu Ser  Thr Ala Phe Pro Val  Cys Ile Trp Ser Leu  Gly
            1035                 1040                 1045

tgg cac tgt gga  gtg cct cca ctg agt  gcc tca gat gag tct  agg      3328
Trp His Cys Gly  Val Pro Pro Leu Ser  Ala Ser Asp Glu Ser  Arg
            1050                 1055                 1060

aag agc tgt acc  gtt ggg atg gcc aca  atg att ctg acc ctg  ctc      3373
Lys Ser Cys Thr  Val Gly Met Ala Thr  Met Ile Leu Thr Leu  Leu
            1065                 1070                 1075

tcg tca gct tgg  ttc cca ttg gat ctc  tca gcc cat caa gat  gct      3418
Ser Ser Ala Trp  Phe Pro Leu Asp Leu  Ser Ala His Gln Asp  Ala
            1080                 1085                 1090

ttg att ttg gcc  gga aac ttg ctt gca  gcc agt gct ccc aaa  tct      3463
Leu Ile Leu Ala  Gly Asn Leu Leu Ala  Ala Ser Ala Pro Lys  Ser
            1095                 1100                 1105

ctg aga agt tca  tgg gcc tct gaa gaa  gaa gcc aac cca gca  gcc      3508
Leu Arg Ser Ser  Trp Ala Ser Glu Glu  Glu Ala Asn Pro Ala  Ala
            1110                 1115                 1120

acc aag caa gag  gag gtc tgg cca gcc  ctg ggg gac cgg gcc  ctg      3553
Thr Lys Gln Glu  Glu Val Trp Pro Ala  Leu Gly Asp Arg Ala  Leu
            1125                 1130                 1135

gtg ccc atg gtg  gag cag ctc ttc tct  cac ctg ctg aag gtg  att      3598
Val Pro Met Val  Glu Gln Leu Phe Ser  His Leu Leu Lys Val  Ile
            1140                 1145                 1150

aac att tgt gcc  cac gtc ctg gat gac  gtg gct cct gga ccc  gca      3643
Asn Ile Cys Ala  His Val Leu Asp Asp  Val Ala Pro Gly Pro  Ala
            1155                 1160                 1165

ata aag gca gcc  ttg cct tct cta aca  aac ccc cct tct cta  agt      3688
Ile Lys Ala Ala  Leu Pro Ser Leu Thr  Asn Pro Pro Ser Leu  Ser
            1170                 1175                 1180

ccc atc cga cga  aag ggg aag gag aaa  gaa cca gga gaa caa  gca      3733
Pro Ile Arg Arg  Lys Gly Lys Glu Lys  Glu Pro Gly Glu Gln  Ala
            1185                 1190                 1195

tct gta ccg ttg  agt ccc aag aaa ggc  agt gag gcc agt gca  gct      3778
Ser Val Pro Leu  Ser Pro Lys Lys Gly  Ser Glu Ala Ser Ala  Ala
            1200                 1205                 1210

tct aga caa tct  gat acc tca ggt cct  gtt aca aca agt aaa  tcc      3823
Ser Arg Gln Ser  Asp Thr Ser Gly Pro  Val Thr Thr Ser Lys  Ser
            1215                 1220                 1225

tca tca ctg ggg  agt ttc tat cat ctt  cct tca tac ctc aaa  ctg      3868
Ser Ser Leu Gly  Ser Phe Tyr His Leu  Pro Ser Tyr Leu Lys  Leu
            1230                 1235                 1240

cat gat gtc ctg  aaa gct aca cac gct  aac tac aag gtc acg  ctg      3913
His Asp Val Leu  Lys Ala Thr His Ala  Asn Tyr Lys Val Thr  Leu
            1245                 1250                 1255

gat ctt cag aac  agc acg gaa aag ttt  gga ggg ttt ctc cgc  tca      3958
Asp Leu Gln Asn  Ser Thr Glu Lys Phe  Gly Gly Phe Leu Arg  Ser
            1260                 1265                 1270

gcc ttg gat gtt  ctt tct cag ata cta  gag ctg gcc aca ctg  cag      4003
Ala Leu Asp Val  Leu Ser Gln Ile Leu  Glu Leu Ala Thr Leu  Gln
            1275                 1280                 1285

gac att ggg aag  tgt gtt gaa gag atc  cta gga tac ctg aaa  tcc      4048
Asp Ile Gly Lys  Cys Val Glu Glu Ile  Leu Gly Tyr Leu Lys  Ser
```

```
            1290                1295                1300

tgc ttt agt cga  gaa cca atg atg gca  act gtt tgt gtt caa  caa      4093
Cys Phe Ser Arg  Glu Pro Met Met Ala  Thr Val Cys Val Gln  Gln
            1305                1310                1315

ttg ttg aag act  ctc ttt ggc aca aac  ttg gcc tcc cag ttt  gat      4138
Leu Leu Lys Thr  Leu Phe Gly Thr Asn  Leu Ala Ser Gln Phe  Asp
            1320                1325                1330

ggc tta tct tcc  aac ccc agc aag tca  caa ggc cga gca cag  cgc      4183
Gly Leu Ser Ser  Asn Pro Ser Lys Ser  Gln Gly Arg Ala Gln  Arg
            1335                1340                1345

ctt ggc tcc tcc  agt gtg agg cca ggc  ttg tac cac tac tgc  ttc      4228
Leu Gly Ser Ser  Ser Val Arg Pro Gly  Leu Tyr His Tyr Cys  Phe
            1350                1355                1360

atg gcc ccg tac  acc cac ttc acc cag  gcc ctc gct gac gcc  agc      4273
Met Ala Pro Tyr  Thr His Phe Thr Gln  Ala Leu Ala Asp Ala  Ser
            1365                1370                1375

ctg agg aac atg  gtg cag gcg gag cag  gag aac gac acc tcg  gga      4318
Leu Arg Asn Met  Val Gln Ala Glu Gln  Glu Asn Asp Thr Ser  Gly
            1380                1385                1390

tgg ttt gat gtc  ctc cag aaa gtg tct  acc cag ttg aag aca  aac      4363
Trp Phe Asp Val  Leu Gln Lys Val Ser  Thr Gln Leu Lys Thr  Asn
            1395                1400                1405

ctc acg agt gtc  aca aag aac cgt gca  gat aag aat gct att  cat      4408
Leu Thr Ser Val  Thr Lys Asn Arg Ala  Asp Lys Asn Ala Ile  His
            1410                1415                1420

aat cac att cgt  ttg ttt gaa cct ctt  gtt ata aaa gct tta  aaa      4453
Asn His Ile Arg  Leu Phe Glu Pro Leu  Val Ile Lys Ala Leu  Lys
            1425                1430                1435

cag tac acg act  aca aca tgt gtg cag  tta cag aag cag gtt  tta      4498
Gln Tyr Thr Thr  Thr Thr Cys Val Gln  Leu Gln Lys Gln Val  Leu
            1440                1445                1450

gat ttg ctg gcg  cag ctg gtt cag tta  cgg gtt aat tac tgt  ctt      4543
Asp Leu Leu Ala  Gln Leu Val Gln Leu  Arg Val Asn Tyr Cys  Leu
            1455                1460                1465

ctg gat tca gat  cag gtg ttt att ggc  ttt gta ttg aaa cag  ttt      4588
Leu Asp Ser Asp  Gln Val Phe Ile Gly  Phe Val Leu Lys Gln  Phe
            1470                1475                1480

gaa tac att gaa  gtg ggc cag ttc agg  gaa tca gag gca atc  att      4633
Glu Tyr Ile Glu  Val Gly Gln Phe Arg  Glu Ser Glu Ala Ile  Ile
            1485                1490                1495

cca aac atc ttt  ttc ttc ttg gta tta  cta tct tat gaa cgc  tat      4678
Pro Asn Ile Phe  Phe Phe Leu Val Leu  Leu Ser Tyr Glu Arg  Tyr
            1500                1505                1510

cat tca aaa cag  atc att gga att cct  aaa atc att cag ctc  tgt      4723
His Ser Lys Gln  Ile Ile Gly Ile Pro  Lys Ile Ile Gln Leu  Cys
            1515                1520                1525

gat ggc atc atg  gcc agt gga agg aag  gct gtg aca cat gcc  ata      4768
Asp Gly Ile Met  Ala Ser Gly Arg Lys  Ala Val Thr His Ala  Ile
            1530                1535                1540

ccg gct ctg cag  ccc ata gtc cac gac  ctc ttt gta tta aga  gga      4813
Pro Ala Leu Gln  Pro Ile Val His Asp  Leu Phe Val Leu Arg  Gly
            1545                1550                1555

aca aat aaa gct  gat gca gga aaa gag  ctt gaa acc caa aaa  gag      4858
Thr Asn Lys Ala  Asp Ala Gly Lys Glu  Leu Glu Thr Gln Lys  Glu
            1560                1565                1570

gtg gtg gtg tca  atg tta ctg aga ctc  atc cag tac cat cag  gtg      4903
Val Val Val Ser  Met Leu Leu Arg Leu  Ile Gln Tyr His Gln  Val
            1575                1580                1585

ttg gag atg ttc  att ctt gtc ctg cag  cag tgc cac aag gag  aat      4948
```

-continued

```
Leu Glu Met Phe Ile Leu Val Leu Gln Gln Cys His Lys Glu Asn
            1590                1595                1600

gaa gac aag tgg aag cga ctg tct cga cag ata gct gac atc atc      4993
Glu Asp Lys Trp Lys Arg Leu Ser Arg Gln Ile Ala Asp Ile Ile
            1605                1610                1615

ctc cca atg tta gcc aaa cag cag atg cac att gac tct cat gaa      5038
Leu Pro Met Leu Ala Lys Gln Gln Met His Ile Asp Ser His Glu
            1620                1625                1630

gcc ctt gga gtg tta aat aca tta ttt gag att ttg gcc cct tcc      5083
Ala Leu Gly Val Leu Asn Thr Leu Phe Glu Ile Leu Ala Pro Ser
            1635                1640                1645

tcc ctc cgt ccg gta gac atg ctt tta cgg agt atg ttc gtc act      5128
Ser Leu Arg Pro Val Asp Met Leu Leu Arg Ser Met Phe Val Thr
            1650                1655                1660

cca aac aca atg gcg tcc gtg agc act gtt caa ctg tgg ata tcg      5173
Pro Asn Thr Met Ala Ser Val Ser Thr Val Gln Leu Trp Ile Ser
            1665                1670                1675

gga att ctg gcc att ttg agg gtt ctg att tcc cag tca act gaa      5218
Gly Ile Leu Ala Ile Leu Arg Val Leu Ile Ser Gln Ser Thr Glu
            1680                1685                1690

gat att gtt ctt tct cgt att cag gag ctc tcc ttc tct ccg tat      5263
Asp Ile Val Leu Ser Arg Ile Gln Glu Leu Ser Phe Ser Pro Tyr
            1695                1700                1705

tta atc tcc tgt aca gta att aat agg tta aga gat ggg gac agt      5308
Leu Ile Ser Cys Thr Val Ile Asn Arg Leu Arg Asp Gly Asp Ser
            1710                1715                1720

act tca acg cta gaa gaa cac agt gaa ggg aaa caa ata aag aat      5353
Thr Ser Thr Leu Glu Glu His Ser Glu Gly Lys Gln Ile Lys Asn
            1725                1730                1735

ttg cca gaa gaa aca ttt tca agg ttt cta tta caa ctg gtt ggt      5398
Leu Pro Glu Glu Thr Phe Ser Arg Phe Leu Leu Gln Leu Val Gly
            1740                1745                1750

att ctt tta gaa gac att gtt aca aaa cag ctg aag gtg gaa atg      5443
Ile Leu Leu Glu Asp Ile Val Thr Lys Gln Leu Lys Val Glu Met
            1755                1760                1765

agt gag cag caa cat act ttc tat tgc cag gaa cta ggc aca ctg      5488
Ser Glu Gln Gln His Thr Phe Tyr Cys Gln Glu Leu Gly Thr Leu
            1770                1775                1780

cta atg tgt ctg atc cac atc ttc aag tct gga atg ttc cgg aga      5533
Leu Met Cys Leu Ile His Ile Phe Lys Ser Gly Met Phe Arg Arg
            1785                1790                1795

atc aca gca gct gcc act agg ctg ttc cgc agt gat ggc tgt ggc      5578
Ile Thr Ala Ala Ala Thr Arg Leu Phe Arg Ser Asp Gly Cys Gly
            1800                1805                1810

ggc agt ttc tac acc ctg gac agc ttg aac ttg cgg gct cgt tcc      5623
Gly Ser Phe Tyr Thr Leu Asp Ser Leu Asn Leu Arg Ala Arg Ser
            1815                1820                1825

atg atc acc acc cac ccg gcc ctg gtg ctg ctc tgg tgt cag ata      5668
Met Ile Thr Thr His Pro Ala Leu Val Leu Leu Trp Cys Gln Ile
            1830                1835                1840

ctg ctg ctt gtc aac cac acc gac tac cgc tgg tgg gca gaa gtg      5713
Leu Leu Leu Val Asn His Thr Asp Tyr Arg Trp Trp Ala Glu Val
            1845                1850                1855

cag cag acc ccg aaa aga cac agt ctg tcc agc aca aag tta ctt      5758
Gln Gln Thr Pro Lys Arg His Ser Leu Ser Ser Thr Lys Leu Leu
            1860                1865                1870

agt ccc cag atg tct gga gaa gag gag gat tct gac ttg gca gcc      5803
Ser Pro Gln Met Ser Gly Glu Glu Glu Asp Ser Asp Leu Ala Ala
            1875                1880                1885
```

-continued

```
aaa ctt gga atg  tgc aat aga gaa ata  gta cga aga ggg gct  ctc      5848
Lys Leu Gly Met  Cys Asn Arg Glu Ile  Val Arg Arg Gly Ala  Leu
            1890                 1895                 1900

att ctc ttc tgt  gat tat gtc tgt cag  aac ctc cat gac tcc  gag      5893
Ile Leu Phe Cys  Asp Tyr Val Cys Gln  Asn Leu His Asp Ser  Glu
            1905                 1910                 1915

cac tta acg tgg  ctc att gta aat cac  att caa gat ctg atc  agc      5938
His Leu Thr Trp  Leu Ile Val Asn His  Ile Gln Asp Leu Ile  Ser
            1920                 1925                 1930

ctt tcc cac gag  cct cca gta cag gac  ttc atc agt gcc gtt  cat      5983
Leu Ser His Glu  Pro Pro Val Gln Asp  Phe Ile Ser Ala Val  His
            1935                 1940                 1945

cgg aac tct gct  gcc agc ggc ctg ttc  atc cag gca att cag  tct      6028
Arg Asn Ser Ala  Ala Ser Gly Leu Phe  Ile Gln Ala Ile Gln  Ser
            1950                 1955                 1960

cgt tgt gaa aac  ctt tca act cca acc  atg ctg aag aaa act  ctt      6073
Arg Cys Glu Asn  Leu Ser Thr Pro Thr  Met Leu Lys Lys Thr  Leu
            1965                 1970                 1975

cag tgc ttg gag  ggg atc cat ctc agc  cag tcg gga gct gtg  ctc      6118
Gln Cys Leu Glu  Gly Ile His Leu Ser  Gln Ser Gly Ala Val  Leu
            1980                 1985                 1990

acg ctg tat gtg  gac agg ctt ctg tgc  acc cct ttc cgt gtg  ctg      6163
Thr Leu Tyr Val  Asp Arg Leu Leu Cys  Thr Pro Phe Arg Val  Leu
            1995                 2000                 2005

gct cgc atg gtc  gac atc ctt gct tgt  cgc cgg gta gaa atg  ctt      6208
Ala Arg Met Val  Asp Ile Leu Ala Cys  Arg Arg Val Glu Met  Leu
            2010                 2015                 2020

ctg gct gca aat  tta cag agc agc atg  gcc cag ttg cca atg  gaa      6253
Leu Ala Ala Asn  Leu Gln Ser Ser Met  Ala Gln Leu Pro Met  Glu
            2025                 2030                 2035

gaa ctc aac aga  atc cag gaa tac ctt  cag agc agc ggg ctc  gct      6298
Glu Leu Asn Arg  Ile Gln Glu Tyr Leu  Gln Ser Ser Gly Leu  Ala
            2040                 2045                 2050

cag aga cac caa  agg ctc tat tcc ctg  ctg gac agg ttt cgt  ctc      6343
Gln Arg His Gln  Arg Leu Tyr Ser Leu  Leu Asp Arg Phe Arg  Leu
            2055                 2060                 2065

tcc acc atg caa  gac tca ctt agt ccc  tct cct cca gtc tct  tcc      6388
Ser Thr Met Gln  Asp Ser Leu Ser Pro  Ser Pro Pro Val Ser  Ser
            2070                 2075                 2080

cac ccg ctg gac  ggg gat ggg cac gtg  tca ctg gaa aca gtg  agt      6433
His Pro Leu Asp  Gly Asp Gly His Val  Ser Leu Glu Thr Val  Ser
            2085                 2090                 2095

ccg gac aaa gac  tgg tac gtt cat ctt  gtc aaa tcc cag tgt  tgg      6478
Pro Asp Lys Asp  Trp Tyr Val His Leu  Val Lys Ser Gln Cys  Trp
            2100                 2105                 2110

acc agg tca gat  tct gca ctg ctg gaa  ggt gca gag ctg gtg  aat      6523
Thr Arg Ser Asp  Ser Ala Leu Leu Glu  Gly Ala Glu Leu Val  Asn
            2115                 2120                 2125

cgg att cct gct  gaa gat atg aat gcc  ttc atg atg aac tcg  gag      6568
Arg Ile Pro Ala  Glu Asp Met Asn Ala  Phe Met Met Asn Ser  Glu
            2130                 2135                 2140

ttc aac cta agc  ctg cta gct cca tgc  tta agc cta ggg atg  agt      6613
Phe Asn Leu Ser  Leu Leu Ala Pro Cys  Leu Ser Leu Gly Met  Ser
            2145                 2150                 2155

gaa att tct ggt  ggc cag aag agt gcc  ctt ttt gaa gca gcc  cgt      6658
Glu Ile Ser Gly  Gly Gln Lys Ser Ala  Leu Phe Glu Ala Ala  Arg
            2160                 2165                 2170

gag gtg act ctg  gcc cgt gtg agc ggc  acc gtg cag cag ctc  cct      6703
Glu Val Thr Leu  Ala Arg Val Ser Gly  Thr Val Gln Gln Leu  Pro
            2175                 2180                 2185
```

-continued

```
gct gtc cat cat  gtc ttc cag ccc gag  ctg cct gca gag ccg  gcg      6748
Ala Val His His  Val Phe Gln Pro Glu  Leu Pro Ala Glu Pro  Ala
            2190                 2195                 2200

gcc tac tgg agc  aag ttg aat gat ctg  ttt ggg gat gct gca  ctg      6793
Ala Tyr Trp Ser  Lys Leu Asn Asp Leu  Phe Gly Asp Ala Ala  Leu
            2205                 2210                 2215

tat cag tcc ctg  ccc act ctg gcc cgg  gcc ctg gca cag tac  ctg      6838
Tyr Gln Ser Leu  Pro Thr Leu Ala Arg  Ala Leu Ala Gln Tyr  Leu
            2220                 2225                 2230

gtg gtg gtc tcc  aaa ctg ccc agt cat  ttg cac ctt cct cct  gag      6883
Val Val Val Ser  Lys Leu Pro Ser His  Leu His Leu Pro Pro  Glu
            2235                 2240                 2245

aaa gag aag gac  att gtg aaa ttc gtg  gtg gca acc ctt gag  gcc      6928
Lys Glu Lys Asp  Ile Val Lys Phe Val  Val Ala Thr Leu Glu  Ala
            2250                 2255                 2260

ctg tcc tgg cat  ttg atc cat gag cag  atc ccg ctg agt ctg  gat      6973
Leu Ser Trp His  Leu Ile His Glu Gln  Ile Pro Leu Ser Leu  Asp
            2265                 2270                 2275

ctc cag gca ggg  ctg gac tgc tgc tgc  ctg gcc ctg cag ctg  cct      7018
Leu Gln Ala Gly  Leu Asp Cys Cys Cys  Leu Ala Leu Gln Leu  Pro
            2280                 2285                 2290

ggc ctc tgg agc  gtg gtc tcc tcc aca  gag ttt gtg acc cac  gcc      7063
Gly Leu Trp Ser  Val Val Ser Ser Thr  Glu Phe Val Thr His  Ala
            2295                 2300                 2305

tgc tcc ctc atc  tac tgt gtg cac ttc  atc ctg gag gcc gtt  gca      7108
Cys Ser Leu Ile  Tyr Cys Val His Phe  Ile Leu Glu Ala Val  Ala
            2310                 2315                 2320

gtg cag cct gga  gag cag ctt ctt agt  cca gaa aga agg aca  aat      7153
Val Gln Pro Gly  Glu Gln Leu Leu Ser  Pro Glu Arg Arg Thr  Asn
            2325                 2330                 2335

acc cca aaa gcc  atc agc gag gag gag  gag gaa gta gat cca  aac      7198
Thr Pro Lys Ala  Ile Ser Glu Glu Glu  Glu Glu Val Asp Pro  Asn
            2340                 2345                 2350

aca cag aat cct  aag tat atc act gca  gcc tgt gag atg gtg  gca      7243
Thr Gln Asn Pro  Lys Tyr Ile Thr Ala  Ala Cys Glu Met Val  Ala
            2355                 2360                 2365

gaa atg gtg gag  tct ctg cag tcg gtg  ttg gcc ttg ggt cat  aaa      7288
Glu Met Val Glu  Ser Leu Gln Ser Val  Leu Ala Leu Gly His  Lys
            2370                 2375                 2380

agg aat agc ggc  gtg ccg gcg ttt ctc  acg cca ttg cta agg  aac      7333
Arg Asn Ser Gly  Val Pro Ala Phe Leu  Thr Pro Leu Leu Arg  Asn
            2385                 2390                 2395

atc atc atc agc  ctg gcc cgc ctg ccc  ctt gtc aac agc tac  aca      7378
Ile Ile Ile Ser  Leu Ala Arg Leu Pro  Leu Val Asn Ser Tyr  Thr
            2400                 2405                 2410

cgt gtg ccc cca  ctg gtg tgg aag ctt  gga tgg tca ccc aaa  ccg      7423
Arg Val Pro Pro  Leu Val Trp Lys Leu  Gly Trp Ser Pro Lys  Pro
            2415                 2420                 2425

gga ggg gat ttt  ggc aca gca ttc cct  gag atc ccc gtg gag  ttc      7468
Gly Gly Asp Phe  Gly Thr Ala Phe Pro  Glu Ile Pro Val Glu  Phe
            2430                 2435                 2440

ctc cag gaa aag  gaa gtc ttt aag gag  ttc atc tac cgc atc  aac      7513
Leu Gln Glu Lys  Glu Val Phe Lys Glu  Phe Ile Tyr Arg Ile  Asn
            2445                 2450                 2455

aca cta ggc tgg  acc agt cgt act cag  ttt gaa gaa act tgg  gcc      7558
Thr Leu Gly Trp  Thr Ser Arg Thr Gln  Phe Glu Glu Thr Trp  Ala
            2460                 2465                 2470

acc ctc ctt ggt  gtc ctg gtg acg cag  ccc ctc gtg atg gag  cag      7603
Thr Leu Leu Gly  Val Leu Val Thr Gln  Pro Leu Val Met Glu  Gln
```

-continued

```
            2475                2480                2485

gag gag agc cca  cca gaa gaa gac aca  gag agg acc cag atc  aac      7648
Glu Glu Ser Pro  Pro Glu Glu Asp Thr  Glu Arg Thr Gln Ile  Asn
            2490                2495                2500

gtc ctg gcc gtg  cag gcc atc acc tca  ctg gtg ctc agt gca  atg      7693
Val Leu Ala Val  Gln Ala Ile Thr Ser  Leu Val Leu Ser Ala  Met
            2505                2510                2515

act gtg cct gtg  gcc ggc aac cca gct  gta agc tgc ttg gag  cag      7738
Thr Val Pro Val  Ala Gly Asn Pro Ala  Val Ser Cys Leu Glu  Gln
            2520                2525                2530

cag ccc cgg aac  aag cct ctg aaa gct  ctc gac acc agg ttt  ggg      7783
Gln Pro Arg Asn  Lys Pro Leu Lys Ala  Leu Asp Thr Arg Phe  Gly
            2535                2540                2545

agg aag ctg agc  att atc aga ggg att  gtg gag caa gag att  caa      7828
Arg Lys Leu Ser  Ile Ile Arg Gly Ile  Val Glu Gln Glu Ile  Gln
            2550                2555                2560

gca atg gtt tca  aag aga gag aat att  gcc acc cat cat tta  tat      7873
Ala Met Val Ser  Lys Arg Glu Asn Ile  Ala Thr His His Leu  Tyr
            2565                2570                2575

cag gca tgg gat  cct gtc cct tct ctg  tct ccg gct act aca  ggt      7918
Gln Ala Trp Asp  Pro Val Pro Ser Leu  Ser Pro Ala Thr Thr  Gly
            2580                2585                2590

gcc ctc atc agc  cac gag aag ctg ctg  cta cag atc aac ccc  gag      7963
Ala Leu Ile Ser  His Glu Lys Leu Leu  Leu Gln Ile Asn Pro  Glu
            2595                2600                2605

cgg gag ctg ggg  agc atg agc tac aaa  ctc ggc cag gtg tcc  ata      8008
Arg Glu Leu Gly  Ser Met Ser Tyr Lys  Leu Gly Gln Val Ser  Ile
            2610                2615                2620

cac tcc gtg tgg  ctg ggg aac agc atc  aca ccc ctg agg gag  gag      8053
His Ser Val Trp  Leu Gly Asn Ser Ile  Thr Pro Leu Arg Glu  Glu
            2625                2630                2635

gaa tgg gac gag  gaa gag gag gag gag  gcc gac gcc cct gca  cct      8098
Glu Trp Asp Glu  Glu Glu Glu Glu Glu  Ala Asp Ala Pro Ala  Pro
            2640                2645                2650

tcg tca cca ccc  acg tct cca gtc aac  tcc agg aaa cac cgg  gct      8143
Ser Ser Pro Pro  Thr Ser Pro Val Asn  Ser Arg Lys His Arg  Ala
            2655                2660                2665

gga gtt gac atc  cac tcc tgt tcg cag  ttt ttg ctt gag ttg  tac      8188
Gly Val Asp Ile  His Ser Cys Ser Gln  Phe Leu Leu Glu Leu  Tyr
            2670                2675                2680

agc cgc tgg atc  ctg ccg tcc agc tca  gcc agg agg acc ccg  gcc      8233
Ser Arg Trp Ile  Leu Pro Ser Ser Ser  Ala Arg Arg Thr Pro  Ala
            2685                2690                2695

atc ctg atc agt  gag gtg gtc aga tcc  ctt cta gtg gtc tca  gac      8278
Ile Leu Ile Ser  Glu Val Val Arg Ser  Leu Leu Val Val Ser  Asp
            2700                2705                2710

ttg ttc acc gag  cgc aac cag ttt gag  ctg atg tat gtg acg  ctg      8323
Leu Phe Thr Glu  Arg Asn Gln Phe Glu  Leu Met Tyr Val Thr  Leu
            2715                2720                2725

aca gaa ctg cga  agg gtg cac cct tca  gaa gac gag atc ctc  gct      8368
Thr Glu Leu Arg  Arg Val His Pro Ser  Glu Asp Glu Ile Leu  Ala
            2730                2735                2740

cag tac ctg gtg  cct gcc acc tgc aag  gca gct gcc gtc ctt  ggg      8413
Gln Tyr Leu Val  Pro Ala Thr Cys Lys  Ala Ala Ala Val Leu  Gly
            2745                2750                2755

atg gac aag gcc  gtg gcg gag cct gtc  agc cgc ctg ctg gag  agc      8458
Met Asp Lys Ala  Val Ala Glu Pro Val  Ser Arg Leu Leu Glu  Ser
            2760                2765                2770

acg ctc agg agc  agc cac ctg ccc agc  agg gtt gga gcc ctg  cac      8503
```

-continued

```
Thr Leu Arg Ser  Ser His Leu Pro Ser  Arg Val Gly Ala Leu  His
            2775                 2780                 2785

ggc gtc ctc tat  gtg ctg gag tgc gac  ctg ctg gac gac act  gcc      8548
Gly Val Leu Tyr  Val Leu Glu Cys Asp  Leu Leu Asp Asp Thr  Ala
            2790                 2795                 2800

aag cag ctc atc  ccg gtc atc agc gac  tat ctc ctc tcc aac  ctg      8593
Lys Gln Leu Ile  Pro Val Ile Ser Asp  Tyr Leu Leu Ser Asn  Leu
            2805                 2810                 2815

aaa ggg atc gcc  cac tgc gtg aac att  cac agc cag cag cac  gta      8638
Lys Gly Ile Ala  His Cys Val Asn Ile  His Ser Gln Gln His  Val
            2820                 2825                 2830

ctg gtc atg tgt  gcc act gcg ttt tac  ctc att gag aac tat  cct      8683
Leu Val Met Cys  Ala Thr Ala Phe Tyr  Leu Ile Glu Asn Tyr  Pro
            2835                 2840                 2845

ctg gac gta ggg  ccg gaa ttt tca gca  tca ata ata cag atg  tgt      8728
Leu Asp Val Gly  Pro Glu Phe Ser Ala  Ser Ile Ile Gln Met  Cys
            2850                 2855                 2860

ggg gtg atg ctg  tct gga agt gag gag  tcc acc ccc tcc atc  att      8773
Gly Val Met Leu  Ser Gly Ser Glu Glu  Ser Thr Pro Ser Ile  Ile
            2865                 2870                 2875

tac cac tgt gcc  ctc aga ggc ctg gag  cgc ctc ctg ctc tct  gag      8818
Tyr His Cys Ala  Leu Arg Gly Leu Glu  Arg Leu Leu Leu Ser  Glu
            2880                 2885                 2890

cag ctc tcc cgc  ctg gat gca gaa tcg  ctg gtc aag ctg agt  gtg      8863
Gln Leu Ser Arg  Leu Asp Ala Glu Ser  Leu Val Lys Leu Ser  Val
            2895                 2900                 2905

gac aga gtg aac  gtg cac agc ccg cac  cgg gcc atg gcg gct  ctg      8908
Asp Arg Val Asn  Val His Ser Pro His  Arg Ala Met Ala Ala  Leu
            2910                 2915                 2920

ggc ctg atg ctc  acc tgc atg tac aca  gga aag gag aaa gtc  agt      8953
Gly Leu Met Leu  Thr Cys Met Tyr Thr  Gly Lys Glu Lys Val  Ser
            2925                 2930                 2935

ccg ggt aga act  tca gac cct aat cct  gca gcc ccc gac agc  gag      8998
Pro Gly Arg Thr  Ser Asp Pro Asn Pro  Ala Ala Pro Asp Ser  Glu
            2940                 2945                 2950

tca gtg att gtt  gct atg gag cgg gta  tct gtt ctt ttt gat  agg      9043
Ser Val Ile Val  Ala Met Glu Arg Val  Ser Val Leu Phe Asp  Arg
            2955                 2960                 2965

atc agg aaa ggc  ttt cct tgt gaa gcc  aga gtg gtg gcc agg  atc      9088
Ile Arg Lys Gly  Phe Pro Cys Glu Ala  Arg Val Val Ala Arg  Ile
            2970                 2975                 2980

ctg ccc cag ttt  cta gac gac ttc ttc  cca ccc cag gac atc  atg      9133
Leu Pro Gln Phe  Leu Asp Asp Phe Phe  Pro Pro Gln Asp Ile  Met
            2985                 2990                 2995

aac aaa gtc atc  gga gag ttt ctg tcc  aac cag cag cca tac  ccc      9178
Asn Lys Val Ile  Gly Glu Phe Leu Ser  Asn Gln Gln Pro Tyr  Pro
            3000                 3005                 3010

cag ttc atg gcc  acc gtg gtg tat aag  gtg ttt cag act ctg  cac      9223
Gln Phe Met Ala  Thr Val Val Tyr Lys  Val Phe Gln Thr Leu  His
            3015                 3020                 3025

agc acc ggg cag  tcg tcc atg gtc cgg  gac tgg gtc atg ctg  tcc      9268
Ser Thr Gly Gln  Ser Ser Met Val Arg  Asp Trp Val Met Leu  Ser
            3030                 3035                 3040

ctc tcc aac ttc  acg cag agg gcc ccg  gtc gcc atg gcc acg  tgg      9313
Leu Ser Asn Phe  Thr Gln Arg Ala Pro  Val Ala Met Ala Thr  Trp
            3045                 3050                 3055

agc ctc tcc tgc  ttc ttt gtc agc gcg  tcc acc agc ccg tgg  gtc      9358
Ser Leu Ser Cys  Phe Phe Val Ser Ala  Ser Thr Ser Pro Trp  Val
            3060                 3065                 3070
```

-continued

```
gcg gcg atc ctc  cca cat gtc atc agc  agg atg ggc aag ctg  gag      9403
Ala Ala Ile Leu  Pro His Val Ile Ser  Arg Met Gly Lys Leu  Glu
            3075                 3080                 3085

cag gtg gac gtg  aac ctt ttc tgc ctg  gtc gcc aca gac ttc  tac      9448
Gln Val Asp Val  Asn Leu Phe Cys Leu  Val Ala Thr Asp Phe  Tyr
            3090                 3095                 3100

aga cac cag ata  gag gag gag ctc gac  cgc agg gcc ttc cag  tct      9493
Arg His Gln Ile  Glu Glu Glu Leu Asp  Arg Arg Ala Phe Gln  Ser
            3105                 3110                 3115

gtg ctt gag gtg  gtt gca gcc cca gga  agc cca tat cac cgg  ctg      9538
Val Leu Glu Val  Val Ala Ala Pro Gly  Ser Pro Tyr His Arg  Leu
            3120                 3125                 3130

ctg act tgt tta  cga aat gtc cac aag  gtc acc acc tgc tga           9580
Leu Thr Cys Leu  Arg Asn Val His Lys  Val Thr Thr Cys
            3135                 3140

gcgccatggt gggagagact gtgaggcggc agctggggcc ggagcctttg gaagtctgcg   9640

cccttgtgcc ctgcctccac cgagccagct tggtccctat gggcttccgc acatgccgcg   9700

ggcggccagg caacgtgcgt gtctctgcca tgtggcagaa gtgctctttg tggcagtggc   9760

caggcaggga gtgtctgcag tcctggtggg gctgagcctg aggccttcca gaaagcagga   9820

gcagctgtgc tgcaccccat gtgggtgacc aggtcctttc tcctgatagt cacctgctgg   9880

ttgttgccag gttgcagctg ctcttgcatc tgggccagaa gtcctccctc ctgcaggctg   9940

gctgttggcc cctctgctgt cctgcagtag aaggtgccgt gagcaggctt tgggaacact  10000

ggcctgggtc tccctggtgg ggtgtgcatg ccacgccccg tgtctggatg cacagatgcc  10060

atggcctgtg ctgggccagt ggctgggggt gctagacacc cggcaccatt ctcccttctc  10120

tcttttcttc tcaggattta aaatttaatt atatcagtaa agagattaat tttaacgtaa  10180

ctctttctat gcccgtgtaa agtatgtgaa tcgcaaggcc tgtgctgcat gcgacagcgt  10240

ccggggtggt ggacagggcc cccggccacg ctccctctcc tgtagccact ggcatagccc  10300

tcctgagcac ccgctgacat ttccgttgta catgttcctg tttatgcatt cacaaggtga  10360

ctgggatgta gagaggcgtt agtgggcagg tggccacagc aggactgagg acaggccccc  10420

attatcctag gggtgcgctc acctgcagcc cctcctcctc gggcacagac gactgtcgtt  10480

ctccacccac cagtcaggga cagcagcctc cctgtcactc agctgagaag gccagccctc  10540

cctggctgtg agcagcctcc actgtgtcca gagacatggg cctcccactc ctgttccttg  10600

ctagccctgg ggtggcgtct gcctaggagc tggctggcag gtgttgggac ctgctgctcc  10660

atggatgcat gccctaagag tgtcactgag ctgtgttttg tctgagcctc tctcggtcaa  10720

cagcaaagct tggtgtcttg gcactgttag tgacagagcc cagcatccct tctgcccccg  10780

ttccagctga catcttgcac ggtgacccct tttagtcagg agagtgcaga tctgtgctca  10840

tcggagactg ccccacggcc ctgtcagagc cgccactcct atccccaggc caggtccctg  10900

gaccagcctc ctgtttgcag gcccagagga gccaagtcat taaaatggaa gtggattctg  10960

gatggccggg ctgctgctga tgtaggagct ggatttggga gctctgcttg ccgactggct  11020

gtgagacgag gcaggggctc tgcttcctca gccctagagg cgagccaggc aaggttggcg  11080

actgtcatgt ggcttggttt ggtcatgccc gtcgatgttt tgggtattga atgtggtaag  11140

tggaggaaat gttggaactc tgtgcaggtg ctgccttgag acccccaagc ttccacctgt  11200

ccctctccta tgtggcagct ggggagcagc tgagatgtgg acttgtatgc tgcccacata  11260

cgtgaggggg agctgaaagg gagcccctcc tctgagcagc ctctgccagg cctgtatgag  11320

gcttttccca ccagctccca acagaggcct cccccagcca ggaccacctc gtcctcgtgg  11380
```

```
cggggcagca ggagcggtag aaaggggtcc gatgtttgag gaggccctta agggaagcta  11440
ctgaattata acacgtaaga aaatcaccat tccgtattgg ttgggggctc ctgtttctca  11500
tcctagcttt ttcctggaaa gcccgctaga aggtttggga acgaggggaa agttctcaga  11560
actgttggct gctccccacc cgcctcccgc ctcccccgca ggttatgtca gcagctctga  11620
gacagcagta tcacaggcca gatgttgttc ctggctagat gtttacattt gtaagaaata  11680
acactgtgaa tgtaaaacag agccattccc ttggaatgca tatcgctggg ctcaacatag  11740
agtttgtctt cctcttgttt acgacgtgat ctaaaccagt ccttagcaag ggctcagaa  11800
caccccgctc tggcagtagg tgtcccccac ccccaaagac ctgcctgtgt gctccggaga  11860
tgaatatgag ctcattagta aaaatgactt cacccacgca tatacataaa gtatccatgc  11920
atgtgcatat agacacatct ataattttac acacacacct ctcaagacgg agatgcatgg  11980
cctctaagag tgcccgtgtc ggttcttcct ggaagttgac tttccttaga cccgccaggt  12040
caagttagcc gcgtgacgga catccaggcg tgggacgtgg tcagggcagg gctcattcat  12100
tgcccactag gatcccactg gcgaagatgg tctccatatc agctctctgc agaagggagg  12160
aagactttat catgttccta aaaatctgtg gcaagcaccc atcgtattat ccaaattttg  12220
ttgcaaatgt gattaatttg gttgtcaagt tttgggggtg ggctgtgggg agattgcttt  12280
tgttttcctg ctggtaatat cgggaaagat tttaatgaaa ccagggtaga attgtttggc  12340
aatgcactga agcgtgtttc tttcccaaaa tgtgcctccc ttccgctgcg ggcccagctg  12400
agtctatgta ggtgatgttt ccagctgcca agtgctcttt gttactgtcc accctcattt  12460
ctgccagcgc atgtgtcctt tcaaggggaa aatgtgaagc tgaacccccct ccagacaccc  12520
agaatgtagc atctgagaag gccctgtgcc ctaaaggaca cccctcgccc ccatcttcat  12580
ggagggggtc atttcagagc cctcggagcc aatgaacagc tcctcctctt ggagctgaga  12640
tgagccccac gtggagctcg ggacggatag tagacagcaa taactcggtg tgtggccgcc  12700
tggcaggtgg aacttcctcc cgttgcgggg tggagtgagg ttagttctgt gtgtctggtg  12760
ggtggagtca ggcttctctt gctacctgtg agcatccttc ccagcagaca tcctcatcgg  12820
gctttgtccc tcccccgctt cctccctctg cggggaggac ccgggaccac agctgctggc  12880
cagggtagac ttggagctgt cctccagagg ggtcacgtgt aggagtgaga agaaggaaga  12940
tcttgagagc tgctgaggga ccttggagag ctcaggatgg ctcagacgag gacactcgct  13000
tgccgggcct gggcctcctg ggaaggaggg agctgctcag aatgccgcat gacaactgaa  13060
ggcaacctgg aaggttcagg ggccgctctt cccccatgtg cctgtcacgc tctggtgcag  13120
tcaaaggaac gccttcccct cagttgtttc taagagcaga gtctcccgct gcaatctggg  13180
tggtaactgc cagccttgga ggatcgtggc caacgtggac ctgcctacgg agggtgggct  13240
ctgacccaag tggggcctcc ttgtccaggt ctcactgctt tgcaccgtgg tcagagggac  13300
tgtcagctga gcttgagctc ccctggagcc agcagggctg tgatgggcga gtcccggagc  13360
cccacccaga cctgaatgct tctgagagca aagggaagga ctgacgagag atgtatattt  13420
aattttttaa ctgctgcaaa cattgtacat ccaaattaaa ggaaaaaaat ggaaaccatc  13480
a                                                                  13481
```

<210> SEQ ID NO 3
<211> LENGTH: 15
<212> TYPE: DNA
<213> ORGANISM: Artificial sequence
<220> FEATURE:

<223> OTHER INFORMATION: Synthetic oligonucleotide

<400> SEQUENCE: 3
taaattgtca tcacc 15

<210> SEQ ID NO 4
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 4
ataaattgtc atcacc 16

<210> SEQ ID NO 5
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 5
ataaattgtc atcacca 17

<210> SEQ ID NO 6
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 6
aataaattgt catcaccag 19

<210> SEQ ID NO 7
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 7
ataaattgtc atcaccaga 19

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
taaattgtca tcaccagaa 19

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
aaattgtcat caccagaaa 19

<210> SEQ ID NO 10
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 10
aattgtcatc accagaaaa 19

<210> SEQ ID NO 11
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 11
attgtcatca ccagaaaaa 19

<210> SEQ ID NO 12
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 12
taataaattg tcatcacca 19

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
ttaataaatt gtcatcacc 19

<210> SEQ ID NO 14
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 14
aaattgtcat caccaga 17

<210> SEQ ID NO 15
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 15
taaattgcca tcacc 15

<210> SEQ ID NO 16
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 16
ataaattgcc atcacca 17

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
ataaattgcc atcacc 16

<210> SEQ ID NO 18
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 18
attgccatca ccaga 15

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
taaattgcca tcacca 16

<210> SEQ ID NO 20
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 20
taaattgcca tcaccag 17

<210> SEQ ID NO 21
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 21
taattttcta gacttta 17

<210> SEQ ID NO 22
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 22
aattttctag actttat 17

<210> SEQ ID NO 23
<211> LENGTH: 15

<212> TYPE: DNA
<213> ORGANISM: Artificial sequence
<220> FEATURE:
<223> OTHER INFORMATION: Synthetic oligonucleotide

<400> SEQUENCE: 23
attgtcatca ccaga 15

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
ttgtcatcac cagaaa 16

<210> SEQ ID NO 25
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 25
ttgtcatcac cagaaaa 17

<210> SEQ ID NO 26
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 26
aattgtcatc accag 15

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
aattgtcatc accaga 16

<210> SEQ ID NO 28
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 28
aattgtcatc accagaa 17

<210> SEQ ID NO 29
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 29

-continued attgtcatca ccagaaa 17

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
attgtcatca ccagaa 16

<210> SEQ ID NO 31
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 31
aattgtcatc acccgaa 17

<210> SEQ ID NO 32
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 32
attgtcatca cccgaaa 17

<210> SEQ ID NO 33
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 33
ttgtcatcac cagcaaa 17

<210> SEQ ID NO 34
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 34
attgtcatca ccagtaa 17

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
ccttccctga aggttcctcc 20

<210> SEQ ID NO 36
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 36

tctctattgc acattccaag                                                20


<210> SEQ ID NO 37
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 37

ttgtcatcac cagaa                                                     15


<210> SEQ ID NO 38
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 38

aatacgggta acatttt                                                   17


<210> SEQ ID NO 39
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 39

gaatacgggt aacattt                                                   17
```